(12) United States Patent
Biasini et al.

(10) Patent No.: US 10,391,068 B2
(45) Date of Patent: Aug. 27, 2019

(54) PRION PROTEIN LIGANDS AS THERAPEUTIC AGENTS FOR NEURODEGENERATIVE DISORDERS

(71) Applicants: TRUSTEES OF BOSTON UNIVERSITY, Boston, MA (US); UNIVERSITA DI PERUGIA, Perugia (IT)

(72) Inventors: Emiliano Biasini, Newton, MA (US); David A. Harris, Boston, MA (US); Aaron Beeler, Cambridge, MA (US); Brian R. Fluharty, Boston, MA (US); Maria Letizia Barreca, Perugia (IT); Nunzio Iraci, Perugia (IT); Oscar Ingham, Boston, MA (US)

(73) Assignees: TRUSTEES OF BOSTON UNIVERSITY, Boston, MA (US); UNIVERSITA DI PERUGIA, Perugia (IT)

( * ) Notice: Subject to any disclaimer, the term of this patent is extended or adjusted under 35 U.S.C. 154(b) by 231 days.

(21) Appl. No.: 14/419,797

(22) PCT Filed: Aug. 6, 2013

(86) PCT No.: PCT/US2013/053796
§ 371 (c)(1),
(2) Date: Feb. 5, 2015

(87) PCT Pub. No.: WO2014/025785
PCT Pub. Date: Feb. 13, 2014

(65) Prior Publication Data
US 2015/0196508 A1    Jul. 16, 2015

Related U.S. Application Data

(60) Provisional application No. 61/679,974, filed on Aug. 6, 2012, provisional application No. 61/835,314, filed on Jun. 14, 2013.

(51) Int. Cl.
| | | |
|---|---|---|
| *A61K 31/18* | (2006.01) | |
| *A61K 31/41* | (2006.01) | |
| *A61K 45/06* | (2006.01) | |
| *A61K 31/145* | (2006.01) | |
| *A61K 31/365* | (2006.01) | |
| *C07C 337/08* | (2006.01) | |
| *C07D 307/33* | (2006.01) | |
| *C07D 309/14* | (2006.01) | |
| *A61K 31/7008* | (2006.01) | |

(52) U.S. Cl.
CPC ............ *A61K 31/145* (2013.01); *A61K 31/18* (2013.01); *A61K 31/365* (2013.01); *A61K 31/41* (2013.01); *A61K 31/7008* (2013.01); *A61K 45/06* (2013.01); *C07C 337/08* (2013.01); *C07D 307/33* (2013.01); *C07D 309/14* (2013.01); *C07C 2601/14* (2017.05)

(58) Field of Classification Search
CPC combination set(s) only.
See application file for complete search history.

(56) References Cited

U.S. PATENT DOCUMENTS

| | | |
|---|---|---|
| 6,866,849 B2 | 3/2005 | Schenk |
| 6,913,745 B1 | 7/2005 | Schenk |
| 2005/0170359 A1 | 8/2005 | Zlokovic |
| 2006/0239996 A1 | 10/2006 | Prusiner et al. |
| 2010/0291090 A1 | 11/2010 | Strittmatter et al. |
| 2011/0250630 A1 | 10/2011 | Burton et al. |

FOREIGN PATENT DOCUMENTS

| | | |
|---|---|---|
| EP | 0920630 | 7/2002 |
| EP | 2311506 A1 | 4/2011 |
| WO | 03/104466 A1 | 12/2003 |
| WO | 2005/072770 A1 | 8/2005 |
| WO | WO 2006083019 * | 8/2006 |
| WO | 2007/028133 A2 | 3/2007 |
| WO | 20070302804 | 3/2007 |
| WO | 2010/013717 A1 | 2/2010 |

OTHER PUBLICATIONS

Kumar et al. (E J of Medicinal Chem. 124, 2016, 1105-1120).*
Gershell 326, col. 2, Nature Reviews, 321-327, 2003.*
Hann, Med. Chem. Commn, Feb. 2011, 349.*
Fluharty et al. "An N-terminal Fragment of the Prior Protein Binds to Amyloid-B Oligomers and Inhibits Their Neurotoxicity in Vivo" The Journal of Biological Chemistry 288:7857-7866 (2013).
Baumann et al., "Lethal recessive myelin toxicity of prion protein lacking its central domain", The EMBO Journal 26(2):538-547 (2007).
Biasini E., "Targeting the Functional Activity of PrPC as a Novel Strategy for Drug Discovery in Prion Diseases", CJD 2011 and the Ninth Annual CJD Foundation Family Conference (2011). (24 pages).
Biasini et al., "Prion Protein At the Crossroads of Physiology and Disease", Trends in Neurosciences 35(2):92-103 (2012).

(Continued)

*Primary Examiner* — Umamaheswari Ramachandran
(74) *Attorney, Agent, or Firm* — Nixon Peabody LLP

(57) ABSTRACT

The invention provides compositions and methods for treatment of neurodegenerative diseases or disorders, particularly neurodegenerative diseases and disorders associated with protein aggregation. The present invention is based on the discovery of binding regions on the surface of PrPc, referred to as PrPc Binding Domains (PBD). In particular, the inventors have identified six different binding regions on PrPc, referred to herein as PrP-binding domain-1 (PBD-1), PrP-binding domain-2 (PBD-2), PrP-binding domain-3 (PBD-3), PrP-binding domain-4 (PBD-4), PrP-binding domain-5 (PBD-5), and PrP-binding domain-6 (PBD-6), herein. The PBD-1 to PBD-6 are each defined by a cluster of amino acids located in the globular domain of the protein, e.g., in the C-terminal half of the protein (i.e., in residues 120-230). One embodiment uses residues 127-226.

2 Claims, 53 Drawing Sheets

Specification includes a Sequence Listing.

(56) References Cited

OTHER PUBLICATIONS

Chung et al., "Anti-PrPC monoclonal antibody infusion as a novel treatment for cognitive deficits in an alzheimer's disease model mouse", BMC Neuroscience 11:130 (2010). (11 pages).
Kuwata et al., "Hot spots in prion protein for pathogenic conversion", Proceedings of the National Academy of Sciences 104(29):11921-11926 (2007).
Li et al., "Neonatal lethality in transgenic mice expressing prion protein with a deletion of residues 105-125", The EMBO Journal 26(2):548-558 (2007).
MolPort Compound No. MolPort-001-9I9-237.
PubChem Compound ID No. 361310.
PubChem Compound ID No. 2829394.
PubChem Compound ID No. 3589074.
Riek et al., "NMR structure of the mouse prion protein domain PrP (121-231)", Nature 382:180-182 (1996).
Sigma-Aldrich Catalog No. R161209.
Viles et al., "Copper binding to the prion protein: Structural implications of four identical cooperative binding sites", Proceedings of the National Academy of Sciences 96:2042-2047 (1999).

\* cited by examiner

Reproduced from Biasini et al. TINS. 2012.

*FIG. 4A*
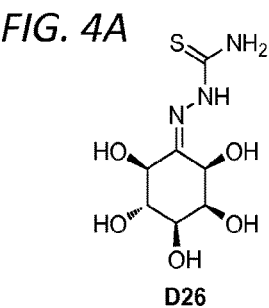
D26
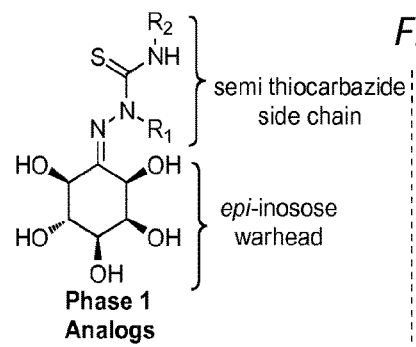
semi thiocarbazide side chain
epi-inosose warhead
Phase 1 Analogs
*FIG. 4C*
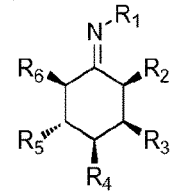
$R_1$ = alkyl, hetero alkyl, aryl
$R_2$-$R_6$ = OH, H, $NH_2$, OR, NHR
*FIG. 4B*
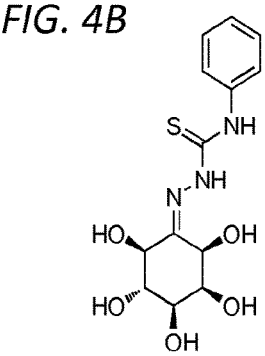 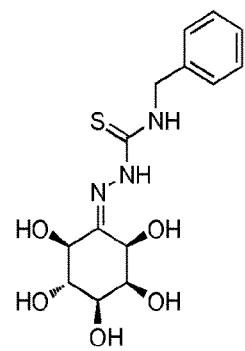 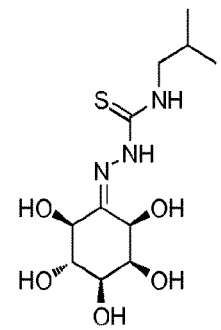
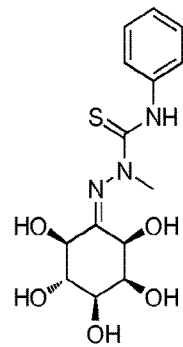 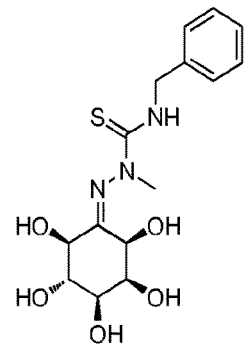 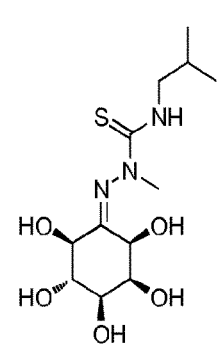
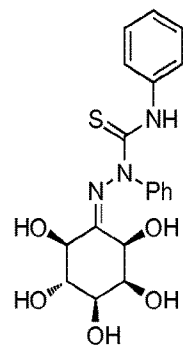 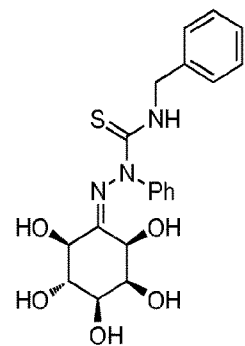 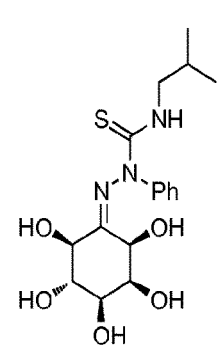

Potential Analogs of DS86

X = O or N
R1 = H, aryl, alkyl, acyl
R2 = H, aryl, alkyl, acyl
R3 = H, aryl, alkyl, acyl Potential Analogs of DS40

X = O or N
R1 = H, aryl, alkyl, acyl
R2 = H, aryl, alkyl, acyl
R3, R4 = aryl, alkyl, heterocycle Potential Analogs of DS5

X = O or N
R1 = H, aryl, alkyl, acyl
R2 = H, aryl, alkyl, acyl
R3 = H, aryl, alkyl, acyl

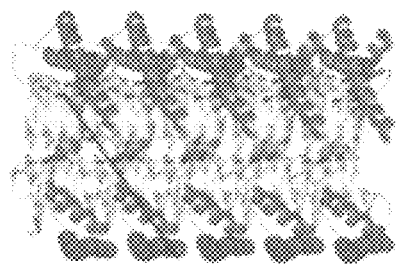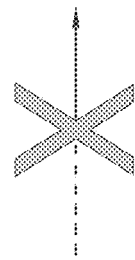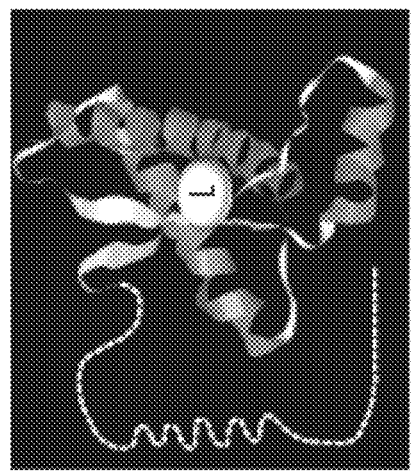
FIG. 9

FIG. 13A
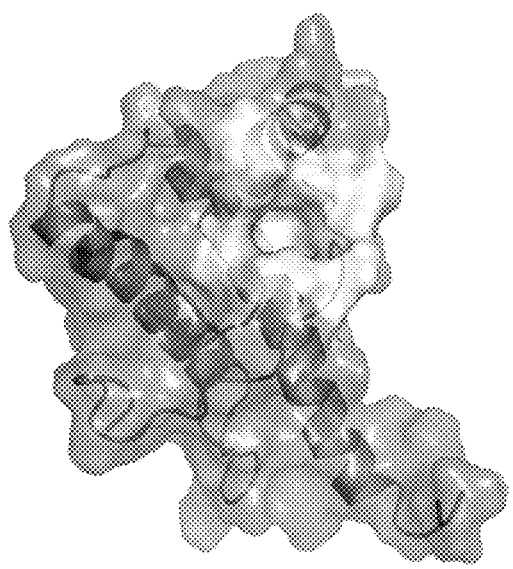
FIG. 13B
17 million compounds
↓ HTVS docking
200,000 Compounds
↓ SP/XP docking and refinement
10,000 Compounds
↓ Removal of low efficiency ligand compounds / clustering / visual inspection
121 Compounds
↓ Molecular Dynamics Ranking
52 Compounds
↓
16 Compounds from NCI
↓ Test by SPR
DS26
FIG. 13C
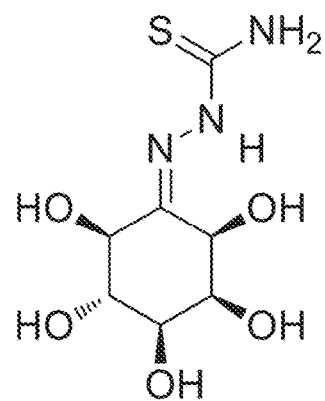

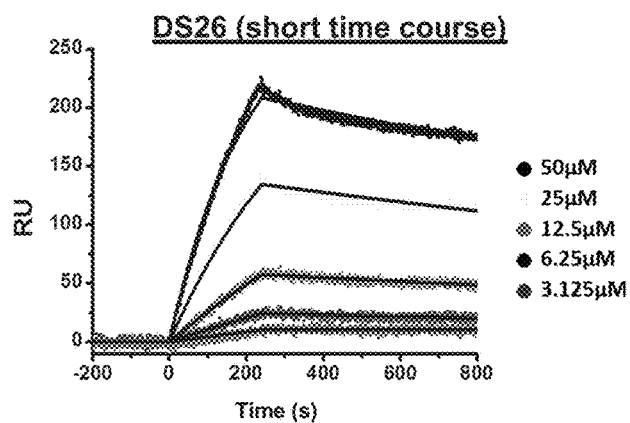
FIG. 14A
FIG. 14B
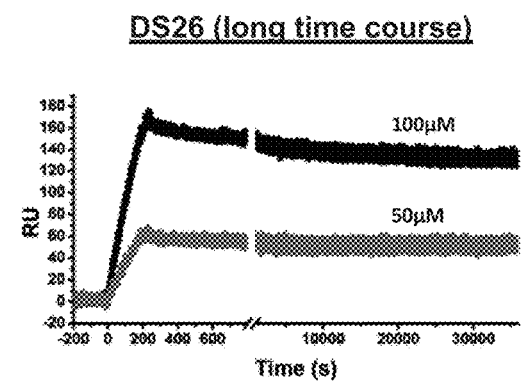
FIG. 14C
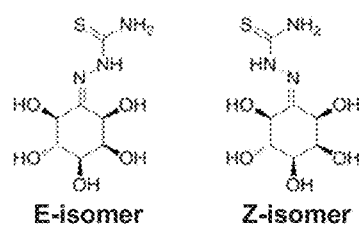
FIG. 14D
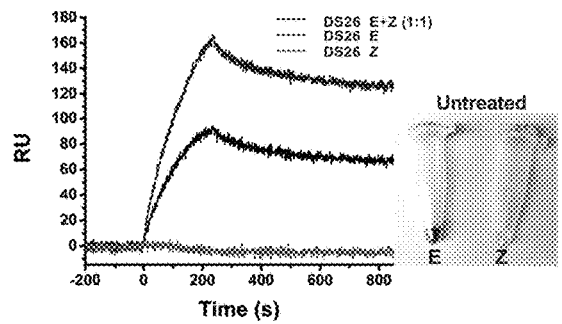

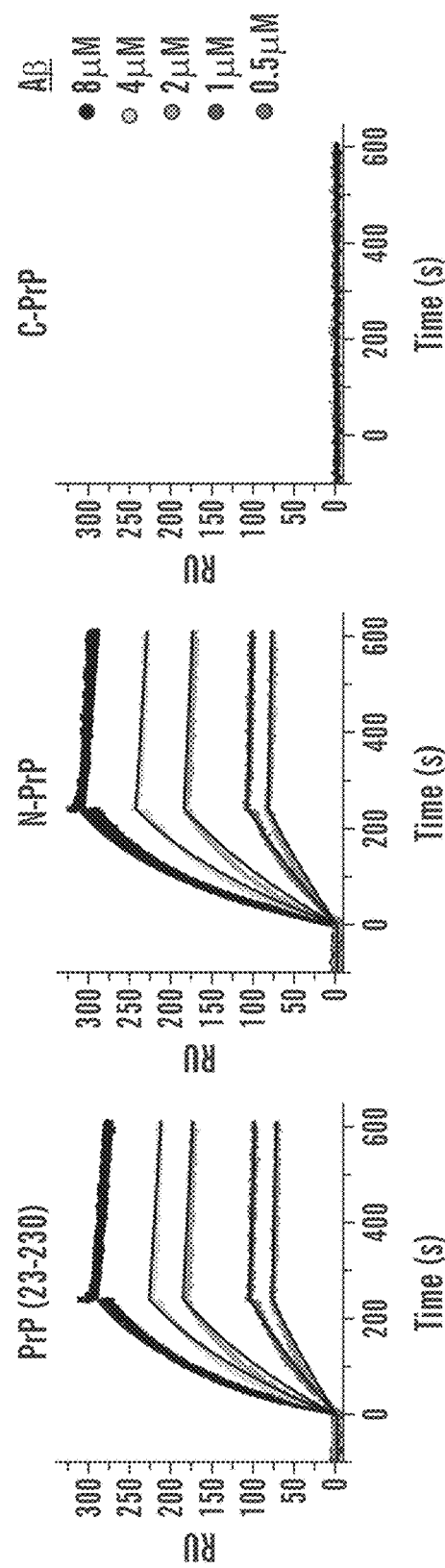

FIG. 18A PrP(23-230)
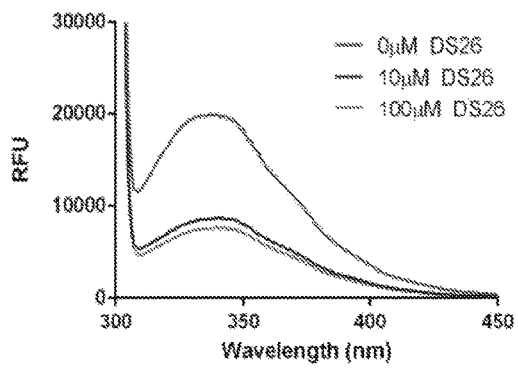
FIG. 18B N-PrP
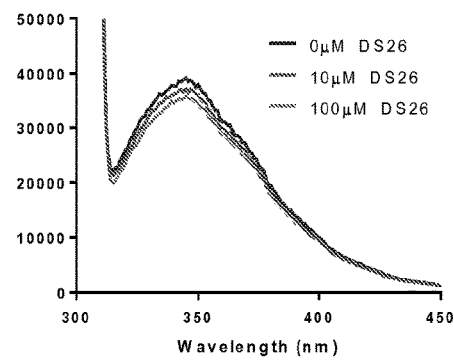
FIG. 18C PrP(23-230)
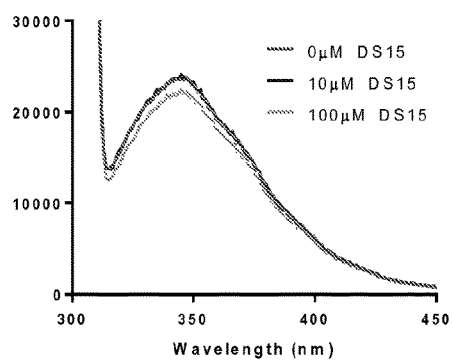
FIG. 18D
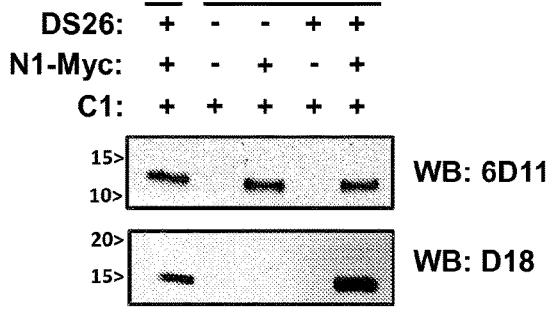
FIG. 18E
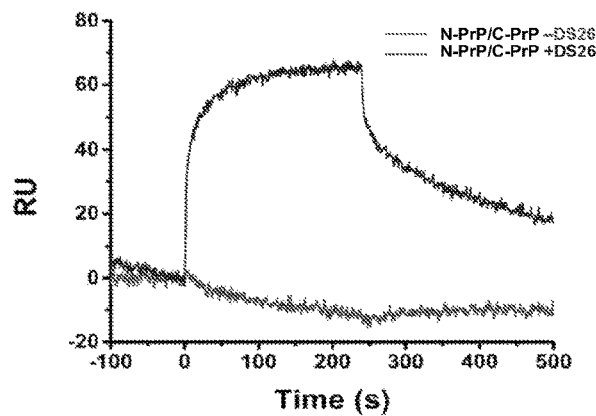

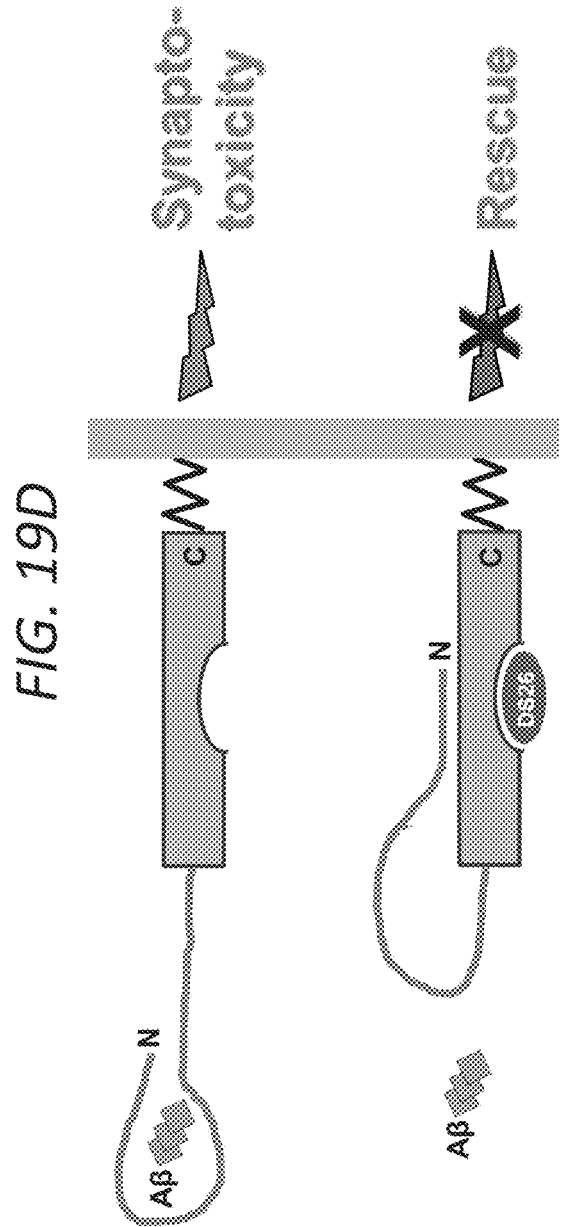

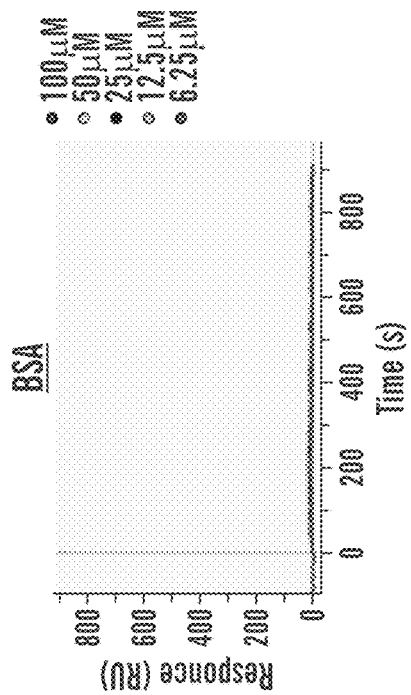
FIG. 20E
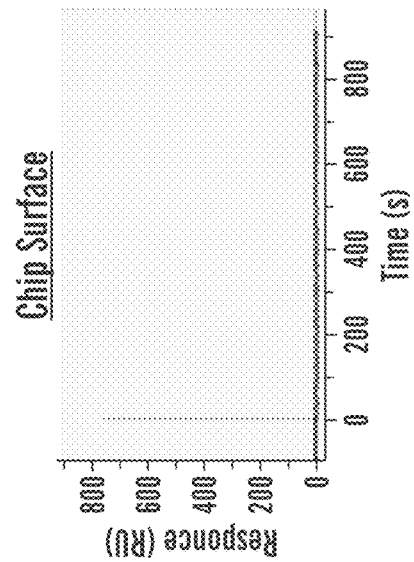
FIG. 20F
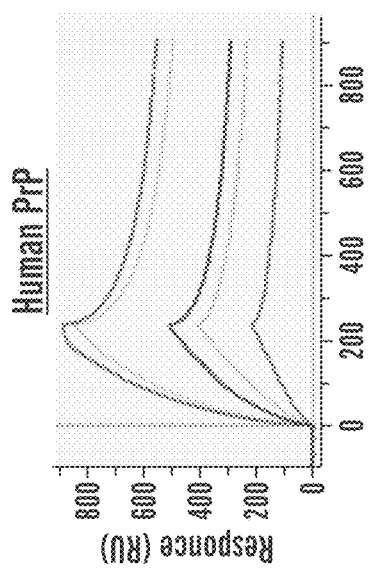
FIG. 20G
FIG. 20H

FIG. 24B
DS35
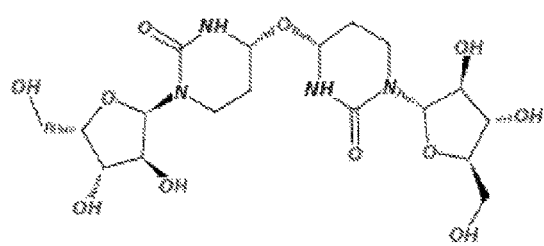
DS37
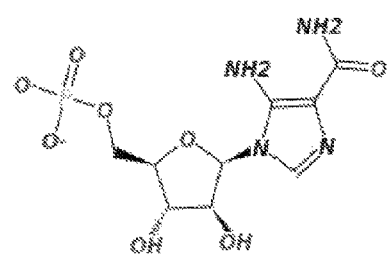
DS38
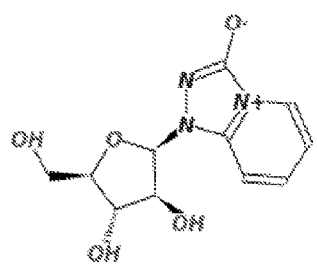
DS39
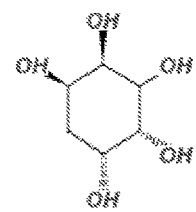
DS41
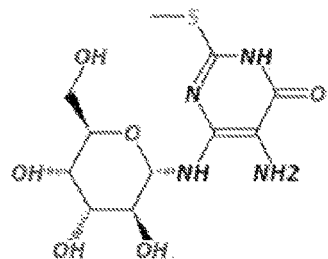

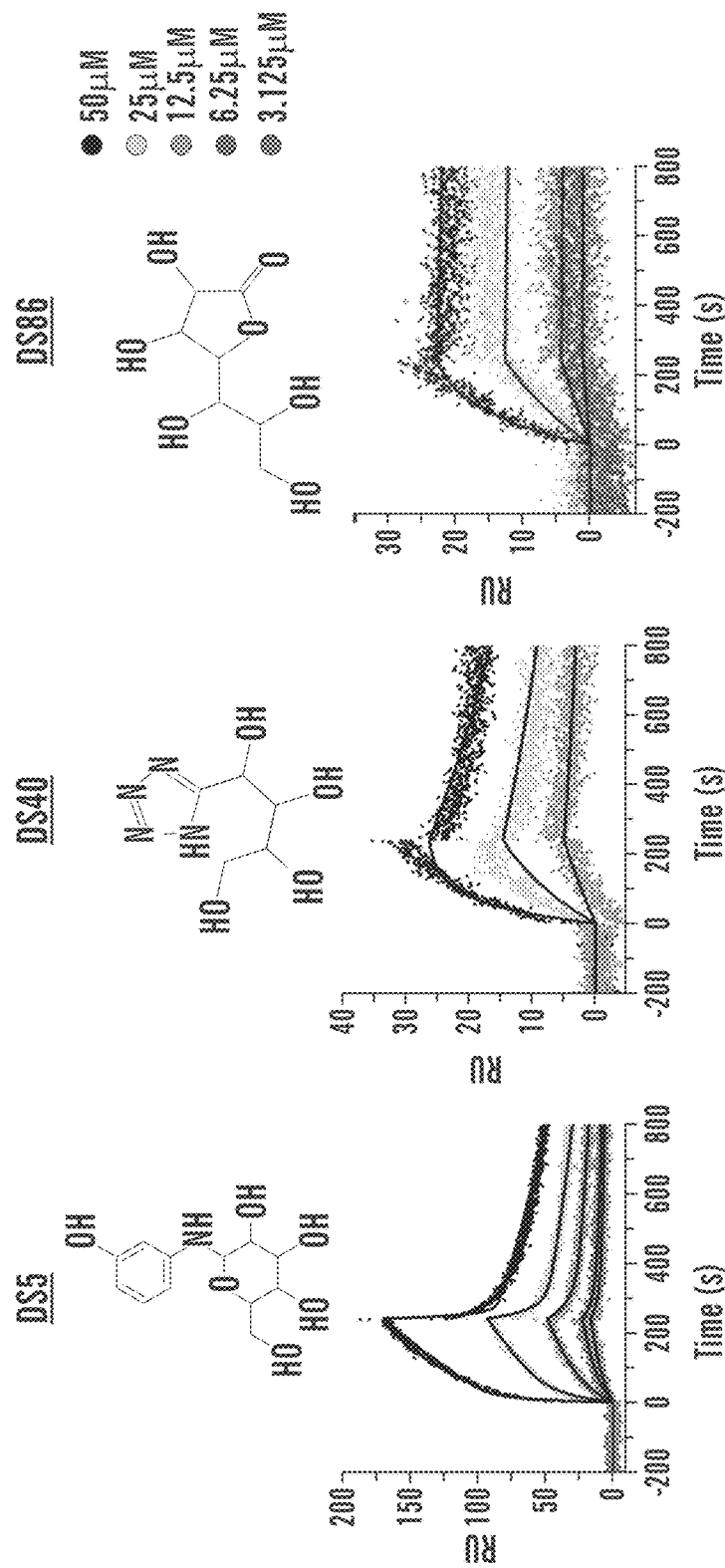

FIG. 30A
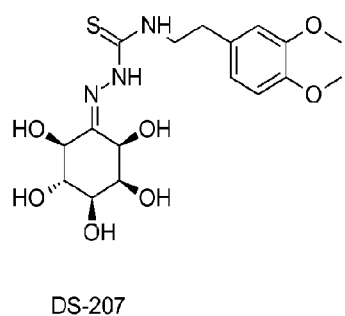
DS-207
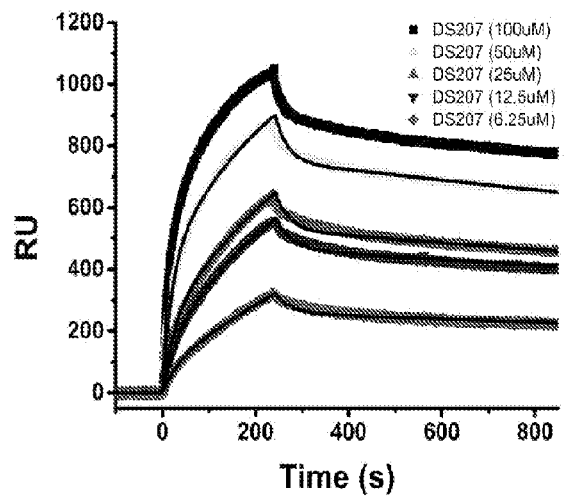
FIG. 30B
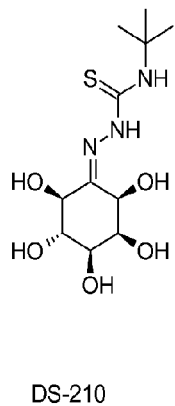
DS-210
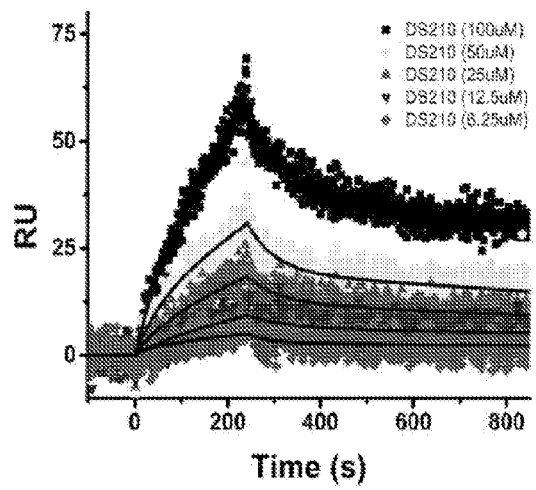
FIG. 30C
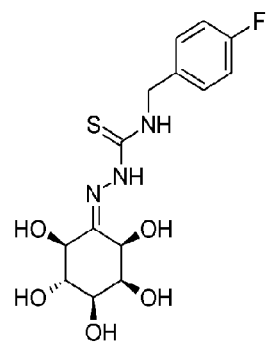
DS-211
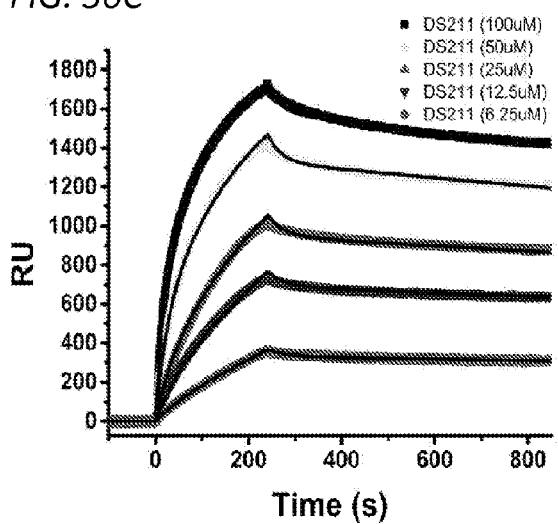

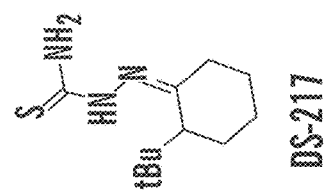
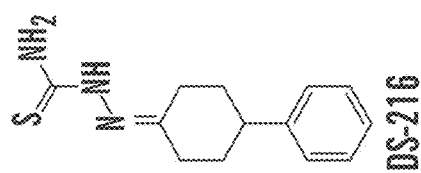
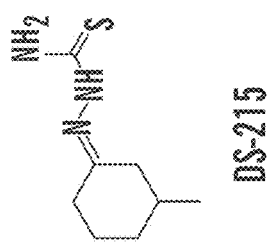
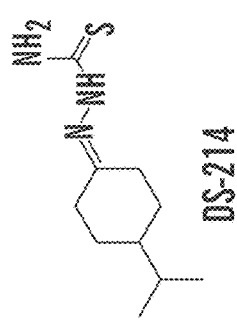
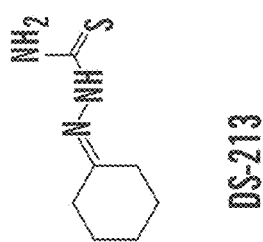
FIG. 31A

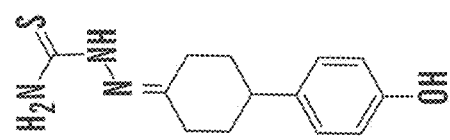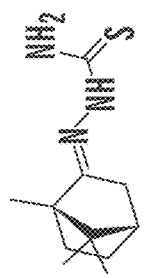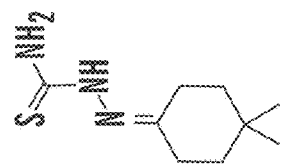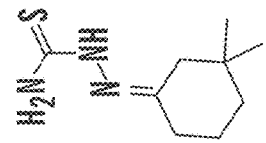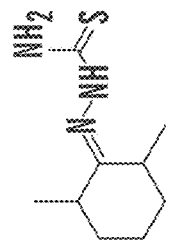
FIG. 31A (cont.)

PRION PROTEIN LIGANDS AS THERAPEUTIC AGENTS FOR NEURODEGENERATIVE DISORDERS

CROSS REFERENCE TO RELATED APPLICATIONS

This application is a 35 U.S.C. § 371 National Phase Entry Application of International Application No. PCT/US2013/053796 filed Aug. 6, 2013, which designates the U.S. and which claims benefit under 35 U.S.C. § 119(e) of U.S. Provisional Application No. 61/679,974, filed Aug. 6, 2012 and U.S. Provisional Application No. 61/835,314, filed Jun. 14, 2013, the contents of each are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 29, 2015, is named 701586-074802_PCT_SL.txt and is 7.98 KB in size.

TECHNICAL FIELD

The present invention relates generally to compositions and methods for treatment of neurodegenerative diseases or disorders.

BACKGROUND

Despite the enormous scientific effort devoted in the last two decades to developing pharmacological approaches for neurodegenerative diseases, very few effective drugs have been discovered. Thus, there are no effective therapies for most of these devastating disorders. A clear example is provided by Alzheimer's disease (AD) Alzheimer's disease is the most common cause of memory loss in the elderly population, and the 5th leading cause of death in this group, currently affecting almost 50 million individuals worldwide. The number will increase dramatically in the coming decades as the population ages, producing devastating medical and socio-economic consequences. Although some of the basic molecular mechanisms underlying AD have been identified, this has not resulted in effective treatments for this devastating disorder. The disease is associated with accumulation in the brain of the 40-42 amino acid amyloid-β (Aβ) peptide, a cleavage product of the amyloid precursor protein (APP). Aβ spontaneously forms polymers ranging from small, soluble oligomers to large, insoluble fibrils. Compelling evidence suggests that soluble Aβ oligomers, rather than fibrillar aggregates, are primarily responsible for the synaptic dysfunction underlying the cognitive decline in Alzheimer's disease. Aβ oligomers are believed to act by binding to cell surface receptors that transduce their detrimental effects on synapses. However, the identity of these receptors remains uncertain. The identification of neuronal receptor sites for Aβ oligomers has important therapeutic implications, since these represent potential targets for pharmacological intervention. Drugs that block Aβ binding to its neuronal receptors and inhibit downstream neurotoxic effects may offer a significant advantage over current therapies, since such compounds target the earliest molecular abnormalities in synaptic function.

The two major neuronal systems previously targeted for preventing this disease are the cholinergic and the glutamatergic systems. Currently approved treatments for Alzheimer's disease, including cholinesterase inhibitors such as Donepezil (Aricept) and the NMDA receptor antagonist memantine, offer temporary symptomatic relief, but do not significantly delay the course of the disease. The reason for the lack of efficacy of these compounds is likely due the fact that their targets are not involved in the earliest alterations in synaptic function that initiate the pathogenic process.

Following the amyloid cascade hypothesis, additional targets have been considered in recent years. Alternative strategies have included: (i) decreasing production of the Aβ peptide by inhibition of β- and γ-secretases, or stimulation of the α-secretases (the cleaving enzymes responsible for the processing of the APP protein); (ii) increasing Aβ clearance by either active (vaccination) or passive (monoclonal antibodies) immunization, up-regulation of degrading enzymes (Neprelysin and the insulin degrading enzyme), or stimulation of Aβ transport out of the brain (by altering the RAGE/LRP-1 pathway). Unfortunately, however, none of these approaches (some of which have reached phase III clinical trials) has shown significant effects in preventing the cognitive decline in Alzheimer's patients.

Recently, a novel and surprising candidate has emerged as a receptor for Aβ oligomers: the cellular form of the prion protein ($PrP^C$), a membrane glycoprotein expressed on the neuronal surface, $PrP^C$. $PrP^C$ is an endogenous, cell-surface glycoprotein, plays an important role in transmissible neurodegenerative disorders such as Creutzfeldt-Jakob disease and bovine spongiform encephalopathy (commonly referred to as prion diseases), by serving as the substrate for formation of $PrP^{Sc}$, the infectious form of PrP. It has been previously reported that Aβ oligomers (but not monomers or fibrils) bind with low nanomolar affinity to $PrP^C$ via two sites within the unstructured N-terminal tail (residues 23-27 and 95-105). Binding was not observed with Aβ monomers or fibrils, suggesting that $PrP^C$ is specifically a receptor for oligomers. Importantly, $PrP^C$ was also found to be a mediator of Aβ-induced synaptotoxicity. As a consequence of this interaction, $PrP^C$ transduces the synaptotoxic effects of Aβ oligomers via intracellular signaling cascades. Although some studies have challenged this model, others have shown that $PrP^C$ could be targeted to block Aβ in vivo. For example, application of anti-PrP antibodies, or genetic ablation of $PrP^C$, can prevent Aβ-induced synaptic dysfunction in hippocampal slices or transgenic mice. In particular, hippocampal slices derived from PrP null mice were found to be resistant to Aβ oligomer-induced suppression of long-term potentiation (LTP), an in vitro correlate of memory and synaptic function. Additionally, $PrP^C$ was required for both the cognitive deficits and reduced survival observed in transgenic mouse models of Alzheimer's disease. The identification of $PrP^C$ as a cell-surface receptor that mediates the neurotoxic effects of the Aβ oligomers therefore suggests that alterations in the normal function of $PrP^C$ could play a role in the pathogenesis of Alzheimer's diseases (see FIGS. 1A and 1C). Thus, there is a need to identify molecules and inhibitors to block Aβ oligomer binding to $PrP^C$ as a treatment for AD Prion Diseases and $PrP^C$. Amazingly, $PrP^C$ has been studied for the last two decades in the context of a different group of neurodegenerative disorders, known as prion diseases. Prion diseases, including bovine spongiform encephalopathy ("mad cow disease") and its human counterparts, are rare neurodegenerative disorders caused by an unusual type of infectious agent (prion) that consist of a self-propagating protein molecule. Prion diseases are caused by conversion of PrP$^C$, a normal cell-surface glycoprotein, into PrP$^{Sc}$, a conformationally altered isoform that serves as a molecular template for generation of additional molecules of PrP$^{Sc}$. While much research has focused on characterizing the mechanisms of formation and replication of prions, little progress has been made in defining the neurodegenerative pathways operative in prion diseases. Recent evidence indicates that the toxicity of PrP$^{Sc}$ requires the presence of membrane-anchored PrP$^C$ at the cell surface, and suggests that the normal, physiological activity of PrP$^C$ is subverted to produce toxicity (see FIGS. 1B and 1D). Previous attempts to treat prion diseases by simply lowering the load of PrP$^{Sc}$ have been largely unsuccessful. This may be due to the fact that PrP$^C$-mediated neurotoxicity, once unleashed, remains active even if formation of PrP$^{Sc}$ is inhibited. Therefore, the most effective anti-prion treatments could be those that block prion-induced toxic pathways, as well as PrP$^{Sc}$ formation.

The physiological activity of PrP$^C$ has so far remained elusive. In an attempt to provide insights into the normal activity of PrP$^C$, the inventors recently demonstrated that deletions in the conserved central region endow the protein with a highly toxic activity that is likely related to its normal function. In particular, the inventors found that mutations in the central region of PrP (residues 105-125), including artificial deletions as well as point mutations associated with familial prion diseases of humans, induce a powerful ion channel activity at the plasma membrane that can be detected in transfected cells by patch-clamping techniques. This activity is dose-dependently suppressed by co-expression of wild-type PrP, indicating that it is related to a normal physiological activity of PrP$^C$.

Accordingly, PrP$^C$ could act as a receptor not only for PrP$^{Sc}$ and Aβ oligomers, but also for other β-rich proteins. Amazingly, the same two sites involved in binding of PrP$^C$ to Aβ oligomers and other aggregated proteins (residues 23-28 and 95-105) also determine the ion channel activity of mutant PrP, which could contribute to protein aggregate-mediated increased ion channel activity in PrP$^C$ similar to that caused by mutant PrP. Therefore, a PrP-dependent ion channel activity may contribute to the pathogenesis of prion disease, Alzheimer's disease, and several other neurodegenerative disorders.

Accordingly, there is a need in the art for identification of small molecule ligands for PrP$^C$ that prevent binding of toxic protein aggregates and providing a new therapeutic strategy for treatment of prion and Alzheimer's diseases, as well as other neurodegenerative disorders due to protein aggregation.

SUMMARY

The present invention is based on the discovery of binding regions on the surface of PrP$^C$, referred to as PrP$^C$ Binding Domains (PBD). In particular, the inventors have identified six different binding regions on PrP$^C$, referred to herein as PrP-binding domain-1 (PBD-1), PrP-binding domain-2 (PBD-2), PrP-binding domain-3 (PBD-3), PrP-binding domain-4 (PBD-4), PrP-binding domain-5 (PBD-5), and PrP-binding domain-6 (PBD-6), herein. The PBD-1 to PBD-6 are each defined by a cluster of amino acids located in the globular domain of the protein, e.g., in the C-terminal half of the protein (i.e., in residues 120-230). One embodiment uses residues 127-226.

Herein, the inventors have combined technologies of computer modeling and virtual screening with biochemical and biophysical binding assays to identify small-molecule ligands which bind to PrP$^C$. Accordingly, another aspect of the present invention relates to compounds which function as PrP$^C$ ligands that bind to the PBDs at the surface of PrP$^C$, e.g., bind to one or more of PBD-1 to PBD-6 as disclosed herein. In some embodiments, compounds which bind to one or more of PBD-1 to PBD-6 can be small molecules, proteins, peptides, nucleic acids etc., and are referred to herein as "PrP$^C$ ligands".

An exemplary PrP$^C$ ligand as disclosed herein is a compound of Formula (I) as disclosed herein, such as an exemplary compound designated DS26, which the inventors demonstrate blocks the toxic effects of Aβ oligomers on long-term potentiation in hippocampal slices, mimicking the effects of genetic deletion of PrP$^C$ in this system. Additionally, the inventors demonstrate that DS26 acts via an unusual auto-inhibitory mechanism in which ligand binding to the C-terminal domain of PrP$^C$ (residues 120-230) creates a docking site for the N-terminal tail (residues 23-111 of SEQ ID NO: 1), thereby preventing access to Aβ oligomers. The inventors have thus discovered novel insights into the mechanisms of Aβ toxicity in AD, and have discovered an entirely new class of AD therapeutics that act by inhibiting neurotoxic signaling pathways, rather than by reducing levels of Aβ. Furthermore, such PrP$^C$ ligand can also be useful for treatment of other protein misfolding disorders that involve PrP$^C$-mediated toxic mechanisms.

Accordingly, in some embodiments, PrP$^C$ ligands as disclosed herein can be used in the treatment of neurodegenerative diseases and pathological diseases associated with protein aggregration, e.g., such as, but not limited to, Alzheimer's disease, Parkinson's disease, Huntington's disease, tauopathies, and the like. In alternative embodiments, the PrP$^C$ ligands as disclosed herein can be used to inhibit the function or the formation of PrP$^{SC}$ from PrP$^C$. PrP$^C$ ligands as disclosed herein can function by at least one of the following: (i) inhibit the ion channel activity of PrP$^C$, and/or (ii) inhibit the binding of Aβ oligomers to PrP$^C$, and/or (iii) stabilize PrP$^C$, thus inhibit the formation of PrP$^{SC}$.

In some embodiments, the PBD-1 comprises at least 3 of the following amino acids 133, 134, 135, 136, 149, 153, 154, 156, 157, 158, 159, 208, 209, and 212 of mouse PrP$^C$ (sequence numbering based on GenBank Accession Number NP_035300, which corresponds to SEQ ID NO: 2 herein). In other embodiments, the PBD-1 comprises at least 4, at least 5, at least 6, at least 7, at least 8, at least 9, at least 10, at least 11, at least 12, at least 13, or all of the following amino acids 133, 134, 135, 136, 149, 153, 154, 156, 157, 158, 159, 208, 209, and 212 of mouse PrP$^C$. The corresponding residues in human PrP$^C$ are 134, 135, 136, 137, 150, 154, 155, 157, 158, 159, 160, 209, 210, and 213 (sequence numbering based on GenBank Accession Number AAA60182, which corresponds to SEQ ID NO: 1 herein).

In some embodiments, the PBD-2 comprises at least 3 of the following amino acids 129, 155, 156, 157, 158, 159, 160, 161, 182, 183, 185, 186, 187, 188, 189, 190, 197, and 205 of mouse PrP$^C$ (sequence numbering based on GenBank Accession Number NP_035300). In other embodiments, the PBD-2 comprises at least 4, at least 5, at least 6, at least 7, at least 8, at least 9, at least 10, at least 11, at least 12, at least 13, at least 14, at least 15, at least 16, at least 17, or all of the following amino acids 129, 155, 156, 157, 158, 159, 160, 161, 182, 183, 185, 186, 187, 188, 189, 190, 197, and 205 of mouse PrP$^C$. The corresponding residues in human PrP$^C$ are 130, 156, 157, 158, 159, 160, 161, 162, 183, 184, 186, 187, 188, 189, 190, 191, 198, and 206 (sequence numbering based on GenBank Accession Number AAA60182).

In some embodiments, the PBD-3 comprises at least 3 of the following amino acids 165, 166, 168, 169, 170, 171, 175, 214, 217, 218, 220, 221, 222, 224, 225, and 226 of mouse PrP$^C$ (sequence numbering based on GenBank Accession Number NP_035300). In other embodiments, the PBD-3 comprises at least 4, at least 5, at least 6, at least 7, at least 8, at least 9, at least 10, at least 11, at least 12, at least 13, at least 14, at least 15, or all of the following amino acids 165, 166, 168, 169, 170, 171, 175, 214, 217, 218, 220, 221, 222, 224, 225, and 226 of mouse PrP$^C$. The corresponding residues in human PrP$^C$ are 166, 167, 169, 170, 171, 172, 176, 215, 218, 219, 221, 222, 223, 225, 226, and 227 (sequence numbering based on GenBank Accession Number AAA60182.

In some embodiments, the PBD-4 comprises at least 3 of the following amino acids 127, 163, 164, 167, 168, 169, 170, 173, 174, 175, and 177 of mouse PrP$^C$ (sequence numbering based on GenBank Accession Number NP_035300). In other embodiments, the PBD-4 comprises at least 4, at least 5, at least 6, at least 7, at least 8, at least 9, at least 10, or all of the following amino acids 127, 163, 164, 167, 168, 169, 170, 173, 174, 175, and 177 of mouse PrP$^C$. The corresponding residues in human PrP$^C$ are 128, 164, 165, 168, 169, 170, 171, 174, 175, 176, and 178 (sequence numbering based on GenBank Accession Number AAA60182.

In some embodiments, the PBD-5 comprises at least 3 of the following amino acids 131, 132, 133, 134, 135, 136, 137, 138, 139, 143, 146, 149, 150, 151, 153, 211, 212, 214, 215, 216, 218, 219, 220, 221, 222, and 223 of mouse PrP$^C$ (sequence numbering based on GenBank Accession Number NP_035300). In other embodiments, the PBD-5 comprises at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, or all of the following amino acids 131, 132, 133, 134, 135, 136, 137, 138, 139, 143, 146, 149, 150, 151, 153, 211, 212, 214, 215, 216, 218, 219, 220, 221, 222, and 223 of mouse PrP$^C$. The corresponding residues in human PrP$^C$ are 132, 133, 134, 135, 136, 137, 138, 139, 140, 144, 147, 150, 151, 152, 154, 212, 213, 215, 216, 217, 219, 220, 221, 222, 223, and 224 (sequence numbering based on GenBank Accession Number AAA60182.

In some embodiments, the PBD-6 comprises at least 3 of the following amino acids 171, 175, 176, 179, 180, 183, 184, 187, 205, 206, 207, 209, 210, and 214 of mouse PrP$^C$ (sequence numbering based on GenBank Accession Number NP_035300). In other embodiments, the PBD-6 comprises at least 4, at least 5, at least 6, at least 7, at least 8, at least 9, at least 10, at least 11, at least 12, at least 13, or all of the following amino acids 171, 175, 176, 179, 180, 183, 184, 187, 205, 206, 207, 209, 210, and 214 of mouse PrP$^C$. The corresponding residues in human PrP$^C$ are 172, 176, 177, 180, 181, 184, 185, 188, 206, 207, 208, 210, 211, and 215 (sequence numbering based on GenBank Accession Number AAA60182.

While the specific amino acids are stated, one of skill in the art will appreciate that PBDs (e.g., PBD1 to PBD-6) do not need to comprise only those amino acids. Thus, domains having amino acids arranged in the same or substantially similar (e.g., at least 70%, at least 75%, at least 80%, at least 95%, at least 95%, or 100% similarity) spatial, electrostatic, or hydrophobic arrangement can be considered as PBDs. In other words, PBD-1 to PBD-6 can be composed of amino acids that are similar in size, shape, charge, or pKa of the amino acids specified above and arranged in a similar spatial configuration.

The inventors have discovered inter alia that be PBDs are functional constituent of the PrP$^C$. Further, binding of a PrP$^C$ ligand at one or more of the PBDs described herein can inhibits the ion channel activity of PrP$^C$ and binding of Aβ oligomers to PrP$^C$ Moreover, binding of a ligand at the PBDs also stabilizes PrP$^C$. PrP$^C$ plays a central role in prion diseases and also participates in the pathogenesis of Alzheimer's disease. Thus, compounds that target PrP$^C$ have the clear potential to provide therapeutic benefit for both diseases. Recently, PrP$^C$ has been shown to interact with aggregates of several other proteins, raising the intriguing possibility that this molecule may serve as a cell-surface receptor for a variety of β-sheet rich forms. Therefore, ligands that bind at one of the PBDs described herein can be effective in treatment of a wide range of diseases and disorders. For example, PBD binding ligands can used to treat pathological conditions associated with protein aggregation and neurodegeneration, including Parkinson's disease, Huntington's disease, and tauopathies. Accordingly, provided herein are methods and compositions for treating a disease or disorder associated with protein aggregation and neurodegeneration.

In one aspect, provided herein is a method for treating a disease or disorder associated with protein aggregation or neurodegeneration, the method comprising administering to a subject in need thereof a therapeutically effective amount of a compound that binds to a PrP$^C$ polypeptide, e.g., a PrP$^c$ ligand. While a compound can bind at anywhere with the PrP$^C$ polypeptide, preferably the compound binds to at least one PrP-binding domain 1, 2, 3, 4, 5, or 6 of the PrP$^C$ polypeptide. A compound that binds at, or to at least one PBD is also referred to as a "PBD binding ligand" or a "PrP$^c$ ligand" herein. Further, the terms PrP$^C$ ligand and PBD binding ligand are used interchangeably herein.

Without limitations, a PrP$^C$ ligand can be selected from small organic or inorganic molecules; carbohydrates, saccharines; oligosaccharides; polysaccharides; biological macromolecules; peptides; proteins; peptide analogs and derivatives; antibodies; antigen binding fragments of antibodies; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the PBD binding compound is a small molecule.

In some embodiments, the compound is of formula (I):

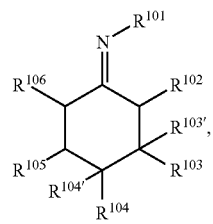

Formula (I)

wherein:
R$^{101}$ is alkyl, hetero alkyl, aryl, acyl, alkenyl, alkynyl, heteroaryl, cyclyl, heterocyclyl, alkylaryl, alkylheteroaryl, alkylcyclyl, alkylheterocyclyl, N(R$^{107}$)C(O) NHR$^{108}$, N(R$^{107}$)C(S)NHR$^{108}$, N(R$^{107}$)C(O)OR$^{109}$, N(R$^{107}$)C(O)SR$^{109}$, or N(R$^{107}$)C(S)OR$^{109}$, each of which can be optionally substituted;

each of $R^{102}$, $R^{103}$, $R^{104}$, $R^{104}$, $R^{105}$, and $R^{106}$ is independently selected from H, alkyl, halogen, OH, $OR^{110}$, $NH_2$, $NHR^{111}$, $N(R^{107})C(O)NHR^{108}$, $N(R^{107})C(S)NHR^{108}$, $N(R^{107})C(O)OR^{109}$, $N(R^{107})C(O)SR^{109}$, or $N(R^{107})C(S)OR^{109}$, each of which can be optionally substituted, $R^{103'}$ is H, alkyl, halogen, OH, $OR^{110}$, $NH_2$, $NHR^{111}$, each of which can be optionally substituted or $R^{103'}$ forms a bond with the carbon attached to $R^{106}$;

$R^{107}$ and $R^{108}$ are independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl;

$R^{109}$ is independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl;

$R^{110}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl;

$R^{111}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl, each of which can be optionally substituted; and isomers and pharmaceutically acceptable salts thereof.

In some embodiments, a $PrP^C$ ligand is a compound of formula (II):

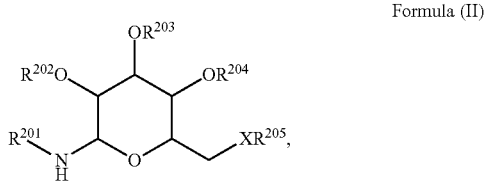

Formula (II)

wherein:

X is O, NH, or S;

each of $R^{201}$, $R^{202}$, $R^{203}$, $R^{204}$ and $R^{205}$ is independently for each occurrence H, aryl, alkyl, acyl, alkenyl, alkynyl, heteroaryl, cyclyl, heterocyclyl, alkylaryl, alkylheteroaryl, alkylcyclyl, or alkylheterocyclyl; and isomers and pharmaceutically acceptable salts thereof In some embodiments, a $PrP^C$ ligand is a compound of formula (III):

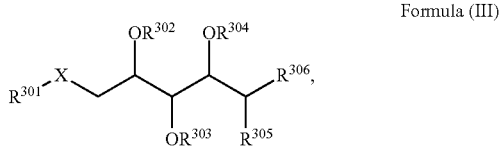

Formula (III)

wherein:

X is O, NH, or S;

each of $R^{301}$, $R^{302}$, $R^{303}$, and $R^{304}$ is independently H, aryl, alkyl, acyl, alkenyl, alkynyl, heteroaryl, cyclyl, heterocyclyl, alkylaryl, alkylheteroaryl, alkylcyclyl, or alkylheterocyclyl;

$R^{305}$ and $R^{306}$ are independently aryl, alkyl, heterocyclyl, heteroaryl, or cyclyl, or $R^{305}$ and $R^{305}$ together with the carbon they are attached to form an aryl, heteroaryl, cyclyl, or heterocyclyl; and isomers and pharmaceutically acceptable salts thereof.

In some embodiments, the compound is of formula (IV):

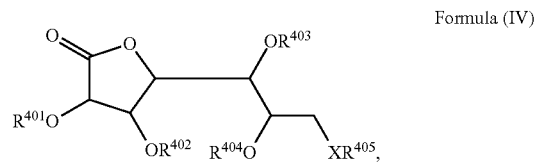

Formula (IV)

wherein:

X is O, NH, or S;

each of $R^{401}$, $R^{402}$, $R^{403}$, $R^{404}$, and $R^{4\text{-}5}$ is independently H, aryl, alkyl, acyl, alkenyl, alkynyl, heteroaryl, cyclyl, heterocyclyl, alkylaryl, alkylheteroaryl, alkylcyclyl, or alkylheterocyclyl, each of which can be optionally substituted; and isomers and pharmaceutically acceptable salts thereof In another aspect, provided herein are novel compounds of formulas (I)-(IV). As discussed herein, these compounds can bind to at least one $PrP^C$-binding domain (PBD) of the $PrP^C$ polypeptide as described herein, e.g., they can bind to at least one of PBD-1 to PBD-6, and are encompassed within the term "$PrP^c$ ligand".

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 1A and 1B illustrate how cell-surface $PrP^C$, as a consequence of its binding to either Aβ oligomers (FIG. 1A) or $PrP^{Sc}$ (FIG. 1B) can deliver a neurotoxic signal in Alzheimer's disease and prion diseases, respectively. FIG. 1C shows that $PrP^C$ is required for inhibition of hippocampal LTP induced by Aβ oligomers. FIG. 1D shows that depletion of neuronal $PrP^C$ reverses spongiosis, but not accumulation of $PrP^{Sc}$, in prion-infected mice. Reproduced from Biasini et al. TINS. 2012.

In FIG. 3A, ΔCR mouse PrP molecules carrying individual mutations within the PBD-1 site (P136G, M153G, N158V, and V208D) were expressed in HEK293 cells and analyzed by whole-cell patch clamping. Recordings were performed at a holding potential −80 mV. FIG. 3B shows quantitation of the currents from FIG. 3A, plotted as the percentage of total time the cells exhibited inward current≥450 pA (mean±S.E.M., n=5 cells). *p<0.01, one-tailed Student's t test.

FIG. 4A-4C illustrate some exemplary analogues and derivatives of DS26. FIG. 4A shows D26 structure and some features for structure-activity relationships. FIG. 4B shows some exemplary analogs of DS26 with modification of the semi-thiocarbazide side chain. FIG. 4C shows an exemplary genus of compounds based on D26.

FIG. 9 is a schematic representation of a pharmacological approach targeting PrP$^C$ to prevent conversion into PrP$^{Sc}$ in prion diseases.

FIGS. 13A-13D shows in silico identification of PBD-1 and PrP$^C$ ligands. FIG. 13A shows the structure of murine PrP$^C$ (1 XYX) with PrP-binding domain 1(PBD-1) highlighted in yellow. FIG. 13B shows a schematic of the virtual screen used to identify DS26. FIG. 13C shows the chemical structure of DS26. FIG. 13D shows a schematic of DS26 docked in the PBD-1site.

FIGS. 14A-14E shows the binding of DS26 to PrP$^C$ evaluated by SPR. FIG. 14A shows that starting at time 0, the indicated concentrations of DS26 were injected over sensor surfaces on which 17,000 resonance units (RUs) of PrP$^C$ had been previously captured by amine coupling. The chip was then washed with buffer alone to monitor ligand dissociation. Sensorgrams show DS26 binding in RUs. The data were fitted using the Langmuir equation, assuming a simple bimolecular interaction (black lines). The estimated binding constants were: $k_{on}=2.45\times10^2$ M$^{-1}$ s$^{-1}$; $k_{off}=1.4\times10^{-4}$ s$^{-1}$; and $K_D$=571 nM. FIG. 14B shows an experiment similar to that shown in panel 17A was performed with 50 and 100 μM DS26, except that the buffer wash was carried out for 10 hours. FIG. 14C shows the chemical structures of the two isomers (the E or Z stereoisomer) of DS26. FIG. 14D shows an experiment similar to that shown in FIG. 17A, which was performed using samples enriched for either the E or Z stereoisomer, or containing a 1:1 mixture of the two. Only the E isomer displayed detectable binding to PrP$^C$, and the equimolar mixture showed about half the binding observed with the pure E isomer. FIG. 14E shows the results from the same experiment as in FIG. 17D, except the enriched E and Z isomers were heated at 80° C. for 16 hrs to equilibrate the two forms. The heated samples of E and Z bind similarly, reflecting interconversion of the two isomers. The insets to the right of the graphs in panels D and E show tubes containing solutions of the indicated samples of DS26. The E isomer is brown, while the Z isomer is colorless. After heating, the Z isomer turns brown, reflecting racemization of the sample. The relative amounts of the two isomers in each sample were confirmed by NMR analysis (not shown).

FIG. 15A shows the chemical structure of DS104, a fluoresceinated derivative of DS26. The colored oval indicates the fluorescein part of the molecule. FIG. 15B shows the results from the measurement of DS104 binding to PrP$^C$ using SPR. Starting at time 0, the indicated concentrations of DS104 were injected over sensor surfaces on which 17,000 RUs of PrP$^C$ had been previously captured by amine coupling. The chip was then washed with buffer alone to monitor ligand dissociation. Sensorgrams show DS104 binding in RUs. The data were fitted using the Langmuir equation, assuming a simple bimolecular interaction (black lines). The calculated $K_D$ was 4.2 μM. FIG. 15C shows the results from a fluorescence polarization (FP) binding assay with DS104 and PrP. Recombinant C-PrP (residues 120-230) at the concentrations shown on the x-axis was incubated for 1 hr with 1 nM DS104 and the polarization values were recorded on the y-axis. There was an increase in the polarization of DS104 with increasing PrP concentration, reflecting binding of DS104 to C-PrP. The values were fitted using a single site receptor model (Graphpad Prism) generating a $K_D$ of 4 uM. FIG. 15D shows the results from a competitive FP binding assay where 5 μM of recombinant C-PrP was incubated with 1 nM of DS104 and various concentrations of DS5,

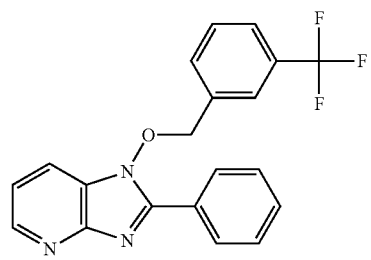 [SMILES: FC(F)(F)c1cccc(COn2c(-c3ccccc3)nc3ncccc32)c1]

(DS15), DS26, DS40, and N,N'-(methylenedi-4,1-phenylene)bis[2-(1-pyrrolidinyl)acetamide] (GN8). DS5, DS26 and DS40 competed with DS104 for binding to C-PrP, leading to a loss of polarization. The values were fitted using a single receptor site completive model (Graphpad Prism), yielding a $K_D$ of 0.3 μM for DS26.

Figure 16A:
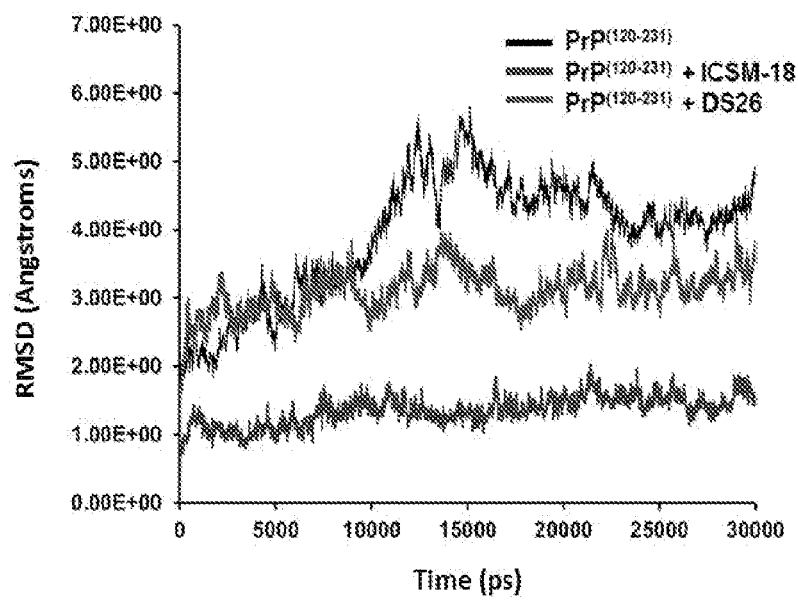
Figure 16B:
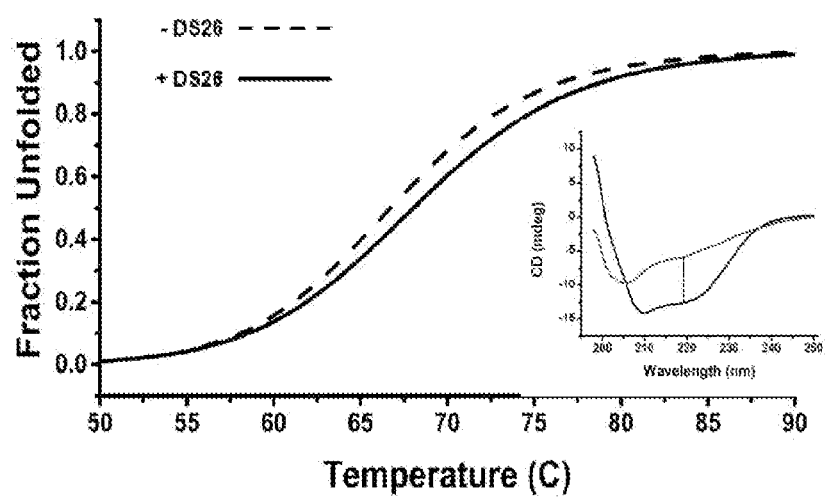
Figure 16C:
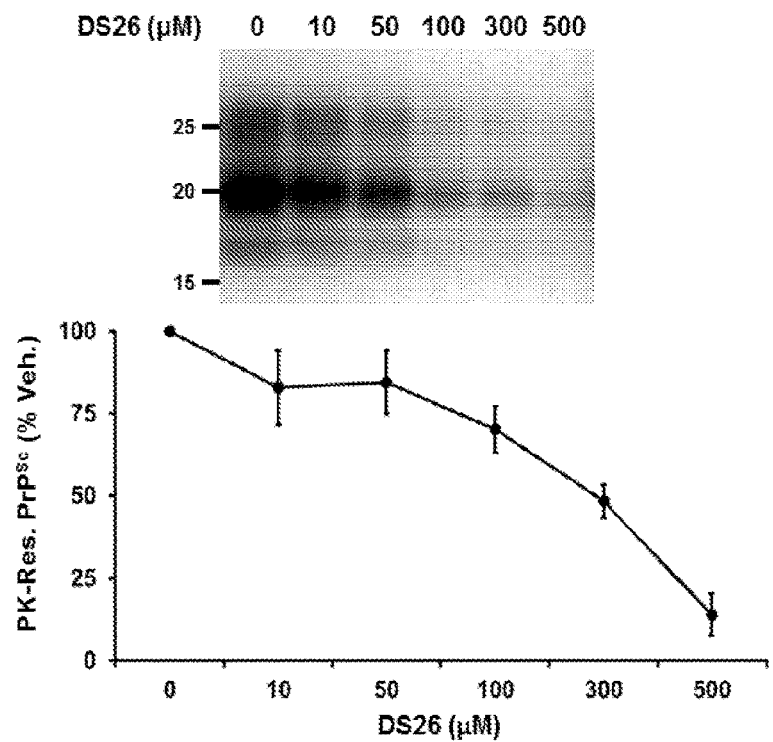
Figure 16D:
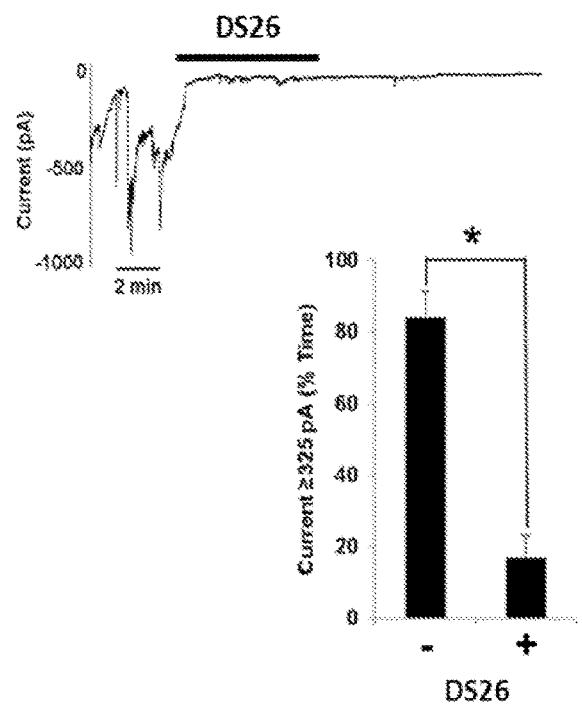

FIGS. 16A-16D shows that DS26 stabilizes the structure of PrP$^C$, and alters its biological activity FIG. 16A shows the results from molecular dynamic simulation of PrP bound to ICSM-18 antibody or DS26. FIG. 16B shows the melting curves of moPrP (23-230) alone or with DS26. The curves represent the fraction of unfolded protein as measured at 220 nm during melting. $T_m$ values for PrP alone and PrP with DS26 were 66.8 and 68.9° C., respectively. The inset shows the far-UV CD spectrum of moPrP (23-230) at 25° C. (black) and 95° C. (red). The dashed line represents the wavelength (220 nm) where the protein was monitored for melting data in the main panel. FIG. 16C shows that DS26 inhibits formation of PrP$^{Sc}$ in scrapie-infected N2 neuroblastoma cells. FIG. 16D shows the results from whole-cell patch clamp recording from HEK cell expressing ΔCR PrP, recorded at a holding potential of −80 mV. DS26 (5 μM) was perfused locally for 2 min. The graph beneath the trace shows quantitation of currents from 9 cells, expressed as the percentage of time cells exhibited inward currents≥325 pA (mean±S.E.M.). The asterisk (*) indicates a statistically significant difference in spontaneous current activity between cells before and after treatment with DS26 (p<0.05, one-tailed Student's t-test).

Figure 17A:
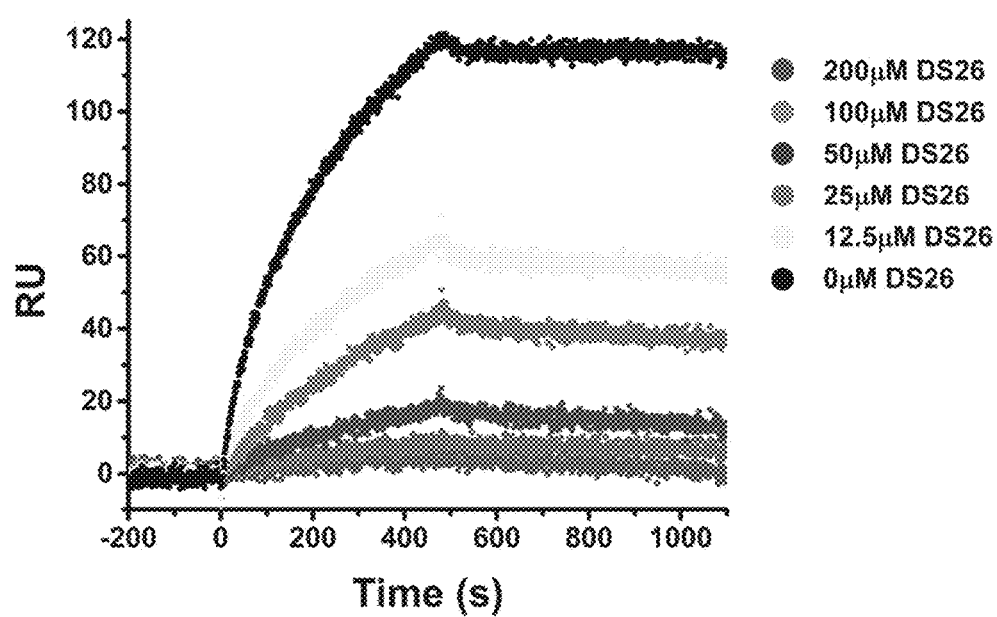
Figure 17B:
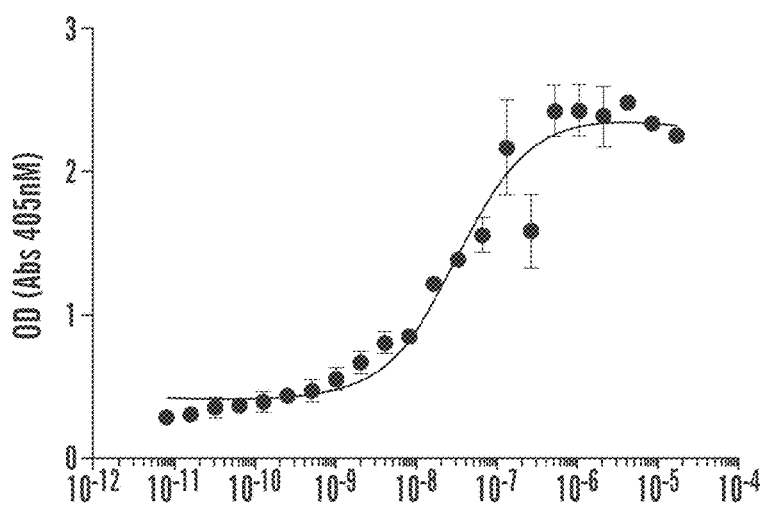

FIGS. 17A-17J shows that DS26 inhibits binding of PrP$^C$ to Aβ oligomers by a non-competitive mechanism. FIG. 17A shows the indicated concentrations of DS26 were injected for 300 seconds over an SPR surface with myc-tagged, full-length PrP that had been captured with an anti-myc antibody. After a PBST wash, 1 uM of Aβ oligomers was injected for 480 sec (starting at time 0), followed by a wash with PBST. Binding of Aβ was measured in RU. DS26 decreased the binding of Aβ oligomers to PrP$^C$ in a dose-dependent manner. FIG. 17B shows the results of binding of Aβ oligomers to PrP$^C$ as measured using an ELISA format.

Figure 17C:
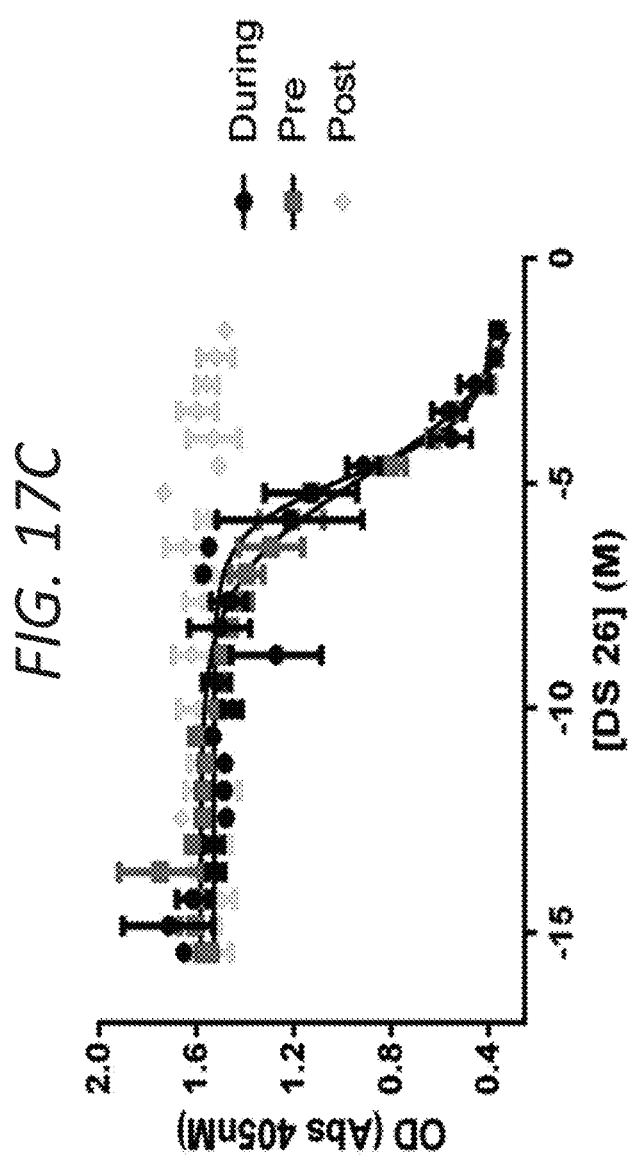
Figures 17G, 17H, 17I:
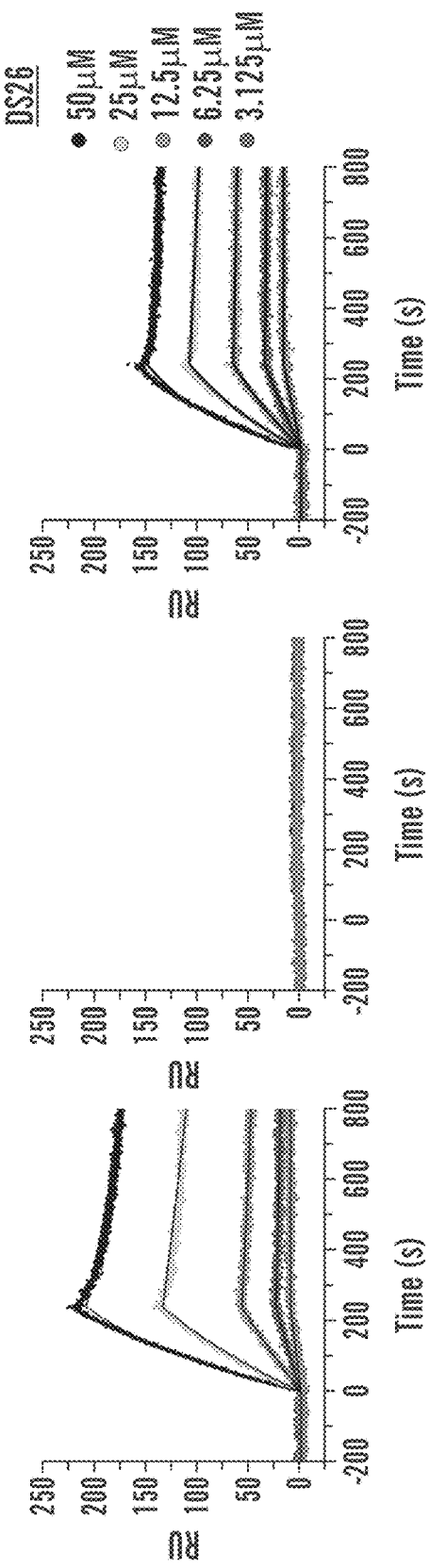
Figure 17J:
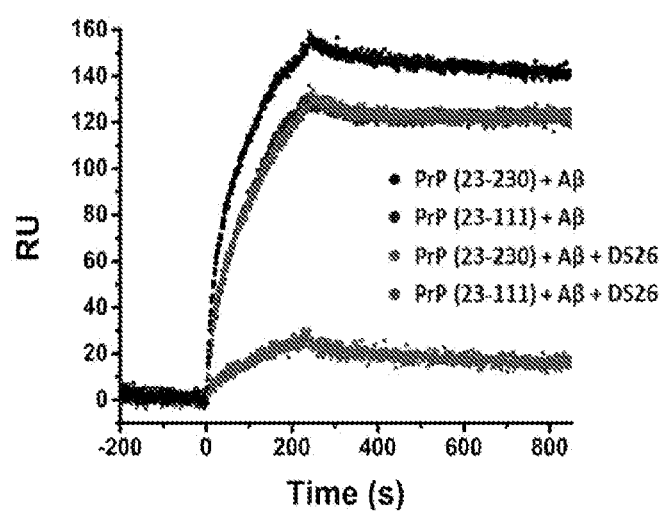

The $K_D$ was calculated to be 28.4 nM. FIG. 17C shows the effect of DS26 on binding of A β oligomers to PrP$^c$ as measured by ELISA using three different procedures: pre-treatment of PrP$^C$ with DS26 prior to addition of Aβ oligomers; simultaneous addition of DS26 and Aβ oligomers; and addition of DS26 after pre-binding of Aβ oligomers. Aβ oligomers were added at 100 nM in each condition. DS26 reduced binding of Aβ oligomers when added prior to or simultaneously with DS26, with a half-maximal inhibitory concentration (IC$_{50}$) of 15 μM. However, DS26 was unable to dislodge Aβ oligomers that had been pre-bound to PrP$^C$. Samples were run in triplicate and error bars represent standard error of the mean. FIGS. 17D-17F show the binding of Aβ oligomers at the indicated concentrations to full-length moPrP(23-230) (FIG. 17D), N-PrP (FIG. 17E), or C-PrP (FIG. 17F) as analyzed by SPR. Aβ oligomers were passed over a chip containing immunocaptured PrP starting at time 0, after which the chip was washed with buffer. Aβ oligomers bind to full-length PrP and N-PrP, but not C-PrP. FIG. 17G-17I show the binding of DS26 at the indicated concentrations to full-length moPrP(23-230) (FIG. 17G), N-PrP (FIG. 17H), or C-PrP (FIG. 17I) as analyzed by SPR. DS26 was passed over a chip containing amine-coupled PrP starting at time 0, after which the chip was washed with buffer. DS26 binds to full-length PrP and C-PrP, but not N-PrP. In D-I, the curves were fitted using the Langmuir equation, assuming a simple bimolecular interaction (black lines). FIG. 17J shows that DS26 prevents binding of Aβ oligomers to full-length PrP, but not N-PrP. DS26 (50 μM) was injected for 300 sec over an SPR chip containing immunocaptured full-length PrP or N-PrP. After a PBST wash, 1 uM of Aβ oligomers was injected, and binding of the oligomers was monitored.

FIGS. 18A-18E show that DS26 alters the conformation of the N-terminal domain of PrP$^C$, and promotes its interaction with the C-terminal domain. FIG. 18A show Trp fluorescence emission spectra of full length moPrP (23-230) alone (red line), and in the presence of 10 uM (blue line) and 100 uM (green line) DS26. Excitation was at 280 nm DS26 quenched the trp fluorescence in a dose-dependent manner. FIG. 18B show Trp fluorescence emission spectra of N-PrP (23-111) in the presence of DS26 at 0, 10, and 100 uM. DS26 did not alter the trp fluorescence of N-PrP. FIG. 18C shows Trp fluorescence emission spectra of moPrP (23-230) in the presence of DS15 at 0, 10, and 100 uM. DS15, which does bind to PrP, did not alter the trp fluorescence of the protein. FIG. 18D shows that recombinant, C-PrP (120-230) was incubated with or without myc-tagged N-PrP (23-111) in the presence and absence of DS26. N-PrP was then immunoprecipitated using anti-myc antibody, 4A6, and the immunoprecipitated proteins were blotted with anti-PrP antibodies 6D11 (which recognizes only N-PrP), or D18 (which recognizes only C-PrP). The input lanes show samples prior to immunoprecipitation. C-PrP was immunoprecipitated with N-PrP only in the presence of DS26. FIG. 18E shows that N-PrP (10 uM) was injected for 300 sec over an SPR ship containing immunocaptured C-PrP, following an injection of either 100 μM DS26 or PBST buffer. N-PrP bound to C-PrP that had been pre-treated with DS26 (blue line), but not to C-PrP that had been pre-treated with buffer (red line).

Figure 19A:
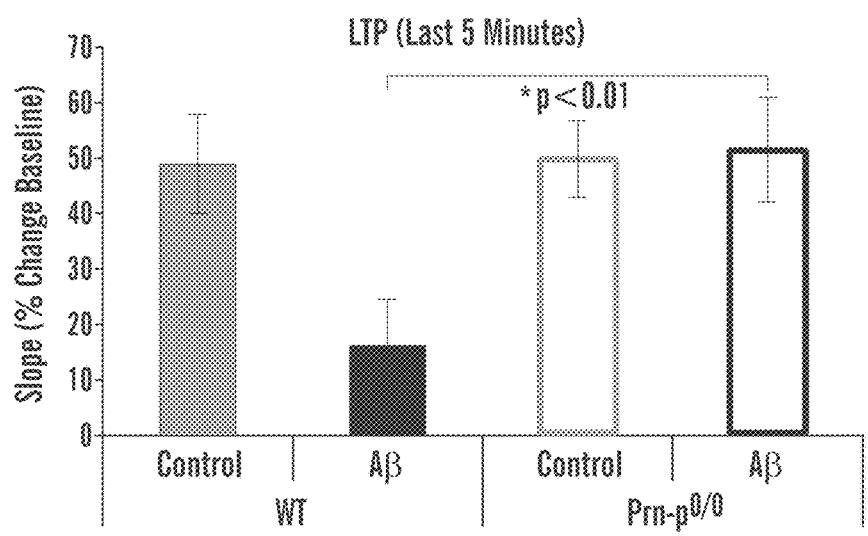
Figure 19B:
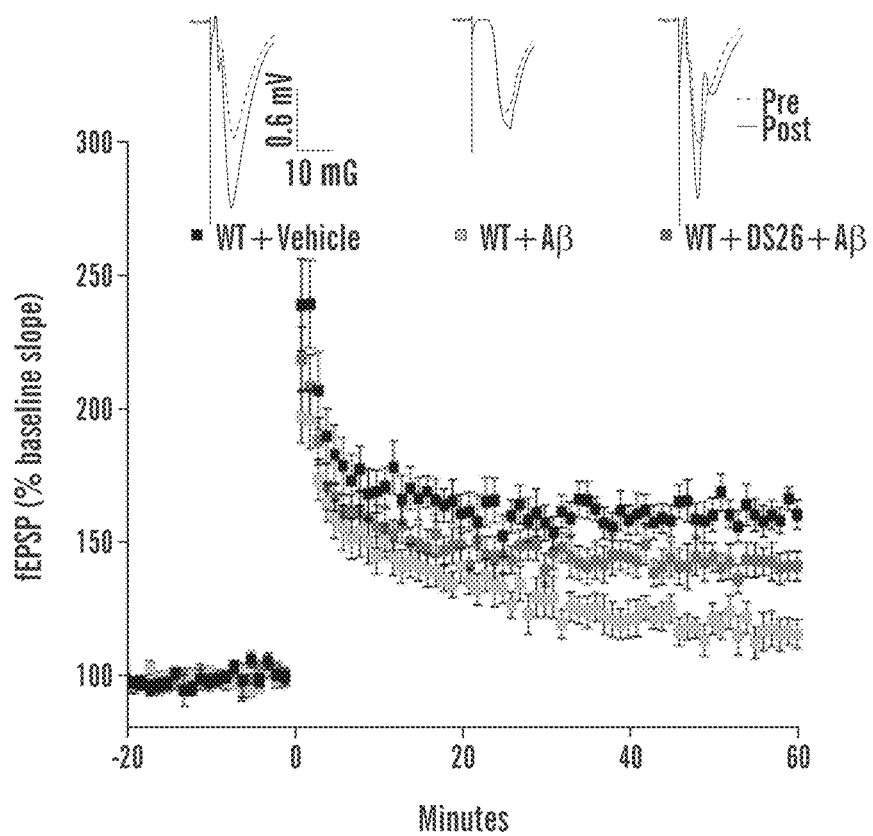
Figure 19C:
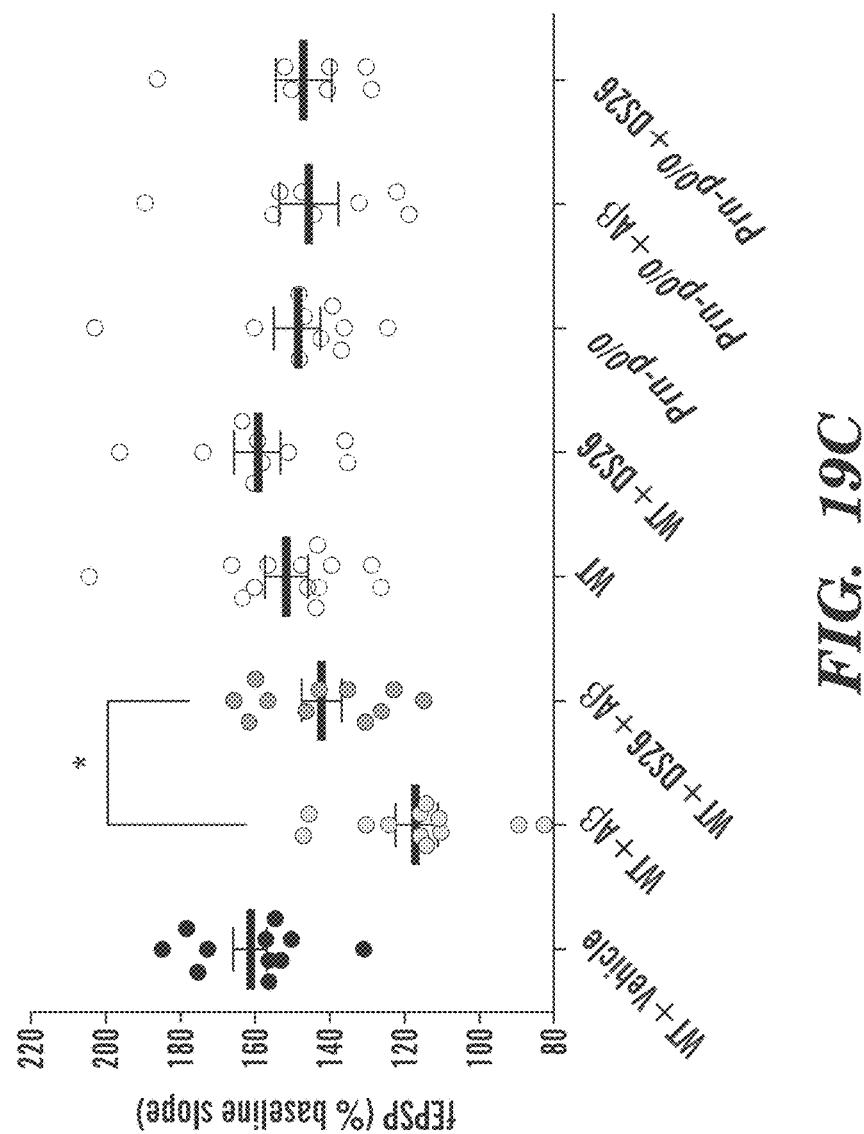

FIGS. 19A-19D shows the synaptotoxicity of Aβ oligomers in hippocampal slices is dependent on expression of PrP$^C$, and is suppressed by DS26. FIG. 19A shows PrP$^C$-dependence of Aβ inhibition of LTP. FIG. 19B shows that DS26 prevents Aβ inhibition of LTP. FIG. 19C shows a summary of the LTP data. Hippocampal slices from wild-type (WT) mice, or PrP knock-out (Prn-p$^{0/0}$) mice were incubated for 20 min in the presence or absence of DS26 (100 μm), followed by treatment with or without Aβ oligomers (500 nM) for 20 mins. Baseline field excitatory postsynaptic potentials (fEPSPs) were then recorded at CA3-CA1 pyramidal cell synapses for 20 min, after which LTP was evoked with theta-burst stimulation. The plot shows fEPSPs (as a percentage of baseline slope) at 55-60 min after theta burst stimulation (points represent individual slices, with mean±SEM indicated). Treatment with DS26, as well as deletion of the PrP gene, significantly (*p<0.05) enhances LTP after Aβ exposure, restoring LTP nearly to control levels (compare WT+Aβ to WT+DS26+Aβ; and WT+Aβ to Prn-p$^{0/0}$+Aβ). FIG. 19D is a schematic diagram deplicing an exemplary model for the auto-inhibitory mechanism of action of DS26. Upper schematic: Aβ oligomer binding to the N-terminal domain of membrane-anchored PrP$^C$ elicits a synaptotoxic signal. Lower schematic: binding of DS26 to the C-terminal domain of PrP$^C$ causes interaction of the N- and C-terminal domains, thereby preventing binding of Aβ oligomers and blocking synaptotoxicity.

Figure 20A:
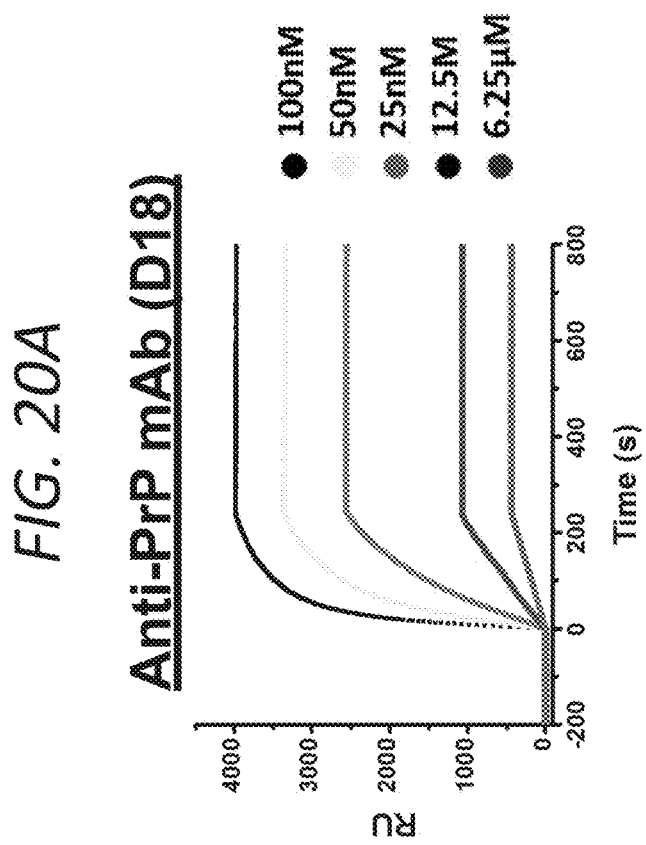

FIGS. 20A-20H show positive and negative controls for PrP$^C$ ligand binding in SPR experiments. FIGS. 20A-20D shows the binding of control analytes to PrP$^C$. The indicated concentrations of anti-PrP antibody D18 (FIG. 20A), DS15 (FIG. 20B), GN8 (FIG. 20C), and (RS)—N'-(6-chloro-2-methoxy-acridin-9-yl)-N,N-diethyl-pentane-1,4-diamine (quinacrine) (FIG. 20D) were injected for 4 min over sensor surfaces on which 17,000 RU of PrP$^C$ had been previously captured by amine coupling. Sensorgrams show analyte binding in resonance units (RUs). FIGS. 20E-20H shows the binding of DS26 to control proteins or the chip surface. The indicated concentrations of DS26 were injected for 4 min over sensor surfaces on which 17,000 units of the following proteins were immobilized by amine coupling: human PrP$^C$ (FIG. 20E), bovine serum albumin (FIG. 20F), and myoglobin (FIG. 20G). FIG. 20H shows results when no protein was coupled to the chip surface. Sensorgrams show binding in resonance units (RUs).

Figure 21:
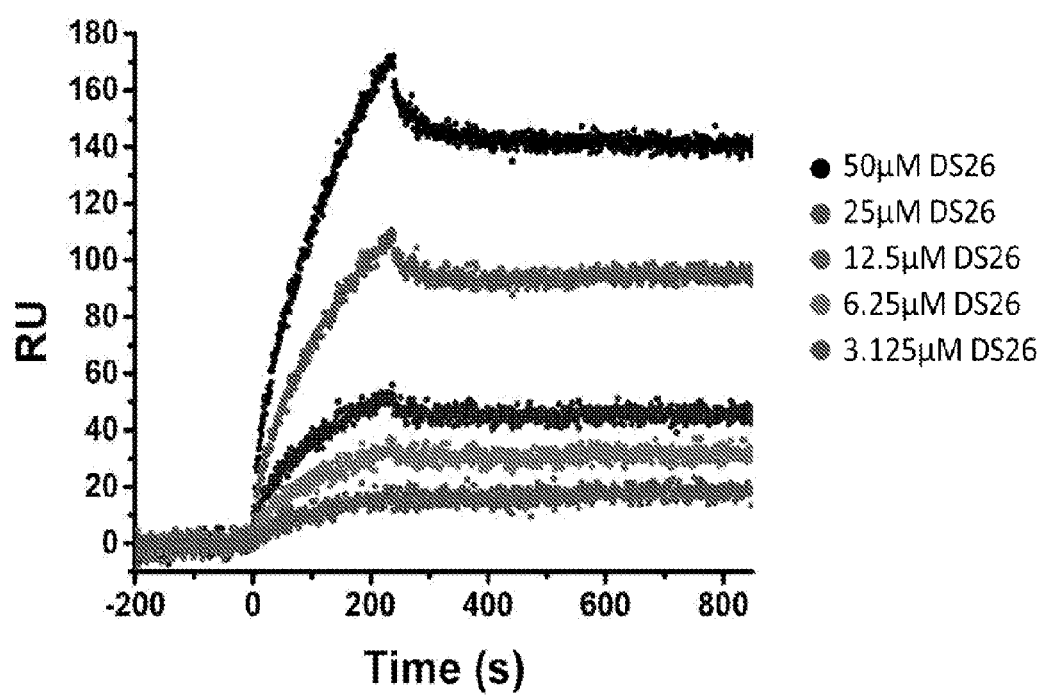

FIG. 21 shows that DS26 binds to ΔCR PrP. DS26 at the indicated concentrations was injected for 4 min over sensor surfaces on which 17,000 RU of ΔCR PrP had been previously captured by amine coupling. Sensorgrams show small molecule binding in resonance units (RUs). The data were fitted using the Langmuir equation, with a calculated $K_D$ of 0.9 uM.

Figure 22A:
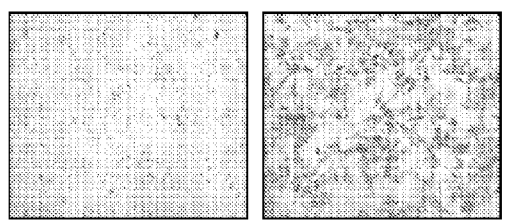
Figure 22B:
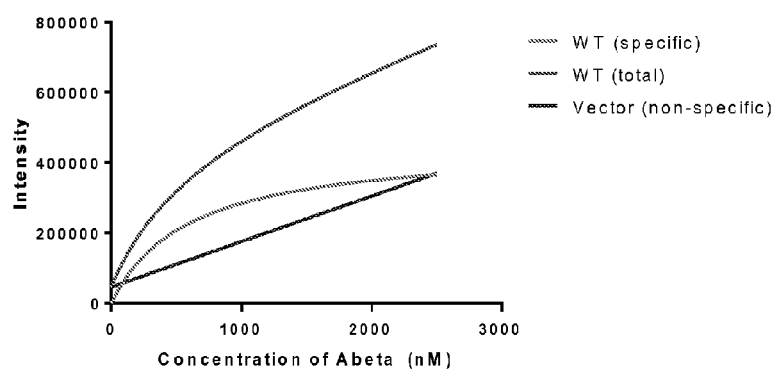
Figure 22C:
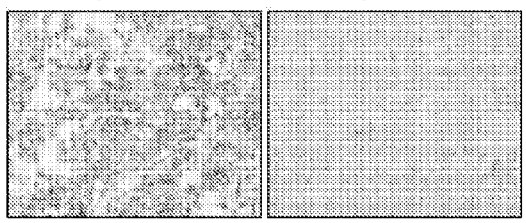
Figure 22D:
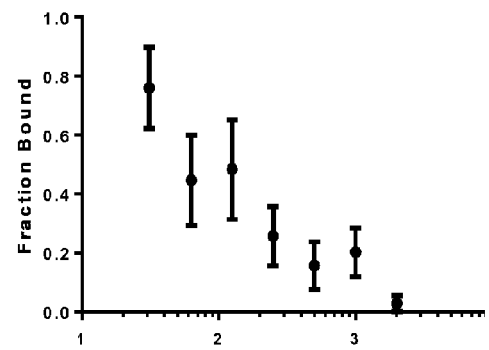

FIG. 22A-22D shows DS26 inhibits binding of Aβ oligomers to PrP$^C$ on cells. FIG. 22A shows micrographs of HEK cells transfected with empty vector or with vector encoding mouse PrP were incubated with biotinylated Aβ oligomers. Cells were then fixed, incubated with alkaline phosphatase-conjugated streptavidin, and bound oligomers visualized with NBT/BCIP. FIG. 22B shows HEK cells transfected with empty vector or with vector encoding mouse PrP were incubated with different concentrations of biotinylated Aβ oligomers, and the amount of bound oligomers was quantitated from micrographs using Image J. The curves show total binding to PrP-transfected cells (pink line), non-specific binding to vector-transfected cells (blue line), and specific binding (total—non-specific; green line). Each point represents the mean±SEM of triplicates. FIG. 22C shows micrographs of PrP-expressing HEK cells were incubated with biotinylated Aβ oligomers (500 nM), following a 30 pre-treatment with either 0 or 250 μM DS26. FIG. 22D shows PrP-expressing HEK cells were pre-incubated with different concentrations of DS26, and specific Aβ oligomer binding was quantitated. Each point represents the mean±SEM of triplicates.

Figure 23:
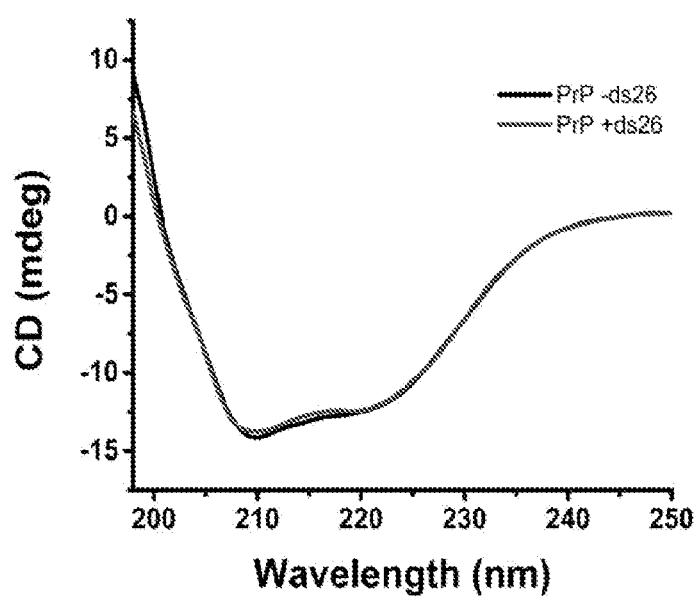

FIG. 23 shows that DS26 does not affect the far-UV CD spectrum of PrP$^C$. Far-UV CD spectra were recorded at 25° C. from 10 μM moPrP (23-230), either alone (black line) or in the presence of 50 μM DS26 (red line).

Figure 24A:
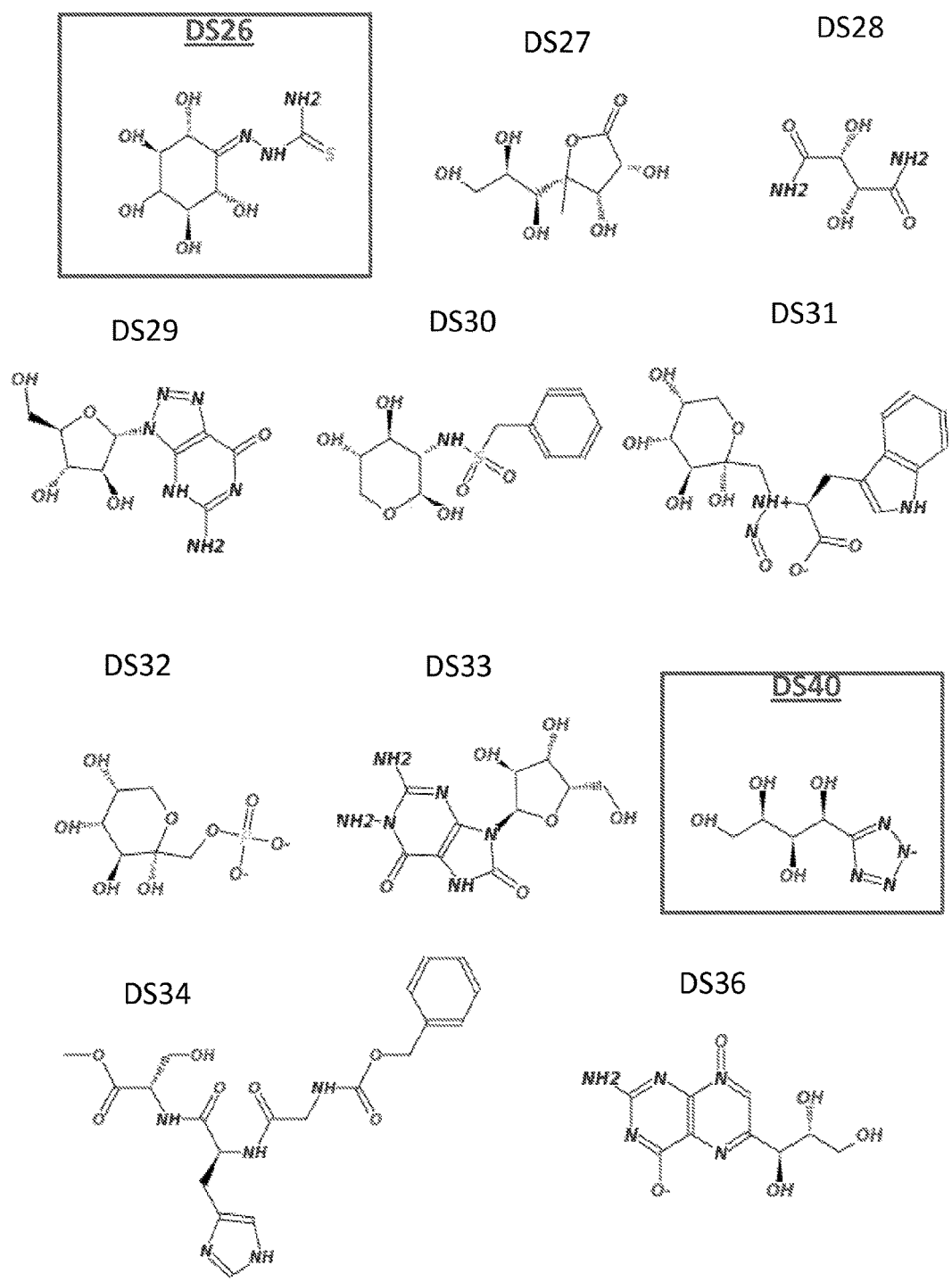

FIG. 24A-24B show the chemical structures of the 16 candidate PrP$^C$ ligand compounds from the National Cancer Institute (NCI) library which were tested by SPR for binding to PrP$^C$. These compounds were identified in a large-scale virtual screen of 17 million compounds (see Examples section, in the Methods and materials section). Of the 16 compounds, only DS26 and DS40 bind to PrP$^C$. (DS5 and DS86 PrP$^c$ ligand compounds, which also bind to PrP$^C$, emerged from smaller, pilot-scale virtual screens.

Figure 25:
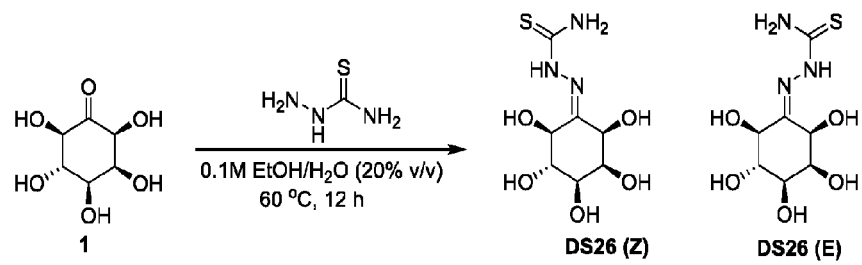

FIG. 25 shows the synthesis of DS26 (E and Z isomers).

Figure 26A:
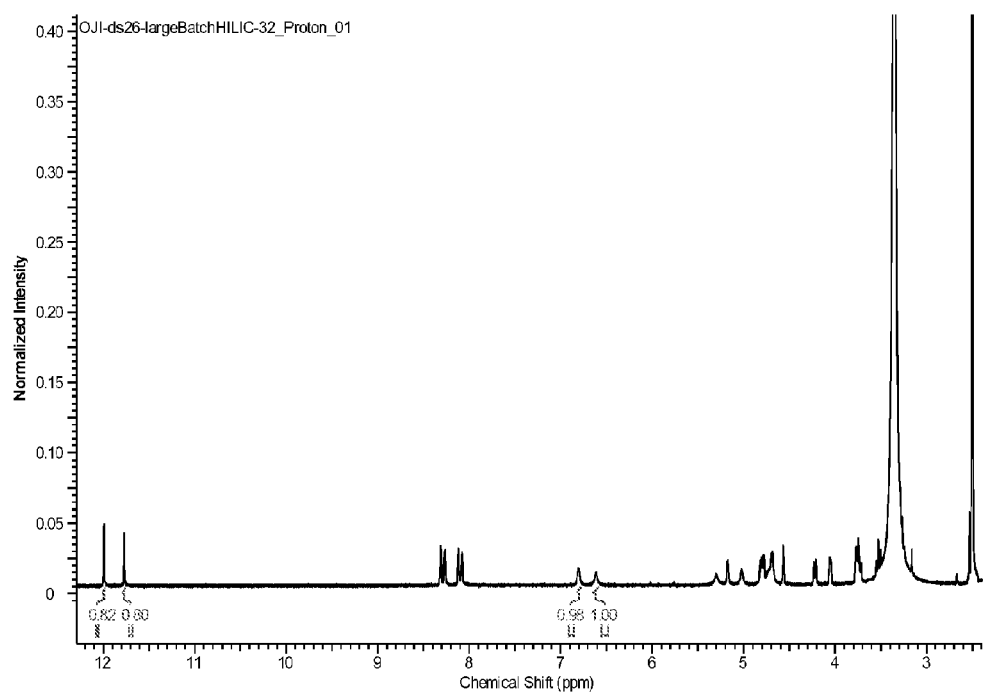
Figure 26B:
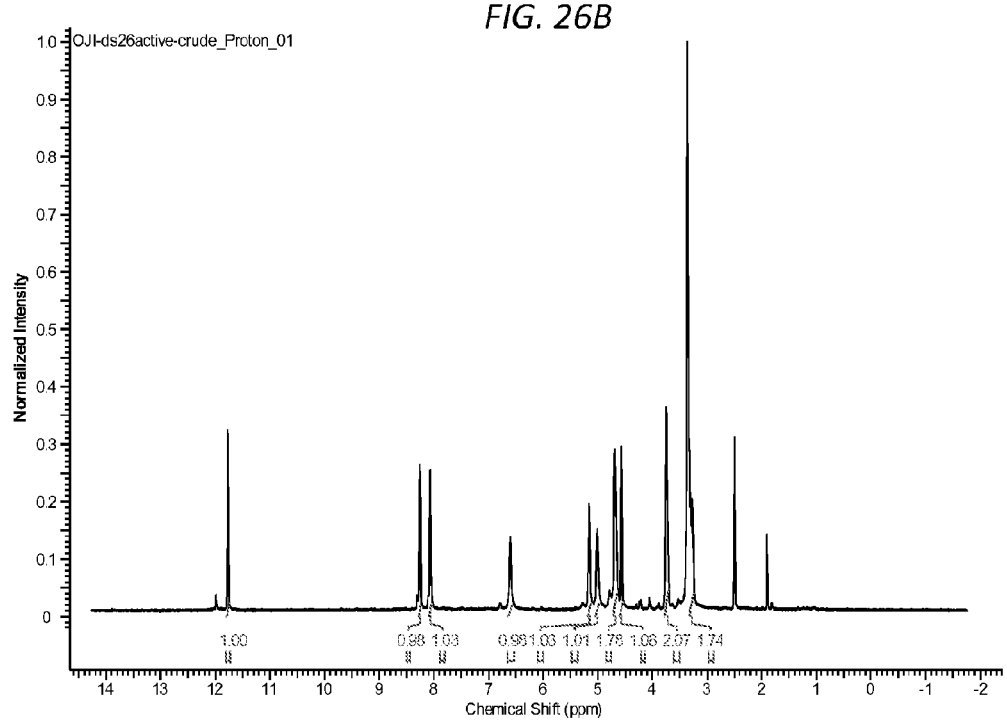
Figure 26C:
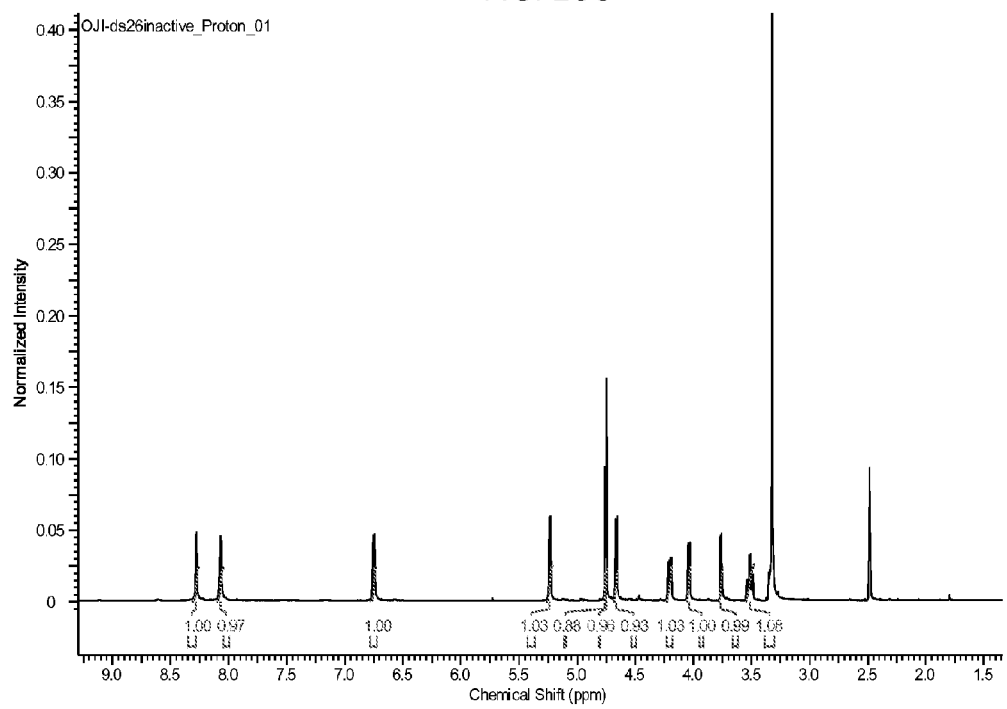

FIG. 26A-26C shows NMR spectruma of DS26 isoforms. FIG. 26A shows the NMR spectrum of DS26 as a 1:1 mixture of E and Z isomers. FIG. 26B shows the NMR spectrum of the Z isomer of DS26. FIG. 26C shows the NMR spectrum of the E isomer of DS26.

FIGS. 27A-27C show the binding of other PrP$^C$ ligands DS5, DS40 and DS86 as evaluated by SPR. FIG. 27A shows the structure and binding of DS5 to recombinant mouse PrP$^C$. FIG. 27B shows the structure and binding of DS40 to recombinant mouse PrP$^C$. FIG. 27C shows the structure and binding of DS86 to recombinant mouse PrP$^C$. DS5, DS26, DS40 and DS86 were assessed at 3.125 μM, 6.25 μM, 12.5 μM, 25 μM and 50 μM.

Figure 28A:
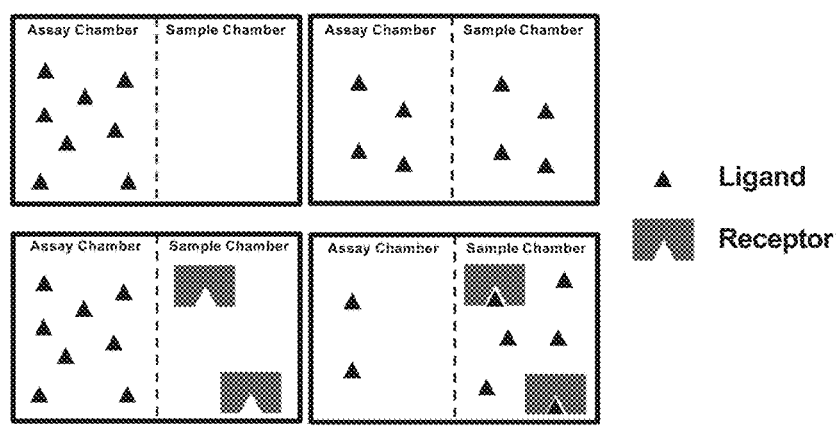
Figure 28B:
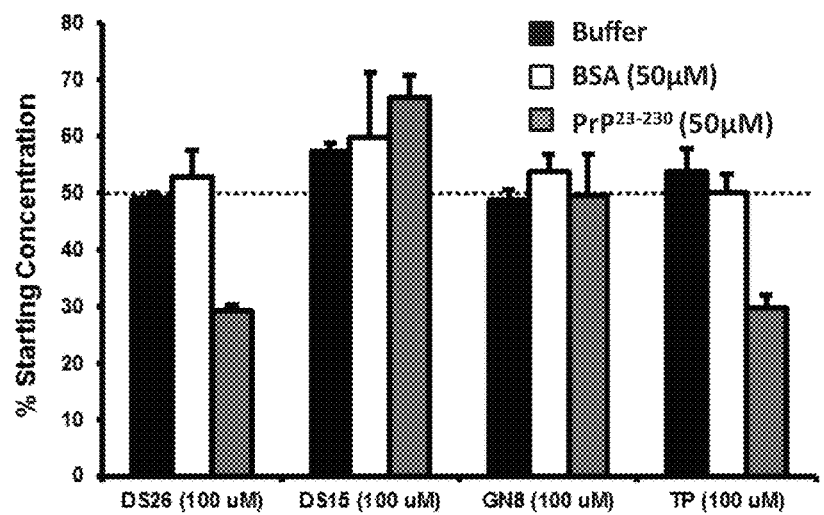

FIGS. 28A-28B show images to validate DS26 binding to PrP$^C$. FIG. 28A is a schematic to test DS26 binding by equilibrium dialysis (EqD), where the ability of a small molecule to equilibrate between two chambers, one containing the target protein (referred to as sample chamber) and one empty (assay chamber), separated by a membrane permeable only to the small molecule is shown. FIG. 28B shows results of the binding equilibrium dialysis (EqD) of 50 μM PrP$^{23-230}$ in the presence of 100 μM of DS26, DS15, GN8 or tetrapyrrole (TP).

Figure 29A:
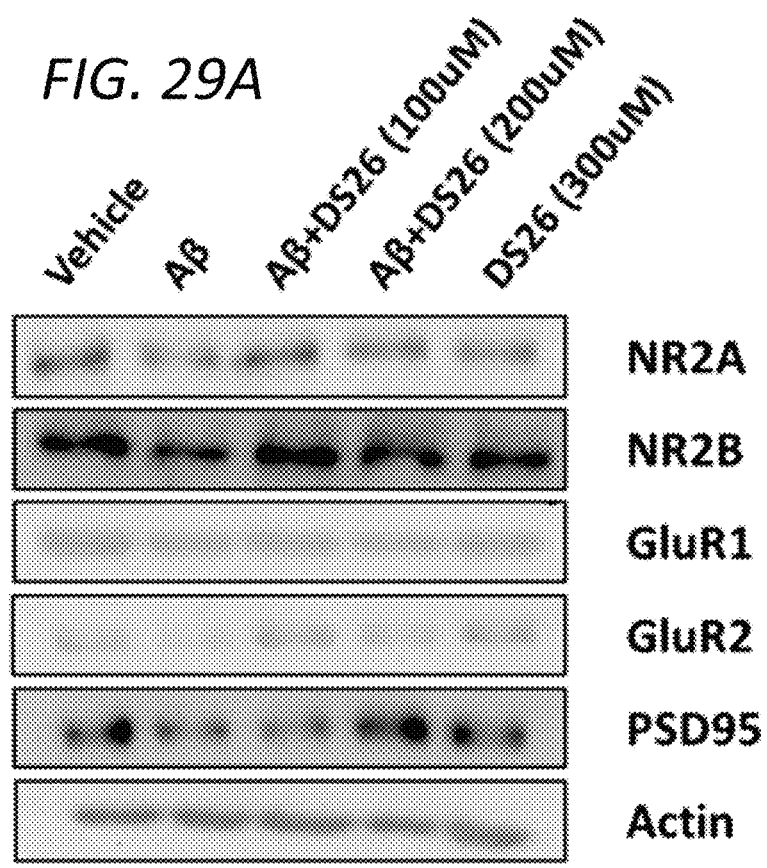
Figure 29B:
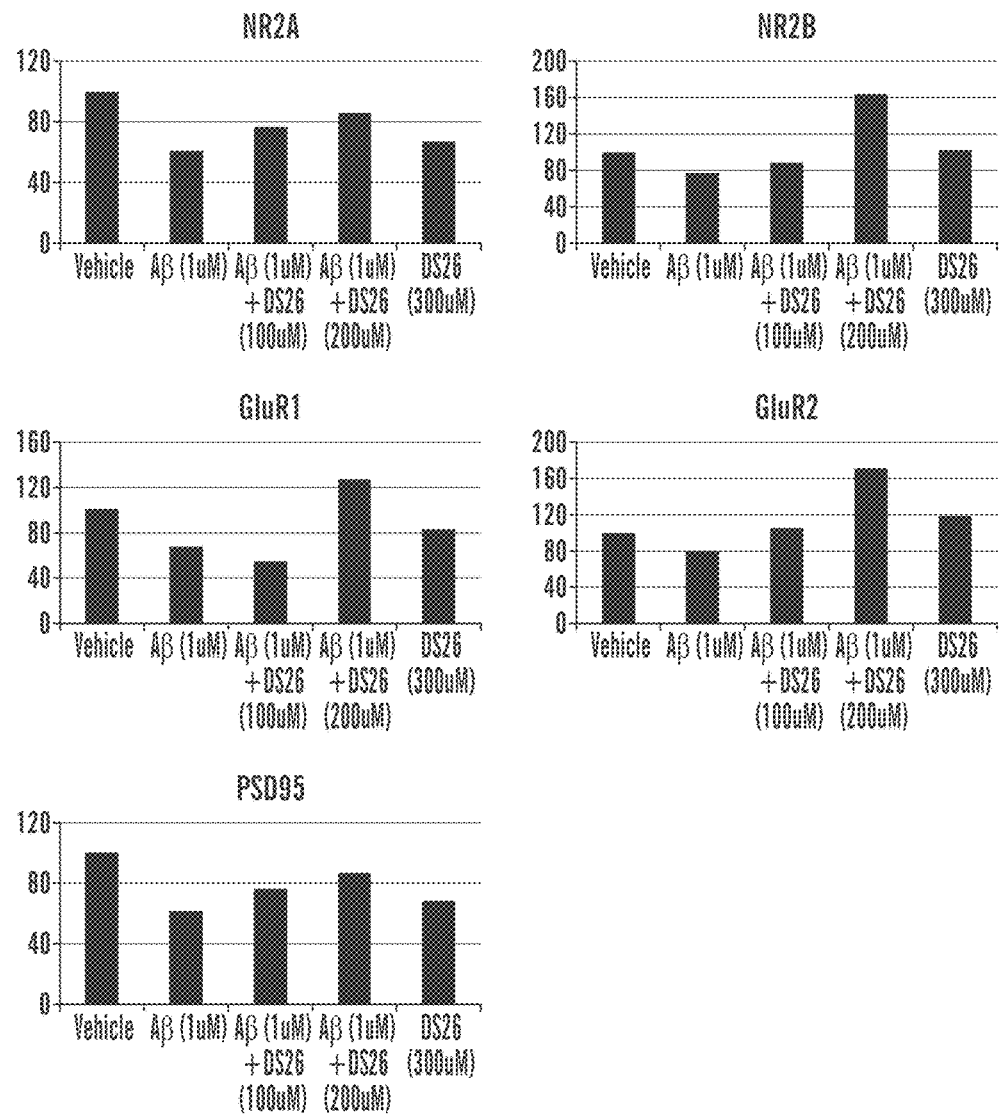

FIGS. 29A-29B show that DS26 blocks the toxic effects of Aβ oligomers. FIG. 29A is a western blot of primary cultures of postnatal mouse hippocampal neurons treated with Aβ oligomers (1 μM) in the presence of DS26 (at 100 μM and 200 μM) and levels of NR2A, NR2B, GluR1, GluR2, PSD95 and actin loading control. FIG. 29B are graphs quantitating the protein expression of NR2A, NR2B, GluR1, GluR2, PSD95 in postnatal mouse hippocampal neurons treated with Aβ oligomers (1 μM) in the presence of DS26 (at 100 μM and 200 μM).

FIG. 30A-30C shows the chemical structures of exemplary derivatives of DS26 which bind to PrP$^C$. Different concentrations of DS207 (FIG. 30A), DS210 (FIG. 30B), and DS211 (FIG. 30C) were injected for 4 min over sensor surfaces on which 19,000 RU of recombinant PrP$^C$ had been previously captured by amine coupling. Sensorgrams show small molecule binding in resonance units (RU), and show that DS207 (FIG. 30A), DS210 (FIG. 30B), and DS211 (FIG. 30C) bind to PrP$^C$. The data were fitted using the Langmuir equation, modeling a simple bimolecular interaction as indicated by the black line. Estimated affinities were: $K_D$=6.48×10$^{-5}$ M for DS207 (FIG. 30A), $K_D$=6.31×10$^{-5}$ M for DS210 (FIG. 30B), $K_D$=6.23×10$^{-5}$ M for DS211 (FIG. 30C).

Figure 31A:
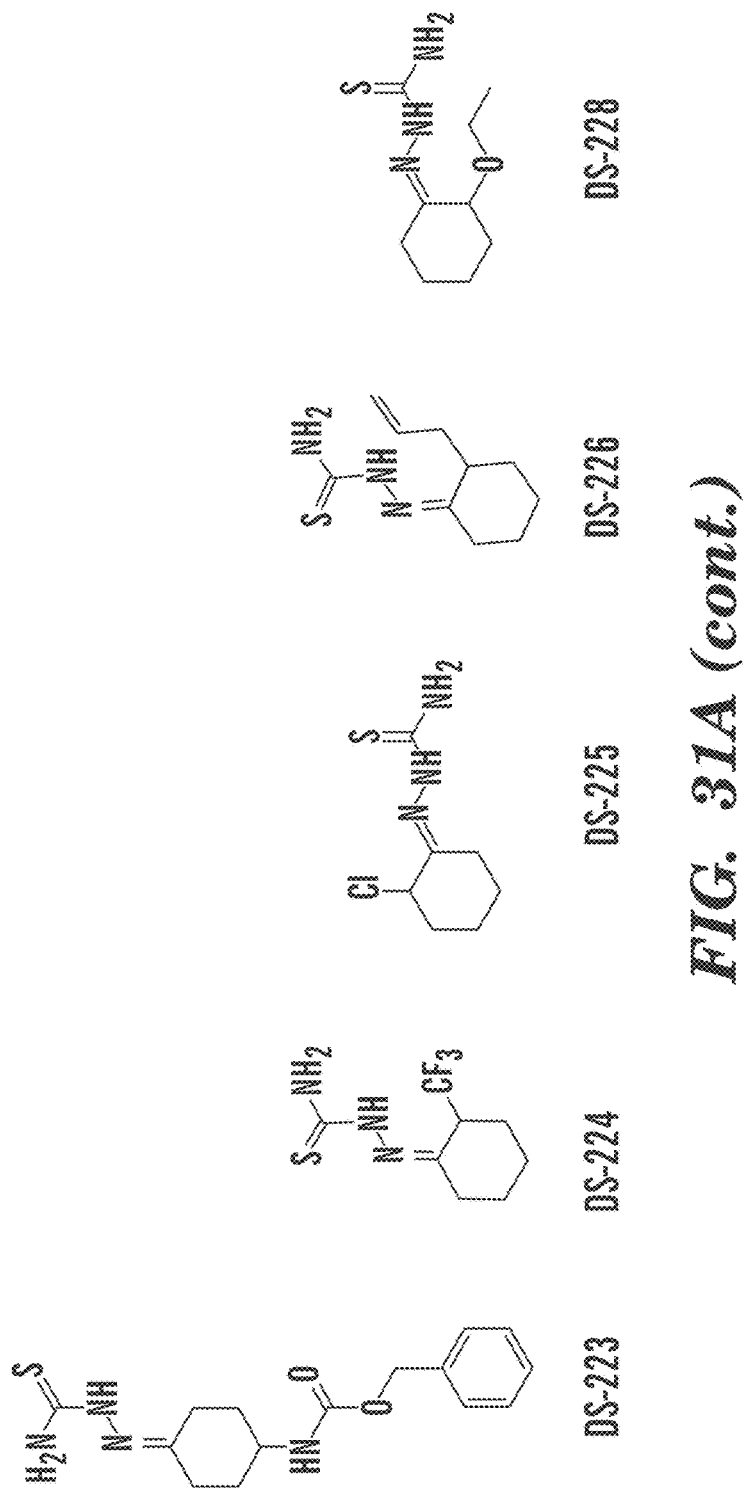
Figure 31B:
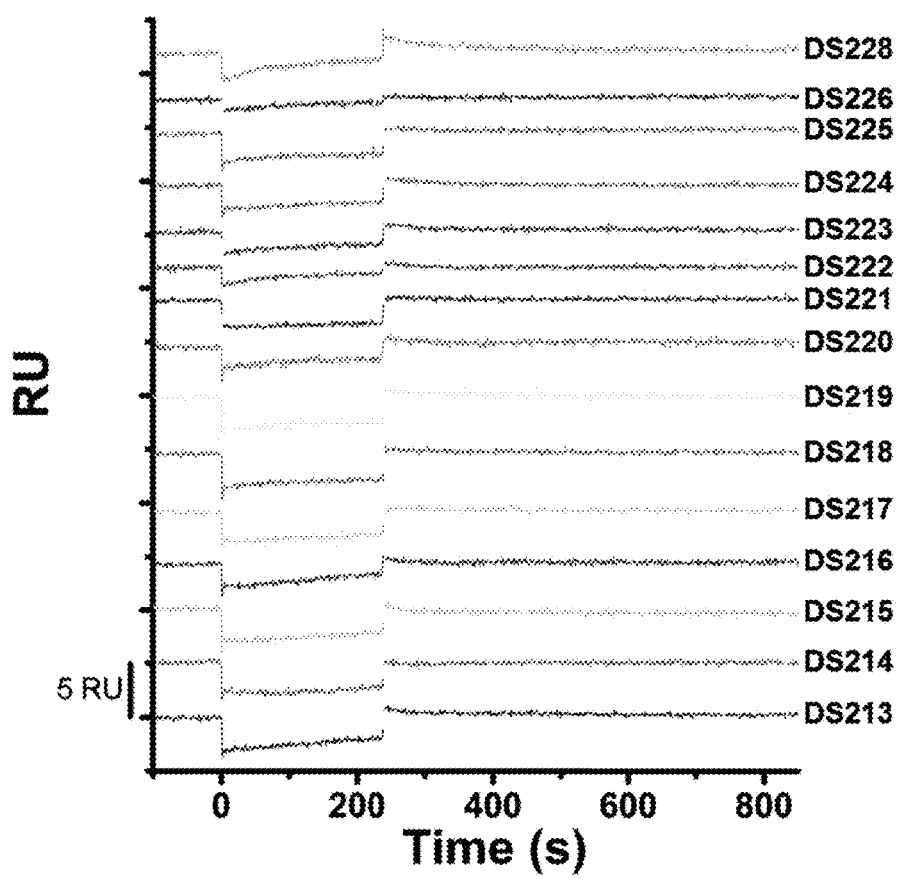

FIG. 31A-31B shows the chemical structures of exemplary derivatives of DS26 which do not bind to PrP$^C$. FIG. 31A shows the chemical structures of the derivatives DS213-DS226 and DS228. FIG. 31B shows different concentrations of DS213-DS226 and DS228 which were injected for 4 min over sensor surfaces on which 19,000 RU of recombinant PrP$^C$ had been previously captured by amine coupling. Sensorgrams showing small molecule binding in resonance units (RU). No binding was detected for the DS213-DS226 and DS228 compounds.

DETAILED DESCRIPTION OF EXEMPLARY EMBODIMENTS

It has been previously reported that PrP$^C$ interacts with aggregates of several other proteins, raising the intriguing possibility that PrP$^C$ can serve as a cell-surface receptor for a variety of β-sheet rich forms. Herein the inventors have discovered inter alia six common binding regions on the surface of PrP$^C$. The inventors have named these domains PrP-binding domains or PBDs and numbered them 1 to 6. Thus, inventors have discovered PBD-1 to PBD-6. As described in more detail below, the inventors have discovered that these PBDs are functional constituent of the PrP$^C$, and identified ligands that bind to the PBDs, and discovered that binding of ligands to the PBDs inhibits the ion channel activity of PrP$^C$, inhibits formation of PrP in cultured cells, structurally abilizes PrP$^C$, inhibits binding of Aβ oligomers to PrP$^C$, and suppresses the toxicity of Aβ oligomers in hippocampal slices. The inventors also demonstrated how some PBD ligands affect Aβ binding to PrP$^C$ via an allosteric mechanism. Accordingly, aspects described herein are based on the discovery of the PBDs and their role in activity of PrP$^C$.

Prion (PrP$^C$) Protein

The protein that prions are made of (PrP) is found throughout the body, even in healthy people and animals. However, PrP found in infectious material has a different structure and is resistant to proteases, the enzymes in the body that can normally break down proteins. The normal form of the protein is called PrP$^C$, while the infectious form is called PrP$^{Sc}$—the C refers to 'cellular', while the Sc refers to 'scrapie', a prion disease occurring in sheep. While PrP$^C$ is structurally well-defined, PrP$^{Sc}$ is hetergenous at a molecular level, and its three-dimensional structure has not yet been defined by high-resolution techniques.

PrP$^C$ is a normal protein found on the membranes of cells. It is produced as a proprotein comprising 254 amino acids corresponding to SEQ ID NO: 1, which is post-translationally processed to a polypeptide having 209 amino acids (in humans), one disulfide bond, and a molecular mass of 35-36 kDa. Its structure consists of a globular C-terminal domain containing three alpha-helices and two beta-strands, and an N-terminal domain that is flexible and unstructured. PrP$^C$ binds copper (II) ions with high affinity. PrP$^C$ has been reported to play important roles in cell-cell adhesion and intracellular signaling in vivo, and may therefore be involved in cell-cell communication in the brain.

Full-length prion protein (PrP) corresponding to SEQ ID NO: 1 consists of a N-terminal signal sequence (residues 1-23 of SEQ ID NO: 1), an N-terminal octapeptide repeat domain, a central domain which includes a charge cluster and a segment with hydrophobic character, a globular C-terminal domain and a C-terminal GPI anchor (residues 230-254 of SEQ ID NO: 1). Cleavage of the N-terminal signal sequence and the C-terminal GPI anchor results in the 209 amino acid of mature PrP. PrP is also known in the art by the names PrP27-30 (which refers to protease-digested PrP$^{Sc}$), PrP33-35C, ASCR, and CD230 antigen.

Different forms of PrP have been identified in the nervous system. The usual cellular form is called PrP$^C$. Another form, PrP$^{Sc}$, has a different 3-dimensional structure and has been associated with inherited, sporadic (non-inherited), and infectious disorders of the brain and nervous system. In a process that is not fully understood, PrP$^C$ can transform into the abnormal PrP$^{Sc}$. This abnormal protein can further promote the transformation of PrP$^C$ into PrP$^{Sc}$, leading to transmissible spongiform encephalopathy.

The amino acid sequence of the human PrP is available under GenBank Accession Number AAA60182, and is presented herein as SEQ ID NO:1:

```
MANLGCWMLV LFVATWSDLG LCKKRPKPGG WNTGGSRYPG

QGSPGGNRYP PQGGGGWGQP HGGGWGQPHG GGWGQPHGGG

WGQPHGGGWG QGGGTHSQWN KPSKPKTNMK HMAGAAAAGA

VVGGLGGYML GSAMSRPIIH FGSDYEDRYY RENMHRYPNQ

VYYRPMDEYS NQNNFVHDCV NITIKQHTVT TTTKGENFTE

TDVKMMERVV EQMCITQYER ESQAYYQRGS SMVLFSSPPV

ILLISFLIFL IVG
```

Variants of the human PrP polypeptide can include, but are not limited to, the following amino acid substitutions: P102L, P105L, L108F. A117V, M129V, G131V, N171S, D178N, V180I, T188K, T188R, T189V, E196K, F198S, E200K, D202N, V203I, R208H, V210I, E211Q, Q212P, Q217R, E219K, M232R, and P238S The amino acid sequence of the mouse PrP is available under GenBank Accession Number NP_035300, and is presented herein as SEQ ID NO:2:

```
MANLGYWLLA LFVTMWTDVG LCKKRPKPGG WNTGGSRYPG

QGSPGGNRYP PQGGTWGQPH GGGWGQPHGG SWGQPHGGSW

GQPHGGGWGQ GGGTHNQWNK PSKPKTNLKH VAGAAAAGAV

VGGLGGYMLG SAMSRPMIHF GNDWEDRYYR ENMYRYPNQV

YYRPVDQYSN QNNFVHDCVN ITIKQHTVTT TTKGENFTET

DVKMMERVVE QMCVTQYQKE
```

The amino acid sequence of the rat PrP is available under GenBank Accession Number NP_036763, and is presented herein as SEQ ID NO:3:

```
MANLGYWLLA LFVTTCTDVG LCKKRPKPGG WNTGGSRYPG

QGSPGGNRYP PQSGGTWGQP HGGGWGQPHG GGWGQPHGGG

WGQPHGGGWS QGGGTHNQWN KPSKPKTNLK HVAGAAAAGA

VVGGLGGYML GSAMSRPMLH FGNDWEDRYY RENMYRYPNQ

VYYRPVDQYS NQNNFVHDCV NITIKQHTVT TTTKGENFTE

TDVKMMERVV EQMCVTQYQK ESQAYYDGRR SSAVLFSSPP

VILLISFLIF LIVG
```

Different domains of PrP$^C$ are associated with various activities in vitro and in vivo. For example, the N-terminal octapeptide repeat domain (aa 60-95) mediates extracellular copper ion binding. Viles, et al., *Proc Natl Acad Sci USA* 96: 2042-2047 (1999). The central domain (aa 95-134) includes a charge cluster (aa 95-110) and a segment with hydrophobic character (aa 112-134). This central domain, particularly residues 105-125, has been implicated in masking a neurodegenerative activity of PrP$^C$ (Baumann, et al., *Embo J* 26: 538-547 (2007) and Li, et al., *Embo J* 26: 548-558 (2007)). The C-terminal domain is globular (aa 125-231) (Riek, et al., *Nature* 382: 180-182 (1996)) and the protein is GPI anchored to the plasma membrane. As one of skill in the art will appreciate, the beginning and ending residues of the domains listed above can vary depending upon the computer modeling program used or the method used for determining the domain.

In one aspect, provided herein is a method of treating a disease or disorder associated with protein aggregation and/or neurodegeneration, the method comprising administering to a subject in need thereof a therapeutically effective amount of a PrP$^C$ ligand or compound that binds to a PrP-binding domain of PrP$^C$. For example, a PrP$^C$ ligand as described herein, e.g., a compound can bind one or more (e.g., one, two, three, four, five, or six) of PDB-1, PDB-2, PDB-3, PDB-4, PDB-5, and PDB-6. In some embodiments, a PrP$^C$ ligand as described herein, is a compound that specifically binds to one or more (e.g., one, two, three, four, five, or six) of PDB-1, PDB-2, PDB-3, PDB-4, PDB-5, and PDB-6.

As used herein, a disease or disorder associated with protein aggregation or neurodegeneration refers to a pathology characterized by attraction of proteins into filaments in the brain, and the aggregation of these filaments into intracytoplasmic inclusions or extracellular plaque deposits. An example of such filamentous lesions are the intracellular neurofibrillary tangles, composed of tau protein, and extracellular senile plaques composed of amyloid protein, which are seen in both Alzheimer's disease and Down's syndrome. Intraneuronal Lewy bodies, formed by the aggregation of α-synuclein, are seen in Parkinson's disease as well as Down's syndrome brains and other synucleinopathies. Prion diseases, such as Creutzfeldt-Jakob disease (CJD), bovine spongiform encephalopathy (BSE), and scrapie, for instance, involve the conformational change and aggregation of prion proteins. Amyloidosis diseases which are due to too much amyloid proteins include are included in the term diseases associated with protein aggregation and include, for example, AD, multiple myeloma, Hodgkin's disease or familial Mediterranean fever (an intestinal disorder), Fatal Familial Insomnia, and type II diabetes.

Neurodegenerative diseases such as Alzheimer's disease (AD), Parkinson's disease (PD), Huntington's disease (HD), amyotrophic lateral sclerosis (ALS) and prion diseases are increasingly being realized to have common cellular and molecular mechanisms including protein aggregation and inclusion body formation. The aggregates usually consist of fibers containing misfolded protein with a beta-sheet conformation, termed amyloid. There is partial but not perfect overlap among the cells in which abnormal proteins are deposited and the cells that degenerate. Accordingly, a disease or disorder associated with protein aggregation or neurodegeneration can include, but is not limited to, Alzheimer's disease (AD); Parkinson's disease (PD); Down's syndrome; Huntington's disease (HD); amyotrophic lateral sclerosis (ALS), Creutzfeldt-Jakob disease (CJD); fatal familial insomnia (FFI); fatal sporadic insomnia (FSI); Gerstmann-Sträussler Syndrome (GSS); Kuru; Iatrogenic Creutzfeld-Jakob disease (iCJD); variant Creutzfeldt-Jakob disease (vCJD); Familial Creutzfeldt-Jakob disease (fCJD), Sporadic Creutzfeldt-Jakob disease (sCJD), Gerstmann-Sträussler-Scheinker syndrome (GSS), Fatal familial insomnia (FFI), Sporadic Fatal Insomnia (sFI); bovine spongiform encephalopathy (BSE); scrapie; chronic wasting disease (CWD); and tauopathies, such as Progressive supranuclear palsy, Dementia, Dementia pugilistica (chronic traumatic encephalopathy), Frontotemporal dementia and parkinsonism linked to chromosome 17, Lytico-Bodig disease, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, Pick's complex, argyrophilic grain disease (AGD), corticalbasal degeneration, frontotemporal dementia and frontotemporal lobar degeneration.

By "treatment", "prevention" or "amelioration" of a disease or disorder associated with protein aggregation or neurodegeneration is meant delaying or preventing the onset of such a disease or disorder, reversing, alleviating, ameliorating, inhibiting, slowing down or stopping the progression, aggravation or deterioration the progression or severity of a condition associated with such a disease or disorder. For the avoidance of doubt, references herein to "treatment" include references to curative, palliative and prophylactic treatment. In some embodiments, at least one symptom of the pathology is alleviated by at least 5%, at least 10%, at least 20%, at least 30%, at least 40%, at least 50%, at least 60%, at least 70%, at least 80%, or at least 90% or more. A complete amelioration of the pathology is not required.

Further, as used herein, the terms "treat" or "treatment" refer to both therapeutic treatment and prophylactic or preventative measures, wherein the object is to prevent or slow down (lessen) an undesired physiological change or disorder, such as the progression of Alzheimer's disease. Beneficial or desired clinical results can include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Any particular treatment regimen can provide one or more such clinical results in one or more patients, and need not provide all such clinical results. "Treatment" can also mean prolonging survival as compared to expected survival if not receiving treatment. Those in need of treatment include those already with the condition or disorder as well as those prone to have the condition or disorder or those in which the condition or disorder is to be prevented.

In some embodiments, the ligand can bind with $PrP^C$ with an off rate ($k_{off}$) of less than or equal to $5\times10^{-1}$ sec$^{-1}$, $10^{-1}$ sec$^{-1}$, $5\times10^{-2}$ sec$^{-1}$, $10^{-2}$ sec$^{-1}$, $5\times10^{-3}$ sec$^{-1}$, $10^{-3}$ sec$^{-1}$. Alternatively, the ligand can bind with $PrP^C$ with an off rate ($k_{off}$) of less than or equal to $5\times10^{-4}$ sec$^{-1}$, $10^{-4}$ sec$^{-1}$, $5\times10^{-5}$ sec$^{-1}$, or $10^{-5}$ sec$^{-1}$ $5\times10^{-6}$ sec$^{-1}$, $10^{-6}$ sec$^{-1}$, $5\times10^{-7}$ sec$^{-1}$ or $10^{-7}$ sec$^{-1}$.

In some embodiments, the ligand can bind with $PrP^C$ with an on rate ($k_{on}$) of greater than or equal to $10^1 M^{-1}$ sec$^{-1}$, $5\times10^1$ M$^{-1}$, $10^2$ M$^{-1}$ sec$^{-1}$, $5\times10^2$ M$^{-1}$, $10^3$M$^{-1}$ sec$^{-1}$, $5\times10^3$ M$^{-1}$, $10^4$M$^{-1}$ sec$^{-1}$. Alternatively, the ligand can bind with $PrP^C$ with an on rate ($k_{on}$) greater than or equal to $5\times10^4$ M$^{-1}$, $10^5$M$^{-1}$ sec$^{-1}$, $5\times10^5$ M$^{-1}$ sec$^{-1}$, $10^6$M$^{-1}$ sec$^{-1}$, or $5\times10^{-6}$ M$^{-1}$ sec$^{-1}$.

In some embodiments, the ligand can bind to the $PrP^C$ with a dissociation constant ($K_d$) of less than or equal to 500 μM, 400 μM, 300 μM, 200 μM, 100 μM, 50 μM, 40 μM, 30 μM, 30 μM, 10 μM, 1 μM, 900 nM, 800 nM, 700 nM, 600 nM, 500 nM, 400 nM, 300 nM, 200 nM, 100 nM, 50 nM, 40 nM, 30 nM, 20 nM, 10 nM, or 1 nM.

In some embodiments, the $PrP^C$ ligand can inhibit binding of Aβ oligomers to $PrP^C$. For example, binding of the $PrP^C$ ligand can reduce the binding of Aβ oligomers with $PrP^C$ by at least 5%, at least 10%, at least 15%, at least 20%, at least 25%, at least 30%, at least 35%, at least 40%, at least 45%, at least 50%, at least 60%, at least 70%, at least 80%, at least 90%, at least or 100% (i.e., complete inhibition of binding) relative to a control or reference level. A control or reference level can be the binding of Aβ oligomers to $PrP^C$ in the absence of a ligand. Binding of $PrP^C$ ligand to $PrP^C$ can be determined using any binding assay known and available to one of skill in the art. For example, binding can be determined using Surface Plasmon Resonance (SPR) or Fluorescence Polalrization (FP) as described in the Examples section.

In some embodiments, the $PrP^C$ ligand can inhibit the ion-channel activity of $PrP^C$. For example, binding of the $PrP^C$ ligand can reduce the ion-channel activity of the $PrP^C$ by at least 5%, at least 10%, at least 15%, at least 20%, at least 25%, at least 30%, at least 35%, at least 40%, at least 45%, at least 50%, at least 60%, at least 70%, at least 80%, at least 90%, at least or 100% (i.e., complete inhibition of binding) relative to a control or reference level. A control or reference level can be the ion-channel activity in the absence of a ligand. Ion-channel activity of $PrP^C$ can be determined using the patch clamp method described in the Examples section.

In some embodiments, the $PrP^C$ ligands can reduce or inhibit $PrP^{Sc}$ replication. Accordingly, in some embodiments, $PrP^C$ ligand can reduce $PrP^{Sc}$ replication by at least 5%, at least 10%, at least 15%, at least 20%, at least 25%, at least 30%, at least 35%, at least 40%, at least 45%, at least 50%, at least 55%, at least 60%, at least 70%, at least 80%, at least 90%, at least 1-fold, at least 1.25-fold, at least 1.5-fold, at least 2-fold, at least 2.5-fold, at least 3-fold, at least 4-fold, or at least 5-fold relative to a control or reference. $PrP^{Sc}$ replication can be determined or measured using the Protein Misfolding Cyclic Amplification (PMCA) assay, which is well known in the art. See, for example, U.S. Pat. No. 7,351,526 and U.S. Patent Application Pub No. 2006/0263767, content of both of which is incorporated herein by reference. $PrP^{Sc}$ replication can also be determined or measured using scrapie-infected N2a neuroblastoma cells, which are well known in the art. See, for example, Race R E, Caughey B, Graham K, Ernst D, Chesebro B (1988) Analyses of frequency of infection, specific infectivity, and prion protein biosynthesis in scrapie-infected neuroblastoma cell clones. J Virol 62: 2845-2849, content of which is incorporated herein by reference.

The conversion of cellular prion protein ($PrP^C$) to the protease resistant isoform ($PrP^{Sc}$) is considered essential for the progression of transmissible spongiform encephalopathies (TSEs). A potential therapeutic strategy for preventing the accumulation of $PrP^{Sc}$ is to stabilize $PrP^C$ through the direct binding of a small molecule to make conversion less energetically favorable. The inventors have discovered that $PrP^C$ ligands described herein can stabilize the $PrP^C$. In one manifestation of this stabilization, the inventors have also discovered that binding of the $PrP^C$ ligand to the $PrP^C$ polypeptide can increase the thermal melting temperature (Tm) of $PrP^C$. For example, the Tm of the $PrP^C$ is at least 0.5° C., at least 0.75° C., at least 1° C., at least 1.25° C., at least 1.5° C., at least 1.75° C., at least 2° C., at least 2.25° C., at least 2.5° C., at least 2.75° C., at least 3° C., at least 3.5° C., at least 4° C., at least 4.5° C., at least 5° C., at least 5.5° C., or at least 6° C. higher when a $PrP^C$ ligand is bound relative to when a $PrP^C$ ligand is not bound to the $PrP^C$. Accordingly, the inventors have discovered that $PrP^C$ ligands described herein can stabilize the $PrP^C$. By stabilizing is meant that the conversion of PrP$^C$ to PrP$^{Sc}$ is reduced. Binding of a PrP$^C$ ligand to the PrP$^C$ can reduce or inhibit conversion of PrP$^C$ to PrP$^{Sc}$ and can reduce or inhibit PrP$^{Sc}$ replication. Accordingly, in some embodiments, binding of the PrP$^C$ ligand can reduce conversion of PrP$^C$ to PrP$^{Sc}$ by at least 5%, at least 10%, at least 15%, at least 20%, at least 25%, at least 30%, at least 35%, at least 40%, at least 45%, at least 50%, at least 55%, at least 60%, at least 70%, at least 80%, at least 90%, at least 1-fold, at least 1.25-fold, at least 1.5-fold, at least 2-fold, at least 2.5-fold, at least 3-fold, at least 4-fold, or at least 5-fold relative to a control or reference. Conversion of PrP$^C$ to PrP$^{Sc}$ can be determined using SPR-based technology.

In some embodiments, the PBD-1 binding compound is selected from the group consisting of compounds of formulas (I)-(IV) and any combinations thereof.

In some embodiments, the compound is of formula (I):

Formula (I)

wherein:
$R^{101}$ is alkyl, hetero alkyl, aryl, acyl, alkenyl, alkynyl, heteroaryl, cyclyl, heterocyclyl, alkylaryl, alkylheteroaryl, alkylcyclyl, alkylheterocyclyl, $N(R^{107})C(O)NHR^{108}$, $N(R^{107})C(S)NHR^{108}$, $N(R^{107})C(O)OR^{109}$, $N(R^{107})C(O)SR^{109}$, or $N(R^{107})C(S)OR^{109}$, each of which can be optionally substituted;

each of $R^{102}$, $R^{103}$, $R^{104}$, $R^{104'}$, $R^{105}$, and $R^{106}$ is independently selected from H, alkyl, halogen, OH, $OR^{110}$, $NH_2$, $NHR^{111}$, $N(R^{107})C(O)NHR^{108}$, $N(R^{107})C(S)NHR^{108}$, $N(R^{107})C(O)OR^{109}$, $N(R^{107})C(O)SR^{109}$, or $N(R^{107})C(S)OR^{109}$, each of which can be optionally substituted, $R^{103'}$ is H, alkyl, halogen, OH, $OR^{110}$, $NH_2$, $NHR^{111}$, each of which can be optionally substituted or $R^{103'}$ forms a bond with the carbon attached to $R^{106}$;

$R^{107}$ and $R^{108}$ are independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl;

$R^{109}$ is independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl;

$R^{110}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl;

$R^{111}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl, each of which can be optionally substituted; and isomers and pharmaceutically acceptable salts thereof.

It is to be understood that the C═N double bond in the compounds of formula (I) can be in the cis (Z) or trans (E) configuration with respect to the ring carbon attached to $R^{106}$. In some embodiments, the C═N double is in the trans (E) configuration with respect to the ring carbon attached to $R^{106}$. While compounds of formula (I) having the C═N double in the cis (Z) configuration with respect to the ring carbon attached to $R^{106}$ do not bind PrP$^C$, they can be easily converted to PrP$^C$ binders by converting the C═N bond from the cis configuration to the trans configuration by heating the cis compound. Thus, compounds of formula (I) having the trans C═N bond can be useful in synthesis of compounds which bind with PrP$^c$.

In some embodiments, $R^{103'}$ and $R^{104'}$ are both H; $R^{101}$ is alkyl, hetero alkyl, aryl, acyl, alkenyl, alkynyl, heteroaryl, cyclyl, heterocyclyl, alkylaryl, alkylheteroaryl, alkylcyclyl, or alkylheterocyclyl, $N(R^{107})C(O)NHR^{108}$, $N(R^{107})C(S)NHR^{108}$, $N(R^{107})C(O)OR^{109}$, $N(R^{107})C(O)SR^{109}$, $N(R^{107})C(S)OR^{109}$, each of which can be optionally substituted; each of $R^{102}$, $R^{103}$, $R^{104}$, $R^{105}$, and $R^{106}$ is independently selected from H, halogen, OH, $OR^{110}$, $NH_2$, $NHR^{111}$, each of which can be optionally substituted; $R^{107}$ and $R^{108}$ are independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl; $R^{109}$ is independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl; $R^{110}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl; and $R^{111}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl.

In some embodiments, $R^{103'}$ and $R^{104'}$ are both H; $R^{101}$ is alkyl, hetero alkyl, aryl, acyl, alkenyl, alkynyl, heteroaryl, cyclyl, heterocyclyl, alkylaryl, alkylheteroaryl, alkylcyclyl, or alkylheterocyclyl, $N(R^{107})C(O)NHR^{108}$, $N(R^{107})C(S)NHR^{108}$, $N(R^{107})C(O)OR^{109}$, $N(R^{107})C(O)SR^{109}$, $N(R^{107})C(S)OR^{109}$, each of which can be optionally substituted; each of $R^{102}$, $R^{103}$, $R^{104}$, $R^{105}$, and $R^{106}$ is independently selected from H, halogen, OH, $OR^{110}$, $NH_2$, $NHR^{111}$, each of which can be optionally substituted; $R^{107}$ and $R^{108}$ are independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl; $R^{109}$ is independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl; $R^{110}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl; and $R^{111}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl, provided that $R^{102}$-$R^{109}$ are not all H.

In some embodiments, $R^{103'}$ and $R^{104'}$ are both H; $R^{101}$ is alkyl, hetero alkyl, aryl, acyl, alkenyl, alkynyl, heteroaryl, cyclyl, heterocyclyl, alkylaryl, alkylheteroaryl, alkylcyclyl, or alkylheterocyclyl, $N(R^{107})C(O)NHR^{108}$, $N(R^{107})C(S)NHR^{108}$, $N(R^{107})C(O)OR^{109}$, $N(R^{107})C(O)SR^{109}$, $N(R^{107})C(S)OR^{109}$, each of which can be optionally substituted; each of $R^{102}$, $R^{103}$, $R^{104}$, $R^{105}$, and $R^{106}$ is independently selected from H, halogen, OH, $OR^{110}$, $NH_2$, $NHR^{111}$, each of which can be optionally substituted; $R^{107}$ and $R^{108}$ are independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl; $R^{109}$ is independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl; $R^{110}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl; and $R^{111}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl, provided that the compound is not one wherein $R^{101}$ is $NHC(S)NH_2$ and $R^{102}$-$R^{106}$ are all H.

In some compounds of formula (I), $R^{101}$ is alkyl, hetero alkyl, aryl, or $N(R^{107})C(S)NHR^{108}$.

In some compounds of formula (I), $R^{102}$ is H, $C_1$-$C_6$ alkyl, OH, $OR^{110}$, $NH_2$, or $NHR^{111}$. In some embodiments, $R^{102}$ is methyl, propen-3-yl, t-butyl, $CF_3$, Cl, or ethoxy ($OCH_2CH_3$).

In some compounds of formula (I), $R^{103}$ and $R^{103'}$ are independently H, $C_1$-$C_6$ alkyl, OH, $OR^{110}$, $NH_2$, or $NHR^{111}$. In some embodiments, at least one of $R^{103}$ and $R^{103'}$ is H. In some embodiments, both of $R^{103}$ and $R^{103'}$ are H. In some embodiments, one of $R^{103}$ and $R^{103'}$ is H and other is $C_1$-$C_6$ alkyl, OH, $OR^{110}$, $NH_2$, or $NHR^{111}$. In some embodiments, one of $R^{103}$ and $R^{103'}$ is H and the other is methyl. In some embodiments, both of $R^{103}$ and $R^{103'}$ are independently $C_1$-$C_6$ alkyl. In one embodiment, both of both of $R^{103}$ and $R^{103'}$ are methyl. In one embodiments, one of $R^{103}$ and $R^{103'}$ is $C(CH_3)_2$ and is attached to the carbon to which $R^{106}$ is attached.

In some compounds of formula (I), $R^{104}$ and $R^{104'}$ are independently H, $C_1$-$C_6$ alkyl, OH, $OR^{110}$, $NH_2$, $NHR^{111}$, $N(R^{107})C(O)OR^{109}$, optionally substituted aryl, or optionally substituted heteroayl. In some embodiments, at least one of $R^{104}$ and $R^{104'}$ is H. In some embodiments, both of $R^{104}$ and $R^{104'}$ are H. In some embodiments, one of $R^{104}$ and $R^{104'}$ is H and other is $C_1$-$C_6$ alkyl, OH, $OR^{110}$, $NH_2$, $NHR^{111}$, $N(R^{107})C(O)OR^{109}$, optionally substituted aryl, or optionally substituted heteroayl. In some embodiments, one of $R^{104}$ and $R^{104'}$ is H and the other is isopropyl. In some embodiments, one of $R^{104}$ and $R^{104'}$ is H and the other is an optionally phenyl. In one embodiment, one of $R^{104}$ and $R^{104'}$ is H and the other is 4-hydroxy phenyl. In some embodiments, one of $R^{104}$ and $R^{104'}$ is H and the other is $NHC(O)OR^{109}$. In one embodiment, $R^{109}$ is optionally substituted benzyl. In some embodiments, both of $R^{104}$ and $R^{104'}$ are independently $C_1$-$C_6$ alkyl. In one embodiment, both of both of $R^{104}$ and $R^{104'}$ are methyl.

In some embodiments, one of $R^{103}$ and $R^{103'}$ is H and one of $R^{104}$ and $R^{104'}$ is H.

In some compounds of formula (I), $R^{105}$ is H, OH, $OR^{110}$, $NH_2$, or $NHR^{111}$.

In some compounds of formula (I), $R^{106}$ is H, $C_1$-$C_6$ alkyl, OH, $OR^{110}$, Cl, $NH_2$, or $NHR^{111}$. In some embodiments, $R^{106}$ is methyl, ethyl or propyl. In one embodiment, $R^{102}$ and $R^{106}$ are independently $C_1$-$C_6$ alkyl. In one embodiment, both $R^{102}$ and $R^{106}$ are methyl. In one embodiment, $R^{106}$ is $C_1$-$C_6$ alkyl and $R^{103}$ or $R^{103'}$ is further attached to the carbon to which $R^{106}$ is attached.

In some compounds of formula (I), $R^{107}$ is H, optionally substituted alkyl, or optionally substituted aryl. Exemplary alkyls for $R^{107}$ include, but are not limited to, optionally substituted $C_1$-$C_6$ alkyls such as methyl, ethyl, propyl, isopropyl, n-butyl, isobutyl, sec-butyl, pentyl, hexyl, and t-butyl. Exemplary aryls for $R^{107}$ include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl each of which can be optionally substituted. In some embodiments, $R^{107}$ is H, methyl, or phenyl. In one embodiment, $R^{107}$ is not H.

In some compounds of formula (I), $R^{108}$ is H, alkyl, aryl, or alkylaryl. Exemplary alkyls for $R^{108}$ include, but are not limited to, optionally substituted $C_1$-$C_6$ alkyls such as methyl, ethyl, propyl, isopropyl, n-butyl, isobutyl, sec-butyl, pentyl, hexyl, and t-butyl. Exemplary aryls for $R^{108}$ include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl each of which can be optionally substituted. Exemplary alkylaryls for $R^{108}$ include, but are not limited to, benzyl, diphenylmethyl and phenylethyl each of which can be optionally substituted. In some embodiments, $R^{108}$ is H, sec-butyl, phenyl or benzyl. In one embodiment, $R^{108}$ is not H. In some embodiments, $R^{108}$ is 3,4-dimethoxyethyl, t-butyl, or 4-fluorobenzyl.

In some compounds of formula (I), $R^{108}$ is a fluorescent molecule. Exemplary fluorescent molecules include, but are not limited to, Fluorescein, Calcofluor (Calcofluor-white), Hydroxycoumarin, Succinimidyl ester, Aminocoumarin, Succinimidyl ester, Methoxycoumarin, Succinimidyl ester, Cascade Blue, Hydrazide, Pacific Blue, Maleimide, Pacific Orange, Lucifer yellow, NBD, NBD-X, R-Phycoerythrin (PE), a PE-Cy5 conjugate (Cychrome, R670, Tri-Color, Quantum Red), a PE-Cy7 conjugate, Red 613, PE-Texas Red, PerCP, Peridinin chlorphyll protein, TruRed (PerCP-Cy5.5 conjugate), FluorX, Fluoresceinisothyocyanate (FITC), BODIPY-FL, TRITC, X-Rhodamine (XRITC), Lissamine Rhodamine B, Texas Red, Allophycocyanin (APC), an APC-Cy7 conjugate, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, Alexa Fluor 750, Alexa Fluor 790, Cy2, Cy3, Cy3B, Cy3.5, Cy5, Cy5.5, Cy7, and DyLight 594.

In some compounds of formula (I), $R^{101}$ is alkyl, hetero alkyl, aryl, or $N(R^{107})C(S)NHR^{108}$; and each of $R^{102}$-$R^{106}$ is independently selected from H, $C_1$-$C_6$ alkyl, $CF_3$, OH, $OR^{110}$, Cl, $NH_2$, and $NHR^{111}$.

In some compounds of formula (I), $R^{102}$-$R^{106}$ are all OH. In some embodiments, $R^{102}$-$R^{106}$ are all OH; $R^{101}$ is $N(R^{107})C(S)NHR^{108}$; and at least one of $R^{107}$ or $R^{108}$ is not H.

In some compounds of formula (I), $R^{102}$-$R^{106}$ are all OH and $R^{103'}$ and $R^{104'}$ are both H.

In some compounds of formula (I), when $R^{102}$-$R^{106}$ are all H, at least one of $R^{107}$ or $R^{108}$ is not H.

In some compounds of formula (I), at least one of (e.g., one, two, three, four, or five) $R^{102}$-$R^{106}$ is independently $OR^{110}$, $C_1$-$C_6$ alkyl, Cl, $CF_3$, $NH_2$, and $NHR^{111}$.

In some compounds of formula (I) all of $R^{102}$-$R^{106}$ are the same or all are different. In some embodiments, at least two of (e.g., one, two, three or four) $R^{102}$-$R^{106}$ are the same and at least one of (e.g., one, two or three) $R^{102}$-$R^{106}$ are different.

In some compounds of formula (I), $R^{107}$ and $R^{108}$ are both H.

In some embodiments, a compound for formula (I) has the stereochemistry as shown in formula (Ia):

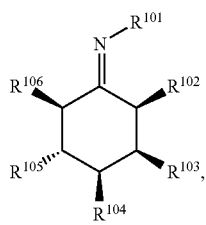

Formula (Ia)

wherein substituents are as defined above for formula (I). While formula (Ia) is shown with the C=N double bond having the trans configuration with respect to carbon to which $R^{106}$ is attached, in some compounds of formula (Ia), the C=N double bond can have the cis (Z) configuration.

In some embodiments, a compound for formula (I) has the structure shown in formula (Ib):

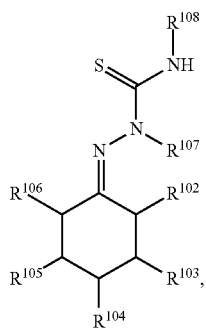

Formula (Ib)

wherein substituents are as defined above for formula (I). While formula (Ib) is shown with the C=N double bond having the trans configuration with respect to carbon to which $R^{106}$ is attached, in some compounds of formula (Ib), the C=N double bond can have the cis (Z) configuration In some embodiments, a compound for formula (Ib) has the stereochemistry shown in formula (Ic):

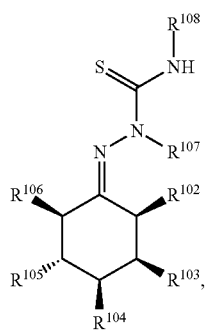

Formula (Ic)

wherein substituents are as defined above for formula (I). While formula (Ic) is shown with the C=N double bond having the trans configuration with respect to carbon to which $R^{106}$ is attached, in some compounds of formula (Ic), the C=N double bond can have the cis (Z) configuration.

In some embodiments, the compound of formula (I) is 2-(2R,3S,5R,6S-pentahydroxycyclohexylidene)hydrazinecarbothioamide (DS26). The structure of DS26 is shown in FIGS. 2, 4A, 14C, 24A and 25. In some compounds of formula (I), all of $R^{102}$-$R^{106}$ are OH; both of $R^{103'}$ and $R^{104'}$ are H; $R^{101}$ is NHC(S)NHR$^{109}$; and $R^{109}$ is 3,4-dimethoxyphenylethyl (DS-207). Structure of DS-207 is shown in FIG. 30A. In some compounds of formula (I), all of $R^{102}$-$R^{106}$ are OH; both of $R^{103'}$ and $R^{104'}$ are H; $R^{101}$ is NHC(S)NHR$^{109}$; andR$^{109}$; is t-butyl (DS-210). Structure of DS-210 is shown in FIG. 30B. In some compounds of formula (I), all of $R^{102}$-$R^{106}$ are OH; both of $R^{103'}$ and $R^{104'}$ are H; $R^{101}$ is NHC(S)NHR$^{109}$ is 4-fluorobenzyl (DS-211) Structure of DS-211 is shown in FIG. 30C.

In some embodiments, the compound of formula (I) is not a compound wherein $R^{101}$ is NHC(S)NH$_2$, $R^{102}$-$R^{106}$ are all H, and $R^{103'}$ and $R^{104'}$ are both H.

In some embodiments, the compound of formula (I) is a compound selected from the group of compounds consisting of the compound shown in Table 1.

TABLE 1

| Some exemplary compounds of formula (I) | |
|---|---|
| Compound | Structure |
| DS95 | |
| DS96 | |
| DS97 | |

TABLE 1-continued

Some exemplary compounds of formula (I)

| Compound | Structure |
|---|---|
| DS98 | (structure) |
| DS99 | (structure) |
| DS100 | (structure) |
| DS101 | (structure) |
| DS102 | (structure) |
| DS103 | (structure) |
| DS104 | (structure) |

TABLE 1-continued

Some exemplary compounds of formula (I)

| Compound | Structure |
|---|---|
| DS207 | 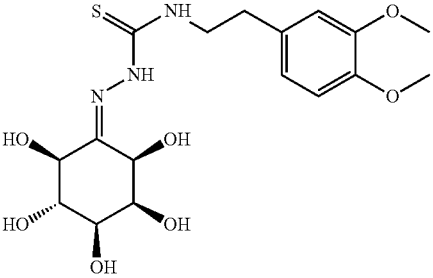<br>DS-207 |
| DS210 | 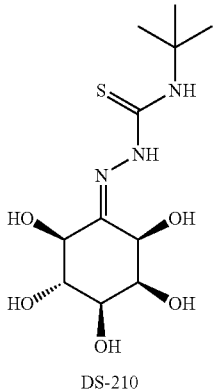 [SMILES: CC(C)(C)NC(=S)N/N=C1\[C@@H](O)[C@@H](O)[C@@H](O)[C@H](O)[C@H]1O]<br>DS-210 |
| DS211 | 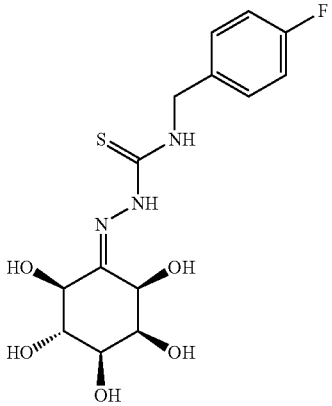 [SMILES: O[C@@H]1[C@H](O)[C@H](O)/C(=N\NC(=S)NCc2ccc(F)cc2)[C@H](O)[C@H]1O]<br>DS-211 |

It is noted that not all compounds of formula (I) bound to $PrP^C$ under the assay conditions described herein. Therefore, in some embodiments of the various aspects described herein, the compounds shown in FIG. 31A are expressly excluded from compounds of formula (I) disclosed herein. For example, in some embodiments of the methods using the compounds of formula (I), the compounds shown in FIG. 31A are specifically excluded.

In some embodiments, the compound is of formula (II):

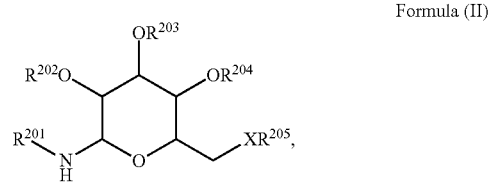

Formula (II)

wherein:

X is O, NH, or S;

each of $R^{201}$, $R^{202}$, $R^{203}$, $R^{204}$ and $R^{205}$ is independently for each occurrence H, aryl, alkyl, acyl, alkenyl, alkynyl, heteroaryl, cyclyl, heterocyclyl, alkylaryl, alkylheteroaryl, alkylcyclyl, or alkylheterocyclyl; and isomers and pharmaceutically acceptable salts thereof In some compounds of formula (II), X is O.

In some compounds of formula (II), $R^{201}$ is selected from the group consisting of H, aryl, alkyl, and acyl, each of which can be optionally substituted. In some embodiments, $R^{201}$ is a an optionally substituted aryl. Exemplary aryls for $R^{201}$ include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl each of which can be optionally substituted. In some embodiments, the aryl is substituted with one, two, or three groups. In some embodiments, the aryl is substituted with at least one group selected from the group consisting of OH, halo, CN, $NO_2$, alkyl, alkoxy, $SO_2H$, $CO_2H$, —SH and any combinations thereof. In some embodiments, aryl is a phenyl substituted with a hydroxyl group, e.g., 2-hydroxyl, 3-hydroxyl, or 4-hydroxyl phenyl.

In some compounds of formula (II), $R^{202}$ is selected from the group consisting of H, aryl, alkyl, and acyl, each of which can be optionally substituted.

In some compounds of formula (II), $R^{203}$ is selected from the group consisting of H, aryl, alkyl, and acyl, each of which can be optionally substituted.

In some compounds of formula (II), $R^{204}$ is selected from the group consisting of H, aryl, alkyl, and acyl, each of which can be optionally substituted.

In some compounds of formula (II), $R^{205}$ is selected from the group consisting of H, aryl, alkyl, and acyl, each of which can be optionally substituted.

In some compounds of formula (II), $R^{201}$ is H, aryl, alkyl or acyl each of which can be optionally substituted; and each of $R^{202}$-$R^{205}$ is independently H, acyl, alkyl or acyl each of which can be optionally substituted.

In some compounds of formula (II), X is O; $R^{201}$ is H, aryl, alkyl or acyl each of which can be optionally substituted; each of $R^{202}$-$R^{205}$ is independently H, acyl, alkyl or acyl each of which can be optionally substituted.

In some compounds of formula (II), X is O, $R^{201}$ is an aryl which can be optionally substituted; and each of $R^{202}$-$R^{205}$ is independently H, acyl, alkyl or acyl each of which can be optionally substituted.

In some compounds of formula (II), each of $R^{202}$-$R^{205}$ is H.

In some compounds of formula (II), at least one of (e.g., one two three, or four) $R^{202}$-$R^{205}$ is not H. In some embodiments, at least one of $R^{202}$-$R^{205}$ is aryl, alkyl, acyl, alkenyl, alkynyl, heteroaryl, cyclyl, heterocyclyl, alkylaryl, alkylheteroaryl, alkylcyclyl, or alkylheterocyclyl.

In some embodiments, when all of $R^{202}$-$R^{205}$, $R^{201}$ is not 3-hydoxyl phenyl.

In some embodiments, when $R^{201}$ is 3-hydroxyl phenyl, at least one of $R^{202}$-$R^{205}$ is not H.

In some embodiments, a compound for formula (II) has the stereochemistry shown in formula (IIa):

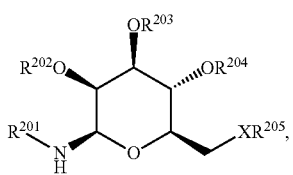

Formula (IIa)

wherein substituents are as defined above for formula (II).

Figures 1A, 1B:
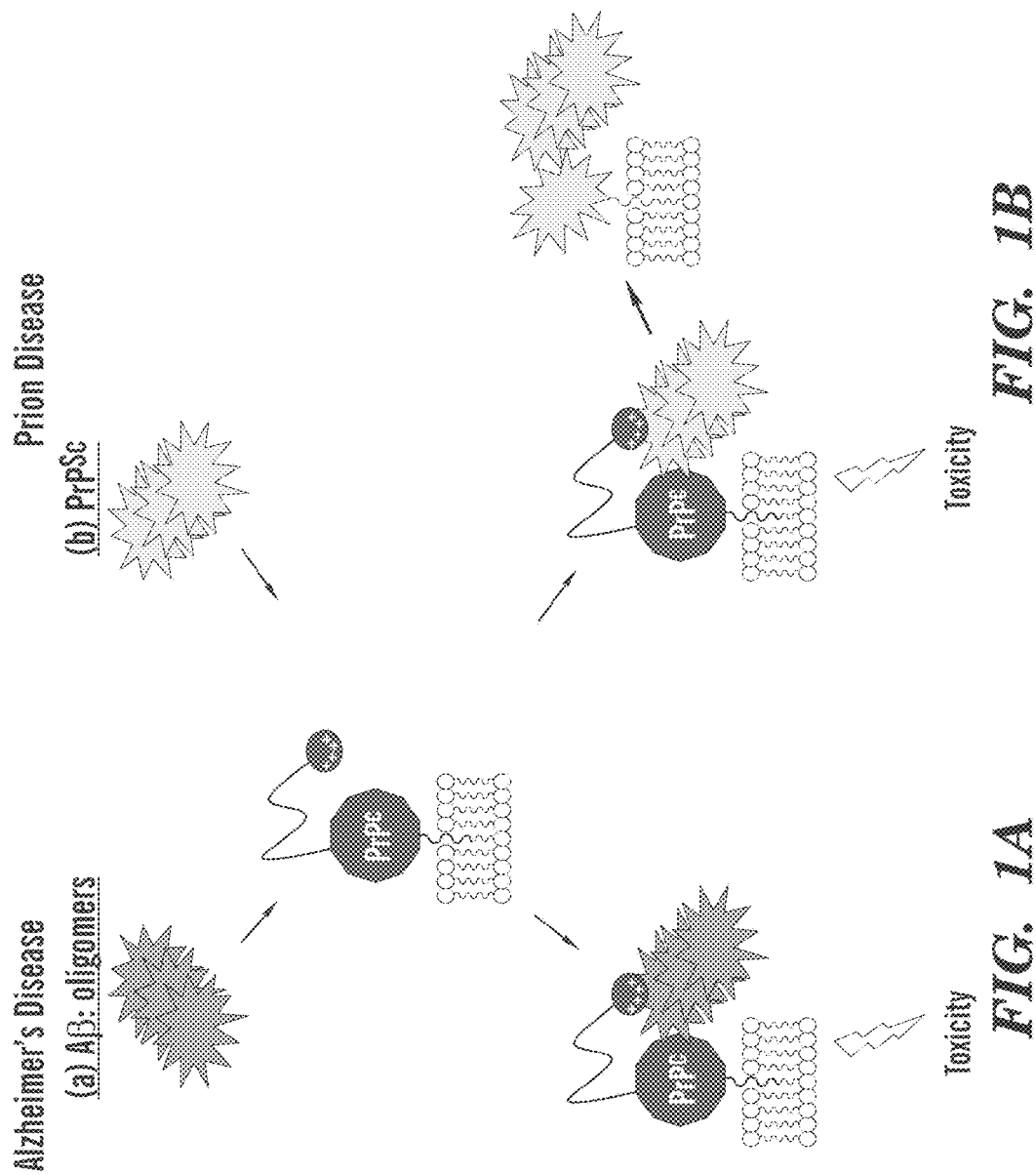
FIGS. 1A-1D has been previously reported and shows that $PrP^C$ may mediate the toxicity of both Aβ oligomers and $PrP^{Sc}$.
Figure 1C:
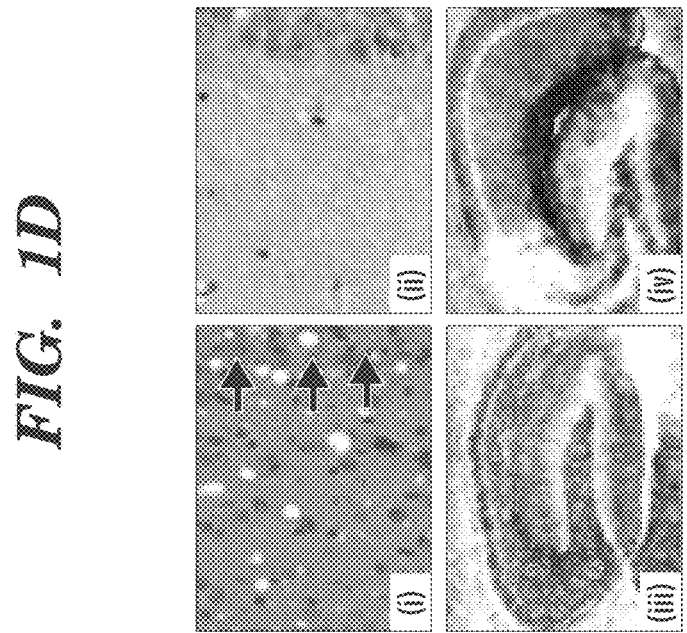
Figure 1D:
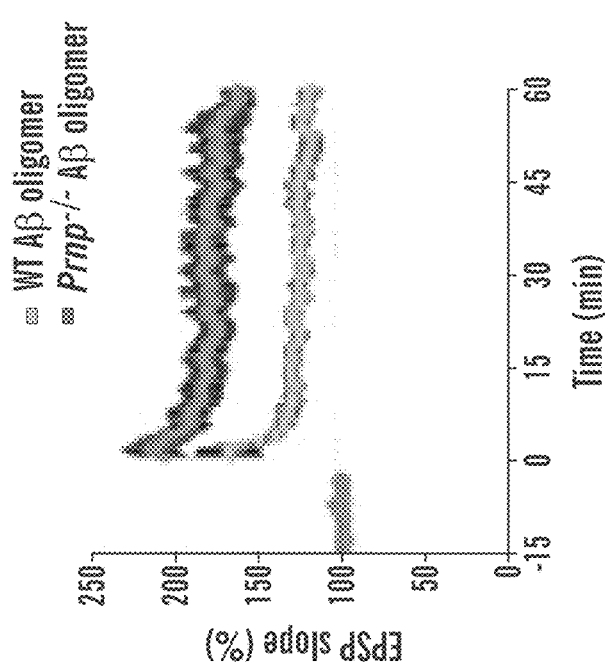
Figure 2:
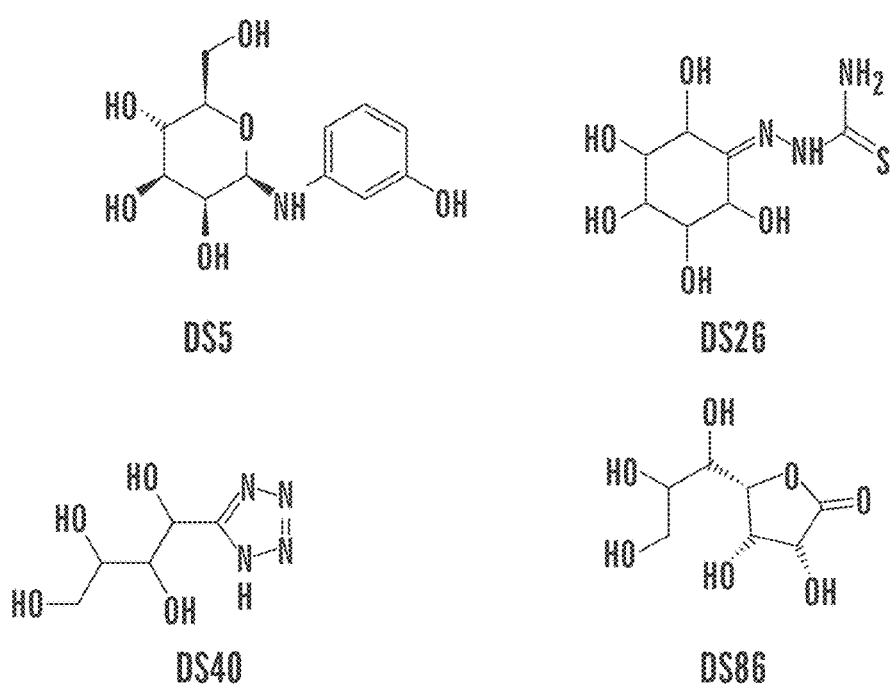
FIG. 2 shows structures of DS5, DS26, DS40, and DS86, ligands that can bind to the PBD-1 site of $PrP^C$.

In some embodiments, a compound of formula (II) is 2R,3S,4S,5S,6R)-2-(hydroxymethyl)-6-[β-hydroxyphenyl) amino]tetrahydro-2H-pyran-3,4,5-triol (DS5). Structure of DS5 is shown in FIG. 2.

In some embodiments, the compound is of formula (III):

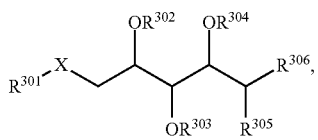

Formula (III)

wherein:
X is O, NH, or S;
each of $R^{301}$, $R^{302}$, $R^{303}$, and $R^{304}$ is independently H, aryl, alkyl, acyl, alkenyl, alkynyl, heteroaryl, cyclyl, heterocyclyl, alkylaryl, alkylheteroaryl, alkylcyclyl, or alkylheterocyclyl;
$R^{305}$ and $R^{306}$ are independently aryl, alkyl, heterocyclyl, heteroaryl, or cyclyl, or $R^{305}$ and $R^{306}$ together with the carbon they are attached to form an aryl, heteroaryl, cyclyl, or heterocyclyl; and isomers and pharmaceutically acceptable salts thereof.

In some compounds of formula (III), X is O.

In some compounds of formula (III), $R^{301}$ is H, aryl, alky, or acyl, each of which can be optionally substituted.

In some compounds of formula (III), $R^{302}$ is H, aryl, alky, or acyl, each of which can be optionally substituted.

In some compounds of formula (III), $R^{303}$ is H, aryl, alky, or acyl, each of which can be optionally substituted.

In some compounds of formula (III), $R^{304}$ is H, aryl, alky, or acyl, each of which can be optionally substituted.

In some compounds of formula (III), $R^{305}$ is aryl, alkyl, or heterocyclyl, each of which can be optionally substituted.

In some compounds of formula (III), $R^{306}$ is aryl, alkyl, or heterocyclyl, each of which can be optionally substituted.

In some compounds of formula (III), $R^{305}$ and $R^{306}$ together with the carbon they are attached to form an aryl, heteroaryl or heterocyclyl. Exemplary aryls, heteroaryls and heterocyclyls for this include, but are not limited to, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, $R^{305}$ and $R^{306}$ together with the carbon they are attached to form an optionally substituted tetrazole group.

In some embodiments, at least one of (e.g., one, two, or three of) $R^{302}$-$R^{304}$ is not H.

In some embodiments, a compound for formula (III) has the stereochemistry shown in formula (IIIa):

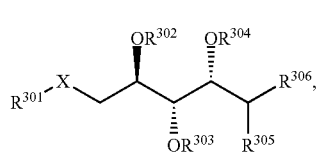

Formula (IIIa)

wherein substituents are as defined above for formula (III).

In some embodiments, a compound for formula (III) is (1S,2R,3R)-1-(1H-tetrazol-5-yl)butane-1,2,3,4-tetrol (DS40). Structure of DS40 is shown in FIG. 2.

In some embodiments, the compound is of formula (IV):

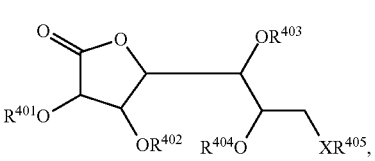

Formula (IV)

wherein:
X is O, NH, or S;
each of $R^{401}$, $R^{402}$, $R^{403}$, $R^{404}$, and $R^{4-5}$ is independently H, aryl, alkyl, acyl, alkenyl, alkynyl, heteroaryl, cyclyl, heterocyclyl, alkylaryl, alkylheteroaryl, alkylcyclyl, or alkylheterocyclyl, each of which can be optionally substituted; and isomers and pharmaceutically acceptable salts thereof.

In some compounds of formula (IV), X is O.

In some compounds of formula (IV), $R^{401}$ is H, aryl, alkyl, or acyl, each of which can be optionally substituted. In some compounds of formula (IV), $R^{401}$ is H.

In some compounds of formula (IV), $R^{402}$ is H, aryl, alkyl, or acyl, each of which can be optionally substituted. In some compounds of formula (IV), $R^{402}$ is H.

In some compounds of formula (IV), $R^{403}$ is H, aryl, alkyl, or acyl, each of which can be optionally substituted. In some compounds of formula (IV), $R^{403}$ is H.

In some compounds of formula (IV), $R^{404}$ is H, aryl, alkyl, or acyl, each of which can be optionally substituted. In some compounds of formula (IV), $R^{404}$ is H.

In some compounds of formula (IV), $R^{405}$ is H, aryl, alkyl, or acyl, each of which can be optionally substituted. In some compounds of formula (IV), $R^{405}$ is H.

Exemplary alkyls for $R^{401}$-$R^{405}$ include, but are not limited to, optionally substituted $C_1$-$C_6$ alkyls such as methyl, ethyl, propyl, isopropyl, n-butyl, isobutyl, sec-butyl, pentyl, hexyl, and t-butyl. Exemplary aryls for $R^{401}$-$R^{405}$ include, but are not limited to, phenyl, naphthyl, anthracenyl, indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl each of which can be optionally substituted.

In some embodiments, a compound for formula (IV) has the stereochemistry shown in formula (IVa):

Formula (IVa)

[chemical structure showing a dihydrofuranone with substituents $R^{401}O$, $OR^{402}$, $R^{404}O$, $OR^{403}$, $XR^{405}$]

wherein substituents are as defined above for formula (IV).

In some embodiments, a compound for formula (IV) is 3R,4S-dihydroxy-5S-(1,2,3-trihydroxypropyl)dihydrofuran-2(3H)-one (DS86). Structure of DS86 is shown in FIG. 2.

In some embodiments, the ligand is a nucleic acid comprising at least three (e.g., three four, five, six, seven, eight, nine, ten or more) nucleotides, wherein the nucleic acid adopts a conformation that is complementary to at least one of the PBDs, e.g., complementary to PBD-1, PBD-2, PBD-3, PBD-4, PBD-5, or PBD-6, In other words, the nucleic acid ligand adopts a conformation which is similar to the shape of a $PrP^C$ ligand described herein.

In some embodiments, the ligand is peptide comprising at least three (e.g., three, four, five, six, seven, eight, nine, ten, eleven, twelve, thirteen, fourteen, fifteen or more) amino acids, wherein the peptide ligand adopts a conformation complementary to a PBD described herein. In other words, the peptide ligand adopts a conformation which is similar to the shape of a $PrP^C$ ligand described herein. In some embodiments, the peptide ligand is a peptidomimetic.

In some embodiments, the ligand is peptide, wherein the peptide comprises at least three (e.g., three, four, five, six, seven, eight, nine, ten, eleven, twelve or more) amino acids from a PBD described herein, e.g., from PBD-1, PBD-2, PBD-3, PBD-4, PBD-5, or PBD-6, wherein the said amino acids are arranged as to mimic the spatial conformation of the PBD. When the ligand is peptide ligand, one or more amino acids in the peptide can be modified.

In some embodiment, the PrPC ligand is not 2-pyrrolidin-1-yl-N-[4-[4-(2-pyrrolidin-1-yl-acetylamino)-benzyl]-phenyl]-acetamide or a compounds described in International patent publication no. WO2010/131717, content of which is incorporated herein by reference. International patent publication no. WO2010/131717 describes 2-pyrrolidin-1-yl-N-[4-[4-(2-pyrrolidin-1-yl-acetylamino)-benzyl]-phenyl]-acetamide and derivatives thereof which are suggested as inhibiting conversion of $PrP^C$ to $PrP^{Sc}$. However, the inventors have found that 2-pyrrolidin-1-yl-N-[4-[4-(2-pyrrolidin-1-yl-acetylamino)-benzyl]-phenyl]-acetamide does not bind PrPC in the SPR assay used for studying the binding of PrPC ligands to PrPC or inhibit binding of Aβ oligomers to $PrP^C$. Further, Kuwata et al., PNAS, 200, 104(29): 11921-11926, content of which is incorporated herein by reference, describes that 2-pyrrolidin-1-yl-N-[4-[4-(2-pyrrolidin-1-yl-acetylamino)-benzyl]-phenyl]-acetamide potentially interacts with amino acids that are not composed in the PBDs described herein. Thus, neither WO2010/131717 nor Kuwata et al., teach or suggest targeting a PBD described herein, e.g., PBD-1, PBD-2, PBD-3, PBD-4, PBD-5, or PBD-6.

The method described herein provides several advantages over previous approaches for treating neurodegenerative diseases. First, the method described herein is directed toward a known pharmacological target: $PrP^C$. As the data presented in this study demonstrate, $PrP^C$ represents a druggable target for the rational design of small molecules that prevent its interaction with toxic protein aggregates and that block its ability to transduce their neurotoxic effects. A well-defined target provides a tremendous opportunity for improvement of the pharmacological properties of effective compounds. The inventors have already identified a number of "druggable pockets" on the surface of $PrP^C$ (e.g., PBD-1, PBD-2, PBD-3, PBD-4, PBD-5, and PBD-6), and demonstrated that these regions are functionally important for $PrP^C$ (e.g. mutations in PBD-1 suppresses the toxicity of a PrP mutant).

Second, the inventors have already found four different high-affinity ligands for $PrP^C$, and demonstrated that one of them (DS26) inhibits a toxic activity of the protein and prevents binding to Aβ oligomers. This small molecule has remarkable pharmacological properties, including sub-micromolar affinity for the target (characterized by an unusually slow dissociation constant) and strong biological activity (it irreversibly suppresses mutant PrP channel activity, inhibits Aβ oligomer binding to $PrP^C$, and significantly suppresses synaptotoxcitiy of Aβ oligomers in hippocampal slices). DS26 is composed of an amino-thiourea tail attached to an epi-inosose ring. Based on the inventors' in silico docking predictions, DS26 enters the PBD-1 site with its inositol ring, leaving the amino-thiourea tail partially outside. This orientation indicates that the pharmacokinetic and pharmacodynamic properties of DS26 can be further improved by introducing chemical modifications in the amino-thiourea tail, without significantly altering the binding property of the small molecule. Importantly, several inositols and derivatives, including epi-inositol and inosose, have been shown to enter the brain by active transport mediated by sodium/myo-inositol co-transporters (SMIT-1 and SMIT-2), proteins expressed at the blood-brain barrier and choroid plexus. Therefore, DS26, or derivatives thereof, can therefore be modified for active transport across the blood-brain barrier using inositol transporters and other transporters, overcoming one of the major problems shared by the vast majority of compounds targeting the brain.

Third, $PrP^C$ plays a central role in prion diseases. Strong experimental evidence now indicates that this protein also participates in the pathogenesis of Alzheimer's disease. Thus, compounds that target $PrP^C$ can provide therapeutic benefit for both diseases. Recently, $PrP^C$ has been shown to interact with aggregates of several other proteins, raising the intriguing possibility that this molecule can serve as a cell-surface receptor for a variety of β-sheet rich forms. Therefore, small molecules, like DS26, that target $PrP^C$ can be effective in several other pathological conditions associated with protein aggregation and neurodegeneration, including Parkinson's disease, Huntington's disease, and tauopathies.

In another aspect, also provided herein, are novel compounds of formulas (I), (II), (III), and (IV).

In some embodiments of this aspect, a compound of formula (I) is not 2-(2R,3S,5R,6S-pentahydroxycyclohexylidene)hydrazinecarbothioamide (also referred to as "DS26").

In some embodiments of this aspect, a compound of formula (I) is selected from the compounds shown in Table 1.

In some embodiments of this aspect, a compound of formula (II) is not 2R,3S,4S,5S,6R)-2-(hydroxymethyl)-6-[β-hydroxyphenyl)amino]tetrahydro-2H-pyran-3,4,5-triol (also referred to as "DS5").

In some embodiments of this aspect, a compound of formula (III) is not (1S,2R,3R)-1-(1H-tetrazol-5-yl)butane-1,2,3,4-tetrol (also referred to herein as "DS40").

In some embodiments of this aspect, a compound of formula (IV) is not 3R,4S-dihydroxy-5S-(1,2,3-trihydroxypropyl)dihydrofuran-2(3H)-one (also referred to herein as "DS86").

Pharmaceutical Compositions

For administration to a subject, the compound, e.g., PBD ligand, can be provided in pharmaceutically acceptable compositions. These pharmaceutically acceptable compositions comprise a $PrP^C$ ligand, formulated together with one or more pharmaceutically acceptable carriers (additives) and/or diluents. As described in detail below, the pharmaceutical compositions described herein can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Examples of solid carriers include starch, sugar, bentonite, silica, and other commonly used carriers. Further non-limiting examples of carriers and diluents which can be used in the formulations comprising a $PrP^C$ ligand as disclosed herein of the present invention include saline, syrup, dextrose, and water.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

The phrase "therapeutically-effective amount" as used herein means that amount of a compound, material, or composition which is effective for producing some desired therapeutic effect in at least a sub-population of cells in an animal at a reasonable benefit/risk ratio applicable to any medical treatment. According, a "therapeutically effective amount" refers to an amount effective, at dosage and periods of time necessary, to achieve a desired therapeutic result. A therapeutic result can be, e.g., lessening of symptoms, prolonged survival, improved mobility, and the like. A therapeutic result need not be a "cure."

As used herein, a "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the composition being delivered to a specific location as compared to the entire body of the subject, whereas, systemic administration results in delivery to essentially the entire body of the subject. In some embodiments, the compound is administered systemically. In other embodiments, the compound is administered peripherally.

An aggregate or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments of the aspects described herein, the compositions are administered by intravenous infusion or injection.

In some embodiments, the compound is administered directly into the central nervous system.

The compounds can be formulated in a gelatin capsule, in tablet form, dragee, syrup, suspension, topical cream, suppository, injectable solution, or kits for the preparation of syrups, suspension, topical cream, suppository or injectable solution just prior to use. Also, compounds can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., *Remington's Pharmaceutical Sciences*, Mack Publishing Co., Easton, Pa. 1985, 17th edition, Nema et al., *PDA J. Pharm. Sci. Tech.* 1997 51:166-171. Methods to make invention formulations include the step of bringing into association or contacting an ActRIIB compound with one or more excipients or carriers. In general, the formulations are prepared by uniformly and intimately bringing into association one or more compounds with liquid excipients or finely divided solid excipients or both, and then, if appropriate, shaping the product.

The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

Examples of injectable form include solutions, suspensions and emulsions. Injectable forms also include sterile powders for extemporaneous preparation of injectable solutions, suspensions or emulsions. The compounds of the present invention can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin. A suitable carrier is 5% dextrose in saline. Frequently, it is desirable to include additives in the carrier such as buffers and preservatives or other substances to enhance isotonicity and chemical stability.

In some embodiments, compounds can be administrated encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., a pituitary cell) can also be used as pharmaceutically acceptable carriers.

In one embodiment, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and Primogel™, and the like.

The compounds can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these compounds may be incorporated with excipients and used in the form of tablets, capsules, elixirs, suspensions, syrups, and the like. Such compositions and preparations should contain at least 0.1% of compound. The percentage of the agent in these compositions may, of course, be varied and may conveniently be between about 2% to about 60% of the weight of the unit. The amount of compound in such therapeutically useful compositions is such that a suitable dosage will be obtained. Preferred compositions according to the present invention are prepared so that an oral dosage unit contains between about 100 and 2000 mg of compound.

Examples of bases useful for the formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives.

The compositions can be given as a bolus dose, to maximize the circulating levels for the greatest length of time after the dose. Continuous infusion may also be used after the bolus dose.

The compounds can also be administered directly to the airways in the form of an aerosol. For administration by inhalation, the compounds in solution or suspension can be delivered in the form of an aerosol spray from pressured container or dispenser which contains a suitable propellant, e.g., a gas such as carbon dioxide, or hydrocarbon propellant like propane, butane or isobutene. The compounds can also be administered in a no-pressurized form such as in an atomizer or nebulizer.

The compounds can also be administered parenterally. Solutions or suspensions of these compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage. As used herein, "dosage unit" refers to physically discrete units suited as unitary dosages for the subject to be treated; each unit containing a predetermined quantity of compound calculated to produce the desired therapeutic effect in association with the required pharmaceutical carrier.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

The compounds can be administered to a subject in combination with an additional pharmaceutically active agent. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians Desk Reference, 50$^{th}$ Edition, 1997, Oradell N.J., Medical Economics Co.; Pharmacological Basis of Therapeutics, 8$^{th}$ Edition, Goodman and Gilman, 1990; United States Pharmacopeia, The National Formulary, USP XII NF XVII, 1990, the complete contents of all of which are incorporated herein by reference. In some embodiments, the pharmaceutically active agent is selected from the group consisting of butyrates, valproic acid, hydroxyuirae and Riluzole.

The compound and the pharmaceutically active agent can be administrated to the subject in the same pharmaceutical composition or in different pharmaceutical compositions (at the same time or at different times).

In some embodiments, the additional pharmaceutically active compound is selected from the group consisting of adrenergic agent; anti-adrenergic agent; anti-androgen agent, anti-anginal agent; anti-anxiety agent; anticonvulsant agent; antidepressant agent; anti-epileptic agent; antihyperlipidemic agent; antihyperlipoproteinemic agent; antihypertensive agent; anti-inflammatory agent; antiobessional agent; antiparkinsonian agent; antipsychotic agent; adrenocortical steroid agent; adrenocortical suppressant agent; aldosterone antagonist agent; amino acid agent; anabolic steroid; analeptic agent; androgen agent; blood glucose regulator; cardioprotectant agent; cardiovascular agent; cholinergic agonist or antagonist; cholinesterase deactivator or inhibitor, such as galantamine, rivastigmine, tacrine and donepezil; cognition adjuvant or enhancer; dopaminergic agent; enzyme inhibitor, estrogen, free oxygen radical scavenger; GABA agonist; glutamate antagonist; hormone; hypocholesterolemic agent; hypolipidemic agent; hypotensive agent; immunizing agent; immunostimulant agent; monoamine oxidase inhibitor, neuroprotective agent; N-methyl D-aspartate (NMDA) antagonist, such as memantine; AMPA antagonist, competitive or -non-competitive NMDA antagonist; opioid antagonist; potassium channel opener; non-hormonal sterol derivative; post-stroke and post-head trauma treatment; prostaglandin; psychotropic agent; relaxant; sedative; sedative-hypnotic agent; selective adenosine antagonist; serotonin antagonist; serotonin inhibitor; selective serotonin uptake inhibitor; serotonin receptor antagonist; sodium and calcium channel blocker; steroid; stimulant; thyroid hormone and inhibitor agents; and any combinations thereof.

In some embodiments, treatment with a $PrP^C$ ligand as disclosed herein can also involve combination with other existing modes of treatment, for example existing agents for treatment of Alzheimer's disease, for example but are not limited to ARICEPT® or donepezil, COGNEX® or tacrine, EXELON® or rivastigmine, REMINYL® or galantamine, antiamyloid vaccine, Abeta-lowering therapies, mental exercise or stimulation; see for review Zlokovic, Adv. Drug Deliv. Rev. 54:1533-1660, 2002).

In some embodiments, a $PrP^c$ ligand as disclosed herein can be combined with other agent, for example therapeutic agent to prevent and/or treat neurodegenerative diseases. Such agents can be any agent currently in use or being developed for the treatment and/or prevention of a neurodegenerative disease or disorder, where the agent can have a prophylactic and/or a curative effect and/or reduce a symptom of a neurodegenerative disorder or disease.

In embodiments where a $PrP^c$ ligand as disclosed herein is used for the prevention and/or treatment of Alzheimer's disease, a $PrP^c$ ligand as disclosed herein can be used in combination with medicaments commonly known by person of ordinary skill in the art that are claimed to be useful as symptomatic treatments of dementia. Examples of such medicaments include, but are not limited to, agents known to modify cholinergic transmission such as M1 muscarinic receptor agonists or allosteric modulators, M2 muscarinic antagonists, acetylcholinesterase inhibitors (such as tetrahydroaminoacridine, donepezil, galantamine and rivastigmine), nicotinic receptor agonists or allosteric modulators (such as α7 agonists or allosteric modulators or α4β2 agonists or allosteric modulators), peroxisome proliferator-activated receptors (PPAR) agonists (such as PPARγ agonists), 5-HT4 receptor partial agonists, histamine H3 antagonists and inverse agonists, 5-HT6 receptor antagonists or 5HT1A receptor antagonists, AMPA positive modulators (alpha-amino-3-hydroxy-5-methylisoxazole-4-propionate, a glutamate receptor subtype) and N-methyl-D-aspartic acid (NMDA) receptor antagonists or modulators (such as memantine).

In some embodiments, where a PrP$^c$ ligand as disclosed herein is used for the treatment of Alzheimer's disease, a PrP$^c$ ligand as disclosed herein can be used in combination with those medicaments mentioned above that are claimed to be useful as symptomatic treatments of dementia and/or disease-modifying agents. Disease modifying agents include, for example but are not limited to, gamma secretase inhibitors and modulators, and human beta-secretase (BACE) inhibitors. Disease modifying agents also are, for example but not limited to gamma secretase inhibitors and modulators, beta-secretase (BACE) inhibitors and any other anti-amyloid approaches including active and passive immunization, for example agents identified by the methods as disclosed in U.S. Patent Application 2005/0170359, as well as agents as disclosed in International Patent Applications WO05/07277, WO03/104466 and WO07/028133, and U.S. Pat. Nos. 6,866,849, 6,913,745, which are incorporated in their entirety herein by reference.

Thus, combination treatment with a PrP$^c$ ligand as disclosed herein with one or more other medical procedures can be practiced.

In addition, treatment can also comprise at least one PrP$^c$ ligand as disclosed herein with one or more additional agents. For example, other agents include the use of statins with Niacin (see http://www.genengnews.com/news/bnitem.aspx?name=6724568) and fenofibrate (see http://www-.genengnews.com/news/bnitem.aspx?name=14817756&taxid=19)

Similarly, diagnosis according to the invention can be practiced with other diagnostic procedures. For example, endothelium of the vascular system, brain, or spinal cord (e.g., blood or leptomeningeal vessels) can be assayed for a change in gene expression profiles using disease-specific molecular diagnostics kits (e.g., custom made arrays, multiplex QPCR, multiplex proteomic arrays). In addition, a noninvasive diagnostic procedure (e.g., CAT, MRI, SPECT, or PET) can be used in combination to improve the accuracy and/or sensitivity of diagnosis. Early and reliable diagnosis is especially useful to for treatments that are only effective for mild to moderate Alzheimer's disease or only delay its progression.

Suitable choices in amounts and timing of doses, formulation, and routes of administration can be made with the goals of achieving a favorable response in the subject with vascular dementia, for example a subject with Alzheimer's disease or a risk thereof (i.e., efficacy), and avoiding undue toxicity or other harm thereto (i.e., safety). Therefore, "effective" refers to such choices that involve routine manipulation of conditions to achieve a desired effect.

For oral or enteral formulations of a PrP$^c$ ligand as disclosed herein for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982.

As regards formulations for administering a PrP$^c$ ligand as disclosed herein, one particularly useful embodiment is a tablet formulation comprising a PrP$^c$ ligand with an enteric polymer casing. An example of such a preparation can be found in WO2005/021002. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropyl-cellulose, polyvinylpyrrolidone, pre-gelatinized starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The active ingredient of a PrP$^c$ ligand preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg as free base of the active ingredient. Particularly preferably, the core contains 20, 30, 40, 50, 60, 80 or 100 mg as free base of the active ingredient. The active ingredient can be present as the free base, or as any pharmaceutically acceptable salt. If the active ingredient is present as a salt, the weight is adjusted such that the tablet contains the desired amount of active ingredient, calculated as free base of the salt. In some embodiments, the active ingredient is present as a hydrochloride salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional cross-linking agents such as epichlorohydrin, dichlorohydrin or 1, 2-, 3, 4-diepoxybutane. The casing can also include starch and/or dextrin.

In some embodiments, an enteric coating materials are the commercially available Eudragit® enteric polymers such as Eudragit® L, Eudragit® S and Eudragit® NE used alone or with a plasticiser. Such coatings are normally applied using a liquid medium, and the nature of the plasticiser depends upon whether the medium is aqueous or non-aqueous. Plasticizers for use with aqueous medium include propylene glycol, triethyl citrate, acetyl triethyl citrate or Citroflex® or Citroflex® A2. Non-aqueous plasticizers include these, and also diethyl and dibutyl phthalate and dibutyl sebacate. A preferred plasticiser is Triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticiser and up to around 50 wt % of anti tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%

In one embodiment, there is a seal coat included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876. Other enteric-coated preparations of this sort can be prepared by one skilled in the art, using these materials or their equivalents.

Subject or Patient

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with auto-immune disease or inflammation. In addition, the methods and compositions described herein can be used to treat domesticated animals and/or pets.

A subject can be one who has been previously diagnosed with or identified as having a disease or disorder associated with protein aggregation or neurodegeneration.

A subject can be one who is currently being treated for a disease or disorder associated with protein aggregation or neurodegeneration.

In some embodiments of the aspects described herein, the method further comprising diagnosing a subject for a disease or disorder associated with protein aggregation or neurodegeneration before onset of treatment with a method described herein. Methods of diagnosing a subject for a disease or disorder associated with protein aggregation or neurodegeneration are known in the art and available to one of ordinary skill in the art.

Alzheimer's Disease

Alzheimer's disease (AD) is a progressive disease resulting in senile dementia. See generally Selkoe, TINS 16, 403-409 (1993); Hardy et al., WO 92/13069; Selkoe, J. Neuropath. Exp. Neurol. 53, 438-447 (1994); Duff et al., Nature 373, 476-477 (1995); Games et al., Nature 373, 523 (1995). Broadly speaking the disease falls into two categories: late onset, which occurs in old age (65+years) and early onset, which develops well before the senile period, i.e, between 35 and 60 years. In both types of disease, the pathology is the same but the β abnormalities tend to be more severe and widespread in cases beginning at an earlier age. The disease is characterized at the macroscopic level by significant brain shrinkage away from the cranial vault as seen in MRI images as a direct result of neuronal loss and by two types of macroscopic lesions in the brain, senile plaques and neurofibrillary tangles. Senile plaques are areas comprising disorganized neuronal processes up to 150 μm across and extracellular amyloid deposits, which are typically concentrated at the center and visible by microscopic analysis of sections of brain tissue. Neurofibrillary tangles are intracellular deposits of tau protein consisting of two filaments twisted about each other in pairs.

The principal constituent of the plaques is a peptide termed Aβ or β-amyloid peptide. Aβ peptide is an internal fragment of 39-43 amino acids of a precursor protein termed amyloid precursor protein (APP). Several mutations within the APP protein have been correlated with the presence of Alzheimer's disease. See, e.g., Goate et al., Nature 349, 704) (1991) (valine$^{717}$ to isoleucine); Chartier Harlan et al. Nature 353, 844 (1991)) (valine$^{717}$ to glycine); Murrell et al., Science 254, 97 (1991) (valine$^{717}$ to phenylalanine); Mullan et al., glycine); Murrell et al., Science 254, 97 (1991) (valine$^{717}$ to phenylalanine); Mullan et al., Nature Genet. 1, 345 (1992) (a double mutation changing lysine$^{595}$-methionine$^{596}$ to asparagine$^{595}$-leucine$^{596}$). Such mutations are thought to cause Alzheimer's disease by increased or altered processing of APP to Aβ, particularly processing of APP to increased amounts of the long form of Aβ (i.e., Aβ 1-42 and Aβ 1-43). Mutations in other genes, such as the presenilin genes, PS1 and PS2, are thought indirectly to affect processing of APP to generate increased amounts of long form Aβ (see Hardy, TINS 20, 154 (1997)). These observations indicate that Aβ, and particularly its long form, is a causative element in Alzheimer's disease.

Aβ, also known as β-amyloid peptide, or A4 peptide (see U.S. Pat. No. 4,666,829; Glenner & Wong, Biochem. Biophys. Res. Commun. 120, 1131 (1984)), is a peptide of 39-43 amino acids, is the principal component of characteristic plaques of Alzheimer's disease. Aβ is generated by processing of a larger protein APP by two enzymes, termed β and γ secretases (see Hardy, TINS 20, 154 (1997)). Known mutations in APP associated with Alzheimer's disease occur proximate to the site of β or γ-secretase, or within A13. For example, position 717 is proximate to the site of γ-secretase cleavage of APP in its processing to Aβ, and positions 670/671 are proximate to the site of β-secretase cleavage. It is believed that the mutations cause AD disease by interacting with the cleavage reactions by which Aβ is formed so as to increase the amount of the 42/43 amino acid form of Aβ generated.

Aβ has the unusual property that it can fix and activate both classical and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000 increase in activation of these cells. This mechanism causes Aβ to generate an immune response in excess of that of other antigens.

Most therapeutic strategies for Alzheimer's disease are aimed at reducing or eliminating the deposition of Aβ42 in the brain, typically via reduction in the generation of Aβ42 from APP and/or some means of lowering existing Aβ42 levels from sources that directly contribute to the deposition of this peptide in the brain (De Felice and Ferreira, 2002). A partial list of aging-associated causative factors in the development of sporadic Alzheimer's disease includes a shift in the balance between Aβ peptide production and its clearance from neurons that favors intracellular accumulation, increased secretion of Aβ peptides by neurons into the surrounding extracellular space, increased levels of oxidative damage to these cells, and global brain hypoperfusion and the associated compensatory metabolic shifts in affected neurons (Cohen et al., 1988; Higgins et al., 1990; Kalaria, 2000; Nalivaevaa et al., 2004; Teller et al., 1996; Wen et al., 2004).

The Aβ42 that deposits within neurons and plaques could also originate from outside of the neurons (exogenous Aβ42) during Alzheimer's disease pathogenesis. Levels of soluble Aβ peptides in the blood are known to be much higher than in the interstitial space and CSF in the brains of healthy individuals (Seubert et al., 1992) with blood as a source of exogenous Aβ peptides that eventually deposit in the Alzheimer's disease brain (Zlokovic et al., 1993). However, except for trace amounts of Aβ that are actively transported across endothelial cells, it is well-known that access of blood-borne Aβ peptides to brain tissue in normal healthy individuals is effectively blocked by the integrity of the blood-brain barrier (BBB) (Kandimalla et al., 2005; Poduslo et al., 1999). The BBB is a complex structure composed of cerebral endothelial cells resting on a basal lamina that is further supported by the foot processes of local astrocytes (Gloor et al., 2001; Risau et al., 1998). It closely regulates the passage of blood components into the brain tissue and is highly impermeable to nearly all proteins and other macromolecules while, at the same time, allowing the selective entry of essential molecules (Mayhan, 2001). Much evidence has revealed that aging is associated with degenerative changes to blood vessels that may compromise the integrity of the BBB. For example, a number of relatively common neurodegenerative diseases in the elderly, including vascular dementia, and AD originate, at least in part, from cerebrovascular pathologies that develop within the microvasculature of the brain (Breteler, 2000; Buee et al., 1997; de la Torre, 1997; Esiri et al., 1999; Kalaria et al., 1996). A link between the neurovasculature and neurodegenerative disease is the well-known fact that Alzheimer pathology, including amyloid plaques and neurofibrillary tangles, develops subsequently within the vicinity of stroke lesions (Jellinger, 2002; Kalaria, 1996; Kalaria, 2002; Natte et al., 1998).

Genetic markers of risk toward Alzheimer's disease include mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of Alzheimer's disease, hypercholesterolemia or atherosclerosis. Subjects presently suffering from Alzheimer's disease can be recognized from characteristic dementia, as well as the presence of risk factors described above. In addition, a number of diagnostic tests are available for identifying subjects who have Alzheimer's disease. These include measurement of CSF tau and Aβ42 levels. Elevated tau and increased Aβ42 levels signify the presence of Alzheimer's disease. Individuals suffering from Alzheimer's disease can also be diagnosed by MMSE or ADRDA criteria. The tissue sample for analysis is typically blood, plasma, serum, mucus or cerebral spinal fluid from the patient. The sample is analyzed for indicia of an immune response to any forms of Aβ peptide, typically Aβ42. The immune response can be determined from the presence of, e.g., antibodies or T-cells that specifically bind to Aβ peptide. ELISA methods of detecting antibodies specific to Aβ are described in the Examples section.

In asymptomatic patients, treatment for AD can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying presence of Aβ peptide in the CSF over time. If the Aβ peptide is still present in the CSF or the BBB remains pearmeable or defective, additional treatment with $PrP^C$ ligands as disclosed herein are recommended, and/or treatment of additional therapies for Alzheimer's disease. In the case of potential Down's syndrome patients, treatment can begin antenatally by administering therapeutic agent to the mother or shortly after birth.

In some embodiments, $PrP^C$ ligands as disclosed herein are also useful in the treatment of other neurodegenerative disorders or cognitive impairment disorders in general: for example, dementia, depression, confusion, Creutzfeldt-Jakob or mad cow disease, Huntington's disease, loss of motor coordination, multiple sclerosis, Parkinson's disease, Pick disease and other brain storage disorders (e.g., amyloidosis, gangliosidosis, lipid storage disorders, mucopolysaccharidosis), syncope, and vascular dementia. Thus, treatment with a $PrP^C$ ligand can be directed to a subject who is affected with unsymptomatic by the neurodegenerative disease; it can improve cognitive function. The efficacy of treatment can be determined by, for example, measuring the presence of Tau or Aβ in the CSF.

Some methods entail determining a baseline value of, for example the level of beta amyloid in the CSF of a subject before administering a dosage of a $PrP^C$ ligands, and comparing this with a value for beta amyloid in the CSF after treatment with a PrP$^C$ ligand. A decrease, for example a 10% decrease in the level of beta amyloid in the CSF indicates a positive treatment outcome (i.e., that administration of the agent has achieved or augmented a decrease in beta amyloid in the CSF). If the value for level of beta amyloid in the CSF does not change significantly, or increases, a negative treatment outcome is indicated. In general, subjects undergoing an initial course of treatment with an agent are expected to show a decrease in beta amyloid in the CSF with successive dosages of a PrP$^C$ ligand as described herein.

In other methods to determine efficacy of treatment, a control value (i.e., a mean and standard deviation) of beta amyloid is determined for a control population. Typically the individuals in the control population have not received prior treatment and do not suffer from Alzheimer's disease. Measured values of beta amyloid in the CSF in a subject after administering a PrP$^C$ ligand as disclosed herein are then compared with the control value. A decrease in the beta amyloid in the CSF of the subject relative to the control value (i.e. a decrease of at least 10% of beta amyloid in a subject) signals a positive treatment outcome. A lack of significant decrease signals a negative treatment outcome.

In other methods, a control value of, for example beta amyloid in the CSF is determined from a control population of subjects who have undergone treatment with a therapeutic agent that is effective at reducing beta amyloid in the CSF. Measured values of CSF beta amyloid in the subject are compared with the control value.

In other methods, a subject who is not presently receiving a treatment with a PrP$^C$ ligand as disclosed herein, but has undergone a previous course of treatment is monitored for beta amyloid in the CSF to determine whether a resumption of treatment is required. The measured value of CSF beta amyloid in the test subject can be compared with a previous level of the CSF beta amyloid in the subject after a previous course of treatment. A significant decrease in CSF beta amyloid relative to the previous measurement (i.e., a decrease of at least 10%) is an indication that treatment can be resumed. Alternatively, the level of beta amyloid in the CSF in the subject can be compared with a control level of CSF beta amyloid determined in a population of subjects after undergoing a course of treatment. Alternatively, the level of CSF beta amyloid in a subject can be compared with a control value in populations of prophylactically treated subjects who remain free of symptoms of disease, or populations of therapeutically treated subjects who show amelioration of disease symptoms.

Methods to Identify a Subject at Risk of Developing or Having Alzheimer's Disease.

Subjects amenable to treatment using the methods as disclosed herein include subjects at risk of a neurodegenerative disease, for example Alzheimer's Disease but not showing symptoms, as well as subjects showing symptoms of the neurodegenerative disease, for example subjects with symptoms of Alzheimer's Disease.

Subjects can be screened for their likelihood of having or developing Alzheimer's Disease based on a number of biochemical and genetic markers.

One can also diagnose a subject with increased risk of developing Alzheimer's Disease using genetic markers for Alzheimer's Disease. Genetic abnormality in a few families has been traced to chromosome 21 (St. George-Hyslop et al., Science 235:885-890, 1987). One genetic marker is, for example mutations in the APP gene, particularly mutations at position 717 and positions 670 and 671 referred to as the Hardy and Swedish mutations respectively (see Hardy, TINS, supra). Other markers of risk are mutations in the presenilin genes, PS1 and PS2, and ApoE4, family history of Alzheimer's Disease, hypercholesterolemia or atherosclerosis. Subjects with APP, PS1 or PS2 mutations are highly likely to develop Alzheimer's disease. ApoE is a susceptibility gene, and subjects with the e4 isoform of ApoE (ApoE4 isoform) have an increased risk of developing Alzheimer's disease. Test for subjects with ApoE4 isoform are disclosed in U.S. Pat. No. 6,027,896, which is incorporated in its entirety herein by reference. Other genetic links have been associated with increased risk of Alzheimer's disease, for example variances in the neuronal sortilin-related receptor SORL1 may have increased likelihood of developing late-onset Alzheimer's disease (Rogaeva at al, Nat Genet. 2007 February; 39(2):168-77). Other potential Alzheimer disease susceptibility genes, include, for example ACE, CHRNB2, CST3, ESR1, GAPDHS, IDE, MTHFR, NCSTN, PRNP, PSEN1, TF, TFAM, TNF CD33, CLU, B1N1, PICALM, CR1, CD2AP, EPHA1, ABCA7, MS4A4A/MS4A6E, and TREM2 and be used to identify subjects with increased risk of developing Alzheimer's disease (Bertram et al, Nat Genet. 2007 January; 39(1):17-23), as well as variances in the alpha-T catenin (VR22) gene (Bertram et al, J Med Genet. 2007 January; 44(1):e63) and Insulin-degrading enzyme (IDE); Kim et al, J Biol Chem. 2007; 282:7825-32; Bettens et al., Lancet Neurol 2013; 12: 92-104; Holton et al., Annals of Human Genetics (2013) 77, 85-105; Griciuc et al., Neuron 78, 1-13, May 22, 2013).

One can also diagnose a subject with increased risk of developing Alzheimer's disease on the basis of a simple eye test, where the presence of cataracts and/or Abeta in the lens identifies a subject with increased risk of developing Alzheimer's Disease. Methods to detect Alzheimer's disease include using a quasi-elastic light scattering device (Goldstein et al., Lancet. 2003; 12; 361:1258-65) from Neuroptix, using Quasi-Elastic Light Scattering (QLS) and Fluorescent Ligand Scanning (FLS) and a Neuroptix™ QEL scanning device, to enable non-invasive quantitative measurements of amyloid aggregates in the eye, to examine and measure deposits in specific areas of the lens as an early diagnostic for Alzheimer's disease. Method to diagnose a subject at risk of developing Alzheimers disease using such a method of non-invasive eye test are disclosed in U.S. Pat. No. 7,107, 092, which is incorporated in its entirety herein by reference.

Individuals presently suffering from Alzheimer's disease can be recognized from characteristic dementia, as well as the presence of risk factors described above. In addition, a number of diagnostic tests are available for identifying individuals who have AD. These include measurement of CSF tau and phospho-tau, and Aβ levels. Elevated tau and phosphor-tau, and decreased AAβ levels signify the presence of Alzheimer's Disease. (Kaj Blennow, Henrik Zetterberg, and Anne M. Fagan. Cold Spring Harb Perspect Med 2012; 2:a006221)

Alternative "criteria" which are utilized to clinically diagnose Alzheimer's Disease include, for example: the DSM-IIIR criteria and the NINCDS-ADRDA criteria (which is an acronym for National Institute of Neurological and Communicative Disorders and Stroke (NINCDS) and the Alzheimer's Disease and Related Disorders Association (ADRDA); see McKhann et al., Neurology 34:939-944, 1984) and Khachaturian, Alz. and Dementia 7:253-256 (2011), Jack et al., Alz. and Dementia 7:257-262 (2011). Briefly, the criteria for diagnosis of Alzheimer's Disease under DSM-IIIR include (1) dementia, (2) insidious onset with a generally progressive deteriorating course, and (3) exclusion of all other specific causes of dementia by history, physical examination, and laboratory tests. Within the context of the DSM-IIIR criteria, dementia is understood to involve "a multifaceted loss of intellectual abilities, such as memory, judgement, abstract thought, and other higher cortical functions, and changes in personality and behaviour." (DSM-1IR, 1987).

In contrast, the NINCDS-ADRDA criteria sets forth three categories of Alzheimer's Disease, including "probable," "possible," and "definite" Alzheimer's Disease. Clinical diagnosis of "possible" Alzheimer's Disease may be made on the basis of a dementia syndrome, in the absence of other neurologic, psychiatric or systemic disorders sufficient to cause dementia. Criteria for the clinical diagnosis of "probable" Alzheimer's Disease include (a) dementia established by clinical examination and documented by a test such as the Mini-Mental test (Foldstein et al., J. Psych. Res. 12:189-198, 1975); (b) deficits in two or more areas of cognition; (c) progressive worsening of memory and other cognitive functions; (d) no disturbance of consciousness; (e) onset between ages 40 and 90, most often after age 65; and (f) absence of systemic orders or other brain diseases that could account for the dementia. The criteria for definite diagnosis of Alzheimer's Disease include histopathologic evidence obtained from a biopsy, or after autopsy. Since confirmation of definite Alzheimer's Disease requires histological examination from a brain biopsy specimen (which is often difficult to obtain), it is rarely used for early diagnosis of Alzheimer's Disease.

One can also use neuropathologic diagnosis of Alzheimer's Disease, where the numbers of plaques and tangles in the neurocortex (frontal, temporal, and parietal lobes), hippocampus and amygdala are analyzed (Khachaturian, Arch. Neurol. 42:1097-1105; Esiri, "Anatomical Criteria for the Biopsy diagnosis of Alzheimer's Disease," Alzheimer's Disease, Current Research in Early Diagnosis, Becker and Giacobini (eds.), pp. 239-252, 1990).

One can also use quantitative electroencephalographic analysis (EEG) to diagnose Alzheimer's Disease. This method employs Fourier analysis of the beta, alpha, theta, and delta bands (Riekkinen et al., "EEG in the Diagnosis of Early Alzheimer's Disease," Alzheimer's Disease, Current Research in Early Diagnosis, Becker and Giacobini (eds.), pp. 159-167, 1990) for diagnosis of Alzheimer's Disease.

One can also diagnose Alzheimer's Disease by quantifying the degree of neural atrophy, since such atrophy is generally accepted as a consequence of Alzheimer's Disease. Examples of these methods include computed tomographic scanning (CT), and magnetic resonance imaging (MRI) (Leedom and Miller, "CT, MRI, and NMR Spectroscopy in Alzheimer's Disease," Alzheimer's Disease, Current Research in Early Diagnosis, Becker and Giacobini (eds.), pp. 297-313, 1990).

One can also diagnose Alzheimer's Disease by assessing decreased cerebral blood flow or metabolism in the posterior temporoparietal cerebral cortex by measuring decreased blood flow or metabolism by positron emission tomography (PET) (Parks and Becker, "Positron Emission Tomography and Neuropsychological Studies in Dementia," Alzheimer's Disease's, Current Research in Early Diagnosis, Becker and Giacobini (eds.), pp. 315-327, 1990), single photon emission computed tomography (SPECT) (Mena et al., "SPECT Studies in Alzheimer's Type Dementia Patients," Alzheimer's Disease, Current Research in Early Diagnosis, Becker and Giacobini (eds.), pp. 339-355, 1990), and xenon inhalation methods (Jagust et al., Neurology 38:909-912; Prohovnik et al., Neurology 38:931-937; and Waldemar et al., Senile Dementias: II International Symposium, pp. 399407, 1988).

One can also immunologically diagnose Alzheimer's disease (Wolozin, "Immunochemical Approaches to the Diagnosis of Alzheimer's Disease," Alzheimer's Disease, Current Research in Early Diagnosis, Becker and Giacobini (eds.), pp. 217-235, 1990). Wolozin and coworkers (Wolozin et al., Science 232:648-650, 1986) produced a monoclonal antibody "Alz50," that reacts with a 68-kDa protein "A68," which is expressed in the plaques and neuron tangles of patients with Alzheimer's disease. Using the antibody Alz50 and Western blot analysis, A68 was detected in the cerebral spinal fluid (CSF) of some Alzheimer's patients and not in the CSF of normal elderly patients (Wolozin and Davies, Ann. Neurol. 22:521-526, 1987).

One can also diagnose Alzheimer's disease using neurochemical markers of Alzheimer's disease. Neurochemical markers which have been associated with Alzheimer's Disease include reduced levels of acetylcholinesterase (Giacobini and Sugaya, "Markers of Cholinergic Dysfunction in Alzheimer's Disease," Alzheimer's Disease, Current Research in Early Diagnosis, Becker and Giacobini (eds.), pp. 137-156, 1990), reduced somatostatin (Tamminga et al., Neurology 37:161-165, 1987), a negative relation between serotonin and 5-hydroxyindoleacetic acid (Volicer et al., Arch Neurol. 42:127-129, 1985), greater probenecid-induced rise in homovanyllic acid (Gibson et al., Arch. Neurol. 42:489-492, 1985) and reduced neuron-specific enolase (Cutler et al., Arch. Neurol. 43:153-154, 1986).

Additionally, PET scanning can be used to visualize amyloid plaques in subjects directly using amyloid-specific probes (Roe et al. (2013). Neurology. 2013 May 7; 80(19): 1784-91), and uses amyloid-specific PET probes referred to as "Amyvid" or ""florbetapir F18" available from Avid Pharmaceuticals/Eli Lilly, which have been approved for patient scans.

Assessment of $PrP^C$ Ligands on Models of Neurodegenerative Diseases.

The suitability of an inhibitor of a $PrP^c$ ligand for the treatment of a neurodegenerative disease can be assessed in any of a number of animal models for neurodegenerative disease. For example, mice transgenic for an expanded polyglutamine repeat mutant of ataxin-1 develop ataxia typical of spinocerebellar ataxia type 1 (SCA-1) are known (Burright et al., 1995, Cell 82: 937-948; Lorenzetti et al., 2000, Hum. Mol. Genet. 9: 779-785; Watase, 2002, Neuron 34: 905-919), and can be used to determine the efficacy of a $PrP^c$ ligand for the treatment or prevention of neurodegenerative disease. Additional animal models, for example, for Huntington's disease (see, e.g., Mangiarini et al., 1996, Cell 87: 493-506, Lin et al., 2001, Hum. Mol. Genet. 10: 137-144), Alzheimer's disease (Hsiao, 1998, Exp. Gerontol, 33: 883-889; Hsiao et al., 1996, Science 274: 99-102), Parkinson's disease (Kim et al., 2002, Nature 418: 50-56), amyotrophic lateral sclerosis (Zhu et al., 2002, Nature 417: 74-78), Pick's disease (Lee & Trojanowski, 2001, Neurology 56 (Suppl. 4): S26-S30, and spongiform encephalopathies (He et al., 2003, Science 299: 710-712) can be used to evaluate the efficacy of a $PrP^c$ ligand as disclosed herein in a similar manner.

Animal models are not limited to mammalian models. For example, *Drosophila* strains provide accepted models for a number of neurodegenerative disorders (reviewed in Fortini & IBonini, 2000, Trends Genet. 16: 161-167; Zoghbi & Botas, 2002, Trends Genet. 18: 463-471). These models include not only flies bearing mutated fly genes, but also flies bearing human transgenes, optionally with targeted mutations. Among the *Drosophila* models available are, for example, spinocerebellar ataxias (e.g., SCA-1 (see, e.g., WO 02/058626), SCA-3 (Warrick et al., 1998, Cell 93: 939-949)), Huntington's disease (Kazemi-Esfarjani & Benzer, 2000, Science 287: 1837-1840), Parkinson's disease (Feany et al, 2000, Nature 404: 394-398; Auluck et al., 2002, Science 295: 809-8 10), age-dependent neurodegeneration (Genetics, 2002, 161:4208), Alzheimer's disease (Selkoe et al., 1998, Trends Cell Biol. 8: 447-453; Ye et al., 1999, J. Cell Biol. 146: 1351-1364), amyotrophic lateral sclerosis (Parkes et al., 1998, Nature Genet. 19: 171-174), and adrenoleukodystrophy.

The use of *Drosophila* as a model organism has proven to be an important tool in the elucidation of human neurodegenerative pathways, as the *Drosophila* genome contains many relevant human orthologs that are extremely well conserved in function (Rubin, G. M., et al., Science 287: 2204-2215 (2000)). For example, *Drosophila melanogaster* carries a gene that is homologous to human APP which is involved in nervous system function. The gene, APP-like (APPL), is approximately 40% identical to APP695, the neuronal isoform (Rosen et al., Proc. Nati. Acad. Sci. U.S.A. 86:2478-2482 (1988)), and like human APP695 is exclusively expressed in the nervous system. Flies deficient for the APPL gene show behavioral defects which can be rescued by the human APP gene, suggesting that the two genes have similar functions in the two organisms (Luo et al., Neuron 9:595-605 (1992)). *Drosophila* models for Alzheimers disease are disclosed in U.S. Patent Applications 2004/0244064, 2005/0132425, 2005/0132424, 2005/0132423, 2005/0132422, 200/50132421, 2005/0108779, 2004/0255342, 2004/0255341, 2004/0250302 which are incorporated herein in their entirety by reference.

In addition, *Drosophila* models of polyglutamine repeat diseases (Jackson, G. R., et al., Neuron 21:633-642 (1998); Kazemi-Esfarani, P. and Benzer, S., Science 287:1837-1840 (2000); Fernandez-Funez et al., Nature 408:101-6 (2000)), Parkinson's disease (Feany, M. B. and Bender, W. W., Nature 404:394-398 (2000)) and other diseases have been established which closely mimic the disease state in humans at the cellular and physiological levels, and have been successfully employed in identifying other genes that can be involved in these diseases. The transgenic flies exhibit progressive neurodegeneration which can lead to a variety of altered phenotypes including locomotor phenotypes, behavioral phenotypes (e.g., appetite, mating behavior, and/or life span), and morphological phenotypes (e.g., shape, size, or location of a cell, organ, or appendage; or size, shape, or growth rate of the fly).

Animals administered the compounds are evaluated for symptoms relative to animals not administered the compounds. A measurable change in the severity a symptom (i.e., a decrease in at least one symptom, i.e. 10% or greater decrease), or a delay in the onset of a symptom, in animals treated with a $PrP^C$ ligand versus untreated animals is indicative of therapeutic efficacy.

One can assess the animals for memory and learning, for instance by performing behavioral testing. One can use any behavioral test for memory and learning commonly known by person of ordinary skill in the art, for but not limited to the Morris water maze test for rodent animal models. A measurable increase in the ability to perform the Morris water maze test in animals administered a $PrP^c$ ligand versus untreated animals is indicative of therapeutic efficacy.

Dosage

The amount of $PrP^C$ ligand that can be combined with a carrier material to produce a single dosage form will generally be that amount of the $PrP^C$ ligand that produces a therapeutic effect. Generally out of one hundred percent, this amount will range from about 0.01% to 99% of $PrP^C$ ligand, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays or animal models. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

The suitability of a $PrP^C$ ligand as disclosed herein for the treatment of a neurodegenerative disease associated with protein aggregration can be assessed in any of a number of animal models for neurodegenerative disease. For example, mice transgenic for an expanded polyglutamine repeat mutant of ataxin-1 develop ataxia typical of spinocerebellar ataxia type 1 (SCA-1) are known (Burright et al., 1995, Cell 82: 937-948; Lorenzetti et al., 2000, Hum. Mol. Genet. 9: 779-785; Watase, 2002, Neuron 34: 905-919), and can be used to determine the efficacy of a $PrP^C$ ligand for the treatment or prevention of neurodegenerative disease. Additional animal models, for example, for Huntington's disease (see, e.g., Mangiarini et al., 1996, Cell 87: 493-506, Lin et al., 2001, Hum. Mol. Genet. 10: 137-144), Alzheimer's disease (Hsiao, 1998, Exp. Gerontol, 33: 883-889; Hsiao et al., 1996, Science 274: 99-102; LaFerla and Green, Cold Spring Harb Perspect Med 2012; 2:a006320; Chin, "Selecting a mouse model of Alzheimer's Disease", Erik D. Roberson (ed.), Alzheimer's Disease and Frontotemporal Dementia, Methods in Molecular Biology, vol. 670, DOI 10.1007/978-1-60761-744-0_130, Parkinson's disease (Kim et al., 2002, Nature 418: 50-56), amyotrophic lateral sclerosis (Zhu et al., 2002, Nature 417: 74-78), Pick's disease (Lee & Trojanowski, 2001, Neurology 56 (Suppl. 4): S26-S30, and spongiform encephalopathies (He et al., 2003, Science 299: 710-712), which are incorporated herein in their entirety, can be used to evaluate the efficacy of a $PrP^C$ ligand as disclosed herein in a similar manner.

Animal models are not limited to mammalian models. For example, *Drosophila* strains provide accepted models for a number of neurodegenerative disorders (reviewed in Fortini & IBonini, 2000, Trends Genet. 16: 161-167; Zoghbi & Botas, 2002, Trends Genet. 18: 463-471). These models include not only flies bearing mutated fly genes, but also flies bearing human transgenes, optionally with targeted mutations. Among the *Drosophila* models available are, for example, spinocerebellar ataxias (e.g., SCA-1 (see, e.g., WO 02/058626), SCA-3 (Warrick et al., 1998, Cell 93: 939-949)), Huntington's disease (Kazemi-Esfarjani & Benzer, 2000, Science 287: 1837-1840), Parkinson's disease (Feany et al, 2000, Nature 404: 394-398; Auluck et al., 2002, Science 295: 809-8 10), age-dependent neurodegeneration (Genetics, 2002, 161:4208), Alzheimer's disease (Selkoe et al., 1998, Trends Cell Biol. 8: 447-453; Ye et al., 1999, J. Cell Biol. 146: 1351-1364), amyotrophic lateral sclerosis (Parkes et al., 1998, Nature Genet. 19: 171-174), and adrenoleukodystrophy.

The use of *Drosophila* as a model organism has proven to be an important tool in the elucidation of human neurodegenerative pathways, as the *Drosophila* genome contains many relevant human orthologs that are extremely well conserved in function (Rubin, G. M., et al., Science 287: 2204-2215 (2000)). For example, *Drosophila melanogaster* carries a gene that is homologous to human APP which is involved in nervous system function. The gene, APP-like (APPL), is approximately 40% identical to APP695, the neuronal isoform (Rosen et al., Proc. Nati. Acad. Sci. U.S.A. 86:2478-2482 (1988)), and like human APP695 is exclusively expressed in the nervous system. Flies deficient for the APPL gene show behavioral defects which can be rescued by the human APP gene, suggesting that the two genes have similar functions in the two organisms (Luo et al., Neuron 9:595-605 (1992)). *Drosophila* models for Alzheimers disease are disclosed in U.S. Patent Applications 2004/0244064, 2005/0132425, 2005/0132424, 2005/0132423, 2005/0132422, 200/50132421, 2005/0108779, 2004/0255342, 2004/0255341, 2004/0250302 which are incorporated herein in their entirety by reference.

In addition, *Drosophila* models of polyglutamine repeat diseases (Jackson, G. R., et al., Neuron 21:633-642 (1998); Kazemi-Esfarani, P. and Benzer, S., Science 287:1837-1840 (2000); Fernandez-Funez et al., Nature 408:101-6 (2000)), Parkinson's disease (Feany, M. B. and Bender, W. W., Nature 404:394-398 (2000)) and other diseases have been established which closely mimic the disease state in humans at the cellular and physiological levels, and have been successfully employed in identifying other genes that can be involved in these diseases. The transgenic flies exhibit progressive neurodegeneration which can lead to a variety of altered phenotypes including locomotor phenotypes, behavioral phenotypes (e.g., appetite, mating behavior, and/or life span), and morphological phenotypes (e.g., shape, size, or location of a cell, organ, or appendage; or size, shape, or growth rate of the fly).

Animals administered the compounds are evaluated for symptoms relative to animals not administered the compounds. A measurable change in the severity a symptom (i.e., a decrease in at least one symptom, i.e. 10% or greater decrease), or a delay in the onset of a symptom, in animals treated with a $PrP^C$ ligand versus untreated animals is indicative of therapeutic efficacy.

One can assess the animals for memory and learning, for instance by performing behavioral testing. One can use any behavioral test for memory and learning commonly known by person of ordinary skill in the art, for but not limited to the Morris water maze test for rodent animal models. A measurable increase in the ability to perform the Morris water maze test in animals administered a $PrP^C$ ligand versus untreated animals is indicative of therapeutic efficacy.

The dosage can be determined by a physician and adjusted, as necessary, to suit observed effects of the treatment. Generally, the compositions are administered so that $PrP^C$ ligand is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 m/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some embodiments, the compositions are administered at a dosage so that $PrP^C$ ligand or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the ligand. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In some embodiments, bolus of a formulation comprising a $PrP^c$ ligand as disclosed herein can be administered to an individual over a short time once a day is a convenient dosing schedule. Alternatively, the effective daily dose can be divided into multiple doses for purposes of administration, for example, two to twelve doses per day. Dosage levels of active ingredients in a pharmaceutical composition can also be varied so as to achieve a transient or sustained concentration of the compound or derivative thereof in an individual, especially in and around vascular endothelium of the brain, and to result in the desired therapeutic response or protection. But it is also within the skill of the art to start doses at levels lower than required to achieve the desired therapeutic effect and to gradually increase the dosage until the desired effect is achieved.

The amount of a $PrP^C$ ligand as disclosed herein administered is dependent upon factors known to a person skilled in the art such as bioactivity and bioavailability of the compound (e.g., half-life in the body, stability, and metabolism); chemical properties of the compound (e.g., molecular weight, hydrophobicity, and solubility); route and scheduling of administration, and the like. It will also be understood that the specific dose level to be achieved for any particular individual can depend on a variety of factors, including age, gender, health, medical history, weight, combination with one or more other drugs, and severity of disease.

In some embodiments, efficacy of treatment can be measured as an improvement in morbidity or mortality (e.g., lengthening of survival curve for a selected population). Prophylactic methods (e.g., preventing or reducing the incidence of relapse) are also considered treatment.

The amount which is administered to a subject is preferably an amount that does not induce toxic effects which outweigh the advantages which result from its administration. Further objectives are to reduce in number, diminish in severity, and/or otherwise relieve suffering from the symptoms of the disease in the individual in comparison to recognized standards of care.

Production of compounds according to present regulations will be regulated for good laboratory practices (GLP) and good manufacturing practices (GMP) by governmental agencies (e.g., U.S. Food and Drug Administration). This requires accurate and complete record keeping, as well as monitoring of QA/QC. Oversight of patient protocols by agencies and institutional panels is also envisioned to ensure that informed consent is obtained; safety, bioactivity, appropriate dosage, and efficacy of products are studied in phases; results are statistically significant; and ethical guidelines are followed. Similar oversight of protocols using animal models, as well as the use of toxic chemicals, and compliance with regulations is required.

Dosages, formulations, dosage volumes, regimens, and methods for analyzing results of administration of a $PrP^C$ ligand as disclosed herein can vary. Thus, minimum and maximum effective dosages vary depending on the method of administration. Suppression of the clinical and histological changes associated with Alzheimer's disease or other neurological or neurodegenerative diseases associated with protein aggregation can occur within a specific dosage range, which, however, varies depending on the organism receiving the dosage, the route of administration, whether a $PrP^C$ ligand as disclosed herein are administered in conjunction with other co-stimulatory molecules, and the specific regimen of $PrP^C$ ligand administration. For example, in general, nasal administration requires a smaller dosage than oral, enteral, rectal, or vaginal administration.

Kits

The invention also provides kits or pharmaceutical packages that comprise a $PrP^C$ ligand as disclosed herein, such as any compound of formula (I)-(IV) and derivatives and analogues thereof for use in the prevention and treatment of the diseases and disorders associated with protein aggregation and neurodegeneration as described herein. In some embodiments, a $PrP^C$ ligand can be in the form of, for example, tablets, capsules, or lyophilized powders. In some embodiments, the kits or packages can optionally include instructions for using the $PrP^C$ ligand in the prevention and/or treatment diseases and disorders associated with protein aggregration and neurodegeneration, such as, but not limited to Alzheimer's disease. In some embodiments, a $PrP^C$ ligand can be provided in the kits or packages in a bottle or another appropriate form (e.g., a blister pack). Optionally, the kits or pharmaceutical packages can also include other pharmaceutically active agents (see, e.g., the agents listed above, such as anti-neurodegenerative disease agents and/or materials used in administration of the drug(s), such as diluents, needles, syringes, applicators, and the like.

A kit may optionally contain additional therapeutics to be co-administered with a $PrP^C$ ligand as disclosed herein. The kit may comprise instructions for administration of a $PrP^C$ ligand as disclosed herein to a subject with a disease and disorder associated with protein aggregation and neurodegeneration.

The kits may also optionally include appropriate systems (e.g. opaque containers) or stabilizers (e.g. antioxidants) to prevent degradation of a $PrP^C$ ligand as disclosed herein by light or other adverse conditions.

In another aspect of the invention provides kits including one or more containers containing a $PrP^C$ ligand as disclosed herein and a pharmaceutically acceptable excipient. The kit may optionally contain additional therapeutics to be co-administered with a $PrP^C$ ligand. The kit may comprise instructions for administration of a subject with a disease or disorder associated with protein aggregation and neurodegeneration.

The kits may optionally include instructional materials containing directions (i.e., protocols) providing for the use of a $PrP^C$ ligand as disclosed herein for the treatment of a disease in a mammal, e.g., for the treatment of a disease or disorder associated with protein aggregration and neurodegeneration.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

Some Selected Definitions

For convenience, certain terms employed herein, in the specification, examples and appended claims are collected herein. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

As used herein the term "comprising" or "comprises" is used in reference to compositions, methods, and respective component(s) thereof, that are essential to the invention, yet open to the inclusion of unspecified elements, whether essential or not.

The singular terms "a," "an," and "the" include plural referents unless context clearly indicates otherwise. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±5% of the value being referred to. For example, about 100 means from 95 to 105.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

The terms "decrease", "reduced", "reduction", "decrease" or "inhibit" are all used herein generally to mean a decrease by a statistically significant amount. However, for avoidance of doubt, ""reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

The term "statistically significant" or "significantly" refers to statistical significance and generally means at least two standard deviation (2SD) away from a reference level. The term refers to statistical evidence that there is a difference. It is defined as the probability of making a decision to reject the null hypothesis when the null hypothesis is actually true.

As used herein, the terms "effective" and "effectiveness" includes both pharmacological effectiveness and physiological safety. Pharmacological effectiveness refers to the ability of the treatment to result in a desired biological effect in the patient. Physiological safety refers to the level of toxicity, or other adverse physiological effects at the cellular, organ and/or organism level (often referred to as side-effects) resulting from administration of the treatment. "Less effective" means that the treatment results in a therapeutically significant lower level of pharmacological effectiveness and/or a therapeutically greater level of adverse physiological effects.

As used herein, the term "binds" in relation to binding of a PrPC ligand to PrPC polypeptide, e.g., at the PBD-1, PBD-2, PBD-3, PBD-4, PBD-5, or PBD-6, refers to the PrPC ligand interacts with at least one (e.g. one, two, three, four, five, six, seven, eight, nine, ten, eleven, twelve, thirteen, fourteen, fifteen or more) amino acids of the PBD. Without limitations, interaction can be hydrogen bonding, electrostatic, ion-pair, Van der Waals or hydrophobic interactions.

The term "specific affinity" or "specifically binds" or "specific binding" are used interchangeably herein refers to an entity, such as a $PrP^C$ ligand that recognizes and binds to $PrP^C$ polypeptide, e.g., at the PBD-1, PBD-2, PBD-3, PBD-4, PBD-5, or PBD-6, but that does not substantially recognize and/or bind to other molecules in a sample, for example, a biological sample which also includes a $PrP^C$ polypeptide. The term "specifically binds" when referring to a $PrP^C$ ligand that binds to a $PrP^C$ polypeptide, e.g., at the PBD-1, PBD-2, PBD-3, PBD-4, PBD-5, or PBD-6, refers to a binding reaction between a $PrP^C$ ligand and the $PrP^C$ polypeptide. A $PrP^C$ ligand that specifically binds to a $PrP^C$ polypeptide has an association constant of at least $10^3$ $M^{-1}$ or $104$ $M^{-1}$, sometimes $10^5$ $M^{-1}$ or $10^6$ $M^{-1}$, in other instances at least $10^6$ $M^{-1}$ or $10^7 M^{-1}$, or at least $10^8$ $M^{-1}$ to $10^9$ $M^{-1}$, or at least $10^{10}$ $M^{-1}$ to $10^{11}$ $M^{-1}$ or higher.

The term "aliphatic", as used herein, means straight-chain, branched or cyclic $C_1$-$C_{12}$ hydrocarbons which are completely saturated or which contain one or more units of unsaturation, but which are not aromatic. For example, suitable aliphatic groups include substituted or unsubstituted linear, branched or cyclic alkyl, alkenyl, alkynyl groups and hybrids thereof, such as cycloalkyl, (cycloalkyl)alkyl, (cycloalkenyl)alkyl or (cycloalkyl)-alkenyl. In various embodiments, the aliphatic group has one to ten, one to eight, one to six, one to four, or one, two, or three carbons.

The terms "alkyl", "alkenyl", and "alkynyl", used alone or as part of a larger moiety, refer to a straight and branched chain aliphatic group having from one to twelve carbon atoms. For purposes of the present invention, the term "alkyl" will be used when the carbon atom attaching the aliphatic group to the rest of the molecule is a saturated carbon atom. However, an alkyl group can include unsaturation at other carbon atoms. Thus, alkyl groups include, without limitation, methyl, ethyl, propyl, allyl, propargyl, butyl, pentyl, and hexyl.

The term "alkoxy" refers to an —O-alkyl radical.

For purposes of the present disclosure, the term "alkenyl" will be used when the carbon atom attaching the aliphatic group to the rest of the molecule forms part of a carboncarbon double bond. Alkenyl groups include, without limitation, vinyl, 1-propenyl, 1-butenyl, 1-pentenyl, and 1-hexenyl.

For purposes of the present disclosure, the term "alkynyl" will be used when the carbon atom attaching the aliphatic group to the rest of the molecule forms part of a carbon-carbon triple bond. Alkynyl groups include, without limitation, ethynyl, 1-propynyl, 1-butynyl, 1-pentynyl, and 1-hexynyl.

The term "cycloaliphatic", used alone or as part of a larger moiety, refers to a saturated or partially unsaturated cyclic aliphatic ring system having from 3 to about 14 members, wherein the aliphatic ring system is optionally substituted. In some embodiments, the cycloaliphatic is a monocyclic hydrocarbon having 3-8 or 3-6 ring carbon atoms. Nonlimiting examples include cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloaliphatic is a bridged or fused bicyclic hydrocarbon having 6-12, 6-10, or 6-8 ring carbon atoms, wherein any individual ring in the bicyclic ring system has 3-8-members.

In some embodiments, two adjacent substituents on a cycloaliphatic ring, taken together with the intervening ring atoms, form an optionally substituted fused 5- to 6-membered aromatic or 3- to 8-membered non-aromatic ring having 0-3 ring heteroatoms selected from the group consisting of O, N, and S. Thus, the term "cycloaliphatic" includes aliphatic rings that are fused to one or more aryl, heteroaryl, or heterocyclyl rings, where the radical or point of attachment is on the aliphatic ring. Nonlimiting examples include indanyl, 5,6,7,8-tetrahydroquinoxalinyl, decahydronaphthyl, or tetrahydronaphthyl, where the radical or point of attachment is on the aliphatic ring.

The terms "haloaliphatic", "haloalkyl", "haloalkenyl" and "haloalkoxy" refer to an aliphatic, alkyl, alkenyl or alkoxy group, as the case can be, which is substituted with one or more halogen atoms. As used herein, the term "halogen" or "halo" means F, Cl, Br, or I. The term "fluoroaliphatic" refers to a haloaliphatic wherein the halogen is fluoro. Nonlimiting examples of fluoroaliphatics include —$CH_2F$, —$CHF_2$, —$CH_3$, —$CH_2CH_3$, —$CH_2CH_3$, and —$CH_2CH_3$.

The terms "aryl" and "ar-", used alone or as part of a larger moiety, e.g., "aralkyl", "aralkoxy", or "aryloxyalkyl", refer to a $C_6$ to $C_{14}$ aromatic hydrocarbon, comprising one to three rings, each of which is optionally substituted. Preferably, the aryl group is a $C_{6-10}$ aryl group. Aryl groups include, without limitation, phenyl, naphthyl, and anthracenyl. In some embodiments, two adjacent substituents on an aryl ring, taken together with the intervening ring atoms, from an optionally substituted fused 5- to 6-membered aromatic or 4- to 8-membered non-aromatic ring having 0-3 ring heteroatoms selected from the group consisting of O, N, and S. Thus, the term "aryl", as used herein, includes groups in which an aromatic ring is fused to one or more heteroaryl, cycloaliphatic, or heterocyclyl rings, where the radical or point of attachment is on the aromatic ring. Nonlimiting examples of such fused ring systems include indolyl, isoindolyl, benzothienyl, benzofuranyl, dibenzofuranyl, indazolyl, benzimidazolyl, benzthiazolyl, quinolyl, isoquinolyl, quinolinyl, phthalazinyl, quinazolinyl, quinoxalinyl, carbazolyl, acridinyl, phenazinyl, phenothiazinyl, phenoxazinyl, tetrahydroquinolinyl, tetrahydroisoquinolinyl, fluorenyl, indanyl, phenanthridinyl, tetrahydronaphthyl, indolinyl, phenoxazinyl, benzodioxanyl, and benzodioxolyl. An aryl group can be mono-, bi-, tri-, or polycyclic, preferably mono-, bi-, or tricyclic, more preferably mono- or bicyclic. The term "aryl" can be used interchangeably with the terms "aryl group", "aryl moiety", and "aryl ring."

The term "alkylaryl" refers to aryl-substituted alkyl groups. Preferable alkylaryl groups are "lower alkylaryl" groups having aryl groups attached to alkyl groups having 1 to 6 carbon atoms. Even more preferred lower alkylaryl groups are phenyl attached to alkyl portions having 1 to 3 carbon atoms. Examples of such groups include benzyl, phenylethyl, diphenylmethyl and naphthylmethyl. The aryl in said alkylaryl may be additionally substituted as defined above. When appropriate the number of carbon atoms designated in the hydrocarbon backbone of the alkyl part is assigned (i.e. C1-3 alklylaryl means an alkylaryl group where the alkyl part contains one to three carbon atoms).

The terms "heteroaryl" and "heteroar-", used alone or as part of a larger moiety, e.g., heteroaralkyl, or "heteroaralkoxy", refer to groups having 5 to 14 ring atoms, preferably 5, 6, 9, or 10 ring atoms; having 6, 10, or 14π electrons shared in a cyclic array; and having, in addition to carbon atoms, from one to four heteroatoms. The term "heteroatom" refers to nitrogen, oxygen, or sulfur, and includes any oxidized form of nitrogen or sulfur, and any quaternized form of a basic nitrogen. Thus, when used in reference to a ring atom of a heteroaryl, the term "nitrogen" includes an oxidized nitrogen (as in pyridine N-oxide). Certain nitrogen atoms of 5-membered heteroaryl groups also are substitutable, as, further defined below. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

In some embodiments, two adjacent substituents on a heteroaryl ring, taken together with the intervening ring atoms, form an optionally substituted fused 5- to 6-membered aromatic or 4- to 8-membered non-aromatic ring having 0-3 ring heteroatoms selected from the group consisting of O, N, and S. Thus, the terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzotl1ienyl, benzofuranyl, dibenzofuranyl, indazolyl, benzimidazolyl, benzthiazolyl, quinolyl, isoquinolyl, cirmolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group can be mono-, bi-, tri-, or polycyclic, preferably mono-, bi-, or tricyclic, more preferably mono- or bicyclic. The term "heteroaryl" can be used interchangeably with the terms "heteroaryl ring", or "heteroaryl group", any of which terms include rings that are optionally substituted. The term "heteroaralkyl" refers to an alkyl group substituted by a heteroaryl, wherein the alkyl and heteroaryl portions independently are optionally substituted.

As used herein, the terms "aromatic ring" and "aromatic ring system" refer to an optionally substituted mono-, bi-, or tricyclic group having 0-6, preferably 0-4 ring heteroatoms, and having 6, 10, or 14π electrons shared in a cyclic array. Thus, the terms "aromatic ring" and "aromatic ring system" encompass both aryl and heteroaryl groups.

As used herein, the terms "heterocycle", "heterocyclyl", "heterocyclic radical", and "heterocyclic ring" are used interchangeably and refer to a stable 3- to 7-membered monocyclic, or to a fused 7- to 10-membered or bridged 6- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a heterocyclyl ring having 1-3 heteroatoms selected from oxygen, sulfur or nitrogen, the nitrogen can be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure, and any of the ring atoms can be optionally substituted. Examples of such saturated or partially unsaturated heterocyclic radicals include, without limitation, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl.

In some embodiments, two adjacent substituents on a heterocyclic ring, taken together with the intervening ring atoms, form an optionally substituted fused 5 to 6-membered aromatic or 3- to 8-membered non-aromatic ring having 0-3 ring heteroatoms selected from the group consisting of O, N, and S. Thus, the terms "heterocycle", "heterocyclyl", "heterocyclyl ring", "heterocyclic group", "heterocyclic moiety", and "heterocyclic radical", are used interchangeably herein, and include groups in which a heterocyclyl ring is fused to one or more aryl, heteroaryl, or cycloaliphatic rings, such as indolinyl, 3H-indolyl, cl1romanyl, phenanthridinyl, or tetrahydroquinolinyl, where the radical or point of attachment is on the heterocyclyl ring. A heterocyclyl group can be mono-, bi-, tri-, or polycyclic, preferably mono-, bi-, or tricyclic, more preferably mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond between ring atoms. The term "partially unsaturated" is intended to encompass rings having multiple sites of unsaturation, but is not intended to include aryl or heteroaryl moieties, as herein defined.

The term "linker group" or "linker" means an organic moiety that connects two parts of a compound. Linkers typically comprise an atom such as oxygen or sulfur, a unit such as NH, $CH_2$, C(O), C(O)NH, or a chain of atoms, such as an alkylene chain. The molecular mass of a linker is typically in the range of about 14 to 200, preferably in the range of 14 to 96 with a length of up to about six atoms. In some embodiments, the linker is a $C_1$-$C_6$ alkylene chain which is optionally substituted.

The term "alkylene" refers to a bivalent alkyl group. An "alkylene chain" is a polymethylene group, i.e., —$(CH_4)_n$—, wherein n is a positive integer, preferably from one to six, from one to four, from one to three, from one to two, or from two to three. A substituted alkylene chain is a polymethylene group in which one or more methylene hydrogen atoms is replaced with a substituent. Suitable substituents include those described below for a substituted aliphatic group. An alkylene chain also can be substituted at one or more positions with an aliphatic group or a substituted aliphatic group.

An alkylene chain also can be optionally interrupted by a functional group. An alkylene chain is "interrupted" by a functional group when an internal methylene unit is replaced with the functional group. Examples of suitable "interrupting functional groups" include —C(R*)=C(R*)—, —C≡C—, —O—, —S—S, —S(O)—, —S(O)$_2$—, —S(O)$_2$N(R$^+$)—, —N(R*)—, —N(R$^+$)CO—, N(R$^+$)CO$_2$—, —N(R$^+$)C(O)N(R$^+$)—, —C(O)N(R$^+$)—, —C(O)—, —C(O)—C(O)—, —CO$_2$—, —OCC(O)—, —OC(O)N (R$^+$)—, or N(R$^+$)S(O)$_2$. Each R$^+$, independently, is hydrogen or an optionally substituted aliphatic, aryl, heteroaryl, or heterocyclyl group, or two R$^+$ on the same nitrogen atom, taken together with the nitrogen atom, form a five to eight membered aromatic or non-aromatic ring having, in addition to the nitrogen atom, zero to two ring heteroatoms selected from N, O, and S. Each R* independently is hydrogen or an optionally substituted aliphatic, aryl, heteroaryl, or heterocyclyl group.

Examples of $C_{3-6}$ alkylene chains that have been "interrupted" with —O— include —$CH_2OCH_2$—, —$CH_2O$ $(CH_2)_2$—, —$CH_2O(CH_2)_3$—, —$CH_2O(CH_2)_4$—, —$(CH_2)_2OCH_2$—, —$(CH_2)_2O(CH_2)_2$—, —$(CH_2)_2O$ $(CH_2)_3$—, —$(CH_2)_3OCH_2$—, —$(CH_2)_3O(CH_2)_2$—, and —$(CH_2)_4OCH_2$—. Other examples of alkylene chains that are "interrupted" with functional groups include —$CH_2GCH_2$—, —$CH_2G$ $(CH_2)_2$—, —$CH_2G$ $(CH_2)_3$—, —$CH_2G$ $(CH_2)_4$—, —$(CH_2)_2GCH_2$—, —$(CH_2)_2G$ $(CH_2)_2$—, —$(CH_2)_2G(CH_2)_3$—, —$(CH_2)_3GCH_2$—, —$(CH_2)_3G(CH_2)_2$—, and —$(CH_2)_4GCH_2$—, wherein G is one of the "interrupting" functional groups listed above.

One of ordinary skill in the art will recognize that when an alkylene chain having an interruption is attached to a functional group, certain combinations are not sufficiently stable for pharmaceutical use. Only stable or chemically feasible compounds are within the scope of the present invention. A stable or chemically feasible compound is one in which the chemical structure is not substantially altered when kept at a temperature from about −80° C. to about +40° C., preferably from about −20° C. to about +40° C., in the absence of moisture or other chemically reactive conditions, for at least a week, or a compound which maintains its integrity long enough to be useful for therapeutic or prophylactic administration to a patient.

The term "substituted", as used herein, means that a hydrogen radical of the designated moiety is replaced with the radical of a specified substituent, provided that the substitution results in a stable or chemically feasible compound. The term "substitutable", when used in reference to a designated atom, means that attached to the atom is a hydrogen radical, which can be replaced with the radical of a suitable substituent.

The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group can have a substituent at each substitutable position of the group, and the substituents can be either the same or different. As used herein, the term "independently selected" means that the same or different values can be selected for multiple instances of a given variable in a single compound.

An aryl (including the aryl moiety in aralkyl, aralkoxy, aryloxyalkyl and the like) or heteroaryl (including the heteroaryl moiety in heteroaralkyl and heteroaralkoxy and the like) group can contain one or more substituents. Examples of suitable substituents on the unsaturated carbon atom of an aryl or heteroaryl group include -halo, —$NO_2$, —CN, —R*, —C(R*)=C(R*)$_2$—, —C≡C—R*, —OR*, —SR°, —S(O) R°, —SO$_2$R°, —SO$_2$N(R$^+$)$_2$, —N(R$^+$)$_2$, —NR$^+$C(O)R*, —NR$^+$C(O)N(R$^+$)$_2$, —NR$^+$CO$_2$R°, —OCO$_2$R°, —OC(O)N (R$^+$)$_2$, —C(O)R*, —CO$_2$R*, —C(O)—C(O)R*, —OC(O) R*, —C(O)N(R$^+$)$_2$, —C(O)N(R$^+$)OR*, —C(O)N(R$^+$)C (=NR$^+$)—N(R)$_2$, —C(=NR$^+$)—N(R$^+$)$_2$, —C(=NR$^+$)—N (R$^+$)—OR*, —C(=NR$^+$)—OR*, —C(R°=N—OR*, —N(R$^+$)—N(R$^+$)$_2$, —N(R$^+$)—OR*, —N(R$^+$)C(=NR$^+$)—N (R$^+$)$_2$, —N(R$^+$)C(=NR$^+$)—N(R$^+$)—C(O)R*, —N(R$^+$)C (=NR$^+$)—R°, —N(R$^+$)SO$_2$(R$^+$)$_2$, —P(O)(R*)$_2$, —P(O) (OR*)$_2$, —O—P(O)—OR*, and —P(O)(NR$^+$)—N(R$^+$)$_2$, wherein $R^o$ is an optionally substituted aliphatic or aryl group, and $R^+$ and $R^*$ are as defined above, or two adjacent substituents, taken together with their intervening atoms, form a 5- to 6-membered unsaturated or partially unsaturated ring having 0-3 ring atoms selected from the group consisting of N, O, and S.

An aliphatic group or a non-aromatic heterocyclic ring can be substituted with one or more substituents. Examples of suitable substituents on the saturated carbon of an aliphatic group or of a non-aromatic heterocyclic ring include, without limitation, those listed above for the unsaturated carbon of an aryl or heteroaryl group and the following: =O, =S, =C(R*)$_2$, =N—N(R+)$_2$, =N—NHC(O)R*, =N—NHCO$_2$R$^o$, =N—NHSO$_2$R$^o$, or =N—R*, where = represents a double bond, and each R* and R$^o$ is as defined above. One of ordinary skill in the art will recognize that substituents that are attached by way of a double bond requires replacement of two hydrogen radicals on the substitutable carbon atom. For the purposes of clarity, the term "substituted aliphatic" refers to an aliphatic group having at least one non-aliphatic substituent.

Suitable substituents on a substitutable nitrogen atom of a heteroaryl or heterocyclic ring include —R*, —N(R*)$_2$ C(O)R*, —CO$_2$R$^o$, —C(O)—C(O)R*—C(O)CH$_2$C(O) R*, —SO$_2$R$^o$, —SO$_2$N(R*)$_2$, —C(=S)N(R*)$_2$, —C(=NH)— N(R*)$_2$, and —NR*SO$_2$R$^o$; wherein each R* and R$^o$ is as defined above.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

It also will be apparent to one skilled in the art that certain compounds of this invention can exist in tautomeric forms, all such tautomeric forms of the compounds being within the scope of the invention. Unless stereochemical configuration is expressly defined, structures depicted herein are meant to include all stereochemical forms of the structure; i.e., the R and S configurations for each asymmetric center. Therefore, unless otherwise indicated, single stereochemical isomers as well as enantiomeric and diastereomeric mixtures of the present compounds are within the scope of the invention.

Where stereochemical configuration at a given asymmetric center is defined by structure, unless stated otherwise, the depicted configuration indicates stereochemistry relative to other asymmetric centers in the molecule. Where stereochemical configuration is defined by chemical name, the designations (rel), (R*), and (S*) indicate relative stereochemistry, while the designations (+), (−), (R), (S), and (abs) indicate absolute stereochemistry.

In the compounds of formulas (I), (II), (III) or (IV), where relative stereochemistry is defined, the diastereomeric purity of the compound preferably is at least 80%, more preferably at least 90%, still more preferably at least 95%, and most preferably at least 99%. As used herein, the term. "diastereomeric purity" refers to the amount of a compound having the depicted relative stereochemistry, expressed as a percentage of the total amount of all diastereomers present.

In some embodiments, stereochemical configurations depicted at asterisked positions indicate absolute as well as relative stereochemistry. Preferably, the enantiomeric purity of the compound is at least 80%, more preferably at least 90%, still more preferably at least 95%, and most preferably at least 99%. As used herein, the term "enantiomeric purity" refers to the amount of a compound having the depicted absolute stereochemistry, expressed as a percentage of the total amount of the depicted compound and its enantiomer.

Methods for determining diastereomeric and enantiomeric purity are well-known in the art. Diastereomeric purity can be determined by any analytical method capable of quantitatively distinguishing between a compound and its diastereomers. Examples of suitable analytical methods include, without limitation, nuclear magnetic resonance spectroscopy (NMR), gas chromatography (GC), and high performance liquid chromatography (HPLC). Similarly, enantiomeric purity can be determined by any analytical method capable of quantitatively distinguishing between a compound and its enantiomer. Examples of suitable analytical methods include, without limitation, GC or HPLC, using a chiral column packing material. Enantiomers can also be distinguishable by NMR if first derivatized with an optically enriched derivatizing agent, e.g., Mosher's acid.

As used here in the term "isomer" refers to compounds having the same molecular formula but differing in structure. Isomers which differ only in configuration and/or conformation are referred to as "stereoisomers." The term "isomer" is also used to refer to an enantiomer.

The term "enantiomer" is used to describe one of a pair of molecular isomers which are mirror images of each other and non-superimposable. Other terms used to designate or refer to enantiomers include "stereoisomers" (because of the different arrangement or stereochemistry around the chiral center; although all enantiomers are stereoisomers, not all stereoisomers are enantiomers) or "optical isomers" (because of the optical activity of pure enantiomers, which is the ability of different pure enantiomers to rotate planepolarized light in different directions). Enantiomers generally have identical physical properties, such as melting points and boiling points, and also have identical spectroscopic properties. Enantiomers can differ from each other with respect to their interaction with plane-polarized light and with respect to biological activity.

The designations "R and S" are used to denote the absolute configuration of the molecule about its chiral center(s). The designations may appear as a prefix or as a suffix; they may or may not be separated from the isomer by a hyphen; they may or may not be hyphenated; and they may or may not be surrounded by parentheses.

The designations or prefixes "(+) and (−)" are employed to designate the sign of rotation of plane-polarized light by the compound, with (−) meaning that the compound is levorotatory (rotates to the left). A compound prefixed with (+) is dextrorotatory (rotates to the right).

The term "racemic mixture," "racemic compound" or "racemate" refers to a mixture of the two enantiomers of one compound. An ideal racemic mixture is one wherein there is a 50:50 mixture of both enantiomers of a compound such that the optical rotation of the (+) enantiomer cancels out the optical rotation of the (−) enantiomer.

The term "resolving" or "resolution" when used in reference to a racemic mixture refers to the separation of a racemate into its two enantiomorphic forms (i.e., (+) and (−); (R) and (S) forms). The terms can also refer to enantioselective conversion of one isomer of a racemate to a product.

The term "enantiomeric excess" or "ee" refers to a reaction product wherein one enantiomer is produced in excess of the other, and is defined for a mixture of (+)- and (−)-enantiomers, with composition given as the mole or weight or volume fraction $F_{(+)}$ and $F_{(−)}$ (where the sum of $F_{(+)}$ and $F_{(−)}$=1). The enantiomeric excess is defined as *$F_{(+)}$-$F_{(−)}$* and the percent enantiomeric excess by 100×*

$F_{(+)}$-$F_{(-)}$*. The "purity" of an enantiomer is described by its ee or percent ee value (% ee).

Whether expressed as a "purified enantiomer" or a "pure enantiomer" or a "resolved enantiomer" or "a compound in enantiomeric excess", the terms are meant to indicate that the amount of one enantiomer exceeds the amount of the other. Thus, when referring to an enantiomer preparation, both (or either) of the percent of the major enantiomer (e.g. by mole or by weight or by volume) and (or) the percent enantiomeric excess of the major enantiomer may be used to determine whether the preparation represents a purified enantiomer preparation.

The term "enantiomeric purity" or "enantiomer purity" of an isomer refers to a qualitative or quantitative measure of the purified enantiomer; typically, the measurement is expressed on the basis of ee or enantiomeric excess.

The terms "substantially purified enantiomer," "substantially resolved enantiomer" "substantially purified enantiomer preparation" are meant to indicate a preparation (e.g. derived from non optically active starting material, substrate, or intermediate) wherein one enantiomer has been enriched over the other, and more preferably, wherein the other enantiomer represents less than 20%, more preferably less than 10%, and more preferably less than 5%, and still more preferably, less than 2% of the enantiomer or enantiomer preparation.

The terms "purified enantiomer," "resolved enantiomer" and "purified enantiomer preparation" are meant to indicate a preparation (e.g. derived from non optically active starting material, substrates or intermediates) wherein one enantiomer (for example, the R-enantiomer) is enriched over the other, and more preferably, wherein the other enantiomer (for example the S-enantiomer) represents less than 30%, preferably less than 20%, more preferably less than 10% (e.g. in this particular instance, the R-enantiomer is substantially free of the S-enantiomer), and more preferably less than 5% and still more preferably, less than 2% of the preparation. A purified enantiomer may be synthesized substantially free of the other enantiomer, or a purified enantiomer may be synthesized in a stereopreferred procedure, followed by separation steps, or a purified enantiomer may be derived from a racemic mixture.

The term "enantioselectivity," also called the enantiomeric ratio indicated by the symbol "E," refers to the selective capacity of an enzyme to generate from a racemic substrate one enantiomer relative to the other in a product racemic mixture; in other words, it is a measure of the ability of the enzyme to distinguish between enantiomers. A nonselective reaction has an E of 1, while resolutions with E's above 20 are generally considered useful for synthesis or resolution. The enantioselectivity resides in a difference in conversion rates between the enantiomers in question. Reaction products are obtained that are enriched in one of the enantiomers; conversely, remaining substrates are enriched in the other enantiomer. For practical purposes it is generally desirable for one of the enantiomers to be obtained in large excess. This is achieved by terminating the conversion process at a certain degree of conversion.

The term "analog" as used herein refers to a compound that results from substitution, replacement or deletion of various organic groups or hydrogen atoms from a parent compound. An analog is structurally similar to the parent compound, but can differ by even a single element of the same valence and group of the periodic table as the element it replaces.

The term "derivative" as used herein refers to a chemical substance related structurally to another, i.e., an "original" substance, which can be referred to as a "parent" compound. A "derivative" can be made from the structurally-related parent compound in one or more steps. The phrase "closely related derivative" means a derivative whose molecular weight does not exceed the weight of the parent compound by more than 50%. The general physical and chemical properties of a closely related derivative are also similar to the parent compound.

As used herein, a "prodrug" refers to compounds that can be converted via some chemical or physiological process (e.g., enzymatic processes and metabolic hydrolysis) to a therapeutic agent. Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of β-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J. Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J. Pharm. Sci.* 4: 49-59 (1996); Gangwar et al., "Pro-drug, molecular structure and percutaneous delivery", *Des. Biopharm. Prop. Prodrugs Analogs*, [*Symp.*] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J. Clin. Pharmac.* 28: 497-507 (1989), content of all of which is herein incorporated by reference in its entirety.

As used herein, the term "pharmaceutically-acceptable salts" refers to the conventional nontoxic salts or quaternary ammonium salts of therapeutic agents, e.g., from non-toxic organic or inorganic acids. These salts can be prepared in situ in the administration vehicle or the dosage form manufacturing process, or by separately reacting a therapeutic agent in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of the aspects described herein, representative salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

In Some Embodiments, the Present Invention may be Defined in any of the Following Numbered Paragraphs:

i. A method of treating a disease or disorder associated with protein aggregation or neurodegeneration, the method comprising administering to a subject in need thereof a therapeutically effective amount of a $PrP^C$ ligand, wherein the $PrP^C$ ligand binds with a $PrP^C$ polypeptide at $PrP^C$-binding domain 1 (PBD-1), $PrP^C$-binding domain 2 (PBD-2), $PrP^C$-binding domain 3 (PBD-3), $PrP^C$-binding domain 4 (PBD-4), $PrP^C$-binding domain 5 (PBD-5), or $PrP^C$-binding domain 6 (PBD-6).

ii. The method of paragraph i, wherein the PBD-1 comprises amino acids 133, 134, 135, 136, 149, 153, 154, 156, 157, 158, 159, 208, 209, and 212 of mouse $PrP^C$ (sequence numbering based on SEQ ID NO: 2), or amino acids 134, 135, 136, 137, 150, 154, 155, 157, 158, 159, 160, 209, 210, and 213 of human $PrP^C$ (sequence numbering based on SEQ ID NO: 1); the PBD-2 comprises amino acids 129, 155, 156, 157, 158, 159, 160, 161, 182, 183, 185, 186, 187, 188, 189, 190, 197, and 205 of mouse $PrP^C$ (sequence numbering based on SEQ ID NO: 2) or amino acids 130, 156, 157, 158, 159, 160, 161, 162, 183, 184, 186, 187, 188, 189, 190, 191, 198, and 206 of human $PrP^C$ (sequence numbering based on SEQ ID NO: 1); the PBD-3 comprises amino acids 165, 166, 168, 169, 170, 171, 175, 214, 217, 218, 220, 221, 222, 224, 225, and 226 of mouse $PrP^C$ (sequence numbering based on SEQ ID NO: 2) or amino acids 166, 167, 169, 170, 171, 172, 176, 215, 218, 219, 221, 222, 223, 225, 226, and 227 of human $PrP^C$ (sequence numbering based on SEQ ID NO: 1); the PBD-4 comprises amino acids 127, 163, 164, 167, 168, 169, 170, 173, 174, 175, and 177 of mouse $PrP^C$ (sequence numbering based on SEQ ID NO: 2) or amino acids 128, 164, 165, 168, 169, 170, 171, 174, 175, 176, and 178 of human $PrP^C$ (sequence numbering based on SEQ ID NO: 1); the PBD-5 comprises amino acids 131, 132, 133, 134, 135, 136, 137, 138, 139, 143, 146, 149, 150, 151, 153, 211, 212, 214, 215, 216, 218, 219, 220, 221, 222, and 223 of mouse $PrP^C$ (sequence numbering based on SEQ ID NO: 2) or amino acids 132, 133, 134, 135, 136, 137, 138, 139, 140, 144, 147, 150, 151, 152, 154, 212, 213, 215, 216, 217, 219, 220, 221, 222, 223, and 224 of human $PrP^C$ (sequence numbering based on SEQ ID NO: 1); and the PBD-6 comprises amino acids 171, 175, 176, 179, 180, 183, 184, 187, 205, 206, 207, 209, 210, and 214 of mouse $PrP^C$ (sequence numbering based on SEQ ID NO: 2) or amino acids 172, 176, 177, 180, 181, 184, 185, 188, 206, 207, 208, 210, 211, and 215 of human $PrP^C$ (sequence numbering based on SEQ ID NO: 1).

iii. The method of paragraph i or ii, wherein the $PrP^C$ ligand is selected from the group consisting of small organic or inorganic molecules; carbohydrates, saccharines; oligosaccharides; polysaccharides; biological macromolecules; peptides; proteins; peptide analogs and derivatives; antibodies; antigen binding fragments of antibodies;

peptidomimetics; nucleic acids; nucleic acid analogs and derivatives; an extract made from biological materials such as bacteria, plants, fungi, or animal cells; animal tissues; naturally occurring or synthetic compositions; and any combinations thereof iv. The method of any of paragraphs i-iii, wherein the PrP$^C$ ligand is selected from the group consisting of:
   (i) compound of formula (I):

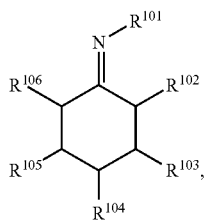

Formula (I)

wherein:
   $R^{101}$ is alkyl, hetero alkyl, aryl, acyl, alkenyl, alkynyl, heteroaryl, cyclyl, heterocyclyl, alkylaryl, alkylheteroaryl, alkylcyclyl, or alkylheterocyclyl, $N(R^{107})C(O)NHR^{108}$, $N(R^{107})C(S)NHR^{108}$, $N(R^{107})C(O)OR^{109}$, $N(R^{107})C(O)SR^{109}$, $N(R^{107})C(S)OR^{109}$, each of which can be optionally substituted;
   each of $R^{102}$, $R^{103}$, $R^{104}$, $R^{105}$, and $R^{106}$ is independently selected from H, halogen, OH, $OR^{110}$, $NH_2$, $NHR^{111}$, each of which can be optionally substituted;
   $R^{107}$ and $R^{108}$ are independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl;
   $R^{109}$ is independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl;
   $R^{110}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl;
   $R^{111}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl; and isomers and pharmaceutically acceptable salts thereof;

(ii) compound formula (II):

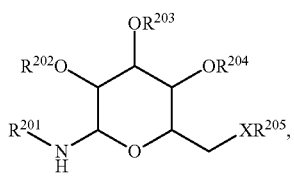

Formula (II)

wherein:
   X is O, NH, or S;
   each of $R^{201}$, $R^{202}$, $R^{203}$, $R^{204}$ and $R^{205}$ is independently for each occurrence H, aryl, alkyl, acyl, alkenyl, alkynyl, heteroaryl, cyclyl, heterocyclyl, alkylaryl, alkylheteroaryl, alkylcyclyl, or alkylheterocyclyl; and isomers and pharmaceutically acceptable salts thereof;

(iii) compound of formula (III):

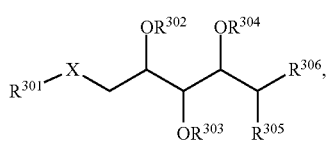

Formula (III)

wherein:
   X is O, NH, or S;
   each of $R^{301}$, $R^{302}$, $R^{303}$, and $R^{304}$ is independently H, aryl, alkyl, acyl, alkenyl, alkynyl, heteroaryl, cyclyl, heterocyclyl, alkylaryl, alkylheteroaryl, alkylcyclyl, or alkylheterocyclyl;
   $R^{305}$ and $R^{306}$ are independently aryl, alkyl, heterocyclyl, heteroaryl, or cyclyl, or $R^{305}$ and $R^{305}$ together with the carbon they are attached to form an aryl, heteroaryl, cyclyl, or heterocyclyl; and isomers and pharmaceutically acceptable salts thereof;

(iv) compound of formula (IV):

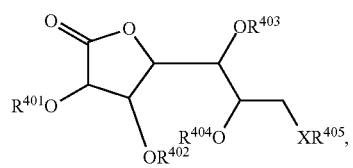

Formula (IV)

wherein:
   X is O, NH, or S;
   each of $R^{401}$, $R^{402}$, $R^{403}$, $R^{404}$, and $R^{4-5}$ is independently H, aryl, alkyl, acyl, alkenyl, alkynyl, heteroaryl, cyclyl, heterocyclyl, alkylaryl, alkylheteroaryl, alkylcyclyl, or alkylheterocyclyl, each of which can be optionally substituted; and
   isomers and pharmaceutically acceptable salts thereof; and (v) any combinations thereof v. The method of paragraph iv, wherein the compound of formula (I) has the stereochemistry shown in formula (Ia):

vi. The method of paragraph iv, wherein the compound of formula (I) has the structure shown in formula (Ib):

vii. The method of paragraph vi, wherein the compound of formula (Ib) has the stereochemistry shown in formula (Ic):

viii. The method of paragraph iv, wherein the compound of formula (II) has the stereochemistry shown in formula (IIa):

ix. The method of paragraph iv, wherein the compound of formula (III) has the stereochemistry shown in formula (Ma):

x. The method of paragraph iv, wherein the compound of formula (IV) has the stereochemistry shown in formula (IVa):

xi. The method of any of paragraphs i-iv, wherein the PrP$^C$ ligand is selected from the group consisting of

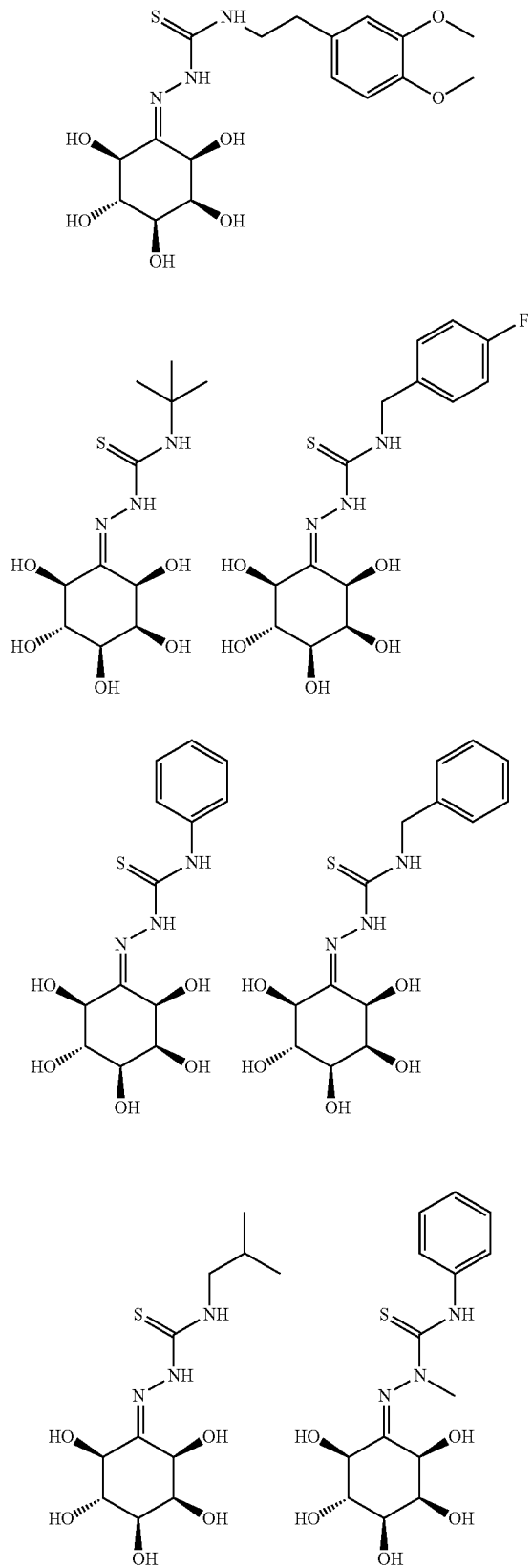
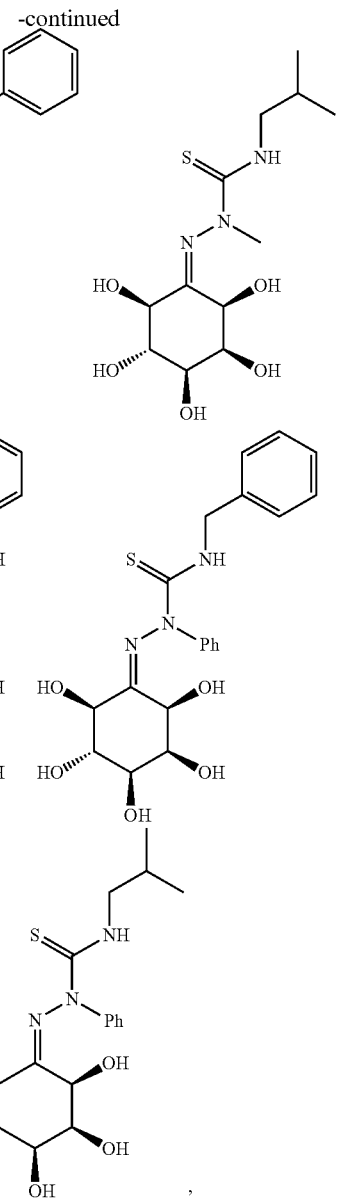

2-(2R,3S,5R,6S-pentahydroxycyclohexylidene) hydrazine carbothioamide, 2R,3S,4S,5S,6R)-2-(hydroxymethyl)-6-[β-hydroxyphenyl)amino]tetrahydro-2H-pyran-3,4,5-triol, (1S,2R,3R)-1-(1H-tetrazol-5-yl) butane-1,2,3,4-tetrol, 3R,4S-dihydroxy-5S-(1,2,3-trihydroxypropyl)dihydrofuran-2(3H)-one, and any combination thereof xii. The method of any of paragraphs i-xi, wherein the PrP$^C$ ligand is co-administered with a pharmaceutically active agent.

xiii. The method of paragraph xii, wherein the pharmaceutically active agent is selected from the group consisting of adrenergic agent; anti-adrenergic agent; anti-androgen agent, anti-anginal agent; anti-anxiety agent; anticonvulsant agent; antidepressant agent; anti-epileptic agent; antihyperlipidemic agent; antihyperlipoproteinemic agent; antihypertensive agent; anti-inflammatory agent; anti-obessional agent; antiparkinsonian agent; antipsychotic agent; adrenocortical steroid agent; adrenocortical suppressant agent; aldosterone antagonist agent; amino acid agent; anabolic steroid; analeptic agent; androgen agent; blood glucose regulator; cardioprotectant agent; cardiovascular agent; cholinergic agonist or antagonist; cholinesterase deactivator or inhibitor, such as galantamine, rivastigmine, tacrine and donepezil; cognition adjuvant or enhancer; dopaminergic agent; enzyme inhibitor, estrogen, free oxygen radical scavenger; GABA agonist; glutamate antagonist; hormone; hypocholesterolemic agent; hypolipidemic agent; hypotensive agent; immunizing agent; immunostimulant agent; monoamine oxidase inhibitor, neuroprotective agent; N-methyl D-aspartate (NMDA) antagonist, such as memantine; AMPA antagonist, competitive or -non-competitive NMDA antagonist; opioid antagonist; potassium channel opener; non-hormonal sterol derivative; post-stroke and post-head trauma treatment; prostaglandin; psychotropic agent; relaxant; sedative; sedative-hypnotic agent; selective adenosine antagonist; serotonin antagonist; serotonin inhibitor; selective serotonin uptake inhibitor; serotonin receptor antagonist; sodium and calcium channel blocker; steroid; stimulant; thyroid hormone and inhibitor agents; and any combinations thereof xiv. The method of any of paragraphs i-xiii, wherein the subject is a mammal.

xv. The method of any of paragraphs i-xiv, wherein the subject is human.

xvi. The method of any of paragraphs i-xv, wherein the PrP$^C$ ligand is administered at a dose from 1 µg/kg to 150 mg/kg of body weight.

xvii. The method of any of paragraphs i-xvi, wherein the PrP$^C$ ligand is administered daily.

xviii. The method of any of paragraphs i-xvii, wherein the PrP$^C$ ligand is administered directly into the central nervous system.

xix. The method of any of paragraphs i-xviii, wherein the disease or disorder associated with protein aggregation or neurodegeneration is Alzheimer's disease; Parkinson's disease; Down's syndrome; Huntington's disease; Creutzfeldt-Jakob disease (CJD); bovine spongiform encephalopathy (BSE); scrapie; or a tauopathy, such as Progressive supranuclear palsy, Dementia pugilistica (chronic traumatic encephalopathy, Frontotemporal dementia and parkinsonism linked to chromosome 17, Lytico-Bodig disease, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease and corticobasal degeneration.

xx. The method of any of paragraphs i-xix, wherein the PrP$^C$ ligand inhibits at least one of the following: binding of Aβ oligomers with PrP$^C$, Aβ oligomer-induced suppression of long-term potentiation, conversion of PrP$^C$ to PrP$^{Sc}$, PrP$^{Sc}$ replication, ion-channel activity of PrP.

xxi. A compound of formula (I):

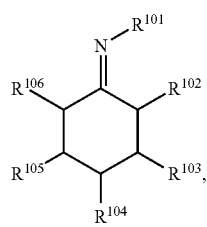

Formula (I)

wherein:

R$^{101}$ is alkyl, hetero alkyl, aryl, acyl, alkenyl, alkynyl, heteroaryl, cyclyl, heterocyclyl, alkylaryl, alkylheteroaryl, alkylcyclyl, or alkylheterocyclyl, N(R$^{107}$)C(O)NHR$^{108}$, N(R$^{107}$)C(S)NHR$^{108}$, N(R$^{107}$)C(O)OR$^{109}$, N(R$^{107}$)C(O)SR$^{109}$, N(R$^{107}$)C(S)OR$^{109}$, each of which can be optionally substituted;

each of R$^{102}$, R$^{103}$, R$^{104}$, R$^{105}$, and R$^{106}$ is independently selected from H, halogen, OH, OR$^{110}$, NH$_2$, NHR$^{111}$, each of which can be optionally substituted;

R$^{107}$ and R$^{108}$ are independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl;

R$^{109}$ is independently for each occurrence H, alkyl, alkenyl, alkynyl, acyl, aryl, heteroaryl, cyclyl, heterocyclyl, alkylaryl, alkylheteroaryl, alkylcyclyl, or alkylheterocyclyl;

R$^{110}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl;

R$^{111}$ is independently for each occurrence alkyl, alkenyl, alkynyl, acyl, aryl, heteroaryl, cyclyl, heterocyclyl, alkylaryl, alkylheteroaryl, alkylcyclyl, or alkylheterocyclyl; and isomers and pharmaceutically acceptable salts thereof, provided that compound of formula (I) is not 2-(2R, 3S,5R,6S-pentahydroxycyclohexylidene) hydrazine carbothioamide.

xxii. The compound of paragraph xxi, wherein the compound has the stereochemistry as shown in formula (Ia):

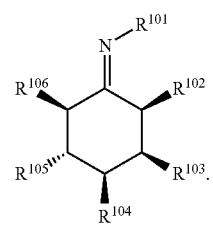

Formula (Ia)

xxiii. The compound of paragraph xxi, wherein the compound has the structure as shown in formula (Ib):

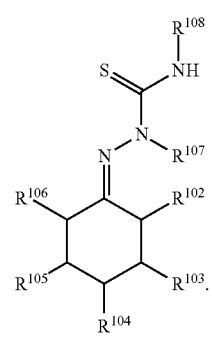

Formula (Ib)

xxiv. The compound of paragraph xxiii, wherein the compound has the structure as shown in formula (Ic):

Formula (Ic)
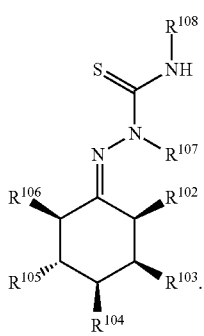
xxv. The compound of paragraph any of paragraphs xxi-xxiv, wherein the compound is selected from the group consisting of
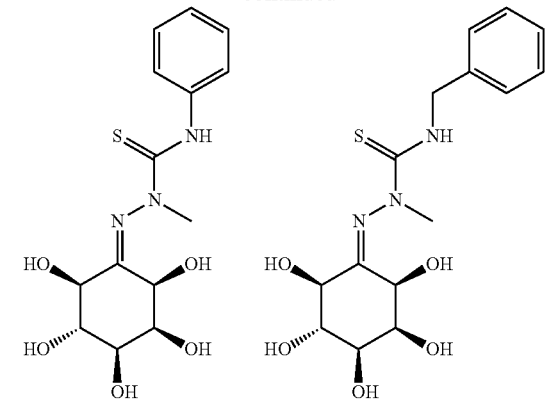
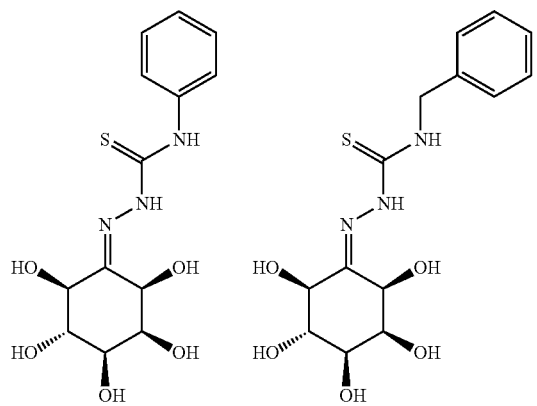
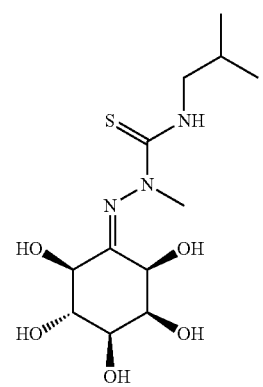
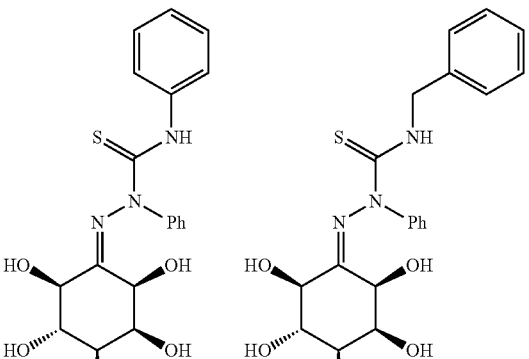
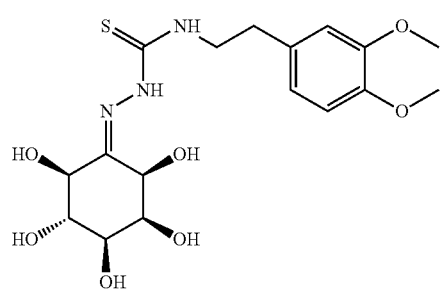
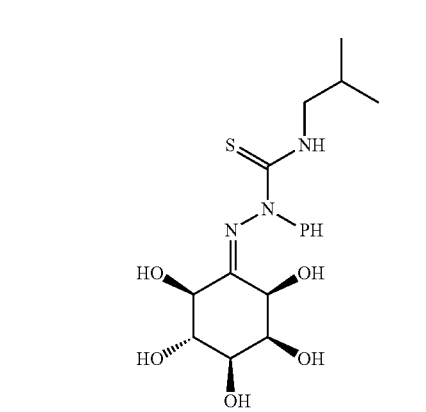

-continued

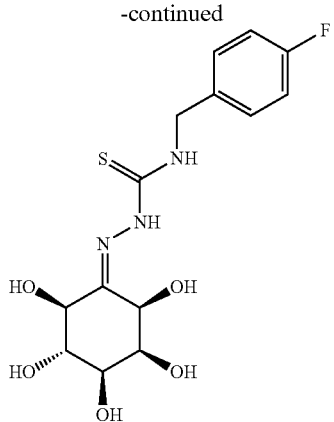

xxvi. A compound of formula (II):

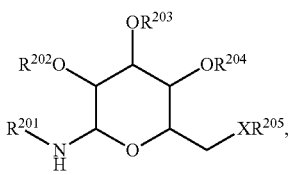

Formula (II)

wherein:
X is O, NH, or S;
each of $R^{201}$, $R^{202}$, $R^{203}$, $R^{204}$ and $R^{205}$ is independently for each occurrence H, aryl, alkyl, acyl, alkenyl, alkynyl, heteroaryl, cyclyl, heterocyclyl, alkylaryl, alkylheteroaryl, alkylcyclyl, or alkylheterocyclyl; and
isomers and pharmaceutically acceptable salts thereof, provided that the compound is not 2R,3S,4S,5S,6R)-2-(hydroxymethyl)-6-[(3-hydroxyphenyl)amino]tetrahydro-2H-pyran-3,4,5-triol.

xxvii. The compound of paragraph xxvi, wherein the compound has the stereochemistry as shown in formula (IIa):

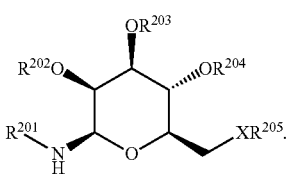

Formula (IIa)

xxviii. A compound of formula (III):

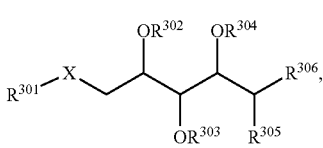

Formula (III)

wherein:
X is O, NH, or S;
each of $R^{301}$, $R^{302}$, $R^{303}$, and $R^{304}$ is independently H, aryl, alkyl, acyl, alkenyl, alkynyl, heteroaryl, cyclyl, heterocyclyl, alkylaryl, alkylheteroaryl, alkylcyclyl, or alkylheterocyclyl;

$R^{305}$ and $R^{306}$ are independently aryl, alkyl, heterocyclyl, heteroaryl, or cyclyl, or $R^{305}$ and $R^{305}$ together with the carbon they are attached to form an aryl, heteroaryl, cyclyl, or heterocyclyl; and isomers and pharmaceutically acceptable salts thereof, provided that the compound is not (1 S,2R,3R)-1-(1H-tetrazol-5-yl)butane-1,2,3,4-tetrol.

xxix. The compound of paragraph xxviii, wherein the compound has the stereochemistry as shown in formula (IIIa):

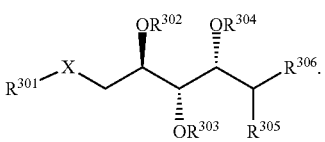

Formula (IIIa)

xxx. A compound of formula (IV):

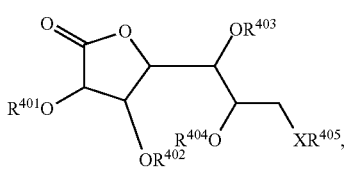

Formula (IV)

wherein:
X is O, NH, or S;
each of $R^{401}$, $R^{402}$, $R^{403}$, $R^{404}$, and $R^{4-5}$ is independently H, aryl, alkyl, acyl, alkenyl, alkynyl, heteroaryl, cyclyl, heterocyclyl, alkylaryl, alkylheteroaryl, alkylcyclyl, or alkylheterocyclyl, each of which can be optionally substituted; and
isomers and pharmaceutically acceptable salts thereof, provided that the compound is not 3R,4S-dihydroxy-5S-(1,2,3-trihydroxypropyl)dihydrofuran-2(3H)-one.

xxxi. The compound of paragraph xxx, wherein the compound has the stereochemistry as shown in formula (IVa):

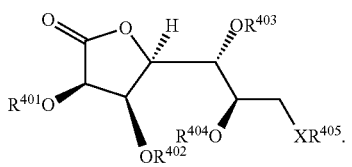

Formula (IVa)

xxxii. A pharmaceutical composition comprising a compound of any of paragraphs xxi-xxxi and a pharmaceutically acceptable carrier.

xxxiii. A compound which binds to $PrP^C$ binding domain 1 (PDB-1) comprising a compound of any of xxi-xxxi for the treatment of a disease or disorder associated with protein aggregation or neurodegeneration.

xxxiv. Use of a compound of any of paragraphs xxi-xxxi in the manufacturer of a composition for the treatment of a disease or disorder associated with protein aggregation or neurodegeneration.

xxxv. The compound of paragraphs xxxiii, wherein the disease or disorder associated with protein aggregation or neurodegeneration is selected from the group consisting of: Alzheimer's disease; Parkinson's disease; Down's syndrome; Huntington's disease; Creutzfeldt-Jakob disease (CJD); bovine spongiform encephalopathy (BSE); scrapie; or a tauopathy, such as Progressive supranuclear palsy, Dementia pugilistica (chronic traumatic encephalopathy, Frontotemporal dementia and parkinsonism linked to chromosome 17, Lytico-Bodig disease, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease and corticobasal degeneration.

xxxvi. The compound of paragraph xxxv, wherein the disease or disorder associated with protein aggregation or neurodegeneration is Alzheimer's disease.

xxxvii. The use of the compound of paragraph xxxiv, wherein the disease or disorder associated with protein aggregration or neurodegeneration is selected from the group consisting of: Alzheimer's disease; Parkinson's disease; Down's syndrome; Huntington's disease; Creutzfeldt-Jakob disease (CJD); bovine spongiform encephalopathy (BSE); scrapie; or a tauopathy, such as Progressive supranuclear palsy, Dementia pugilistica (chronic traumatic encephalopathy, Frontotemporal dementia and parkinsonism linked to chromosome 17, Lytico-Bodig disease, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease and corticobasal degeneration.

xxxviii. The method of any of paragraphs i-xx, wherein the $PrP^C$ ligand is administered to a subject diagnosed with a disease or disorder associated with protein aggregration or neurodegeneration.

xxxix. The method of any of paragraphs i-xx, wherein the $PrP^C$ ligand is administered to a subject who is at subject at risk of, or diagnosed has having developing a disease or disorder associated with protein aggregation or neurodegeneration.

xl. The method of any of paragraphs i-xx and xxxviii-xxxix, wherein the disease or disorder associated with protein aggregration or neurodegeneration is Alzheimer's disease.

xli. A kit comprising a composition one or more compounds of paragraphs xxi-xxxi, and instructions for administration to a subject.

xlii. Use of one or more compounds of any of paragraphs xxi-xxxi for preparation of a medicament for inhibiting Aβ oligomers binding to $PrP^C$ polypeptide.

xliii. A method to treat Alzheimer's disease in a subject, comprising administering to the subject a composition comprising a $PrP^C$ ligand, wherein the $PrP^C$ ligand binds with a $PrP^C$ polypeptide at $PrP^C$-binding domain 1 (PBD-1), $PrP^C$-binding domain 2 (PBD-2), $PrP^C$-binding domain 3 (PBD-3), $PrP^C$-binding domain 4 (PBD-4), $PrP^C$-binding domain 5 (PBD-5), or $PrP^C$-binding domain 6 (PBD-6).

xliv. A method to treat Alzheimer's disease in a subject, comprising administering to the subject a composition comprising at least one or more compounds of any of paragraphs xxi-xxxi.

xlv. The method of any of paragraphs xliii-xliv, wherein the subject has been diagnosed with Alzheimer's disease.

xlvi. The method of any of paragraphs xliii-xliv, wherein the subject is at risk of developing Alzheimer's disease.

xlvii. The method of any of paragraphs i-xx and xxxviii-xl, wherein the $PrP^C$ ligand promotes or induced an auto inhibitory conformational change in PrPc that allows interaction of the N and C terminal promoters.

The disclosure is further illustrated by the following examples which should not be construed as limiting. The examples are illustrative only, and are not intended to limit, in any manner, any of the aspects described herein. The following examples do not in any way limit the invention.

EXAMPLES

Materials and Methods

In Silico Analyses to Identify PDB-1 and DS26.

Protein structures. NMR structures of the mouse PrP (PDB code 1XYX, 20 conformations) were used for target-based, in silico drug discovery experiments. The 20 NMR conformations of $PrP^C$ used in this study were retrieved from the RCSB Protein Data Bank (PDB code 1XYX) and prepared using the Schrödinger Protein Preparation utility to ensure their chemical correctness. The orientation of hydroxyl groups on Ser, Thr and Tyr, the side chains of Asn and Gln residues, and the protonation state of His residues were optimized N- and C-terminal residues were capped with ACE and NMA residues, respectively. Steric clashes were relieved by a limited number of minimization steps, employing OPLS-2005 force field and an RMSD for non-hydrogen atoms of 0.30 Å as convergence criteria.

Sitemap analyses. In order to define potential binding sites on the surface of the $PrP^C$ protein, the 20 NMR conformations of mouse recombinant $PrP^C$ (residues 121-231) were submitted to SiteMap calculations. For each conformation, up to 5 sites composed of at least 15 site points were reported, cropping each site at 4 Å from the nearest site point. Reported sites were scored with the embedded SiteScore scoring function, resulting in the identification of PBD-1, which recurred with relatively high scores across all of the 20 NMR conformations. PBD-1 was targeted in the virtual screening experiments.

Docking grid generation. Docking-based virtual screening simulations were performed using the Glide program. The prepared NMR conformations were used as input to prepare the receptor grids. The grids were centered on the centroid of residues 134-137, 150, 154, 155,157-160, 209, 210, and 213, and the docking space was defined as a 24 Å³ cubic box. The diameter midpoint of docked ligands was required to remain within a smaller, nested 14 Å³ cubic box. No softening was used for the potential of nonpolar parts of the protein.

Virtual Screening. For the virtual screen that led to the identification of DS26, all of the NMR conformations were used as docking targets. The ZINC database (standard purchasable chemical universe) was first screened using Glide HTVS against NMR conformation 8 (which had the highest scoring PBD-1 by SiteMap analysis). A post-docking constraint was applied to the compounds retried: only those molecules able to fit at least one non hydrogen atom in a 5 Å diameter sphere centered on the centroid of PBD-1 were kept. The 10% top scoring molecules retrieved from GLIDE HTVS were then docked using Glide SP against all of the NMR conformations. The top 10% best scoring docking poses from this analysis, consisting of twenty 4,000 member sets of docked molecules, were refined, rescored, and minimized using Glide XP against all of the target structures. Consensus scores were then calculated using the following equation:

$$\text{score} = \left\{ \sum_{r=1}^{n} XPGscore\left(1 + \frac{1}{HA}\right) \right\} / n$$

where n is the total number of r target structures, XPGscore is the score assigned to the pose by Glide XP, and HA is the ligand heavy atom count. The XPGscore/HA term was included in the consensus score calculation in an attempt to overcome molecular weight-related overestimation of binding energies.

Using the Canvas program, the ~80,000 resulting compounds were then subjected to duplicate removal (keeping the best scoring duplicate only), and for the 10,000 best scoring compounds, mol2d 64 bit fingerprints were calculated, with the goal of making a diversity-based selection. After molecular diversity filtering and visual inspection of docking poses, 122 candidates were selected for further analysis. These candidates were submitted to molecular dynamics (MD) simulations performed by means of the MacroModel program. Before running the MD simulations, all of the complexes were relaxed by 200 steps of PRCG energy minimization. A simplified MD model was employed, with the following features: (i) MM-GB/SA was used as solvation treatment; (ii) residues defining PBD-1, residues within a distance of 2 Å from PBD-1, and residues 130-161 were set as fully flexible; (iii) residues within a 3 Å distance from the fully flexible set, and not comprised in it, were constrained by a 100 kcal/mol force; and (iv) the remaining protein residues were kept frozen. RMSDs for non-hydrogen atoms belonging to the fully flexible shell and for ligand non-hydrogen atoms were calculated in function of the 20 ns simulation time. For each simulation, standard deviations (SDs) were calculated for the RMSD time series to see whether a ligand was able to stay bound to the protein and to stabilize the flexible protein set. On the basis of these SD values, 52 molecules were finally selected for SPR assays.

MD simulations of ligand-complexed PrP$^C$. MD simulations were run in explicit solvent, using the TIP4P water model in a Periodic Boundary Conditions orthorhombic box. Desmond molecular dynamics (MD) system (version 30110) was used to setup and run the MD simulations. The simulated environment was built using the system builder utility, with the structures being neutralized by Na$^+$ and Cl$^-$ ions, which were added until a concentration of 0.15 M was reached. The buried regions were solvated using the "solvate pocket" utility. Before performing the simulations, a series of minimizations and short MD simulations was carried out to relax the model system, by means of a relaxation protocol consisting of six stages: (i) minimization with the solute restrained; (ii) minimization without restraints; (iii) simulation (12 ps) in the NVT ensemble using a Berendsen thermostat (10 K) with non-hydrogen solute atoms restrained; (iv) simulation (12 ps) in the NPT ensemble using a Berendsen thermostat (10 K) and a Berendsen barostat (1 atm) with non-hydrogen solute atoms restrained; (v) simulation (24 ps) in the NPT ensemble using a Berendsen thermostat (300 K) and a Berendsen barostat (1 atm) with non-hydrogen solute atoms restrained; (vi) unrestrained simulation (24 ps) in the NPT ensemble using a Berendsen thermostat (300 K) and a Berendsen barostat (1 atm). At this point, 30 ns long MD simulations were carried out at a temperature of 300° K in the NPT ensemble using a Nose-Hoover chain thermostat and a Martyna-Tobias-Klein barostat (1.01325 bar).

Modeling of the PrP/DS26 complex. The conformation of DS26 was optimized by conformational analysis (Macro-Model, OPLS-2005) and DFT optimization (B3LYP, 631-G*). Glide SP was used to dock DS26 against all of the NMR conformations. A maximum of three docking poses was retrieved for each target structure, and poses were discarded as duplicates when RMS deviation was less than 1.5 Å and maximum atomic distance was less than 2.3 Å. The set of bound conformations of DS26 was then refined, rescored and minimized using Glide XP. The best docking pose was then used to build the DS26/PrP complex, which was relaxed using 100 steps of PRCG minimization, using OPLS-2005 force field and GB/SA as solvation treatment.

Synthesis and characterization of DS26 and DS104. All reagents and solvents were purchased directly from commercial sources and used without further purification. Hydrophilic interaction liquid chromatography (HILIC) was accomplished using Interchim brand 35 g, 30µ, columns.

DS26: 2-((2R,3R,4S,5R,6S)-2,3,4,5,6-pentahydroxycyclohexylidene)hydrazinecarbothioamide (FIG. 25). 200 mg (1.12 mmol) of 1 L-epi-2-inosose (1) was dissolved in 11.2 mL (0.1M) of H$_2$O/EtOH (1:4). 102.3 mg (1.12 mmol, 1 eq.) of thiosemicarbazide was added to the reaction mixture as a solid. Into the reaction was added 0.64 mL (10 eq.) of acetic acid and the mixture was stirred for 12 h at 60° C. The solvent was removed in vacuo and the crude mixture was purified using hydrophilic interaction liquid chromatography (0% MeOH/DCM to 50% MeOH/DCM gradient). Macroporous polymer-supported sulfonyl hydrazine was added to the solvent fractions to remove residual ketone (1). After stirring for 30 minutes, the mixture was filtered and concentrated in vacuo to afford 245 mg (87%) of DS26 as a 1:1 mixture of isomers (FIG. 26A).

DS26 (Z-isomer): $^1$H-NMR (400 MHz, d$_6$-DMSO) (FIG. 26B): δ 11.77 (s, 1H), 8.26 (s, 1H), 8.07 (s, 1H), 6.60 (s, 1H), 5.16 (s, 1H), 5.01 (s, 1H), 4.69 (s, 2H), 4.57 (s, 1H), 3.75 (s, 1H); $^{13}$C-NMR (400 MHz, d$_6$-DMSO): δ 177.13, 148.49, 76.80, 75.16, 75.07, 72.53, 71.29

DS26 (E-isomer): $^1$H-NMR (400 MHz, d$_6$-DMSO) (FIG. 26C): δ 11.99 (s, 1H), 8.28 (s, 1H), 8.07 (s, 1H), 6.75 (d, J=4.70 Hz, 1H), 5.24 (d, J=5.09 Hz, 1H), 4.77 (d, J=1.96 Hz, 1H), 4.75 (s, 1H), 4.66 (d, J=5.67 Hz, 1H), 4.21 (dd, J$_1$=9.39 Hz, J$_2$=4.50 Hz, 1H), 3.52 (td, J$_1$=9.39 Hz, J$_2$=4.70 Hz, 1H); $^{13}$C-NMR (400 MHz, d$_6$-DMSO): δ 177.29, 147.63, 76.70, 74.86, 74.11, 71.65, 70.50

DS104: (Z)—N-(3',6'-dihydroxy-3-oxo-3H-spiro[isobenzofuran-1,9'-xanthen]-5-yl)-2-((2R,3R,4S,5R,6S)-2,3,4,5,6-pentahydroxycyclohexylidene)hydrazinecarbothioamide.

100 mg (0.257 mmol) of fluorescein isothiocyanate was dissolved in 2.06 mL (0.08M) of EtOH. Into the reaction was added 8.1 µL (0.257 mmol, 1 eq.) of hydrazine and the resulting solution was stirred for one hour at room temperature. Into the reaction was added 45.8 mg (0.257 mmol, 1 eq.) of 1 L-epi-2-inosose as a solution in 0.52 mL of water followed by 0.15 mL (10 eq.) of acetic acid. The reaction was stirred for 12 h at 40° C. The solvent was evaporated and the crude mixture was purified via hydrophilic interaction liquid chromatography (0% MeOH/DCM to 50% MeOH/DCM gradient). Macroporous polymer-supported sulfonyl hydrazine was then added to the solvent fractions in order to scavenge residual ketone (1). After stirring for 30 minutes, the mixture was filtered and concentrated in vacuo to afford mg (%) of DS104 as a 1:1 mixture of isomers.

Expression and purification of recombinant PrP. cDNAs encoding mouse PrP (23-230, 23-111 [N-PrP], or 120-230 [C-PrP], or human PrP were amplified by PCR with an N-terminal 6×His tag (MRGSHHHHHH; SEQ ID NO: 4) and a C-terminal c-myc tag (EQKLISEEDL; SEQ ID NO: 5), and inserted into the peT101 TOPO E. coli expression vector (Invitrogen) using one step PCR. TOP10 or BL21 Star chemically competent E. coli were transformed with each plasmid, and expression was induced by growing cells in auto-induction media overnight. Inclusion bodies were isolated and solubilized in a buffer containing 8 M urea, 10 mM β-mercaptoethanol, 100 mM Na-phosphate, and 10 mM Tris-HCl (pH 8). The solubilized PrP proteins from inclusion bodies was passed over a nickel-IMAC column, and the bound PrP refolded and oxidized overnight by washing the column with a linear gradient of 8 M to 0 M urea in 100 mM Na-phosphate and 10 mM Tris-HCl (pH 8). The refolded PrP was then eluted from the column using 250 mM imidazole-HCl. The α-helical content was confirmed using far-UV CD.

Preparation of Aβ oligomers. Synthetic Aβ (1-42) peptide (American Peptide, Sunnyvale, Calif.) was dissolved in hexafluoro-2-propanol, sonicated, aliquoted, and stored (after evaporation) at −80° C. Before use, the dried film was dissolved using DMSO and diluted to 100 µM in F12 Medium (Invitrogen). Aβ oligomers were obtained by incubating the peptide for 16 hrs at 25° C. This preparation routinely produces oligomers that elute near the void volume of a Superdex 75 10/300 column (GE Healthcare) size exclusion column, and that react with oligomer-specific antibody A11. Preparations were checked by size-exclusions chromatography before use. Aβ oligomer concentrations are given in monomer equivalents, since the size of the oligomers is heterogeneous Surface Plasmon Resonance (SPR). Binding studies were performed using the ProteOn XPR36 Protein Interaction Array system (Bio-Rad). Detection of $PrP^C$ binding to small compounds was obtained by immobilizing mouse or human recombinant $PrP^C$ molecules on the surface of a sensor chip (GL-H chip, Biorad) by amine-coupling chemistry. For studies involving Aβ oligomers, myc-tagged, recombinant $hPrP^C$ was captured by anti-PrP monoclonal antibody D18 or anti-Myc antibody 4A6 (Millipore), which were previously immobilized on the sensor chip (GL-C chip, Biorad) by amine-coupling chemistry. Binding of Aβ1-42 oligomers (2 µM) to $PrP^C$ was tested after injection of different concentrations (0-100 µM) of DS26 dissolved in doubly distilled $H_2O$ ($ddH_2O$). The resulting sensorgrams (time course of resonance unit signal) were fitted to the simplest 1:1 interaction Langmuir binding model using the ProteOn analysis software to obtain the corresponding association and dissociation rate constants ($k_{on}$ and $k_{off}$, respectively), and the equilibrium dissociation constant ($K_D$) (details in figure legends).

Fluorescence polarization. Samples containing recombinant C-PrP (120-230) were mixed with DS104 and allowed to equilibrate for 60 min. Fluorescence polarization was measured on a Synergy H1MF plate reader (Biotek, Winooski, Vt.) fitted with a 485 nm excitation filter and 528 nm emission filter in both the parallel and perpendicular polarization light paths. Polarization values were calculated using the Synergy Gen 5 software (Biotek Winooski, Vt.) and expressed in millipolarizaiton units (mP).

Circular dichroism (CD) and thermal stability assay. CD spectra for human recombinant $PrP^C$ was recorded at different temperatures and collected using a Jasco J-815 spectropolarimeter equipped with thermoelectric temperature controllers (Jasco Inc., Japan). α-helical content of recombinant PrP was monitored at a wavelength of 220 nm. A temperature ramp rate of 1.0° C./min was applied from 25 to 95° C. Thermal unfolding curves were measured after pre-incubation for 20 min at 20° C. in the presence or absence of 100 µM of DS26. The curves were smoothed using Sigma Plot (Systat Software, San Jose, Calif.) software. The melting temperature ($T_m$) for each sample was determined from the first derivative of the melting curve. Standard deviation was calculated based on three independent Tm measurements.

Tryptophan fluorescence. Tryptophan fluorescence data were collected using a Synergy H1MF (Biotek Winooski, Vt.). PrP (5 uM) was incubated with various concentrations of DS26 or DS15 for 1 hr before fluorescence measurements. The samples were excited at 278 nm and emission spectra were collected from 300 to 450 nm using a monochromator light path. Values represent an average of 3 replicate wells.

N-PrP/C-PrP co-immunoprecipitation assay. C-PrP was incubated with myc-tagged N-PrP in binding buffer (200 mM NaCl, 0.1% NP-40, 50 mM Tris-HCl, pH 7.5), at 4° C. for 4 h, in the absence or presence of DS26. Anti-myc antibody 4A6 was cross-linked onto Dynabeads containing anti-mouse IgG (Invitrogen), and the beads were then incubated with each sample at 4° C. for 2 h. Beads were washed twice with binding buffer and re-suspended in loading buffer for immunoblot analysis using anti-PrP antibodies 6D11 or D18.

Cell-based Aβ binding assay. HEK293 cells (ATCC CRL-1573) were maintained in α-minimum essential medium/Dulbecco's modified Eagle's medium (1:1) supplemented with nonessential amino acids, L-glutamine, 10% fetal bovine serum, penicillin/streptomycin, and 50 µg/ml hygromycin. Stable lines were created by transfecting cells with pcDNA3.1(+)Hygro (Invitrogen) vector alone or with vector containing the cDNA sequence for wild type (WT) murine PrP using Lipofectamine 2000 (Invitrogen) according to the manufacturer's directions. Deletion of residues 105-125 and point mutations (P136G, M153G, N158V, and V208D) were introduced into WT mouse PrP using a QuikChange site-directed mutagenesis kit (Stratagene). Clones were selected for 14 days in 200 µg/ml hygromycin.

HEK293 cells stably expressing either WT PrP or empty vector were grown in PDL-coated, 24-well plates (BD Biosciences). Cells receiving drug treatment were pre-incubated for 30 min with DS26 in F12 media. Cells were incubated with biotinylated-Aβ 1-42 oligomers in F12 media for 1 hr. Unbound Aβ was removed by vigorous washing with PBS. The cells were fixed with 4% paraformaldehyde at room temperature for 10 min and washed with PBS. Next, the cells were blocked for 20 min with 3% goat serum and 0.1% Triton X-100 in PBS, and then incubated at 4° C. overnight with alkaline-phosphatase-conjugated streptavidin in PBS supplemented with 1.5% goat serum and 0.05% Triton X-100. Lastly, alkaline phosphatase was visualized by incubation with 5-bromo-4-chloro-3-indolyl phosphate/nitro blue tetrazolium, according to manufacturer's instructions (Pierce). Digital micrographs of cells were acquired on a Nikon TE-2000E inverted fluorescence microscope (Nikon Instruments, Melville, N.Y., USA), and ImageJ was used to quantify the amount of bound Aµ. This procedure is similar to the one used by Lauren et al.

Patch clamping of HEK cells. Assay of the spontaneous ion channel activity induced by ΔCR PrP in HEK cells was performed by whole-cell patch clamping as previously described (Solomon et al. JBC 2011). Pipettes were pulled from borosilicate glass, coated with Sylgard, and polished to an open resistance of 1-10 megaohms Experiments were conducted at room temperature with the following solutions: internal: 140 mM cesium glucuronate, 5 mM CsCl, 4 mM MgATP, 1 mM Na2GTP, 10 mM EGTA, and 10 mM HEPES (pH7.4 with CsOH); external: 150 mM NaCl, 4 mM KCl, 2 mM CaCl2, 2 mM MgCl2, 10 mM glucose, and 10 mM HEPES (pH 7.4 with NaOH). Current signals were collected from an Axopatch 200B amplifier and digitized with a Digidata 1330 interface (Axon Instruments) or with an EPC-10 amplifier controlled by Patch-Master acquisition software (HEKA Elektronik) and were saved to disc for analysis with PClamp 9 software. Quantification of current activity was obtained by calculating the proportion of total recording time that a cell exhibited inward current≥450 pA.

Analysis of Synaptic Proteins in Primary Hippocampal Culture. Primary neuronal cultures were derived from the hippocampuses of 2-day-old postnatal mice and cultured as described previously. Briefly, neurons were plated on 35-mm dishes (600,000 cells/dish) precoated with 25 g/ml poly-D-lysine (Sigma P6407) in B27/Neurobasal-A medium supplemented with 0.5 mM glutamine, 100 units/ml penicillin, and 100 μg/ml streptomycin (all from Invitrogen). Experiments were performed 12 days after plating. Neurons were exposed for 3 h to Aβ oligomers (1 μM) that had been preincubated for 1 h at 4° C. with DS26 (100 μM) or with vehicle. Subcellular fractionation was performed as reported previously with minor modifications. Briefly, neurons were homogenized using a Potter-Elvehjem homogenizer in 0.32 M ice-cold sucrose buffer (pH 7.4) containing 1 mM HEPES, 1 mM MgCl2, 1 mM EDTA, 1 mM NaHCO3, and 0.1 mM PMSF in the presence of protease (Complete, Roche Applied Science) and phosphatase (Sigma) inhibitor mixtures. Samples were centrifuged at 3000×g for 15 min to obtain a crude membrane fraction. The pellet was resuspended in buffer containing 75 mM KCl and 0.5% Triton X-100 and centrifuged at 100,000×g for 1 h. The final pellet, referred to as the Triton-insoluble fraction, was rehomogenized in 20 mM HEPES supplemented with protease and phosphatase inhibitors and then stored at_80° C. or directly used in further experiments. The protein concentration in each sample was quantified using the Bradford assay (Bio-Rad), and Triton-insoluble fraction-extracted proteins (5 μg) were then analyzed by Western blotting. The primary antibodies used were anti-GluN2A and anti-GluN2B (both 1:2000; Invitrogen), anti-GluA1 and anti-GluA2 (both 1:1000; Millipore), anti-PSD95 (postsynaptic density protein 95; 1:2000; Cayman Chemical), and anti-tubulin (1:5000; Santa Cruz Biotechnology). Western blots were quantified by densitometry using Quantity One software (Bio-Rad). All experiments were repeated on six independent culture preparations (n=6).

Hippocampal slice preparation and electrophysiology. Prn-p$^{0/0}$ mice (Zurich I) on an inbred C57BL6 background were obtained from the European Mouse Mutant Archive (EMMA, Rome). Mice had access to food and water ad libitum and were maintained on a 12 h light/dark cycle. Housing and experimental protocols were in accordance with the Guidelines for Care and Use of Laboratory Animals of the National Institutes of Health and approved by the Boston University Animal Care Committee.

Coronal hippocampal slices (400 mm) from adult (2-4 months of age) male C57BL6 control or Prn-p$^{0/0}$ mice were bathed in oxygenated normal artificial cerebrospinal fluid (naCSF). The composition of the naCSF was as follows: 119 mM NaCl, 2.5 mM KCl, 1.3 mM MgCl$_2$, 2.4 mM CaCl$_2$, 26.2 mM NaHCO$_3$, 11 mM D-glucose, 1.25 mM NaH$_2$PO$_4$. Synaptic responses were evoked with a bipolar electrode (FHC, USA) placed in the Schaffer collateral pathway. Evoked CA1 field potentials were recorded and the slope of the EPSP (fEPSP) determined (Clampfit, Molecular Devices, USA). LTP was induced with ten 100 Hz trains (five pulses) delivered with a 5 Hz inter-burst-interval. Verified Aβ oligomers (500 nM) or DS26 (100 μM) were bath-applied during baseline recordings for 20 min before inducing LTP. In the experiments when both Aβ oligomers and DS26 were utilized, DS26 was applied for 20 min, followed by 20 min of Aβ oligomers application.

The slope of the fEPSP was measured and used for all statistical comparisons of LTP experiments. fEPSP recordings were normalized to the average value of the 20 min baseline and reported as percent change from baseline. LTP was calculated by averaging the last 10 traces (i.e., 55-60 min) of the post-theta burst stimulation recording. Statistical differences were examined with a one-way analysis of variance (ANOVA) and Tukey-HSD post hoc tests. Results were processed for statistical analysis using Prism (Graph-Pad, USA), and differences were considered significant when p<0.05. Data are presented as means±standard error of the mean (SEM).

Example 1

A wide range of devastating human diseases is characterized by abnormal folding of cellular proteins and their deposition in vital organs. Among these are neurodegenerative disorders, such as Alzheimer's, Parkinson's and prion diseases, in which misfolded proteins accumulate in the brain, causing memory loss, movement disturbances, and frequently death Alzheimer's disease is associated with progressive dementia and accumulation in the brain of the amyloid-β (Aβ) peptide, a cleavage product of the amyloid precursor protein. Compelling evidence suggests that soluble, oligomeric assemblies of Aβ are primarily responsible for the synaptic dysfunction underlying the cognitive decline in Alzheimer's disease. So far, the identity of the cellular receptors to which these oligomers bind to exert their neurotoxic effects has remained enigmatic.

Soluble oligomers of the amyloid-β (Aβ) peptide, a cleavage product of the amyloid precursor protein, are primarily responsible for synaptic dysfunction in Alzheimer's disease (AD). The cellular prion protein (PrP$^C$), a cell surface glycoprotein involved in transmissible spongiform encephalopathies, has been shown to bind Aβ oligomers and transduce downstream synaptotoxic signaling. Thus, PrP$^C$ may represent a novel therapeutic target for treatment of AD. Here we describe the identification of a high-affinity ligand for PrP$^C$ that blocks the neurotoxic effects of Aβ oligomers in cell cultures and brain slices. The compound exerts this activity by inducing an unexpected and unusual allosteric, auto-inhibitory change in the conformation of PrP$^C$, which blocks interaction with Aβ oligomers. These results provide the first example of an entirely new class of potential AD therapeutics directed against PrP$^C$-mediated neurotoxic pathways, rather than formation or clearance of Aβ.

Recently, the cellular form of the prion protein (abbreviated PrP$^C$), a membrane glycoprotein expressed at the neuronal surface, has been identified as a receptor for Aβ oligomers and other toxic protein aggregates associated with neurodegenerative disorders. Growing evidence indicates that PrP$^C$ could directly be involved in the pathogenesis of these diseases by transducing the neurotoxic effects of the aggregates. Surprisingly, PrP$^C$ has already been studied in the context of a completely different group of neurodegenerative disorders, known as prion diseases. Thus, PrP$^C$ represents a unique molecular target for the development of therapeutic agents to treat Alzheimer's disease, prion diseases and other neurodegenerative disorders linked to protein aggregation. Drugs that bind to PrP$^C$ have the potential to block the neurotoxic effects of protein aggregates, and thereby prevent neurodegeneration.

Here, the inventors describe the identification of small, high affinity ligands for PrP$^C$ that bind to a defined three-dimensional pocket on the surface of the protein, inhibit its biological activity, prevent binding to Aβ oligomers, and inhibit the synaptotoxic activity of Aβ oligomers in brain slices. These compounds represent an entirely new class of therapeutic agents for Alzheimer's disease, prion diseases, and other neurodegenerative disorders due to protein aggregation.

In order to identify small molecule ligands that bind to PrP$^C$, block its ion channel activity, inhibit formation of PrP$^{Sc}$, prevent binding to protein aggregates, and suppress synaptotoxicity of the aggregates, the inventors undertook a series of computational, biophysical and biochemical analyses to define the potential binding sites in the C-terminal, structured domain of the PrP$^C$ protein. These studies led to discovery of a previously unknown pocket on the surface of PrP$^C$, and identification of four ligands, which have been designated DS5, DS26, DS40 and DS86. DS26, the most promising of the four compounds, binds to PrP$^C$ with sub-micromolar affinity and a very slow off-rate. It inhibits formation of PrP$^{Sc}$ in scrapie-infected cells, and silences the ion channel activity of a neurotoxic PrP mutant. Importantly, binding of DS26 potently inhibits the interaction between PrP$^C$ and Aβ oligomers, and suppresses the synaptotoxic effects of Aβ oligomers in hippocampal slices. DS26 also stabilizes the native fold of PrP$^C$, and causes an allosteric, auto-inhibitory interaction between the N- and C-terminal domains of PrP$^C$. Collectively, these data define a novel pharmacological target and a completely new class of therapeutic agents for Alzheimer's and prion diseases, which act via a novel molecular mechanism, and which may show beneficial effects in other neurodegenerative conditions as well.

Identification of a novel, solvent-accessible pocket on the surface of PrP$^C$. The first step in identifying small molecule ligands that bind to PrP$^C$ with high-affinity is to define potential binding sites on the surface of the protein. The three dimensional structure of the globular domain of mouse recombinant PrP$^C$ (residues 121-231) has been solved using SiteMap software (Schrödinger) to scout the surface of 20 different NMR conformations of mouse PrP$^C$ (PDB 1XYX) using by NMR spectroscopy. Binding sites that recurred in all the available NMR conformations were ranked on the basis of size, functionality, and extent of solvent exposure. This analysis identified a common binding regions on the surface of PrP$^C$ (named PrP-binding domains 1 or PBD-1), defined by twelve non-continuous residues located in the globular domain of the protein. The PBD-1 was determined to comprise amino acids 133, 134, 135, 136, 149, 153, 154, 156, 157, 158, 159, 208, 209, and 212 of mouse PrP$^C$ (sequence numbering based on GenBank Accession Number NP_035300). The corresponding residues of PBD-1 in human PrP$^C$ are 134, 135, 136, 137, 150, 154, 155, 157, 158, 159, 160, 209, 210, and 213 (sequence numbering based on GenBank Accession Number AAA60182), which were recurrent in all conformations of the protein (FIG. 16A). These residues lie within the loops flanking both ends of helix 1 and the N-terminal end of helix 3.

Example 2

Figure 13D:
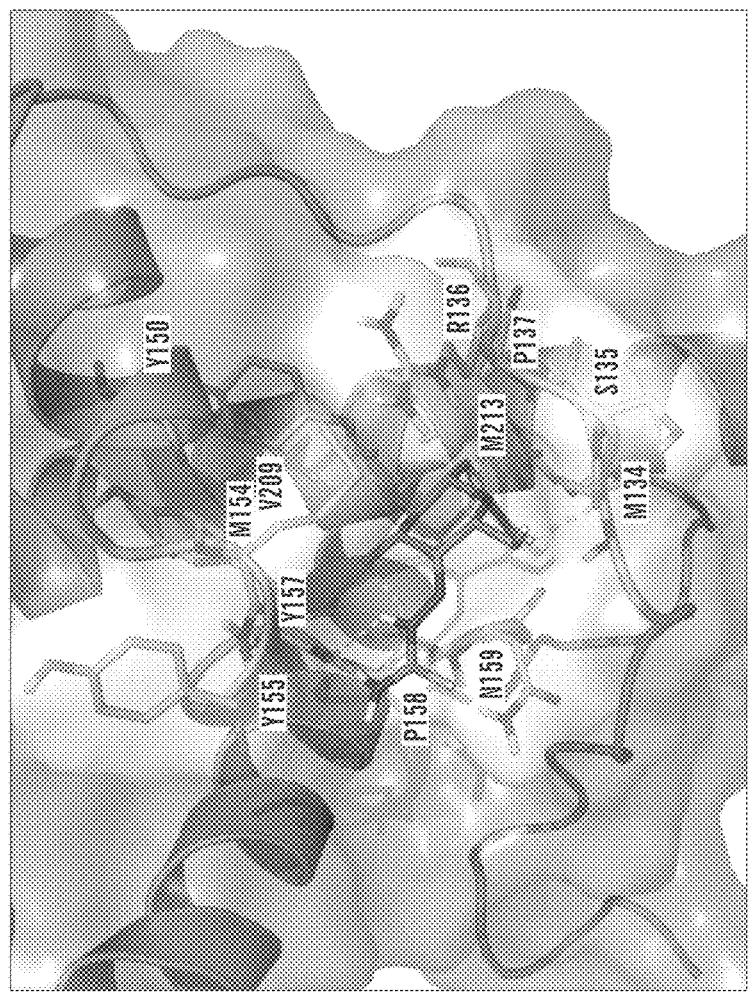

To identify high affinity ligands for PrPC, the inventors performed a set of virtual screens. In the largest of these screens (see workflow in FIG. 13B), the inventors used the GLIDE program to screen the ZINC database, consisting of ~17 million commercially available molecules, using as a target PBD-1 in all of the different NMR conformations of PrPC. Compounds predicted to bind the PBD-1 site were filtered by molecular diversity and visual inspection, and finally prioritized by molecular dynamics (MD) to predict the stability of each protein-ligand complex. These analyses identified 52 candidate molecules. Among these, 16 were available in the compound library of the National Cancer Institute (See FIGS. 24A and 24B), and were tested for binding to PrPC by SPR a label-free technique that allows estimation of kinetic and binding constants for protein-ligand interactions. One of the molecules was found to bind PrPC with sub-micromolar affinity, and was chosen for further analysis: 2-(2R,3S,5R,6S-pentahydroxycyclohexylidene)hydrazinecarbothioamide (designated DS26; FIG. 13C). FIG. 13D shows a model of DS26 docked in the PBD-1 site. Several other molecules that bind to PrPC with lower affinity were also identified in these virtual screens, which include DS5, DS40 and DS86 as disclosed in FIGS. 27A-27C.

Example 3

Identification of additional binding sites on PrP$^C$. The PrP$^C$ ligand DS26 was used as a probe to explore the protein surface of PrP$^C$ and locate additional regions potentially able to bind DS26. The NMR conformation of mouse PrP (PDB code 1XYX, 20 conformations) was submitted to replica-exchange molecular dynamics calculations in explicit solvent, using the TIP4P water model in a Periodic Boundary Conditions cubic box. Desmond molecular dynamics (MD) system (version 2.4) was used to set up and run the MD simulations. After system building and preparation, 20-ns long replica-exchange molecular dynamics simulations were carried at temperatures ranging from 300 to 320 K in the NPT ensemble using a Berendsen thermostat (300 K) and a Berendsen barostat (1 atm); in total, 11 replicas were simulated, with the intermediate temperatures calculated according to the scheme described by Patriksson et al. (Patriksson et al. Phys. Chem. Chem. Phys., 2008, 10, 2073-2077). Configuration swaps between the replicas were attempted every 12 ps and structures were sampled every 10 ps. The trajectories were then clustered in order to select a set of representative structures, which together with the NMR conformations were used as targets in DS26 docking experiments. Sitemap calculations were performed on each representative structure mined from the MD trajectory, and docking grids were built using the centroid of each detected site as grid center. At this point, DS26 was docked using all of the generated grids using Glide SP, and each obtained pose was then refined, rescored and minimized using Glide XP. Clusters of high-scoring, docked DS26 molecules were used to identify potential binding regions, which were called PBD-2 through PBD-6.

The PBD-2 was discloseved to comprise amino acids 129, 155, 156, 157, 158, 159, 160, 161, 182, 183, 185, 186, 187, 188, 189, 190, 197, and 205 of mouse PrP$^C$ (sequence numbering based on GenBank Accession Number NP_035300). The corresponding residues in human PrP$^C$ are 130, 156, 157, 158, 159, 160, 161, 162, 183, 184, 186, 187, 188, 189, 190, 191, 198, and 206 (sequence numbering based on GenBank Accession Number AAA60182).

The PBD-3 was discloseved to comprise amino acids 165, 166, 168, 169, 170, 171, 175, 214, 217, 218, 220, 221, 222, 224, 225, and 226 of mouse PrP$^C$ (sequence numbering based on GenBank Accession Number NP_035300). The corresponding residues in human PrP$^C$ are 166, 167, 169, 170, 171, 172, 176, 215, 218, 219, 221, 222, 223, 225, 226, and 227 (sequence numbering based on GenBank Accession Number AAA60182.

The PBD-4 was discloseved to comprise amino acids 127, 163, 164, 167, 168, 169, 170, 173, 174, 175, and 177 of mouse PrP$^C$ (sequence numbering based on GenBank Accession Number NP_035300). The corresponding residues in human PrP$^C$ are 128, 164, 165, 168, 169, 170, 171, 174, 175, 176, and 178 (sequence numbering based on GenBank Accession Number AAA60182.

The PBD-5 was discovered to comprise amino acids 131, 132, 133, 134, 135, 136, 137, 138, 139, 143, 146, 149, 150, 151, 153, 211, 212, 214, 215, 216, 218, 219, 220, 221, 222, and 223 of mouse PrP$^C$ (sequence numbering based on GenBank Accession Number NP_035300). The corresponding residues in human PrP$^C$ are 132, 133, 134, 135, 136, 137, 138, 139, 140, 144, 147, 150, 151, 152, 154, 212, 213, 215, 216, 217, 219, 220, 221, 222, 223, and 224 (sequence numbering based on GenBank Accession Number AAA60182.

The PBD-6 was discovered to comprise amino acids 171, 175, 176, 179, 180, 183, 184, 187, 205, 206, 207, 209, 210, and 214 of mouse PrP$^C$ (sequence numbering based on GenBank Accession Number NP_035300). The corresponding residues in human PrP$^C$ are 172, 176, 177, 180, 181, 184, 185, 188, 206, 207, 208, 210, 211, and 215 (sequence numbering based on GenBank Accession Number AAA60182.

TABLE 2A

Amino acids in the PDBs of human PrP$^C$(Human sequence numbering is based on GenBank Accession Number AAA60182 (SEQ ID NO: 1))

| Domain | Amino acids |
|---|---|
| PDB-1 | 134, 135, 136, 137, 150, 154, 155, 157, 158, 159, 160, 209, 210, and 213 |
| PDB-2 | 130, 156, 157, 158, 159, 160, 161, 162, 183, 184, 186, 187, 188, 189, 190, 191, 198, and 206 |
| PDB-3 | 166, 167, 169, 170, 171, 172, 176, 215, 218, 219, 221, 222, 223, 225, 226, and 227 |
| PDB-4 | 128, 164, 165, 168, 169, 170, 171, 174, 175, 176, and 178 |
| PDB-5 | 132, 133, 134, 135, 136, 137, 138, 139, 140, 144, 147, 150, 151, 152, 154, 212, 213, 215, 216, 217, 219, 220, 221, 222, 223, and 224 |
| PDB-6 | 172, 176, 177, 180, 181, 184, 185, 188, 206, 207, 208, 210, 211, and 215 |

TABLE 2B

Amino acids in the PDBs of mouse PrP$^C$(Mouse sequence numbering is based on GenBank Accession Number NP_035300 (SEQ ID NO: 2))

| Domain | Amino acids |
|---|---|
| PDB-1 | 133, 134, 135, 136,149,153,154,156, 157, 158, 159, 208, 209, and 212 |
| PDB-2 | 129, 155, 156, 157, 158, 159, 160, 161, 182, 183, 185, 186, 187, 188, 189, 190, 197, and 205 |
| PDB-3 | 165, 166, 168, 169, 170, 171, 175, 214, 217, 218, 220, 221, 222, 224, 225, and 226 |
| PDB-4 | 127, 163, 164, 167, 168, 169, 170, 173, 174, 175, and 177 |
| PDB-5 | 131, 132, 133, 134, 135, 136, 137, 138, 139, 143, 146, 149, 150, 151, 153, 211, 212, 214, 215, 216, 218, 219, 220, 221, 222, and 223 |
| PDB-6 | 171, 175, 176, 179, 180, 183, 184, 187, 205, 206, 207, 209, 210, and 214 |

Example 4

Exemplary analogues of DS26. Based on information from molecular modelling (cf. FIG. 13D) the inventors designed an initial set of D26 analogs with minor modification of the semi thiocarbazide side chain (FIGS. 4A and 4B). Analogs addressed substitution at each nitrogen atom of the semi thiocarbazide. These compounds were evaluated for binding to mouse PrP using SPR. All but two were found to be active. Notably, the two inactive compounds were subsequently analysed and determined to have decomposed. Thus, all of the structurally competent analogs were found to bind mouse PrP with an affinity similar to D26. Additional DS26 analogues which bind to $PrP^C$ are shown in FIG. 30A.

The data from the DS26 analogs show that variability of the side chain is well tolerated, and a wide range of DS26 analogs can be synthesized and used. DS26 analogues which do not bind to $PrP^C$ are shown in FIG. 31A. Furthermore, the inventors are currently investigating the requirement of the inosose warhead. These analogs will include deoxy-sugar derivatives, aza-sugar derivatives and O-substituted derivatives. FIG. 4C illustrates an exemplary generalized chemical scaffold base on DS26 that can be utilized to generate novel chemical matter and improve biological and physiochemical properties.

Preparation of DS26 derivatives. A substituted hydrazine is placed into flame-dried glassware under an atmosphere of argon. An equivalent of an isothiocyanate is added and the flask is charged with anhydrous ethanol to form a 0.1M solution. The mixture is stirred for 2 hours at room temperature. At this time, an equivalent of 1 L-epi-2-inosose and 0.2 equivalents of p-toluenesulfonic acid monohydrate are added to the mixture. The solution is continued to stir until completion of the reaction. The solvent is then removed under vacuum, and the crude product is purified by preparative reverse-phase HPLC.

Exemplary analogues of DS5, DS40 and DS86. DS5 analogs (FIG. 5A) can be synthesized based on literature procedures beginning with L- or D-mannose. Generally, condensation with an amine (R3) followed by cyclization of the subsequent imine affords the sugar bearing free hydroxyls. Appropriate protection schemes for the primary and secondary alcohols the allow diversification for R1 and R2. DS40 and DS86 analogs (FIGS. 5B and 5C) can be synthesized based on literature procedures beginning with L- or D-arabinose. Generally, each synthesis is initiated by opening of arabinose to afford arabinonic acid. Appropriate differential protection of primary and secondary alcohols allow R1 and R2 analogs. DS40 analogs varying R3 and R4 can be derived by transformation of the carboxylic acid to an appropriate functional group for cycloaddition reactions. Synthesis of DS86 analogs varying R2 and R3 can proceed through reduction of the carboxylic acid to the corresponding aldehyde, followed by Wittig homologation and dihydroxylation.

Example 5

Identification of additional high-affinity ligands for $PrP^C$. To identify additional high affinity small molecule ligands for $PrP^C$, the inventors conducted a pilot virtual screening against the PBD-1 pocket using the Glide program (Schrödinger). The analyses was performed using a simplified screening protocol of a small database of commercially available molecules (~300,000 compounds) against four conformations of $PrP^C$, selected on the basis of volume and hydrophobicity of the PBD-1 pocket, plus an additional conformation representing the average of all the 20 different NMR structures. The inventors identified 21 candidate molecules. Three compounds, selected by following the ranking score, were tested in vitro for binding to $PrP^C$ by surface plasmon resonance (SPR), a label-free technique that allows estimation of kinetic and binding constants for protein-ligand interactions. Recombinant, mouse $PrP^C$ was immobilized on the surface of a SPR chip, as confirmed by binding of an anti-PrP antibody (D18, FIG. 20A), and each small molecule flowed through. The inventors detected specific binding to $PrP^C$ for one molecule, referred to as DS5 {2R,3S,4S,5S,6R)-2-(hydroxymethyl)-6-[β-hydroxyphenyl)amino]tetrahydro-2H-pyran-3,4,5-triol}, with an estimated affinity in the micromolar range ($K_d$=10 μM) (FIG. 27A). This demonstrated that the PBD-1 pocket can be targeted to identify high affinity ligands for $PrP^C$.

Therefore, the inventors designed a more sophisticated protocol to screen a larger database of commercially available compounds (ZINC all purchasable set: ~17 million molecules) against the PBD-1 pocket in all of the different NMR conformations of $PrP^C$. Compounds predicted to bind PBD-1 in all the conformations, as well as in additional conformations obtained by molecular dynamics, were then filtered by molecular diversity, ligand efficiency, and visual inspection and finally prioritized by molecular dynamics (MD) to predict the stability of each protein-ligand complex (a schematic representation of the workflow is shown in FIG. 13B). These analyses identified 51 candidate molecules. Among these, 16 were available in the compound library of the National Cancer Institute (FIG. 24A, 24B), and were tested for binding to $PrP^C$ by SPR.

Suprisingly, only two molecules from the 16 molecules tested, called DS26 [2-(2R,3S,5R,6S-pentahydroxycyclohexylidene)hydrazinecarbothioamide] (FIGS. 2 and 14A) and DS40 [3R,4S-dihydroxy-5S-(1,2,3-trihydroxypropyl)dihydrofuran-2(3H)-one] (FIGS. 2 and 27B) showed sub-micromolar affinity for both mouse and human recombinant $PrP^C$ by SPR ($K_d$=0.571 μM and 0.801 μM, respectively; a docking pose of DS26 attached to PBD-1 is shown in FIG. 13D). The remaining 14 compounds from the NCI library tested did not bind to $PrP^C$.

Both molecules, DS26 ad DS40 also showed a particularly slow rate of dissociation ($K_{off}$) from $PrP^C$. As expected, they failed to bind an N-terminal PrP fragment (residues 23-110), while they bound to a C-terminal $PrP^C$ fragment (residues 121-230). Importantly, DS26 and DS40 bound mouse and human recombinant $PrP^C$ with identical affinity, indicating that the spatial properties of PBD-1 are conserved between mice and humans.

Six additional candidate ligands for $PrP^C$ were selected by screening in silico a set of DS26-like molecules, using the NCI, LifeChemicals, Specs, Enamine and Asinex databases (a total of ~2 million molecules).

SPR analyses of these compounds identified one additional molecule (DS86), 3R,4S-dihydroxy-5S-(1,2,3-trihydroxypropyl)dihydrofuran-2(3H)-one (DS86) (FIG. 27C) showing specific binding to $PrP^C$ ($K_d$=4.21 μM). The inventors detected specific binding to $PrP^C$ for one molecule, referred to as DS5 {2R,3S,4S,5S,6R)-2-(hydroxymethyl)-6-[β-hydroxyphenyl)amino]tetrahydro-2H-pyran-3,4,5-triol}, with an estimated affinity in the micromolar range ($K_d$=XX.XX μM) (FIG. 27A).

SPR analyses of these compounds identified one additional molecule (DS40), [3R,4S-dihydroxy-5S-(1,2,3-trihydroxypropyl)dihydrofuran-2(3H)-one] (FIG. 27B) showing specific binding to $PrP^C$ ($K_d$=0.801 μM).

None of the identified $PrP^C$ ligands showed detectable binding to bovine serum albumin (BSA) or myoglobin (results for compound DS26 are shown in FIGS. 20F and 20G). The inventors also failed to observe detectable binding to $PrP^C$ ($K_D$>1 mM) for GN8 (FIG. 20C) or quinacrine (FIG. 23D); two anti-prion compounds with reported affinity for $PrP^C$.

Among the four different $PrP^C$-binding compounds identified by SPR (FIG. 2), DS26 showed higher solubility and higher affinity for $PrP^C$. Binding of DS26 to $PrP^C$ was also characterized by remarkably slow dissociation kinetics (Koff) (FIG. 14B). Based on these properties, DS26 was chosen as lead compound in all the subsequent experiments.

Example 6

Characterization of DS26 binding to $PrP^C$. SPR was used to characterize the kinetics of DS26 binding to $PrP^C$. Recombinant, mouse $PrP^C$ was immobilized on the surface of an SPR chip, as confirmed by binding of an anti-PrP antibody (FIG. 20A). A solution containing DS26 was then flowed over the chip for 240 sec to allow association of the analyte with $PrP^C$, after which the chip was washed with buffer to follow dissociation. Fitting these data to a single-state binding model, we calculated a $k_{on}$ rate of $2.45 \times 10^2$ $M^{-1}$ $sec^{-1}$, a $k_{off}$ rate of $1.40 \times 10^{-4}$ $sec^{-1}$, and a dissociation constant ($K_D$) of 0.57 μM (FIG. 14A). It was discovered that the measured $k_{off}$ rate was remarkably slow for small molecule binding to a protein, with a half-life for the bound state of 83 min. Indeed, when the dissociation phase was monitored for longer periods of time, a substantial amount of DS26 remained bound to $PrP^C$ even after many hours of washing the SPR chip (70% after 10 hrs; FIG. 14B). Thus the inventors have discovered that some DS26 molecules may become locked into an extremely stable association with $PrP^C$.

Figure 20B:
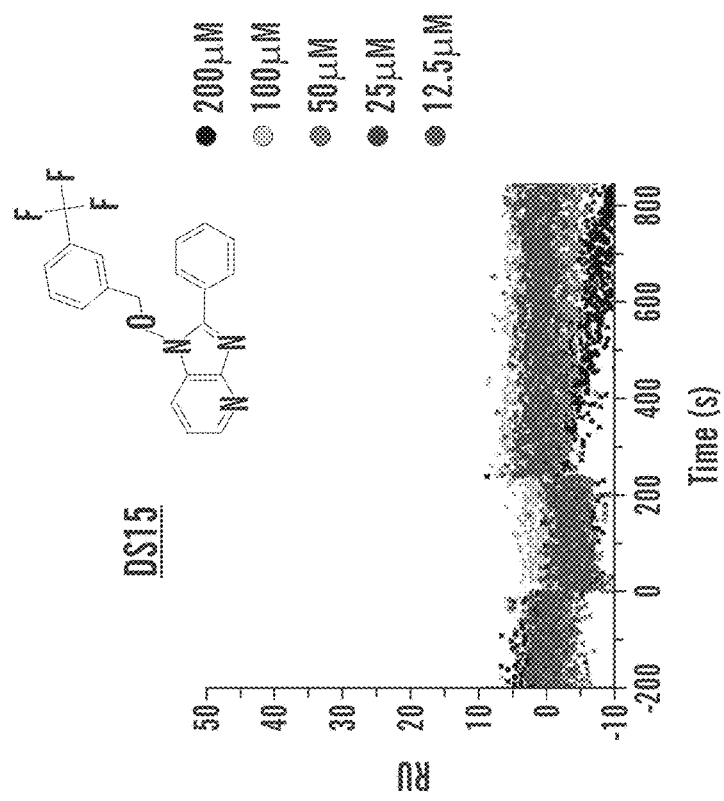
Figure 20D:
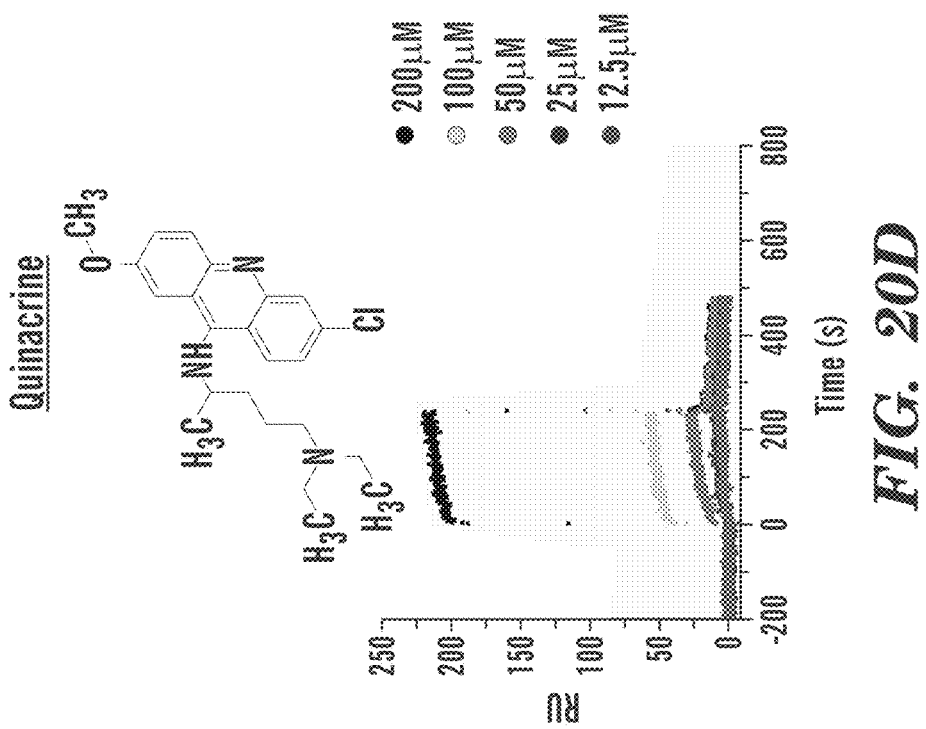
Figure 20C:
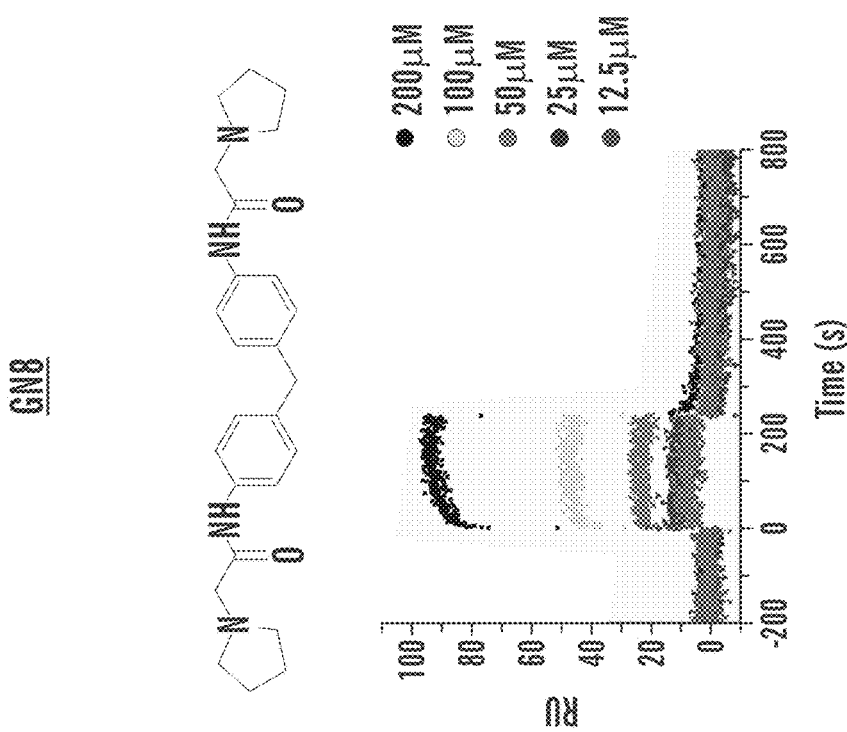

As controls for binding specificity, the inventors demonstrated that DS26 did not bind detectably ($K_D$>1 mM) to the SPR chip surface, or to control proteins, including bovine serum albumin and myoglobin (FIG. 20F-20H). In addition, no detectable binding to $PrP^C$ of GN8 or quinacrine was detected, two anti-prion compounds that were originally reported to bind to $PrP^C$, but which were shown in subsequent studies to have negligible affinity (FIG. 20C, 20D). For comparison, FIG. 20B shows SPR data for an example of a molecule (DS15) that emerged from the virtual screen, but which did not bind to $PrP^C$. The inventors also discovered DS26 binds to human $PrP^C$ as well as mouse $PrP^C$ with similar affinities, indicating that the PBD-1 site is conserved between these two species (FIG. 20E).

Figure 14E:
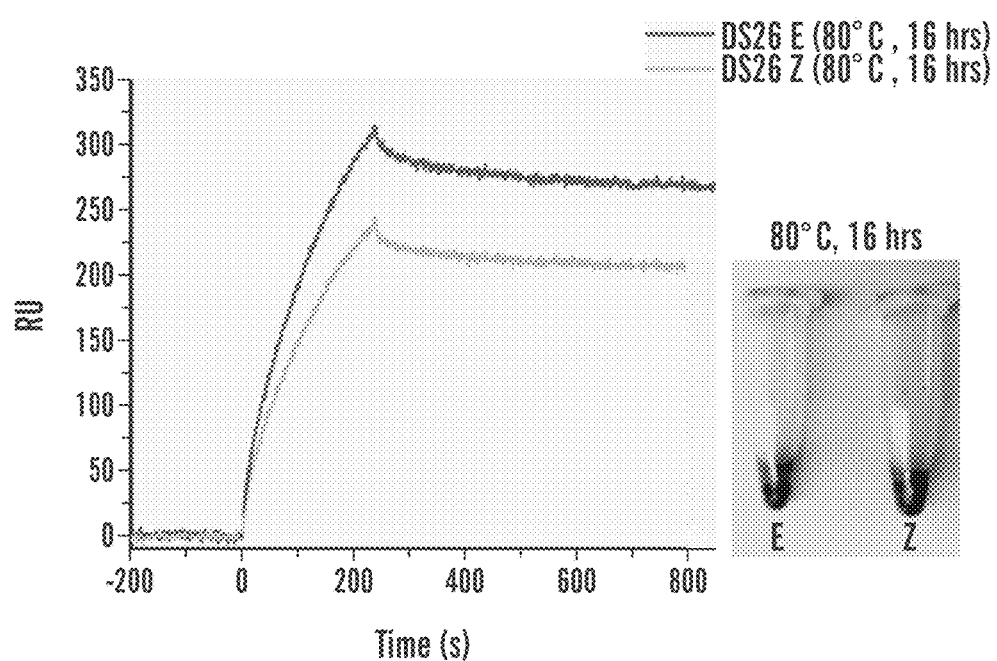

The inventors discovered that binding of DS26 was stereospecific. The D26 compound can exist as two possible stereoisomers, E and Z, based (FIG. 14C). The two forms can be distinguished visibly, based on their color in solution (the E form is brown, while the Z form is colorless (FIG. 14D, inset). DS26 can by synthesized exclusively as either the E or Z isomer (see Experimental Procedures), but these can be interconverted to a mixture of the two isomers by incubation at 80° C. for 16 hrs. The inventors discovered that only the E isomer of DS26 bound to $PrP^C$ (FIG. 14D) and heating of the Z isomer caused a color change and created binding activity, reflecting racemization of the sample (FIG. 14E). The docking pose in FIG. 13D shows the E isomer of DS26 bound to PBD-1.

To confirm binding of DS26 to $PrP^C$ using an alternative method, the inventors performed fluorescence polarization (FP), a technique that detects polarization of fluorescence emission from a small molecule as a result of binding to a target protein. In contrast to SPR, which relies on kinetic parameters to characterize ligand binding to surface-immobilized protein, FP measures equilibrium binding in solution.

Figure 15A:
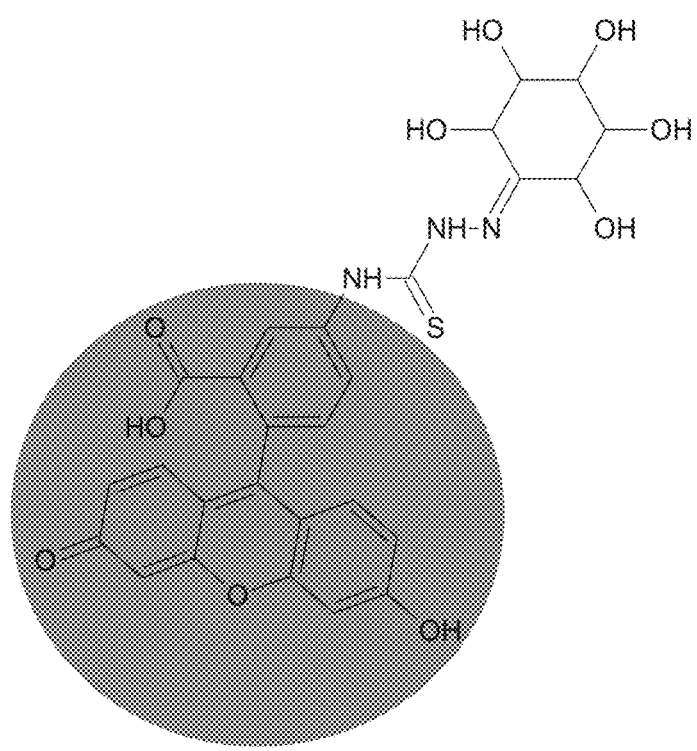
FIGS. 15A-15D shows the validation of DS26 binding to PrP$^C$ using fluorescence polarization (FP).
Figure 15B:
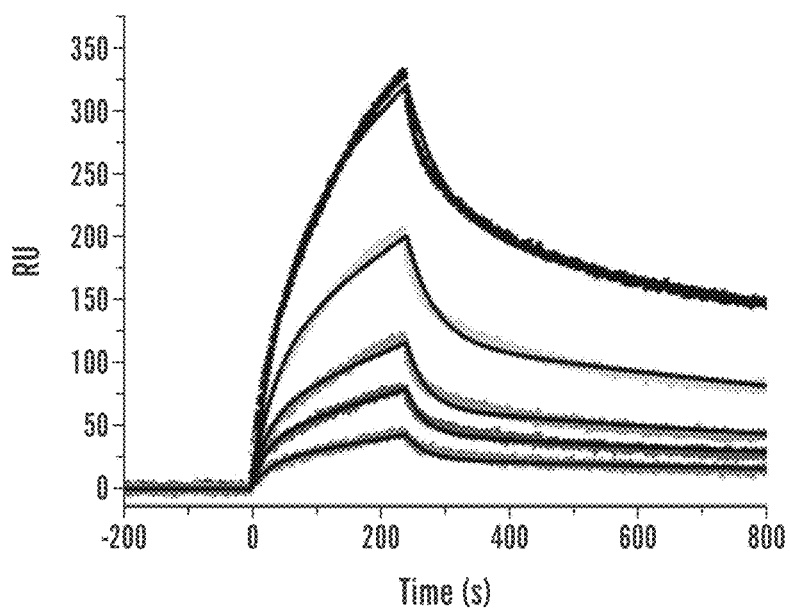

The inventors engineered a fluoresceinated derivative of DS26 (referred to as DS104; see Experimental Procedures) (FIG. 15A). The dissociation constant for binding of DS104 to $PrP^C$, as evaluated by SPR, was slightly higher than that of DS26 ($K_D$=4 μM, FIG. 15B; compared to 0.57 μM, FIG. 14A), presumably reflecting some perturbation of binding by the fluorescein moiety. The binding of DS104 to $PrP^C$ was confirmed by FP. DS104 was incubated with increasing amounts of $PrP^C$, and observed a concentration-dependent increase in polarization, with a calculated $K_D$ similar to the value obtained by SPR (FIG. 15C), indicating that DS104 was binding to $PrP^C$.

Figure 15D:
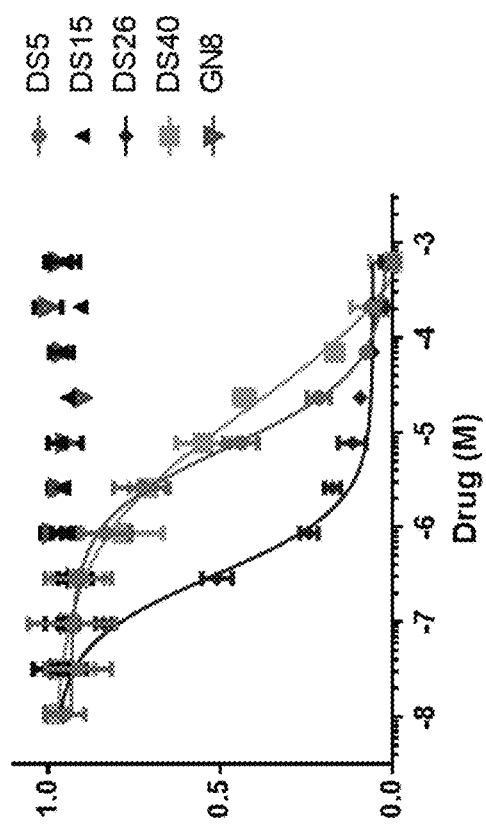
Figure 15C:
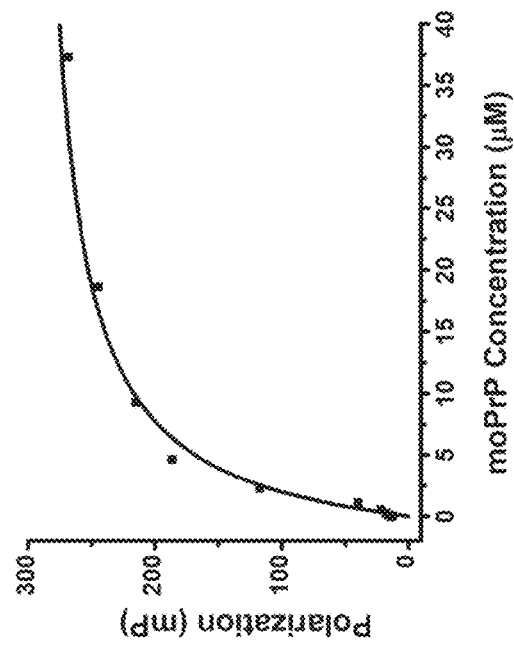

The FP assay was then used to test the ability of DS26 to compete with DS104 for binding to $PrP^C$. It was discovered that DS26, but not GN8 or DS15, were able to displace DS104 from $PrP^C$ (FIG. 15D). The $K_D$ value for DS26 calculated from these experiments was similar to that derived from SPR experiments. Importantly, the FP binding data for both DS26 and DS104 were best fitted assuming a single binding site, consistent with the idea that these compounds are binding to PBD-1. Binding of DS104 to myoglobin or BSA was not detected by FP (data not shown).

It was also discovered that DS26, DS5 and DS40 (but not GN8 or DS15) were able to displace DS104 from $PrP^C$ (FIG. 15D). Thus, the inventors have demonstrated that DS26, DS5 and DS40 share the same binding pocket on $PrP^C$.

Binding of DS26 to $PrP^C$ was also demonstrated by equilibrium dialysis (EqD), a simple method based on the ability of a small molecule to equilibrate between two chambers, one containing the target protein (referred to as sample chamber) and one empty (assay chamber), separated by a membrane permeable only to the small molecule (see schematic in FIG. 28A). As expected, DS26 equilibrated equally between the two chambers when the sample chamber contained BSA or only buffer. Conversely, when $PrP^C$ (50 µM) was added to the sample chamber, a 75% decrease in the concentration of DS26 was detected in the assay chamber, indicating that the compound was retained by $PrP^C$ in the sample chamber (FIG. 28B). As positive control for the assay, the binding of [Fe(III)-TMPyP; abbreviated TP], a cationic porphyrin previously reported to interact with $PrP^C$ was confirmed by EqD. No binding was observed for GN8 or DS15, molecules that also failed to bind $PrP^C$ by SPR.

Example 7

DS26 stabilizes the structure of $PrP^C$. In principle, a small molecule ligand for $PrP^C$ could act as a pharmacological chaperone and stabilize the native structure of the protein. To test this hypothesis, molecular dynamics simulations was performed of $PrP^C$ alone (PDB 1XYX), or complexed with DS26 or with anti-PrP antibody ICSM-18 (PDB 2W9E). It was discovered that both ICSM-18 and DS26 decreased the intrinsic motion of $PrP^C$, although the antibody showed a much stronger stabilization effect (non-H atoms RMSDs for the three models in function of simulation time (30 ns) are plotted in FIG. 16A). These data demonstrate that DS26 could stabilize the native structure of the globular domain of $PrP^C$.

To verify this idea experimentally and to measure the stabilizing effect of DS26 on $PrP^C$, circular dichroism (CD) was performed in a thermal-denaturation assay, a technique that has been previously used to characterize protein-ligand interactions, including binding of ligands to $PrP^C$. This assay is based on the principle that binding of a ligand to a target protein may increase the temperature at which the protein denatures.

The inventors determined the thermal stability of the C-terminal domain of $PrP^C$ (residues 120-231) by CD, monitoring the presence of α-helical content at 220 nm (FIG. 16B, inset). The observed unfolding (melting) temperature ($T_m$) for $PrP^C$ was 66.82±0.1° C. In presence of DS26, the $T_m$ was increased substantially (68.93±0.1° C., a difference of 2.11° C.) (FIG. 19B). Thus, binding of DS26 effectively stabilizes the native folding of $PrP^C$.

Example 8

DS26 alters the biological activity of $PrP^C$. Since DS26 binds to $PrP^C$ and stabilizes its structure, the inventors assessed if DS26 alters the biological activity of the $PrP^C$ protein. The effect of DS26 was assessed on two, readily assayable activities: (i) conversion of $PrP^C$ into $PrP^{Sc}$, and (ii) the ion channel activity associated with a mutant form of PrP.

(i) The inventors also directly tested whether DS26 could act as a pharmacological chaperone and interfere with the conversion of $PrP^C$ into $PrP^{Sc}$. To measure the effect of DS26 on generation of $PrP^{Sc}$, a clone of murine neuroblastoma cells that had been chronically infected with the Rocky Mountain Laboratory (RML) strain of scrapie was used. These cells were exposed for 72 h to different concentrations of DS26 (10-500 µM), or vehicle control, and detected the levels of proteinase K-resistant $PrP^{Sc}$ by Western blot. The inventors discovered that treatment with DS26 reduced $PrP^{Sc}$ levels in the scrapie-infected N2a cells in a dose-dependent fashion (FIG. 16C). The dose required for half-maximal inhibition was considerably higher than the $K_D$ for DS26 binding to $PrP^C$, which may reflect the fact that the cells were chronically infected and already continuously synthesizing $PrP^{Sc}$ at the time of drug application. Collectively, these data indicate that DS26 is an anti-prion compound, likely acting as a pharmacological chaperone for $PrP^C$.

(ii) The inventors have previously reported that $PrP^C$ carrying deletions or point mutations in the conserved, central region are associated with a spontaneous ion channel activity that can be recorded by patch clamping techniques. This activity causes a severe neurodegenerative phenotype when the mutant proteins are expressed in transgenic mice. Since both the ion channel activity and the neurodegenerative phenotype of the mice are dose-dependently suppressed by co-expression of wild-type PrP, it indicates that the mutations lead to a dominant-negative alteration in the normal functional activity of $PrP^C$.

Here, the inventors assessed whether DS26 inhibits the ion channel activity of the most active of these PrP mutants, ΔCR PrP, which lacks the central region residues 105-125. First, the inventors confirmed by SPR that DS26 binds to ΔCR PrP (FIG. 21). Next, whole-cell patch-clamp recordings of HEK293 cells expressing ΔCR PrP was performed. As expected, these cells displayed large, spontaneous inward currents (FIG. 16D) that were absent in cells expressing WT PrP (data not shown). Importantly, channel activity is silenced by over-expression of wild-type $PrP^C$, indicating that this activity is related to a normal, physiological property of the protein. The spontaneous currents in the ΔCR PrP cells were almost completely silenced by treatment with DS26 (5 µM) demonstrating that the molecule remains stably attached to $PrP^C$. The inhibitory activity of DS26 was long-lasting, as the currents were still silenced for several minutes after removing the compound from the solution, consistent with results obtained by molecular dynamics and SPR, which indicate that DS26 has particularly slow dissociation kinetics from $PrP^C$.

The identification of DS26, along with the data showing that it binds to $PrP^C$ with sub-micromolar affinity and inhibits an assayable physiological activity of the protein, demonstrates that DS26 is a functional inhibitor of $PrP^C$.

Figure 3B:
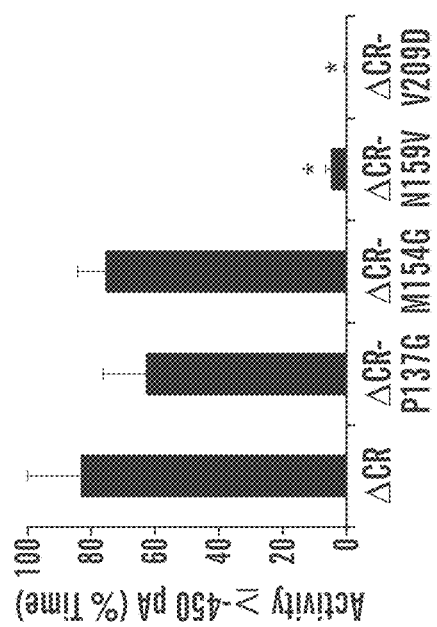
FIGS. 3A and 3B show that mutations in the PBD-1 site silence ΔCR PrP channel activity.
Figure 3A:
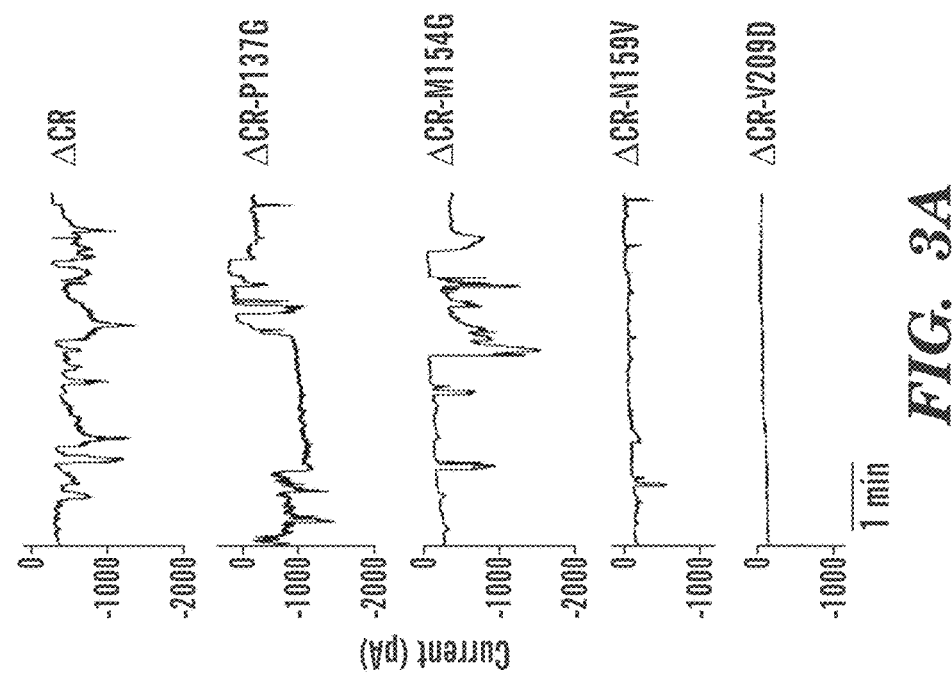
Figure 5C:
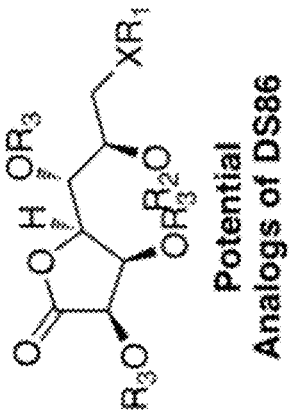
FIGS. 5A-5C illustrate some exemplary analogues and derivatives of DS5 (FIG. 5A), DS40 (FIG. 5B), and DS86 (FIG. 5C).
Figure 5B:
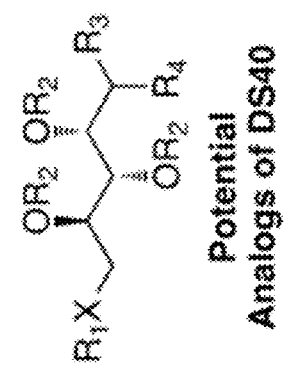
Figure 5A:
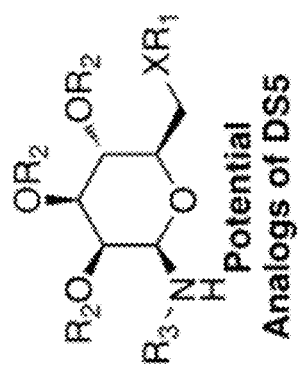
Figure 6:
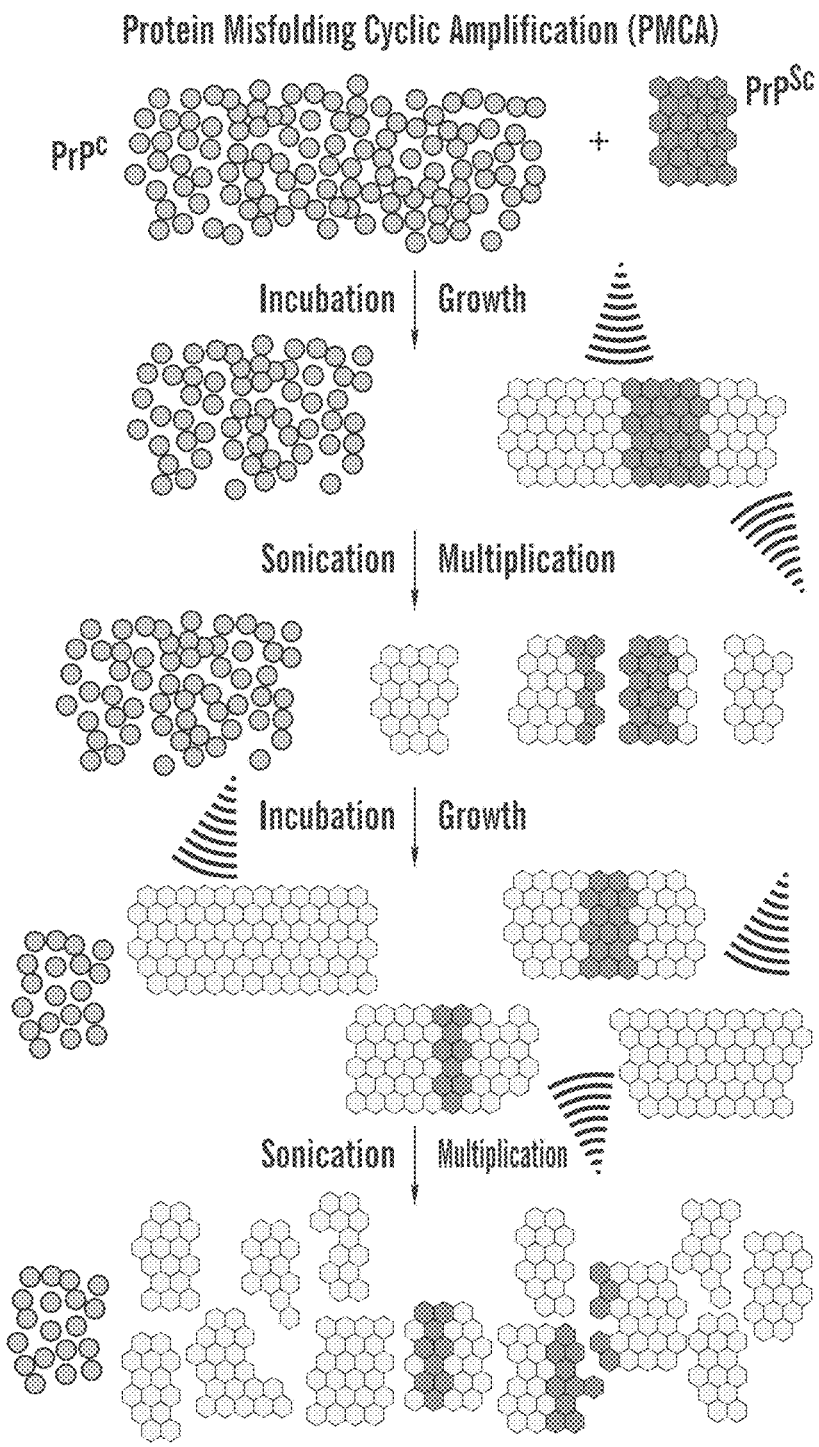
FIG. 6 shows that compound DS26 partially inhibits $PrP^{Sc}$ replication in vitro.
Figure 6:
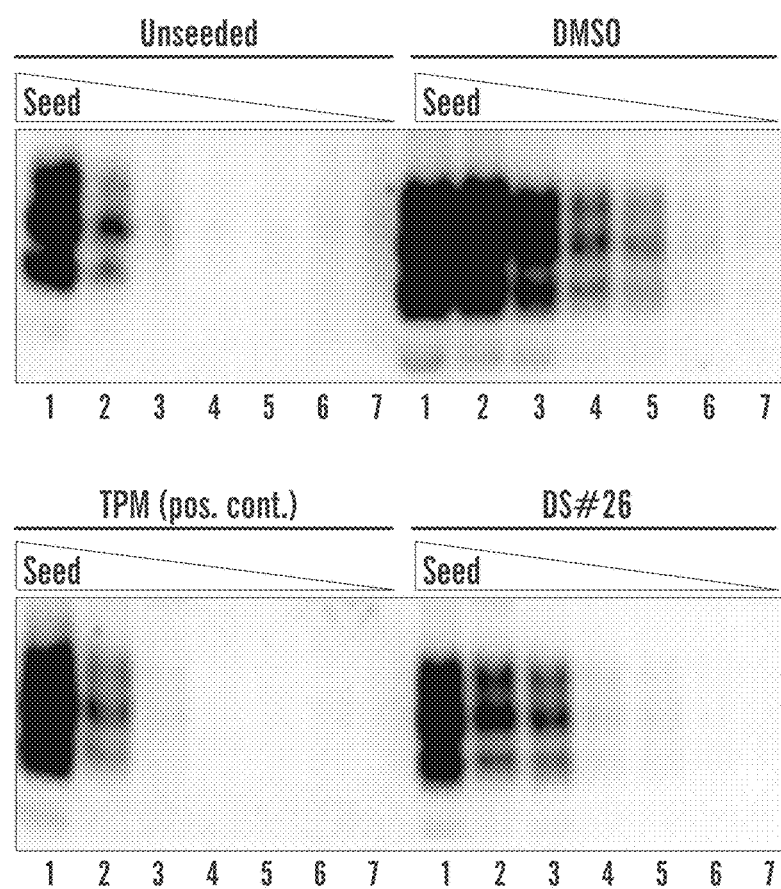
Figure 7:
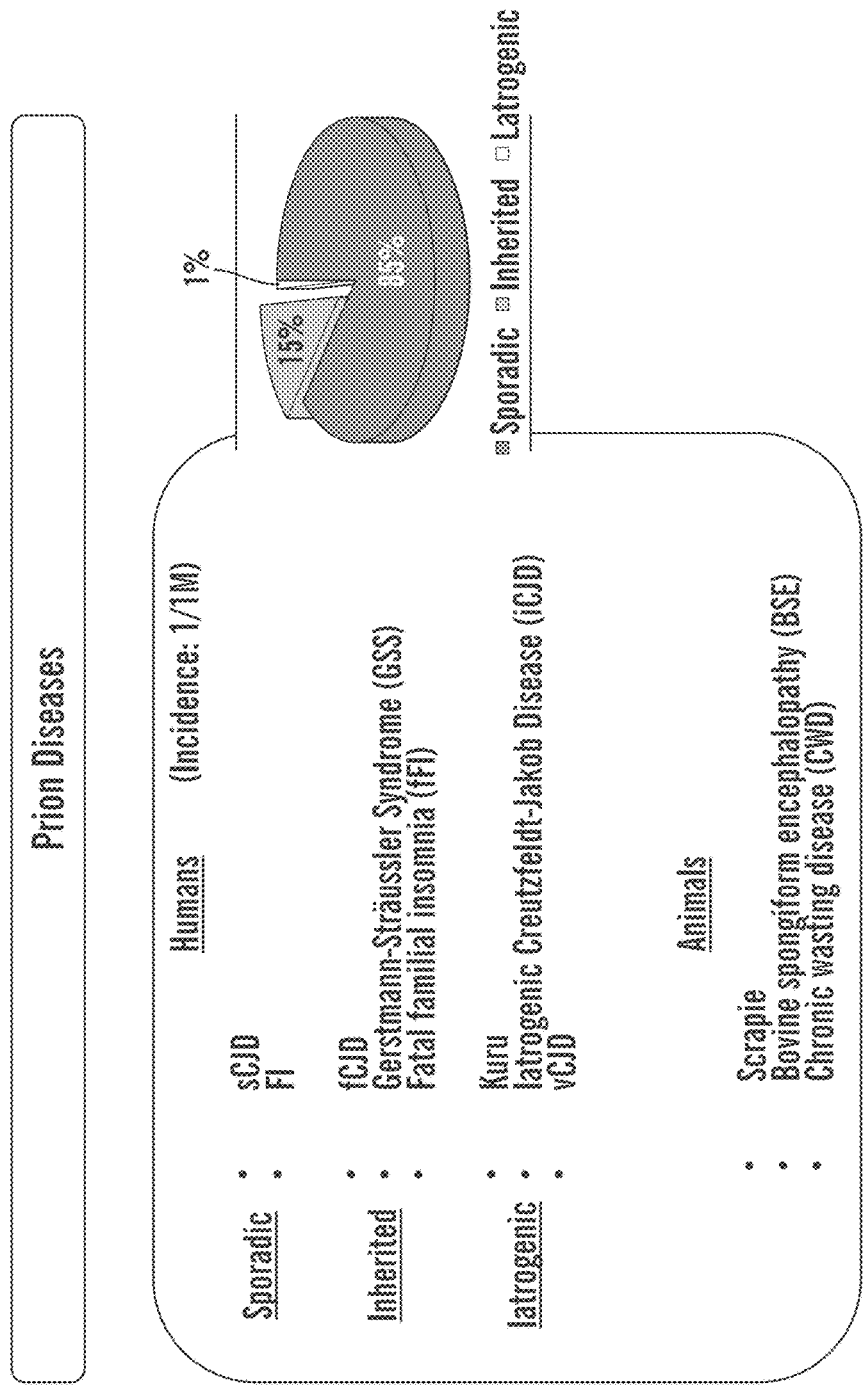
FIG. 7 is a schematic representation of classification of prion disease.
Figure 8:
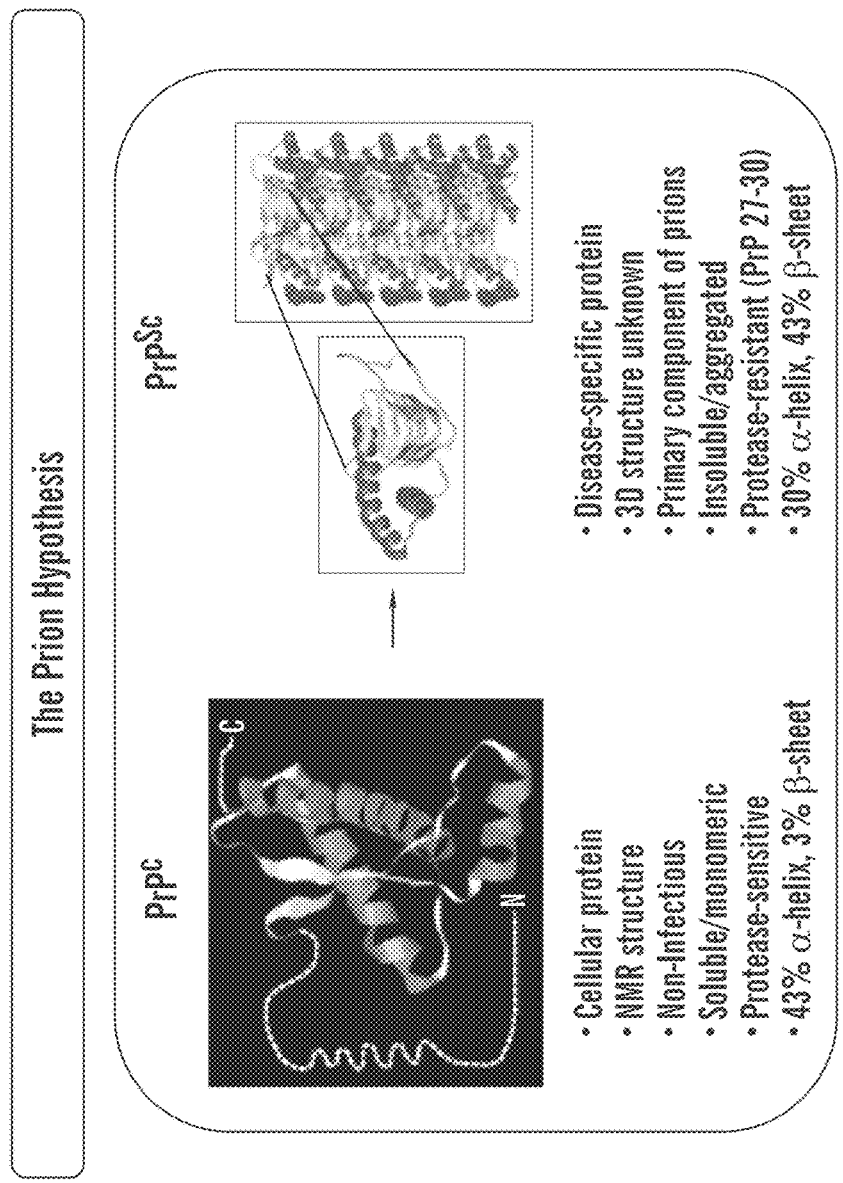
FIG. 8 is a schematic representation of the prion hypothesis.
Figure 10:
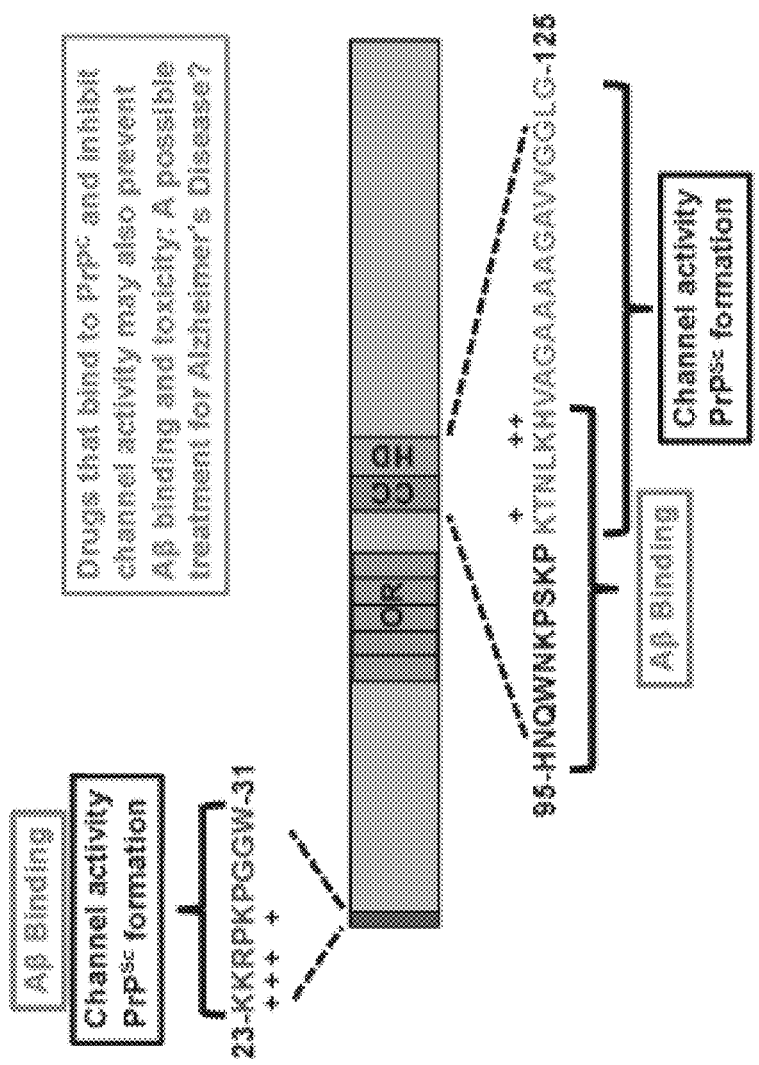
FIG. 10 is a schematic representation of functional domains of PrP$^C$.
Figure 11:
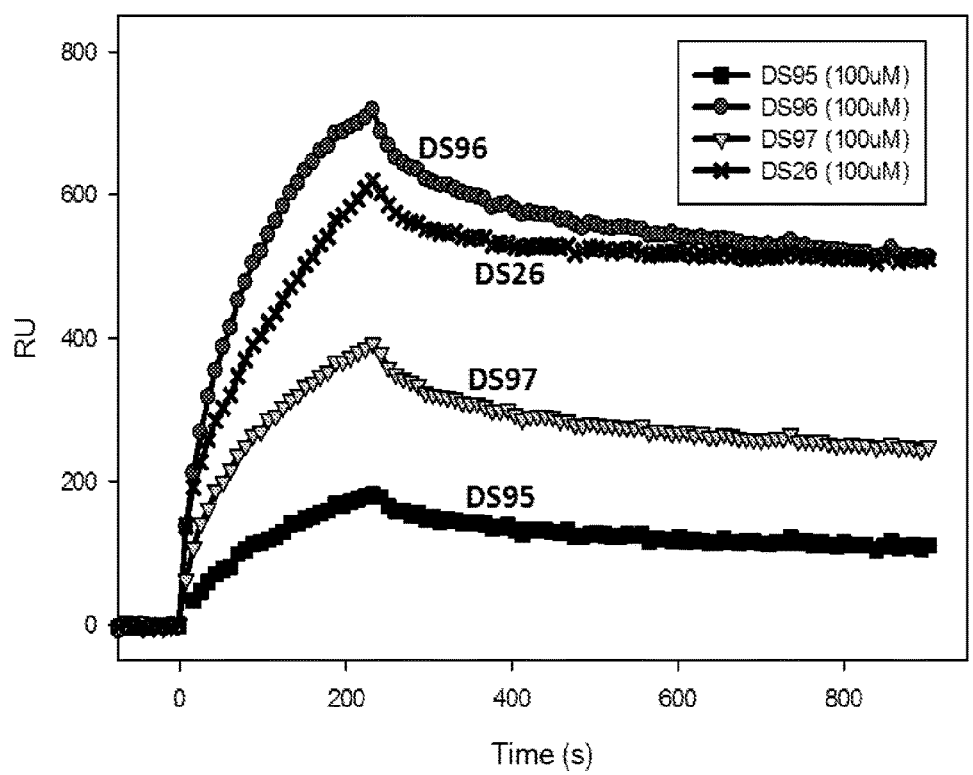
FIG. 11 is a line graph showing SPR analysis of some exemplary PrP$^C$ ligand compounds of formula (I), e.g., DS95, DS96 and DS97. The chemical structures of these exemplary PrP$^C$ ligand as shown in Table 1.
Figure 12:
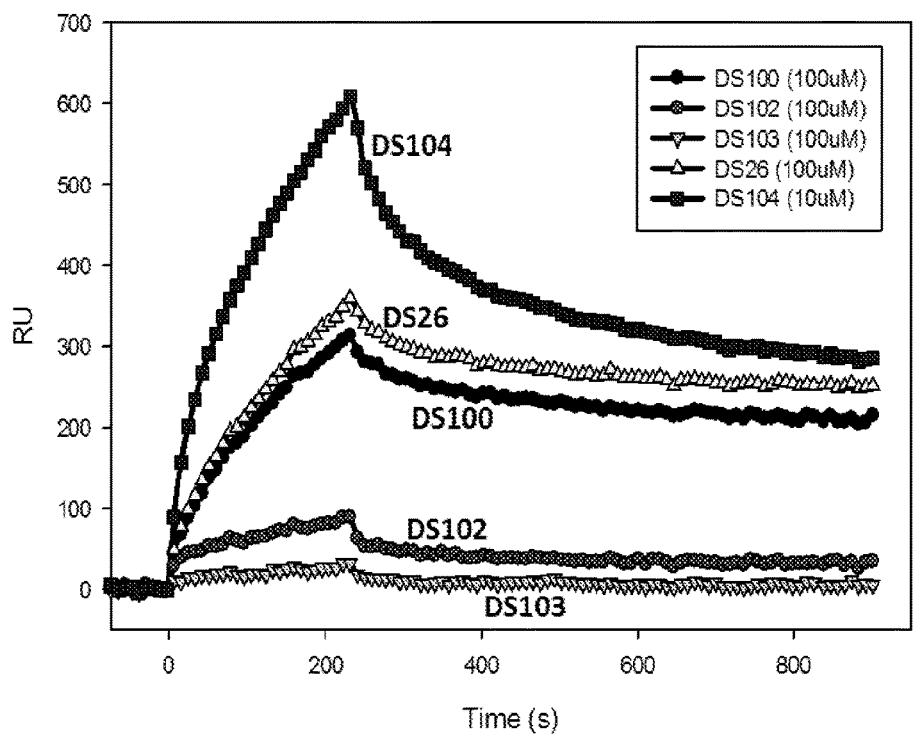
FIG. 12 is a line graph showing SPR analysis of some additional exemplary PrP ligand compounds of formula (I), e.g., DS100, DS102, DS103, DS26 and DS104. The chemical structures of these exemplary PrP$^C$ ligand as shown in Table 1.

In order to confirm whether the PBD-1 represents a functionally important domain of PrP$^C$, the inventors introduced mutations into four of the different residues constituting the conformational pocket (FIG. 3A). Each substitution was chosen to interfere with the binding properties of the pocket, but to have minimal effect on the local folding of PrP$^C$. The inventors introduced each mutation into the ΔCR PrP molecule, and stably expressed the resulting proteins in HEK293 cells. The channel activity of the different mutants was then tested by patch-clamping. The inventors discovered that that mutations at two different residues (159 and 209) completely abrogated ΔCR PrP-induced currents (FIG. 3A). These results demonstrated that the PBD-1 represents a functionally important region of PrP$^C$.

Example 9

DS26 blocks binding of Aβ oligomers to PrP$^C$. Given the proposed role of PrP$^C$ in binding Aβ oligomers and transducing synaptotoxic signals, the inventors assessed the effect of DS26 on Aβ oligomer binding to PrP$^C$ using three different experimental formats. First, the inventors immuno-captured recombinant, mouse PrP$^C$ on the surface of an SPR chip, exposed the chip to different concentrations of DS26, and then evaluated the binding of Aβ oligomers. It was discovered that DS26 inhibited binding of Aβ oligomers to PrP$^C$ in a dose-dependent fashion, with an IC$_{50}$ of ~15 μM (FIG. 17A), with the highest concentration (100 μM) reducing the interaction by more than 90% (FIG. 17A).

These results were confirmed using an ELISA format to assay Aβ oligomer binding to PrP$^C$. To establish optimal conditions for the ELISA, increasing amounts of Aβ was added to wells in which tagged PrP$^C$ had been captured using an anti-myc antibody, and detected bound Aβ using an antibody. Binding of Aβ to PrP$^C$ was saturable, with an estimated K$_D$ of 30 nM (FIG. 17B), similar to the value the inventors previously obtained using SPR (data not shown). When PrP$^C$ in the ELISA wells was pre-incubated with different concentrations of DS26, binding of Aβ was dose-dependently inhibited, with an IC$_{50}$ of 15 μM (FIG. 17C), similar to the value obtained by SPR (FIG. 17A). To test whether DS26 was able to dislodge Aβ oligomers that were already bound to PrP$^C$, PrP$^C$ was incubated with Aβ oligomers and then different concentrations of DS26 was added. DS26, even at high concentrations, was unable to release Aβ that was already attached to PrP$^C$ (FIG. 17C).

The inventors also tested the effect of DS26 on Aβ oligomer binding to PrP$^C$ in a cellular context. Transfected HEK cells expressing PrP$^C$ bound Aβ oligomers above the background levels observed in untransfected cells (FIG. 22A). The K$_D$ for oligomer binding was higher than measured using SPR or ELISA formats, possibly due to the effects of other cell-surface proteins on the Aβ-PrP$^C$ interaction, or the presence of posttranslational modifications on PrP$^C$. Pre-incubation of cells with DS26 showed a dose-dependent inhibition of Aβ binding (FIG. 22C-22D), although the estimated IC$_{50}$ was higher than the corresponding value observed by SPR and ELISA.

Example 10

Molecular mechanism underlying DS26 inhibition of Aβ binding to PrP$^C$—DS26 acts by blocking the interaction between Aβ oligomers and PrP$^C$ in an allosteric fashion. One plausible mechanism by which DS26 rescues the toxic effects of Aβ oligomers in cells and brain slices may involve the ability of this compound to inhibit their interaction with PrP$^C$. The results are shown in FIGS. 22C and 22D, and 17A and 17C.

Two, distinct Aβ oligomer binding sites have been identified on PrP$^C$ (residues 23-27 and 95-105). These binding sites are both encompassed within the flexible, N-terminal tail of the molecule (residues 23-111). In contrast, DS26 is predicted to bind to a pocket in the C-terminal, globular domain (residues 120-230) of PrP$^C$ (see FIG. 13D). To confirm that Aβ oligomers and DS26 bind in two different regions of PrP$^C$, the inventors immobilized on the surface of a SPR chip, recombinant mouse PrP$^C$ or fragments corresponding to its N-terminal (23-111) or C-terminal (120-230) regions (hereafter referred to as N-PrP and C-PrP, respectively). The inventors found that DS26 inhibited binding of Aβ oligomers to PrP$^C$ in a dose-dependent fashion (FIG. 17A). These results were confirmed using an ELISA format (FIG. 17B, 17C), which allowed estimation of the half maximal inhibitory concentration (IC$_{50}$) of DS26 for Aβ oligomer binding to PrP$^C$ (estimated to be approximately 15 μM). The inventors also confirmed that Aβ oligomers bound to both full-length PrP$^C$ and N-PrP, but not C-PrP (FIG. 17D-17F). Conversely, DS26 bound to full-length PrP$^C$ and C-PrP, but not N-PrP (FIG. 17G-17I). Thus, C-PrP was necessary and sufficient for binding of DS26 to PrP$^C$. Thus, the inventors have demonstrated that DS26 and Aβ oligomers bind PrP$^C$ in two different regions. Consistent with this conclusion, DS26 failed to inhibit the binding of Aβ oligomers to N-PrP (FIG. 17J). Accordingly, the inventors have discovered that the ability of DS26 to inhibit binding of Aβ oligomers to PrP$^C$ is not exerted by direct competition (e.g., competitive inhibition) for a common binding site, but through an unexpected allosteric interaction between the two halves of the protein; the DS26 binding site in the C-terminus and the Aβ binding sites in the N-terminus.

To further investigate this mechanism, the inventors first assessed whether DS26 induced a detectable change in the secondary structure of PrP$^C$, as measured by far-UV circular dichroism (CD). The inventors demonstrate that addition of DS26 did not detectably alter the CD spectrum of PrP$^C$, which was consistent with the presence of three α-helices in the C-terminal domain (FIG. 23). These data imply that DS26 does not cause a major change in the folding of the C-terminal domain.

The inventors next assessed the effect of the compound on the N-terminal domain. This unstructured, flexible region of PrP$^C$ (residues 23-111) includes 7 of the 8 tryptophan (Trp) residues present in the mature protein. This feature makes it possible to detect changes in the conformation of the N-terminus by measuring alterations in Trp fluorescence. When excited at 280 nm, full-length, recombinant PrP$^C$ produces a Trp emission peak at 345 nm. Suprisingly, incubation with DS26 caused a dose-dependent quenching of this peak (FIG. 18A). As a negative control, DS15, a small molecule with similar absorbance of DS26 but no detectable affinity for PrP$^C$, did not produce any change in Trp fluorescence (FIG. 18C). Moreover, the fluorescence of N-PrP was unaffected by DS26 (FIG. 18B), consistent with the absence of a ligand binding site in this region.

Thus, these data demonstrate that binding of DS26 in the C-terminal, globular domain of PrP$^C$ alters the conformation of the flexible, N-terminal tail, possibly accounting for reduced Aβ oligomer binding to the tail. One way this conformation change might occur is if DS26 induced an intramolecular interaction between the N-terminal and C-terminal domains. To directly assess this, two kinds of experiments were performed; first, myc-tagged N-PrP was co-immunoprecipitated with C-PrP in presence or absence of DS26. Co-immunoprecipitation of the two PrP fragments occurred only after incubation with DS26 (FIG. 18D). These data were further confirmed by SPR. In this case, myc-tagged C-PrP was captured on the surface of a SPR chip, and N-PrP was flowed over the chip. It was determined that N-PrP interacted with C-PrP only after pre-injection of DS26 (FIG. 18E). Accordingly, the inventors have demonstrated that binding of DS26 promotes interaction between the N- and the C-terminal halves of PrP$^C$, thereby preventing access of Aβ oligomers to sites in the N-terminal tail.

In summary, the inventors demonstrate herein a model by which DS26 induces an auto-inhibitory change in PrP$^C$, caused by the conformational rearrangement of the N-terminal, flexible tail and binding of the tail onto the C-terminal, globular domain of the protein (FIG. 19D). As a result, the compound abrogates binding of Aβ oligomers to the N-terminus of PrP$^C$, and also acts a functional inhibitor of a toxic PrP mutant that relies on the N-terminus to elicit ionic currents. Accordingly, DS26 may mimic an endogenous ligand that modulates the physiological activity of PrP$^C$, or its ability to elicit toxic signaling.

Example 11

DS26 inhibits the synaptotoxic effects of Aβ oligomers in hippocampal neurons and brain slices In addition to its role in prion diseases, it has been recently reported that PrP$^C$ functions as a toxicity-transducing receptor for Aβ oligomers that may contribute to synaptic dysfunction in AD. Given the discovery herein that DS26 inhibits Aβ binding to PrP$^C$, the inventors sought to test whether DS26 is capable of blocking the synaptotoxic effects of Aβ oligomers in a biologically relevant system. For this purpose, the inventors turned to electrophysiological measurements of long-term potentiation (LTP) in hippocampal slices. LTP is one of the cellular mechanisms by which long-lasting changes in synaptic efficacy are encoded in neuronal networks in the hippocampus. A number of laboratories have shown that Aβ oligomers from both synthetic and natural sources potently suppress LTP, and this effect is regarded as a sensitive measure of the synaptotoxic effects of the oligomers.

The inventors first sought to confirm earlier reports that the negative effect of Aβ oligomers on LTP is dependent on expression of PrP$^C$. To do this, the LTP in hippocampal slices from control mice were compared with that of PrP knock-out mice in response to application of synthetic Aβ oligomers. A single, brief theta-burst stimulation (TBS) in the Schaffer collateral pathway between hippocampal CA3 and CA1 regions is sufficient to trigger LTP in slices from both control C57BL/6 mice and Prn-p$^{0/0}$ mice on the C57BL/6 genetic background (Zurich 1 strain) (FIGS. 19A and 19C). Incubation with Aβ oligomers (500 nM) suppresses LTP in control slices, but not in Prn-p$^{0/0}$ slices (FIG. 19A, 19C). Thus, the toxic effect of Aβ oligomers is largely PrP$^C$-dependent, consistent with several previous studies.

In order to assess whether treatment with DS26 could prevent or rescue the negative effect of Aβ oligomers on LTP, slices were perfused with the DS26 compound (100 μM) for 20 minutes prior to Aβ application. The inventors demonstrate that DS26 significantly reversed the inhibitory effect of Aβ oligomers on LTP (FIGS. 19B and 19C). Indeed, the DS26 compound restored LTP to control levels seen in WT slices that were not exposed to Aβ, or to Prn-p$^{0/0}$ slices treated with Aβ. No change in LTP was detected when DS26 alone was administered to either WT or Prn-p$^{0/0}$ slices, demonstrating that the compound does not have significant baseline effects in this protocol (FIG. 19C). Collectively, these results demonstrate that DS26 blocks the PrP$^C$-dependent effects of Aβ oligomers on LTP.

In a second set of experiments, the inventors employed primary cultures of postnatal mouse hippocampal neurons. Treatment of these cells for 3 hours with Aβ oligomers (1 μM) induces a decrease of several postsynaptic markers, as evaluated by western blot of the triton-insoluble fractions (FIG. 29A). Synaptic markers affected by Aβ oligomer treatment included subunits of the glutamate receptors NMDA (GluN2A, GluN2B, decreased) and AMPA (GluA1 and GluA2, decreased) as well as the post-synaptic density protein 95 (PSD-95; reduced; FIG. 29B). The levels of these proteins were not significantly altered by treatment with DS26 (100 μM). However, pre-treatment with DS26 for 1 h prior to incubation with Aβ oligomers significantly rescued the levels of all the synaptic markers (GluN2A, GluN2B, GluA1 and GluA2; and PSD95 levels were increased). The level of a control protein (actin) was not affected by either Aβ oligomers or DS26. These results indicate that DS26 antagonizes the loss of synaptic proteins induced by Aβ oligomers.

Example 12

The inventors have identified DS26, a small molecule that inhibits the neurotoxicity of Aβ oligomers by targeting PrP$^C$. The compound was discovered by virtual screening analyses, and its affinity for PrP$^C$ estimated by biochemical and biophysical binding assays. The inventors demonstrate that DS26 blocks Aβ-induced synaptic loss in cultured hippocampal neurons, and prevents Aβ-dependent suppression of LTP in hippocampal slices. The small molecule operates by an unusual allosteric mechanism in which ligand binding to a site in the structured C-terminal half of PrP$^C$ induces an intramolecular interaction with the N-terminal tail, thereby preventing Aβ binding. Our data validate PrP$^C$ as a pharmacological target in AD. The chemical nature of DS26 and its mode of action suggest the existence of an endogenous ligand that regulates PrP$^C$ activity by determining the conformation of the flexible N-terminus.

DS26 as anti-prion compound. A number of compounds active against PrP$^{Sc}$ replication in cells have previously been proposed to act by targeting PrP$^C$. Examples include sulphated glycans (such as pentosan polysulphate and cyclodextrins) cyclic tetrapyrroles (porphyrins and phthalocyanines), the anti-malaria drug quinacrine, and a small molecule, known as GN8, discovered using an in silico approach as to the one described here. However, these compounds have been shown to possess either poor specificity or low affinity for PrP$^C$, with the exception of GN8, which was reported to bind PrP$^C$ with micromolar affinity. Suprisingly, as disclosed herein, the inventors failed to detect binding of GN8 to PrP$^C$ by either SPR or EqD. This observation was consistent with other reported published data. Conversely, the inventors demonstrate by multiple techniques that DS26 binds stereo-specifically to the C-terminus of PrP$^C$ with sub-micromolar affinity. This compound represents the first member of a novel generation of small, high-affinity ligands for PrP$^C$.

The inventors demonstrated that DS26 inhibits PrP$^{Sc}$ replication in cell cultures, in a dose-dependent fashion. An explanation for this activity is that the compound inhibits the interaction between PrP$^C$ and PrP$^{Sc}$, similar to the effect seen with Aβ oligomers. Indeed, the ability of DS26 to promote the interaction between the N-terminus and the C-terminus of PrP$^C$ could directly disfavor binding to PrP$^{Sc}$. This possibility is consistent with the inventors' prior discovery that a poly-basic domain in the N-terminus of $PrP^C$ determines the efficiency of prion propagation by participating in the initial steps of formation of the $PrP^C$-$PrP^{Sc}$ complex. The analyses of MD and CD thermal denaturation as demonstrated herein indicate that the compound also acts as a pharmacological chaperone, stabilizing the folded state of the globular domain of $PrP^C$. In this case, an anti-prion effect could be exerted by reducing the Gibbs free energy of the PrP polypeptide, with consequent increase of the activation energy ($\Delta G$) necessary for reaching any unfolded state along the pathway of formation of $PrP^{Sc}$. A similar mechanism has already been proposed for explaining the anti-prion effect of TP. Since the relationship between $\Delta G$ and the stability constant of a folded polypeptide is exponential, the inventors' data demonstrate that a second ligand, binding with similar affinity but to a different pocket in $PrP^C$, could act synergistically with DS26 and stabilize the native folding enough to completely block the formation of $PrP^{Sc}$. Thus, the inventors demonstrate a cocktail of two or three of such $PrP^C$ ligands could show unprecedented therapeutic effects against prion diseases.

DS26 as anti-A$\beta$ molecule. The recent identification of $PrP^C$ as a potential receptor for A$\beta$ oligomers has resulted in intense effort to characterize the effects of this interaction at a functional level. Ablation of $PrP^C$, or antibodies directed against it, were shown to rescue neurotoxic effects of A$\beta$ oligomers in hippocampal slices and transgenic mice.

However, a number of conflicting results have left the question of whether $PrP^C$ is essential for transducing the toxicity of A$\beta$ oligomers unsettled. The inventors' discovery as disclosed herein adds a pharmacological perspective that helps to resolve the discrepancy between previous studies. The inventors demonstrate that the A$\beta$-dependent effects on synaptic integrity and hippocampal LTP are suppressed by a small molecule directed against $PrP^C$ that blocks interaction with the oligomers. These data establish strong experimental evidence that $PrP^C$ could be targeted to suppress A$\beta$ toxicity, with important therapeutic implications. In fact, in contrast to existing therapies for AD, most of which aim to reduce the levels of toxic A$\beta$ or tau species, DS26 has the potential to directly block the proximal events leading to synaptic dysfunction and degeneration activated by A$\beta$ oligomers.

In addition, compounds like DS26 may be capable of halting the neurodegenerative process even after substantial amounts of A$\beta$ have already been deposited in the brain. This feature is highly desirable, since recent evidence indicates that A$\beta$ may begin accumulating in the brains of A$\beta$ patients many years prior to the onset of clinical symptoms. Thus, in some embodiments, one can administer DS26 at the time that the earliest, mildest symptoms appear, and thereby arrest the slow, inexorable, cognitive decline that is typical of AD. DS26 administered pre-symptomatically could be capable of completely preventing development of clinical symptoms, particularly if given in combination with A$\beta$-lowering therapies. Finally, $PrP^C$-directed therapeutics like DS26 are likely to have fewer side effects than some other agents (e.g., secretase inhibitors), which act on molecular targets that perform other essential biological functions. In fact, genetic deletion of the $PrP^C$ gene has no observable phenotypic effect in mice or cattle.

Dissecting the mode of action of DS26. One of the striking discoveries herein is that DS26 induces a auto-inhibitory interaction between the N-terminal tail and the structured C-terminus of $PrP^C$. This mechanism explains some of the biological properties of the compound, in particular its ability to prevent binding of A$\beta$ oligomers to $PrP^C$. In principle, an equation describing the DS26 allosteric inhibition of A$\beta$ oligomer binding to $PrP^C$ should include the affinity of the compound for $PrP^C$ ($K_d$=0.5 $\mu$M), the interaction constant of A$\beta$ oligomers binding to $PrP^C$ {$K_d$=1 nM, as estimated herein (FIG. 17A), and, as well as the affinity of the N-terminus for the C-terminus of $PrP^C$ ($K_d$=30 nM; FIG. 19A-19D). Based on these assumptions, the concentration of DS26 necessary to block 50% of A$\beta$ oligomer binding to $PrP^C$ should higher than the $K_d$ of the compound for its target, which is consistent with the value observed experimentally ($IC_{50}$=15 $\mu$M).

The ability of DS26 to modulate the conformation of the N-terminal tail of $PrP^C$ also provides a model for the inhibitory effect of the compound on the ionic currents induced by $\Delta$CR PrP. The neurotoxic effects of this mutant are governed by a polybasic domain in the N-terminus of the protein (residues 23-31; KKRPKPGGW; SEQ ID NO: 6). This region, which has been associated with several cell biological properties of $PrP^C$, is believed to promote the insertion of the N-terminus of $\Delta$CR PrP into the plasma membrane, with consequent formation of transient pores, causing spontaneous ionic currents that can be detected by patch clamping techniques.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:
1. A method for therapeutic treatment of Alzheimer's disease (AD), the method comprising administering to a subject in need thereof a therapeutically effective amount of a compound selected from the group consisting of:
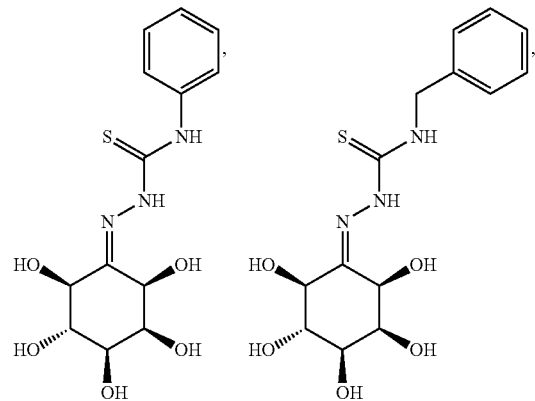
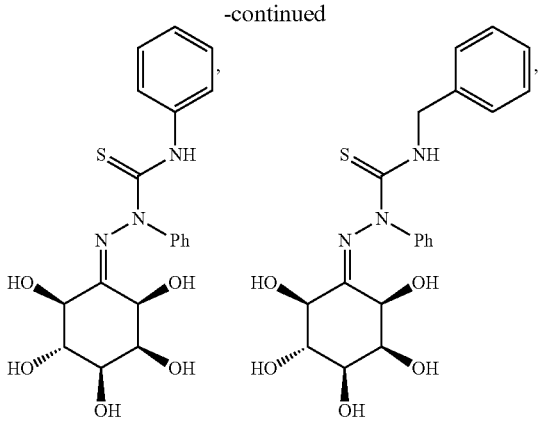
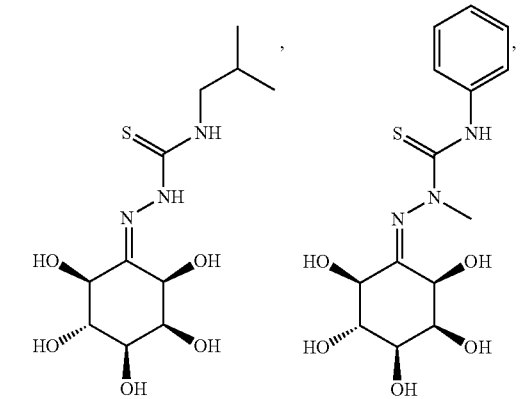
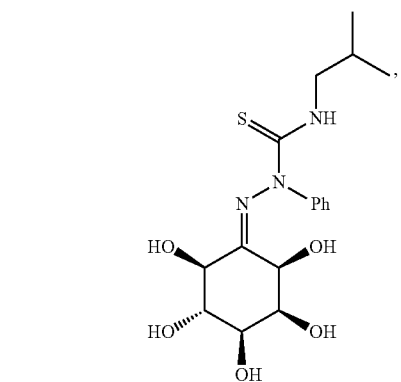
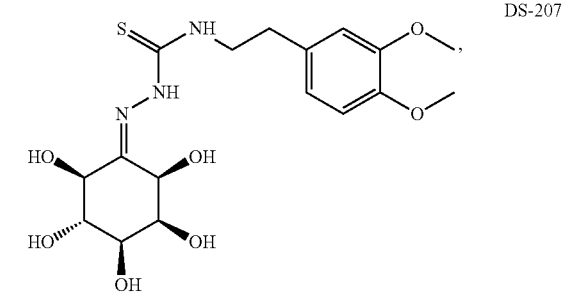
DS-207
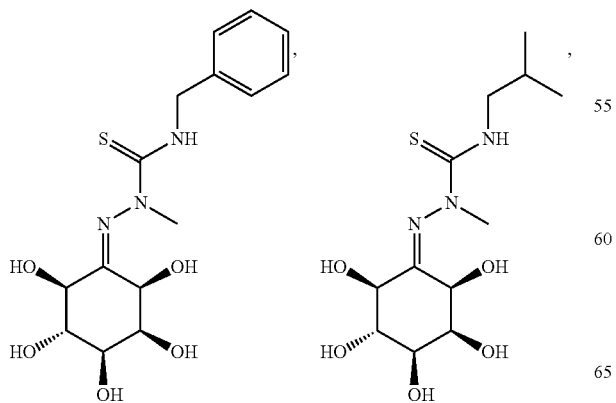
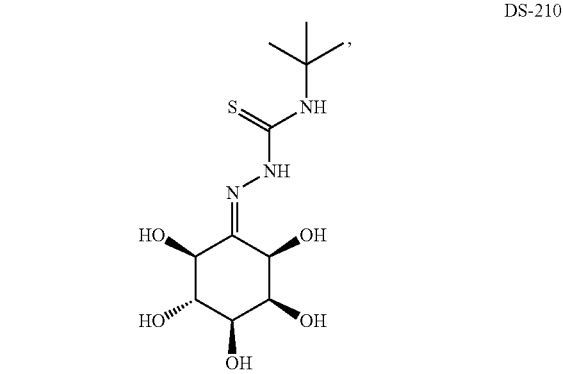
DS-210

(DS-211)
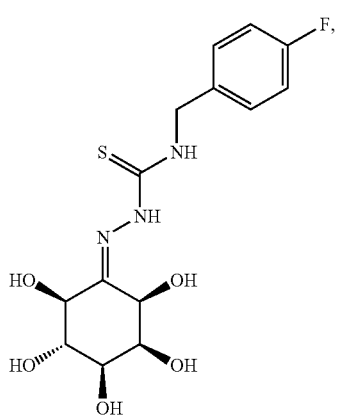
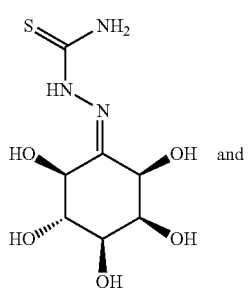
and
(DS26 (E))
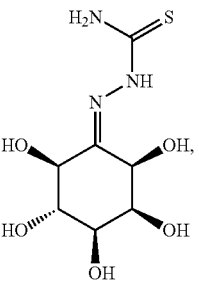
wherein said compound is capable of blocking the binding of Aβ oligomers to PrPC.
2. The method of claim 1, wherein the compound is DS26 having the structure:
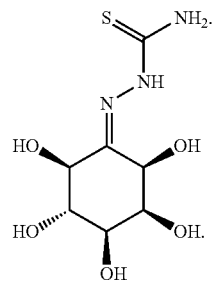
* * * * *

SEQUENCE LISTING

<160> NUMBER OF SEQ ID NOS: 9

<210> SEQ ID NO 1
<211> LENGTH: 253
<212> TYPE: PRT
<213> ORGANISM: Homo sapiens

```
<400> SEQUENCE: 1

Met Ala Asn Leu Gly Cys Trp Met Leu Val Leu Phe Val Ala Thr Trp
1               5                   10                  15

Ser Asp Leu Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Gly Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Gly Gln Gly Gly Gly Thr His
                85                  90                  95

Ser Gln Trp Asn Lys Pro Ser Lys Pro Lys Thr Asn Met Lys His Met
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Ile Ile His Phe Gly Ser Asp
    130                 135                 140

Tyr Glu Asp Arg Tyr Tyr Arg Glu Asn Met His Arg Tyr Pro Asn Gln
145                 150                 155                 160

Val Tyr Tyr Arg Pro Met Asp Glu Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Ile Thr Gln Tyr Arg Glu Ser Gln Ala
    210                 215                 220

Tyr Tyr Gln Arg Gly Ser Ser Met Val Leu Phe Ser Ser Pro Pro Val
225                 230                 235                 240

Ile Leu Leu Ile Ser Phe Leu Ile Phe Leu Ile Val Gly
                245                 250

<210> SEQ ID NO 2
<211> LENGTH: 220
<212> TYPE: PRT
<213> ORGANISM: Mus musculus

<400> SEQUENCE: 2

Met Ala Asn Leu Gly Tyr Trp Leu Leu Ala Leu Phe Val Thr Met Trp
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Gly Gly Thr Trp Gly Gln Pro His Gly Gly Gly Trp
    50                  55                  60

Gly Gln Pro His Gly Gly Ser Trp Gly Gln Pro His Gly Gly Ser Trp
65                  70                  75                  80

Gly Gln Pro His Gly Gly Gly Trp Gly Gln Gly Gly Gly Thr His Asn
                85                  90                  95

Gln Trp Asn Lys Pro Ser Lys Pro Lys Thr Asn Leu Lys His Val Ala
            100                 105                 110
```

Gly Ala Ala Ala Gly Ala Val Val Gly Leu Gly Gly Tyr Met
            115                 120                 125

Leu Gly Ser Ala Met Ser Arg Pro Met Ile His Phe Gly Asn Asp Trp
130                 135                 140

Glu Asp Arg Tyr Tyr Arg Glu Asn Met Tyr Arg Tyr Pro Asn Gln Val
145                 150                 155                 160

Tyr Tyr Arg Pro Val Asp Gln Tyr Ser Asn Gln Asn Asn Phe Val His
                165                 170                 175

Asp Cys Val Asn Ile Thr Ile Lys Gln His Thr Val Thr Thr Thr
            180                 185                 190

Lys Gly Glu Asn Phe Thr Glu Thr Asp Val Lys Met Met Glu Arg Val
            195                 200                 205

Val Glu Gln Met Cys Val Thr Gln Tyr Gln Lys Glu
210                 215                 220

<210> SEQ ID NO 3
<211> LENGTH: 254
<212> TYPE: PRT
<213> ORGANISM: Rattus norvegicus

<400> SEQUENCE: 3

Met Ala Asn Leu Gly Tyr Trp Leu Leu Ala Leu Phe Val Thr Thr Cys
1               5                   10                  15

Thr Asp Val Gly Leu Cys Lys Lys Arg Pro Lys Pro Gly Gly Trp Asn
            20                  25                  30

Thr Gly Gly Ser Arg Tyr Pro Gly Gln Gly Ser Pro Gly Gly Asn Arg
        35                  40                  45

Tyr Pro Pro Gln Ser Gly Gly Thr Trp Gly Gln Pro His Gly Gly Gly
    50                  55                  60

Trp Gly Gln Pro His Gly Gly Gly Trp Gly Gln Pro His Gly Gly Gly
65                  70                  75                  80

Trp Gly Gln Pro His Gly Gly Gly Trp Ser Gln Gly Gly Gly Thr His
                85                  90                  95

Asn Gln Trp Asn Lys Pro Ser Lys Pro Lys Thr Asn Leu Lys His Val
            100                 105                 110

Ala Gly Ala Ala Ala Ala Gly Ala Val Val Gly Gly Leu Gly Gly Tyr
        115                 120                 125

Met Leu Gly Ser Ala Met Ser Arg Pro Met Leu His Phe Gly Asn Asp
    130                 135                 140

Trp Glu Asp Arg Tyr Tyr Arg Glu Asn Met Tyr Arg Tyr Pro Asn Gln
145                 150                 155                 160

Val Tyr Tyr Arg Pro Val Asp Gln Tyr Ser Asn Gln Asn Asn Phe Val
                165                 170                 175

His Asp Cys Val Asn Ile Thr Ile Lys Gln His Thr Val Thr Thr Thr
            180                 185                 190

Thr Lys Gly Glu Asn Phe Thr Glu Thr Asp Val Lys Met Met Glu Arg
        195                 200                 205

Val Val Glu Gln Met Cys Val Thr Gln Tyr Gln Lys Glu Ser Gln Ala
210                 215                 220

Tyr Tyr Asp Gly Arg Arg Ser Ser Ala Val Leu Phe Ser Ser Pro Pro
225                 230                 235                 240

Val Ile Leu Leu Ile Ser Phe Leu Ile Phe Leu Ile Val Gly
                245                 250

-continued

```
<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Arg Gly Ser His His His His His His
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Glu Gln Lys Leu Ile Ser Glu Glu Asp Leu
1               5                   10

<210> SEQ ID NO 6
<211> LENGTH: 9
<212> TYPE: PRT
<213> ORGANISM: Unknown
<220> FEATURE:
<223> OTHER INFORMATION: Description of Unknown: Prion
      polybasic domain peptide

<400> SEQUENCE: 6

Lys Lys Arg Pro Lys Pro Gly Gly Trp
1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 7

His His His His His His
1               5

<210> SEQ ID NO 8
<211> LENGTH: 31
<212> TYPE: PRT
<213> ORGANISM: Unknown
<220> FEATURE:
<223> OTHER INFORMATION: Description of Unknown: Prion
      polybasic domain polypeptide

<400> SEQUENCE: 8

His Asn Gln Trp Asn Lys Pro Ser Lys Pro Lys Thr Asn Leu Lys His
1               5                   10                  15

Val Ala Gly Ala Ala Ala Ala Gly Ala Val Val Gly Gly Leu Gly
            20                  25                  30

<210> SEQ ID NO 9
<211> LENGTH: 4
<212> TYPE: PRT
<213> ORGANISM: Mus musculus
```

```
<400> SEQUENCE: 9
Met Ser Arg Pro
1
```